US008012963B2

(12) United States Patent
Kuo et al.

(10) Patent No.: US 8,012,963 B2

(45) Date of Patent: Sep. 6, 2011

(54) 3,4-DIHYDRO-2H-BENZO[1,4]OXAZINE AND THIAZINE DERIVATIVES AS CETP INHIBITORS

(75) Inventors: Gee-Hong Kuo, Scotch Plains, NJ (US); Thomas Rano, Branchburg, NJ (US); Aihua Wang, Jamison, PA (US); Catherine Prouty, Doylestown, PA (US); Keith T. Demarest, Flemington, NJ (US); Patricia Pelton, Long Valley, NJ (US)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 12/782,280

(22) Filed: May 18, 2010

(65) Prior Publication Data

US 2010/0227857 A1 Sep. 9, 2010

Related U.S. Application Data

(62) Division of application No. 11/746,776, filed on May 10, 2007, now Pat. No. 7,749,995.

(60) Provisional application No. 60/799,604, filed on May 11, 2006, provisional application No. 60/871,148, filed on Dec. 21, 2006.

(51) Int. Cl.
*A61K 31/536* (2006.01)

(52) U.S. Cl. .................................... 514/230.5; 544/105

(58) Field of Classification Search ................ 514/230.5
See application file for complete search history.

(56) References Cited

U.S. PATENT DOCUMENTS

| | | | |
|---|---|---|---|
| 5,580,885 | A | 12/1996 | King et al. |
| 5,616,537 | A | 4/1997 | Yokota et al. |
| 5,770,544 | A | 6/1998 | Yokota et al. |
| 6,051,601 | A | 4/2000 | Dombroski et al. |
| 6,262,074 | B1 | 7/2001 | Otten et al. |
| 6,476,075 | B1 | 11/2002 | Sikorski et al. |
| 6,479,437 | B1 | 11/2002 | Bratz et al. |
| 6,642,228 | B1 | 11/2003 | Hayashi et al. |
| 6,713,508 | B2 | 3/2004 | Sahoo et al. |
| 7,015,219 | B2 | 3/2006 | Dickson et al. |
| 7,125,891 | B2 | 10/2006 | Breslin et al. |
| 2002/0013314 | A1 | 1/2002 | Zhu et al. |
| 2003/0162777 | A1 | 8/2003 | Leonardi et al. |
| 2003/0181446 | A1 | 9/2003 | Leonardi et al. |
| 2004/0034089 | A1 | 2/2004 | Breslin et al. |
| 2005/0113368 | A1 | 5/2005 | Bhuniya et al. |
| 2006/0276509 | A1 | 12/2006 | Breslin et al. |
| 2007/0179165 | A1 | 8/2007 | Gyorkos et al. |

FOREIGN PATENT DOCUMENTS

| | | | |
|---|---|---|---|
| EP | 0198264 | A2 | 3/1986 |
| EP | 0801060 | A1 | 3/1997 |
| WO | WO 93/05038 | | 3/1993 |
| WO | WO 94/01415 | | 1/1994 |
| WO | WO 96/11920 | | 4/1996 |
| WO | WO 96/15099 | | 5/1996 |
| WO | WO 98/12180 | | 3/1998 |
| WO | WO 98/12192 | | 3/1998 |
| WO | WO 00/78716 | A1 | 12/2000 |
| WO | WO 01/12187 | A2 | 2/2001 |
| WO | WO 01/57003 | A1 | 8/2001 |
| WO | WO 02/36116 | A2 | 5/2002 |
| WO | WO 03/031436 | A1 | 4/2003 |
| WO | WO 2004/037788 | A1 | 5/2004 |
| WO | WO 2004/072041 | A1 | 8/2004 |
| WO | WO 2004/072042 | A1 | 8/2004 |
| WO | WO 2005/096688 | | 10/2005 |

OTHER PUBLICATIONS

Chalmers (TiPS vol. 17, pp. 166-172 Apr. 1996).*

Atarashi et al., "Assymetric Reduction of 7,8-Difluoro-3-methyl-2*H*-1, 4-benzoxazine. Synthesis of a Key Intermediate of (S)-(-)-Ofloxacine (DR-3355).", *J.Heterocyclic Chem.*, Feb.-Mar. 1991, pp. 329-331, vol. 28.

Au-Young and Fielding, "Synthesis and secretion of wild-type and mutant human plasma cholesteryl ester transfer protein in baculovirus-transfected insect cells: the carboxyl-terminal region is required for both lipoprotein binding and catalysis of transfer." Proc. Natl. Acad. Sci., 1992, vol. 89(9), pp. 4094-4098.

Berge et al., "Pharmaceutical Salts.", J. Pharm.Sci., 1977, pp. 1-19, vol. 66(1).

Brousseau et al., "Effects of an Inhibitor of Cholesteryl Ester Transfer Protein on HDL Cholesterol.", New England Journal of Medicine, 2004, vol. 350(15), pp. 1505-1515.

Bruce et al., "The implications of the structure of the bactericidal/permeability-increasing protein on the lipid-transfer function of the cholesteryl ester transfer protein.", Curr. Opin. Struct. Biol., 1998, pp. 426-434, vol. 8.

Connolly et al., "Sterospecific Inhibition of CETP by Chiral *N*, *N*-Disubstituted Trifluoro-3-amino-2-propanols.", Biochemistry, 2000, pp. 13870-13879, vol. 39.

Degrooth et al., "Efficacy and Safety of a Novel Cholesteryl Ester Transfer Protein Inhibitor, JTT-705, in Humans: A Randomized Phase II Dose-Response Study.", Circulation, 2002, vol. 105(18), pp. 2159-2165.

Gould P.L., "Salt Selection for Basic Drugs.", International J. Pharm., 1986, vol. 33, pp. 201-217.

Guerin et al., "Action of atorvastatin in combined hyperlipidemia: preferential reduction of cholesteryl ester transfer from HDL to VLDL1 particles.", Arterioscloerosis, Thrombosis and Vascular Biology, 2000, pp. 189-197, vol. 20(1).

Guerin et al., "A new in vitro method for the simultaneous evaluation of cholesteryl ester exchange and mass transfer between HDL and apoB-containing lipoprotein subspecies. Identification of preferential cholesteryl ester acceptors in human plasma .", Arteriosclerosis and Thrombosis: A Journal of Vascular Biology, 1994 pp. 199-206, vol. 14(2).

Guerin et al., "Preferential cholesteryl ester acceptors among the LDL subspecies of subjects with familial hypercholesterolemia.", Arteriosclerosis and Thrombosis: A Journal of Vascular Biology, 1994, pp. 679-685, vol. 14(5).

(Continued)

*Primary Examiner* — Kahsay T Habte

(57) ABSTRACT

The invention is directed to compounds of Formula (I) described herein useful as CETP inhibitors, compositions containing them, and methods of using them.

25 Claims, No Drawings

OTHER PUBLICATIONS

Guerin et al., "Absence of cholesteryl ester transfer protein-mediated cholesteryl ester mass transfer from high-density lipoprotein to low-density lipoprotein particles is a major feature of combined hyperlipidaemia.", European Journal of Clinical Investigation, 1996, pp. 485-494, vol. 26(6).
Hesler et al., "Purification and characterization of human plasma cholesteryl ester transfer protein.", J. Biol. Chem., 1987, pp. 2275-2282, vol. 262(5).
Huang et al., "Cholesteryl ester transfer protein inhibitor (JTT-705) and the development of atherosclerosis in rabbits with severe hypercholesterolaemia.", Clin. Sci., 2002, pp. 587-594, vol. 103(6).
Marcel et al., "Distribution and concentration of cholesteryl ester transfer protein in plasma of normolipemic subjects.", Journal of Clinical Investigation, 1990, pp. 10-17, vol. 85(1).
McPherson et al., "Plasma concentrations of cholesteryl ester transfer protein in hyperlipoproteinemia. Relation to cholesteryl ester transfer protein activity and other lipoprotein variables.", Arteriosclerosis and Thrombosis: A Jounral of Vascular Biology, 1991, pp. 797-804, vol 11(4).
Nishida et al., "Cholesterol ester transfer mediated by lipid transfer protein as influenced by changes in the charge characteristics of plasma lipoproteins.", Journal of Biological Chemistry, 1993, pp. 16352-16360, vol. 268(22).
Okamoto et al., "A cholesteryl ester transfer protein inhibitor attenuates atherosclerosis in rabbits.", Nature, 2000, pp. 203-207, vol. 406.
Packard, C. and Shepherd, J., "Lipoprotein Heterogeneity and Apolipoprotein B Metabolism.", Arterscler. Thromb. Vasc. Biol., 1997, pp. 3542-3556, vol. 17(12).
Rittershause et al., "Vaccine-Induced Antibodies Inhibit CETP Activity in Vivo and Reduce Aortic Lesions in a Rabbit Model of Atherosclerosis.", Arteriosclerosis, Thrombosis and Vascular Biology, 2000, pp. 2106-2112, vol. 20(9).
Still et al., "Rapid Chromatographic Technique for Preparative Separations with Moderate Resolution.", J. Org. Chem., 1978, pp. 2923-2925, vol. 43(14).
Sugano et al., "Effect of Antisense Oligonucleotides against Cholesteryl Ester Transfer Protein on the Development of Atherosclerosis in Cholesterol-fed Rabbits.", Journal of Biological Chemistry, 1998, pp. 5033-5036, vol. 273(9)
Tashiro et al., "Preparation of Bromobenzoic Acids From the Corresponding Bromotoluenes Via the Krohke Method.", Organic Preparations and Procedures International, 1987, pp. 379-383, vol. 16(5).
Tin, K.C. & Durst, T., "a-Chlorination of Sulfoxides With Sulfuryl Chloride.", Tetra. Lett., 1970, vol. 53, pp. 4643-4644, Pergamon Press, Great Britain.
Whitlock et al., "Monoclonal antibody inhibition of cholesteryl ester transfer protein activity in the rabbit. Effects on lipoprotein composition and high density lipoprotein cholesteryl ester metabolism.", Journal of Clinical Investigation, 1989, pp. 129-137, vol. 84(1).
Vippagunta, et al., "Crystalline Solids.", Advanced Drug Delivery Reviews, 2001, pp. 3-26, vol. 48.
Gavezzotti, A., "Are Crystal Structures Predictable?", Acc. Chem. Res., 1994, vol. 27, pp. 309-314.
Wolff, Manfred E., "Burger's Medicinal Chemistry, 5ed., Part 1", John Wiley & Sons, 1995, pp. 975-977.
Banker et al., "Modern Pharmaceutics, 3ed.", Marcel Dekker, New York, 1996, pp. 451 and 596.
PCT International Search Report, dated Nov. 13, 2007 for PCT Appln. No. PCT/US2007/68636 which relates to U.S. Appl. No. 11/746,776, filed May 7, 2007.
Written Opinion of the International Searching Authority for PCT Application No. PCT/US/2007/68636, Date of Mailing of Written Opinion, Nov. 13, 2007.

* cited by examiner

3,4-DIHYDRO-2H-BENZO[1,4]OXAZINE AND THIAZINE DERIVATIVES AS CETP INHIBITORS

CROSS-REFERENCE TO RELATED APPLICATIONS

This Application is a divisional application of U.S. Application Ser. No. 11/746,776, filed May 10, 2007 now U.S. Pat. No. 7,749,995, which claims priority to U.S. Provisional Patent Applications Nos. 60/799,604, filed May 11, 2006, and 60/871,148, filed Dec. 21, 2006 which are hereby incorporated by reference herein in their entireties.

FIELD OF THE INVENTION

The present invention is directed to compounds useful as CETP inhibitors, compositions containing them, and methods of using them, for example, for the treatment of disorders and conditions modulated by cholesteryl ester transfer protein (CETP).

STATEMENT REGARDING FEDERALLY SPONSORED RESEARCH OR DEVELOPMENT

The research and development of the invention described below was not federally sponsored.

BACKGROUND OF THE INVENTION

Cholesterol homeostasis is maintained by dietary intake, biosynthesis, metabolism to bile acids, absorption and a process known as reverse cholesterol transport (RCT). Cholesterol is transported in the blood by lipoproteins, which contain different apolipoproteins that are recognized by different receptors on the liver and cells such as macrophages. RCT is involved in the movement of cholesterol from peripheral tissues to the liver for excretion. This pathway may represent up to 70% of the flux of cholesterol to the liver. Inherent in this process is the remodeling of the lipoprotein particles. A key player in RCT is the cholesteryl ester transfer protein (CETP), a glycoprotein that mediates the transfer of cholesteryl ester from the cardioprotective High Density Lipoprotein (HDL) particles to the pro-atherogenic LDL (Low Density Lipoprotein), VLDL (Very Low Density Lipoprotein) and IDL (Intermediate Density Lipoprotein).

CETP is a glycoprotein with a molecular weight of about 74 kDa and a primary sequence containing 476 amino acids. Although the amino acid sequence would suggest the protein to be highly hydrophobic, most of the hydrophobic residues reside mainly on the interior, as the protein is soluble in water (Hesler et al., J. Biol. Chem., 262:2275-2282, 1987). This hydrophobic pocket allows for the binding of neutral lipids (Au-Young and Fielding, Proc. Natl. Acad. Sci., 89:4094-4098, 1992). Using the crystallographic structure of a related protein, BPI (bactericidal/permeability increasing protein) with about 20% homology to CETP, a model of CETP was published by Bruce et al., Curr. Opin. Struct. Biol., 8:426-434, 1998. The C-terminal residues were predicted to form an amphipathic helix that covers the opening of an N-terminal pocket. Lipid transfer is thought to occur through a disordering of the lipids in the lipoprotein surface followed by flipping open of the hydrophobic pocket with entry of the neutral lipid.

CETP facilitates exchange and net transfer of neutral lipids, mainly cholesteryl esters and triglycerides between plasma lipoproteins. Phospholipids can also be transferred to a lesser degree. CETP inhibitors have emerged with the potential to increase HDL cholesterol (HDL-C) to levels exceeding those of the currently available therapies.

In normal human plasma, the CETP concentration is around 1-3 μg/ml; however, in patients with hypercholesterolemia, or mixed hyperlipidemias with hypertriglyceridemia, the CETP concentrations have been reported to be 2-3 fold higher (Marcel et al., Journal of Clinical Investigation, 85:10-17, 1990, and McPherson et al., Arteriosclerosis and Thrombosis: A Journal of Vascular Biology, 11(4):797-804, 1991). Plasma CETP activity is modulated by a variety of factors including: plasma CETP concentration, plasma levels of lipoprotein acceptors and donors, plasma triglyceride levels, physical exercise, alcohol and smoking. Circulating CETP is associated with HDL, VLDL and LDL particles (Nishida et al., Journal of Biological Chemistry, 268(22):16352-60, 1993). Most seems to be associated with HDL and only about 1% is reported to be present in free form.

In patients with Type IIa hypercholesterolemia (familial hypercholesterolemia, LDL-C>160 mg/dL), elevated levels of CETP have been reported as well as increased transfer of cholesteryl ester from HDL to VLDL and LDL (Guerin et al., Arteriosclerosis and Thrombosis: A Journal of Vascular Biology, 14(5):679-85, 1994, and Guerin et al., Arteriosclerosis and Thrombosis: A Journal of Vascular Biology, 14(2):199-206, 1994) thereby generating the smaller more dense LDL particles, which are considered to be atherogenic. Type IV hypertriglyceridemia is characterized by elevated levels of VLDL and VLDL remnants with plasma triglycerides measuring >150 mg/dL. Associated with these elevations are reduced levels of HDL and apoA-I. This may be due to an increase in the CETP-mediated transfer of cholesterol esters to VLDL. This results in the formation of large VLDL1 subfractions, which are the preferential precursors of small dense proatherogenic LDL particles (Packard and Shepard, Arterscler. Thromb. Vasc. Biol., 17:3542-3556, 1997). Type IIB is a mixed hyperlipidemia characterized by simultaneous elevations in both plasma cholesterol and triglycerides with increases in VLDL and LDL and decreases in HDL. The LDL particles are shifted to the small dense LDL 4 and 5 subfractions. Plasma CETP concentrations are elevated and a higher rate of transfer activity has also been reported (Guerin et al., European Journal of Clinical Investigation, 26(6):485-94, 1996). In the case of secondary dyslipidemias such as those found in diabetes, there are also reports of elevated CETP activity particularly in the presence of hypertriglyceridemia (Guerin et al, Arterioscloerosis, Thrombosis and Vascular Biology, 20(1):189-97, 2001).

The first studies with CETP inhibitors were done in rabbits, which express high levels of CETP and are highly susceptible to atherosclerosis when fed a high cholesterol diet. Anti-sense oligonucleotides, antibodies, vaccines and small molecule inhibitors have been tested (Sugano et al., Journal of Biological Chemistry, 273(9):5033-6, 1996; Rittershaus et al., Arteriosclerosis, Thrombosis and Vascular Biology, 20(9):2106-2112, 2000; Whitlock et al., Journal of Clinical Investigation, 84(1):129-37, 1989; and Okamoto et al., Nature, 406:203-207, 2000). These studies showed that inhibition of CETP increased plasma HDL-C levels and particle size as well as decreasing aortic cholesterol content and lesion development. Administration of the small molecule inhibitor JTT-705, which irreversibly inactivated CETP by binding to a crucial cysteine residue (Cys13), to rabbits at a dose of 30 mg/kg inhibited CETP activity, increased HDL-C (+90%), reduced non-HDL-C cholesterol and lesion size (−50% and −70%, respectively, Okamoto et al., Nature, 406:203-207, 2000). However, in another study where rabbits had severe hypercholesterolemia, JTT-705 was not efficacious in preventing lesion development (Huang et al., Clin. Sci., 103(6):587-594, 2002). Interestingly there were significant elevations of plasma triglycerides in this study with JTT-705 treatment. In later clinical studies, JTT-705 was found to raise HDL-C, modestly lower LDL-C and not alter triglyceride levels (DeGrooth et al., Circulation, 105(18):2159-2165, 2002). A more potent CETP inhibitor, Torcetrapib, has shown positive results in Phase II trials, particularly in combination with Atorvastatin (Brousseau et al., New England Journal of Medicine, 350(15):1505-1515, 2004). The references cited herein are hereby incorporated by reference in their entries.

There is a continuing need for new CETP inhibitors. There is a further need for new CETP inhibitors that increase HDL-C, increase the ratio of HDL-C/total cholesterol, increase the ratio of HCL-C/LDL-C, and/or lower LDL-C and/or lower non-HDL-C cholesterol.

It is an object of the present invention to provide compounds that are CETP inhibitors. It is also an object of the invention to provide a method of treating or ameliorating a condition mediated by CETP. It is a further object of the invention to provide a useful pharmaceutical composition comprising a compound of the present invention useful as a CETP inhibitor.

SUMMARY OF THE INVENTION

In one aspect, the present invention is directed to a compound of Formula (I):

Formula (I)

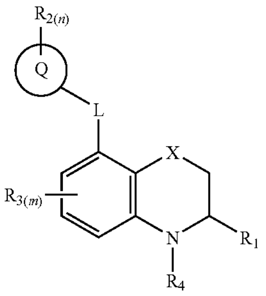

wherein:

L is a covalent bond or O;

X is O or S;

Q is $C_{6-10}$ aryl or 5- or 6-membered heteroaryl;

n is 0 to 3;

m is 0 to 3;

$R_1$ is $C_{1-10}$ alkyl, $C_{2-10}$ alkenyl, $C_{2-10}$ alkynyl, $C_{3-10}$cycloalkyl, 5- or 6-membered heteroaryl, wherein each of $C_{1-10}$ alkyl, $C_{2-10}$ alkenyl, $C_{2-10}$ alkynyl, $C_{3-10}$cycloalkyl, 5- or 6-membered heteroaryl may be optionally substituted;

or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated$C_{1-4}$alkoxy, optionally substituted $C_{1-4}$ alkylthio, halo, cyano, and hydroxy, or $R_a$ and $R_b$ together with the carbon atoms of the phenyl ring to which they are attached form an optionally substituted 5- or 6-membered heterocyclyl fused to the phenyl ring;

each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;

each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;

$R_4$ is $C_{1-10}$ alkyl optionally substituted with 1-3 members independently selected from halo, oxo, hydroxy, halogenated$C_{1-4}$alkyl, $C_{1-4}$ alkoxy, $C_{3-8}$ cycloalkyl, CN, tert-butyldimethylsilyloxy, optionally substituted heterocyclyl and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$ alkyl; or $R_4$ is $C_{1-6}$alkyl substituted with heteroaryl or phenyl substituted with 1 to 3 members independently selected from halo, hydroxy, $C_{1-3}$alkyl, halogenated$C_{1-3}$alkyl, $C_{1-4}$alkoxy, or halogenated$C_{1-4}$alkoxy;

and enantiomers, diastereomers, tautomers, solvates, or pharmaceutically acceptable salts thereof.

In another aspect, the present invention is directed to pharmaceutical compositions containing one or more compounds of Formula (I), enantiomers, diastereomers, tautomers, solvates, or pharmaceutically acceptable salts thereof as described herein admixed with a pharmaceutically acceptable carrier, excipient or diluent, wherein the compositions can be used to treat a condition directly or indirectly mediated by CETP.

In yet another aspect, the present invention is directed to a method of treating or preventing a disease or condition in a mammal which disease or condition is affected by the modulation of CETP, which method comprises administering to a mammal in need of such treatment or prevention a therapeutically effective amount of one or more compounds of Formula (I), enantiomers, diastereomers, tautomers, solvates, or pharmaceutically acceptable salts thereof as described herein.

In a further aspect, the present invention is directed to a method for treating or preventing a disease or condition selected from atherosclerosis, peripheral vascular disease, dyslipidemia (including hypertriglyceridemia, hypercholesterolemia, mixed hyperlipidemia, and hypo-HDL-cholesterolemia), hyper-LDL-cholesterolemia hyperbetaliproteinemia, hypoalphalipoproteinemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and Metabolic Syndrome, said method comprising the step of administering to a mammal in need of such treatment a therapeutically effective amount of a compound of Formula (I), or an enantiomer, diastereomer, tautomer, solvate, or pharmaceutically acceptable salt thereof.

DETAILED DESCRIPTION OF THE INVENTION

As used herein, the following underlined terms are intended to have the following meanings unless otherwise noted:

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

"$C_{a-b}$" (where a and b are integers) refers to a radical containing from a to b carbon atoms inclusive. For example, $C_{1-3}$ denotes a radical containing 1, 2 or 3 carbon atoms.

"Alkyl" whether used alone or as part of a substituent group refers to straight and branched carbon chains having 1 to 10 carbon atoms or any number within this range. Typical alkyl groups include, but are not limited to, methyl, ethyl, propyl, and butyl. In preferred embodiments, the alkyl group is $C_{1-8}$ alkyl, with $C_{1-3}$alkyl being particularly preferred. The term "alkoxy" refers to an —Oalkyl substituent group, wherein alkyl is defined supra. Similarly, the terms "alkenyl" and "alkynyl" refer to straight and branched carbon chains having 2 to 10 carbon atoms or any number within this range, wherein an alkenyl chain has at least one double bond in the chain and an alkynyl chain has at least one triple bond in the chain.

The term "cycloalkyl" refers to saturated or partially unsaturated, monocyclic or polycyclic hydrocarbon rings of from 3 to 20 carbon atom members (preferably from 3 to 14 carbon atom members). Examples of such rings include, but are not limited to, cyclopropyl, cyclobutyl, cyclopentyl, cyclohexyl, cycloheptyl or adamantyl.

In certain embodiments, wherein the alkyl, alkenyl, alkynyl, alkoxy, and/or cycloalkyl as defined herein can be optionally substituted, such alkyl, alkenyl, alkynyl, alkoxy, and cycloalkyl can be substituted with one, two or three groups independently selected from halo (F, Cl, Br, or I), oxo, cyano, amino, alkoxy, cycloalkyl, carboxy, hydroxy, heterocyclyl, and halogenatedalkyl; and/or one group selected from optionally substituted aryl and optionally substituted heteroaryl.

"Halogenated alkyl" refers to a saturated branched or straight chain alkyl radical derived by removal of at least 1 hydrogen atom from the parent alkyl and substituting it with a halogen; the parent alkyl chain contains from 1 to 10 carbon atoms with 1 or more hydrogen atoms substituted with halogen atoms up to and including substitution of all hydrogen atoms with halogen. Preferred halogenated alkyl groups are fluorinated alkyls, including trifluoromethyl substituted alkyls and perfluorinated alkyls; more preferred fluorinated alkyls include trifluoromethyl, perfluoroethyl, 1,1,2,2-tetrafluoroethyl, 2,2,2-trifluoroethyl, perfluoropropyl, 1,1,2,2,3,3-Hexafluoro-propyl, 3,3,3-trifluoroprop-1-yl, 3,3,3-trifluoroprop-2-yl; a particularly preferred fluorinated alkyls are trifluoromethyl and 1,1,2,2-tetrafluoroethyl.

"Halogenated alkoxy" refers to a radical derived from a halogenated alkyl radical attached to an oxygen atom having one open valence for attachment to a parent structure. Preferred halogenated alkoxy groups are fluorinated alkoxy groups, including trifluoromethoxy and 1,1,2,2-tetrafluoroethoxy.

"Alkylthio" refers to an alkyl group as defined herein attached through one or more sulfur (S) atoms. For example, an alkylthio group can include —S—$C_{1-6}$alkyl optionally substituted with, for example, one, two, or three groups selected from, halo (F, Cl, Br, or I), amino, alkoxy, carboxy, and hydroxy.

"Oxo" whether used alone or as part of a substituent group refers to an O═ to either a carbon or a sulfur atom. For example, phthalimide and saccharin are examples of compounds with oxo substituents.

The term "aryl" refers to an unsaturated monocyclic or polycyclic ring, preferably an aromatic monocyclic ring of 6 carbon members or to an unsaturated, aromatic polycyclic ring of from 10 to 14 carbon members. Preferred aryl groups for the practice of this invention are phenyl and naphthalenyl. In certain embodiments, the aryl ring is a $C_{6-10}$aryl. "Ph" when used herein refers to phenyl. In certain embodiments, wherein the aryl is optionally substituted, the aryl can be substituted with one, two or three groups independently selected from optionally substituted alkyl, halogenated alkyl, optionally substituted alkenyl, optionally substituted alkynyl, halo, —CHO, cyano, amino, optionally substituted alkoxy, halogenated alkoxy, carboxy, hydroxy, and optionally substituted heterocyclyl.

The term "arylalkyl" means an alkyl group substituted with an aryl group (e.g., benzyl, phenylethyl, naphthylmethyl). Similarly, the term "arylalkoxy" indicates an alkoxy group substituted with an aryl group (e.g., benzyloxy). In particularly preferred embodiments, the alkyl moiety of the arylalkyl group is ($C_{1-3}$) and the aryl moiety is ($C_{6-10}$).

"Heterocyclyl" or "heterocycle" is a 3- to 8-member, preferably 5-7 membered saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 1,3-dioxolane, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone. A "heterocyclyl" can be a partially unsaturated ring such as 2-pyrroline, 3-pyrroline, 2-imidazoline, 2-pyrazoline, or indolinone. In certain embodiments, wherein the "heterocyclyl" or "heterocycle" is optionally substituted, the "heterocyclyl" or "heterocycle" can be substituted with, one, two or three groups independently selected from $C_{1-6}$alkyl, halogenated$C_{1-6}$alkyl, $C_{2-6}$alkenyl, $C_{2-6}$alkynyl, halo, hydroxy, —CN, and/or one group selected from aryl, heteroaryl, heterocyclyl, —$SO_3$H, —C(O)OH, —C(O)O—$C_{1-4}$alkyl, C(O)NR'R", —OR', —SR', —C(O)R', —N(R')(R"), —$S(O)_2$—R', and —$S(O)_2$—N(R)(R"), wherein R' and R" are independently selected from H, $C_{1-6}$-alkyl, aryl, and heteroaryl.

"Heteroaryl" refers to a monovalent heteroaromatic radical derived by the removal of one hydrogen atom from a single atom of a parent heteroaromatic ring system. Preferably, the term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclic ring. For such compounds in which the heteroaryl ring is fused to a moiety as described above, the point of attachment is through the heteroaryl ring portion of the compound. Examples of heteroaryl groups include, and are not limited to, furyl, thienyl, pyrrolyl, oxazolyl, thiazolyl, tetrazolyl, imidazolyl, pyrazolyl, isoxazolyl, isothiazolyl, oxadiazolyl, triazolyl, thiadiazolyl, pyranyl, pyridinyl, pyridazinyl, pyrimidinyl or pyrazinyl; fused heteroaryl groups include indolyl, isoindolyl, indolinyl, isoindolinyl, indolizinyl, benzofuryl, benzothienyl, indazolyl, benzimidazolyl, benzthiazolyl, benzoxazolyl, benzisoxazolyl, benzothiadiazolyl, benzotriazolyl, purinyl, quinolizinyl, quinoxalinyl, quinolinyl, isoquinolinyl or quinazolinyl. Preferred are thienyl, oxazolyl, thiazolyl, isoxazolyl, pyridinyl, and pyridazinyl. In certain embodiments, wherein the heteroaryl is optionally substituted, the heteroaryl can be optionally substituted with one, two or three groups independently selected from alkyl, halogenatedalkyl, alkenyl, alkynyl, halo, —CHO, cyano, amino, optionally substituted alkoxy, halogenatedalkoxy, carboxy, hydroxy, and heterocyclyl.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "halogen" or "halo" refers to fluorine, chlorine, bromine and iodine. Substituents that are substituted with multiple halogens are substituted in a manner that provides compounds, which are stable.

Throughout this disclosure, unless otherwise indicated, the terminal portion of the designated side chain is described first, followed by the adjacent functionality toward the point of attachment. Thus, for example, a "phenyl$C_{1-6}$alkylaminocarbonyl$C_{1-6}$alkyl" substituent refers to a group of the formula

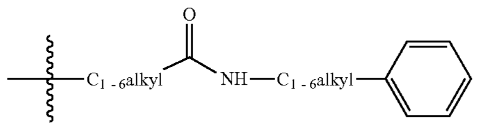

The present invention is directed to compositions comprising a compound of Formula (I) for uses as CETP inhibitors:

Formula (I)

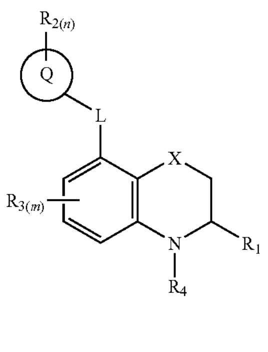

wherein:

L is a covalent bond or O;

X is O or S;

Q is $C_{6-10}$ aryl or 5- or 6-membered heteroaryl;

n is 0 to 3;

m is 0 to 3;

$R_1$ is $C_{1-10}$ alkyl, $C_{2-10}$ alkenyl, $C_{2-10}$ alkynyl, $C_{3-10}$cycloalkyl, 5- or 6-membered heteroaryl, wherein each of $C_{1-10}$ alkyl, $C_{2-10}$ alkenyl, $C_{2-10}$ alkynyl, $C_{3-10}$cycloalkyl, 5- or 6-membered heteroaryl may be optionally substituted;

or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated$C_{1-4}$alkoxy, optionally substituted $C_{1-4}$ alkylthio, halo, cyano, and hydroxy, or $R_a$ and $R_b$ together with the carbon atoms of the phenyl ring to which they are attached form an optionally substituted 5- or 6-membered heterocyclyl fused to the phenyl ring;

each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;

each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;

$R_4$ is $C_{1-10}$ alkyl optionally substituted with 1-3 members independently selected from halo, oxo, hydroxy, halogenated$C_{1-4}$alkyl, $C_{1-4}$ alkoxy, $C_{3-8}$ cycloalkyl, CN, tert-butyldimethylsilyloxy, optionally substituted heterocyclyl and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$ alkyl; or $R_4$ is $C_{1-6}$alkyl substituted with heteroaryl or phenyl substituted with 1 to 3 members independently selected from halo, hydroxy, $C_{1-3}$alkyl, halogenated$C_{1-3}$alkyl, $C_{1-4}$alkoxy, or halogenated$C_{1-4}$alkoxy;

and enantiomers, diastereomers, tautomers, solvates, or pharmaceutically acceptable salts thereof.

Particularly, the present invention features a compound of Formula (I) wherein m is 0.

Particularly, the present invention features a compound of Formula (I) wherein n is 1 or 2.

Particularly, the present invention features a compound of Formula (I) wherein L is a covalent bond.

Particularly, the present invention features a compound of Formula (I) wherein Q is phenyl.

Particularly, the present invention features a compound of Formula (I) wherein Q is thienyl or pyridinyl.

Particularly, the present invention features a compound of Formula (I) wherein X is O.

Particularly, the present invention features a compound of Formula (I) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, hydroxy, halogenated $C_{1-4}$alkylthio, or an optionally substituted five membered heterocyclyl ring fused to the phenyl ring forming a bicyclic ring system.

Particularly, the present invention features a compound of Formula (I) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

Particularly, the present invention features a compound of Formula (I) wherein $R_1$ is phenyl substituted with halogenated $C_{1-4}$alkyl or halogenated $C_{1-4}$alkoxy, preferably $R_1$ is phenyl substituted with —$OCF_2CF_2H$, —$CF_3$, or —$OCF_3$.

Particularly, the present invention features a compound of Formula (I) wherein $R_1$ is $C_{1-6}$ alkyl substituted with hydroxy, $C_{1-4}$alkoxy, oxo, halo, or cyano.

Particularly, the present invention features a compound of Formula (I) wherein $R_1$ is furanyl or thienyl optionally substituted with $C_{1-3}$alkyl, $C_{1-3}$alkoxy, hydroxy, or cyano.

Particularly, the present invention features a compound of Formula (I) wherein n is 1, 2, or 3 and each $R_2$ is independently selected from halo, halogenated $C_{1-4}$alkyl, and halogenated $C_{1-4}$alkoxy, preferably $R_2$ is —$OCF_2CF_2H$, —$OCF_3$ or F.

Particularly, the present invention features a compound of Formula (I) wherein n is 1 and $R_2$ is halogenated $C_{1-4}$alkoxy, preferably $R_2$ is —$OCF_2CF_2H$.

Particularly, the present invention features a compound of Formula (I) wherein $R_4$ is $C_{1-5}$ alkyl optionally substituted with 1 or 2 members each independently selected from halo, oxo, hydroxy, halogenated$C_{1-4}$alkyl, and optionally substituted heterocyclyl; preferably $R_4$ is $C_{1-3}$ alkyl substituted with 2 members each independently selected from halo, hydroxy, and halogenated$C_{1-3}$alkyl.

In particular, the present invention is directed to a compound of Formula (I) wherein X is O;

Q is phenyl;

m is 0;

n is 1, 2, or 3;

L is a covalent bond;

$R_1$ is phenyl optionally substituted with $C_{1-4}$ alkyl, halogenated$C_{1-4}$alkyl, $C_{1-4}$alkoxy, halogenated$C_{1-4}$ alkoxy, or cyano;

Each $R_2$ is independently selected from halo, hydroxy, cyano, $C_{1-4}$ alkoxy, halogenated$C_{1-4}$ alkoxy, $C_{1-4}$alkyl, halogenated$C_{1-4}$alkyl, and —C(O)H; and $R_4$ is $C_{1-6}$ alkyl substituted with 1-3 members independently selected from halo, hydroxy, oxo, halogenated$C_{1-4}$ alkyl, $C_{1-4}$alkoxy, and halogenated$C_{1-4}$alkoxy.

In particular, the present invention is directed to a compound of Formula (I) wherein Q is phenyl;

n is 1;

m is 0; and

L is a covalent bond.

In particular, the present invention is directed to a compound of Formula (I) as shown above, wherein (n) is 1; (m) is 0; and the Q-$R_2$ group is

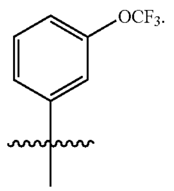

In particular, the present invention is directed to a compound of Formula (I) as shown above, wherein (m) is 0; and $R_1$ is

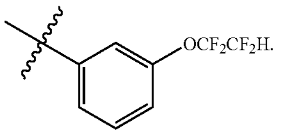

In particular, the present invention is directed to a compound of Formula (I) as shown above wherein (m) is 0, and $R_4$ is

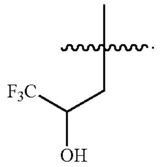

In particular, the present invention is directed to a compound of Formula (I) wherein X is O;

Q is phenyl;

m is 0;

n is 1 or 2;

L is a covalent bond;

$R_1$ is $C_{1-5}$alkyl substituted with oxo, hydroxy, or $C_{1-3}$alkoxy, thienyl optionally substituted with $C_{1-3}$alkyl or $C_{1-3}$alkoxy, furanyl, or phenyl optionally substituted with halogenated$C_{1-4}$alkyl, halogenated$C_{1-4}$alkoxy, $C_{1-4}$alkoxy, or halo;

Each $R_2$ is independently selected from halo, $C_{1-4}$alkyl, halogenated$C_{1-4}$alkyl, halogenated$C_{1-4}$alkoxy, and $C_{1-4}$alkoxy; and $R_4$ is $C_{1-5}$ alkyl optionally substituted with 1-3 members independently selected from —OH, halogenated$C_{1-3}$alkyl, and $C_{1-4}$alkoxy.

In particular, the present invention is directed to a compound of Formula (I) wherein X is O;

Q is phenyl;

m is 0;

n is 1 or 2;

L is a covalent bond;

$R_1$ is $C_{1-5}$alkyl substituted with oxo, hydroxy, or $C_{1-3}$alkoxy, thienyl optionally substituted with $C_{1-3}$alkyl or $C_{1-3}$alkoxy, furanyl, or phenyl optionally substituted with —$OCF_2CF_2H$, —$CF_3$, —F, —$OCH_3$, —Cl, or —$OCF_3$;

Each $R_2$ is independently selected from —$OCF_3$, —$CF_3$, and —F; and $R_4$ is $C_{1-5}$ alkyl optionally substituted with 1-3 members independently selected from —OH, halogenated$C_{1-3}$alkyl, and $C_{1-4}$alkoxy.

In particular, the present invention is directed to a compound of Formula (I) wherein Q is thienyl or pyridinyl;

X is O;

m is 0;

n is 0;

L is a covalent bond;

$R_1$ is $C_{1-5}$alkyl substituted with oxo, hydroxy, or $C_{1-3}$alkoxy, thienyl optionally substituted with $C_{1-3}$alkyl or $C_{1-3}$alkoxy, furanyl, or phenyl optionally substituted with halogenated$C_{1-4}$alkyl, halogenated$C_{1-4}$alkoxy, $C_{1-4}$alkoxy, or halo; and $R_4$ is $C_{1-5}$ alkyl optionally substituted with 1-3 members independently selected from —OH, halogenated$C_{1-3}$alkyl, and $C_{1-4}$alkoxy.

In particular, the present invention is directed to a compound of Formula (I) as shown above wherein:

(a) X is O;

(b) X is S;

(c) $R_1$ is $C_{1-6}$alkyl substituted with hydroxy, oxo, or $C_{1-3}$alkoxy;

(d) $R_1$ is thienyl optionally substituted with $C_{1-3}$alkyl or $C_{1-3}$alkoxy;

(e) $R_1$ is phenyl optionally substituted with 1 or 2 members selected from $R_a$ and $R_b$, wherein $R_a$ and $R_b$ are independently selected from the group consisting of $C_{1-4}$ alkyl, halogenated$C_{1-4}$ alkyl, $C_{1-4}$ alkoxy, halogenated $C_{1-4}$ alkoxy, phenyl$C_{1-3}$alkoxy, —S—$CF_3$, halo, cyano, and hydroxy, or $R_a$ and $R_b$ together with the carbon atoms they are attached to form 5- or 6-membered heterocyclyl fused to the phenyl ring; preferably $R_1$ is phenyl,

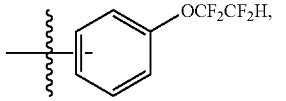 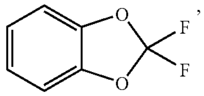,

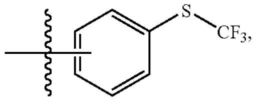, 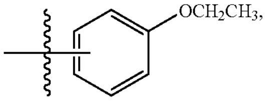

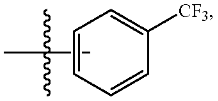 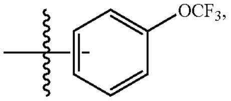

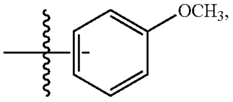

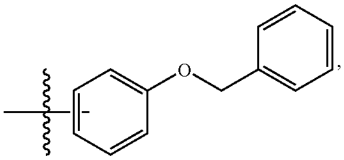

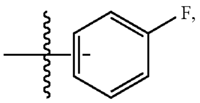 or 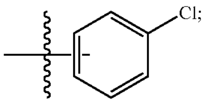

(f) $R_1$ is optionally substituted 5- or 6-membered heteroaryl, preferably,

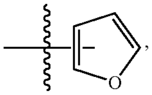, 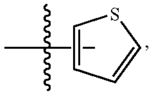, 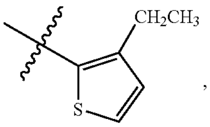,

-continued

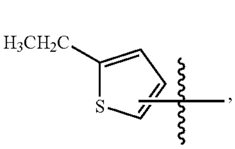, 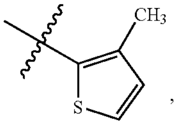,

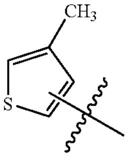 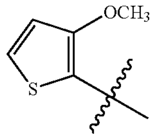 or 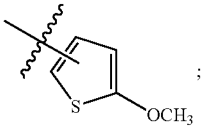;

(g) L is a covalent bond;

(h) Q is $C_{6-10}$ aryl, and preferably Q is phenyl;

(i) Q is 5- or 6-membered heteroaryl; preferably thienyl, oxazolyl, thiazolyl, isoxazolyl, pyridinyl, and pyridazinyl; and more preferably thienyl and pyridinyl;

(j) each $R_2$ is independently selected from halo, hydroxy, cyano, $C_{1-4}$ alkoxy, halogenated$C_{1-4}$ alkoxy, $C_{1-4}$alkyl, halogenated$C_{1-4}$alkyl, and —C(O)H; preferably —$CH_3$, —$CH_2CH_3$, —C(O)H, —O—$CH_3$, —O—$CF_3$, —O—$CH(CH_3)_2$, —$CH(CH_3)_2$, CN, OH, F, Cl, and —$CF_3$; more preferably —O—$CF_3$, F, and —$CF_3$;

(k) n is 1, 2, or 3;

(l) m is 0;

(m) $R_4$ is —C(O)O—$C_{1-4}$alkyl, preferably —C(O)O—$CH_3$ or —C(O)O—$CH_2CH_3$;

(n) $R_4$ is $C_{1-5}$ alkyl optionally substituted with 1-3 members independently selected from halo, oxo, hydroxy, halogenated$C_{1-3}$alkyl, $C_{1-4}$ alkoxy, tert-butyldimethylsilyloxy, $C_{3-8}$ cycloalkyl, CN, heterocyclyl, and —$NR_cR_d$, wherein $R_c$ and $R_d$ are independently selected from H, —$S(O)_2$—$C_{1-4}$alkyl, $C_{1-3}$ alkyl, —C(O)—$C_{1-3}$ alkyl, and —C(O)O—$C_{1-3}$ alkyl, more preferably $R_4$ is $C_{1-5}$ alkyl optionally substituted with 1-2 members independently selected from oxo, F, —$CF_3$, hydroxy, tert-tert-butyldimethylsilyloxy, —$NH_2$, —$N(CH_3)_2$, —O—$CH_3$, —O—$CH_2CH_3$,

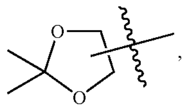, 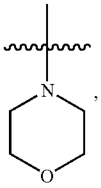, 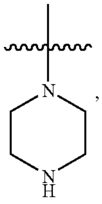, 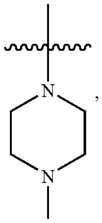,

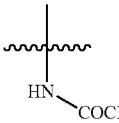, 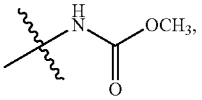 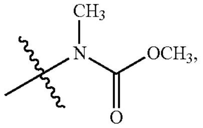

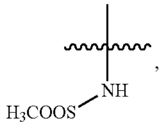, and 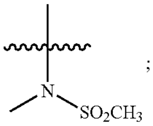;

more preferably $R_4$ is $C_{1-3}$ alkyl substituted with OH and —$CF_3$, more preferably

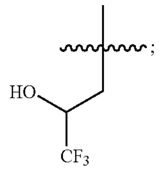;

and enantiomers, diastereomers, tautomers, solvates, or pharmaceutically acceptable salts thereof; or any possible combinations of examples (a)-(n) above.

More particularly, the present invention is directed to a compound of Formula (I) as shown above wherein:

m is 0;

n is 1, 2, or 3;

$R_1$ is $—CH_2—CH{=}CH_2$, $—CH_2CH_2CH_2OH$, $—CH_2CH_2CH_2—O—CH_3$, or $—CH_2—C(O)—C(CH_3)_3$, Ph,

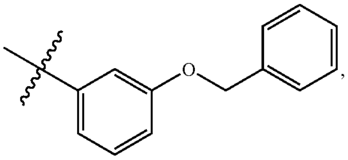, 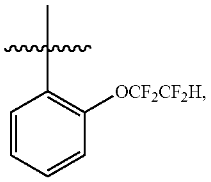

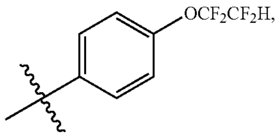 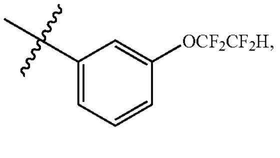

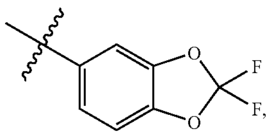 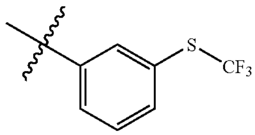,

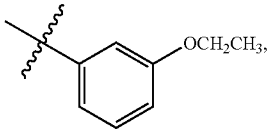 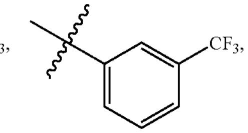

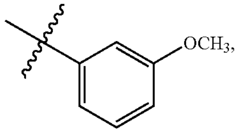 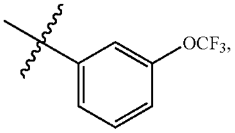

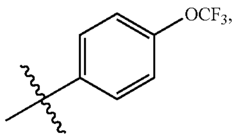 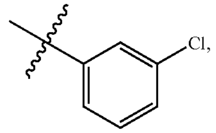

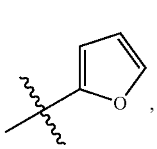, 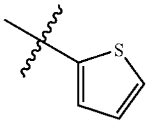, 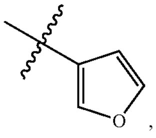,

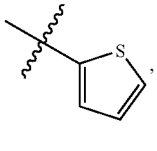, 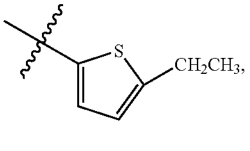

-continued

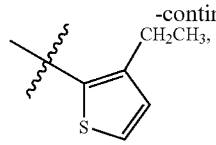 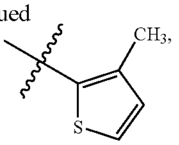

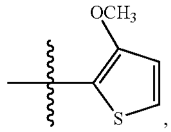, or 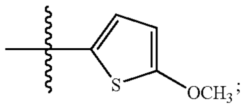;

Each $R_2$ is independently selected from $—O—CF_3$, F, or $—CF_3$; and $R_4$ is $—C(O)O—CH_3$, $—C(O)O—CH_2CH_3$, or $C_{1-5}$ alkyl optionally substituted with 1-2 members independently selected from oxo, F, $—CF_3$, hydroxy, $NH_2$, $—N(CH_3)_2$, $—O—CH_3$,

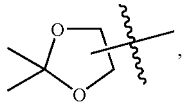, 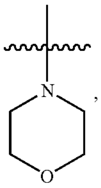, 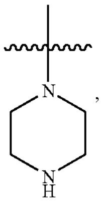, 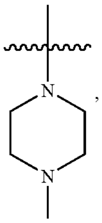,

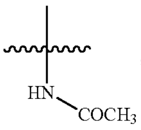, 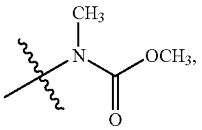 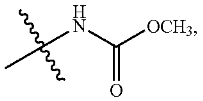

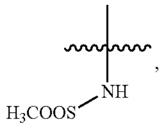, and 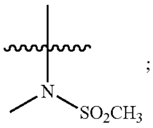;

and enantiomers, diastereomers, tautomers, solvates, or pharmaceutically acceptable salts thereof.

In one aspect, the present invention is directed to a compound of Formula (Ia):

Formula (Ia)

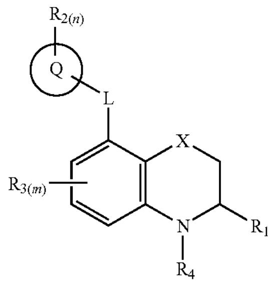

wherein:

X is O or S;

L is a covalent bond or O;

Q is phenyl, naphthalenyl, or a heteroaryl selected from the group consisting of thienyl, oxazolyl, thiazolyl, isoxazolyl, pyridinyl, and pyridazinyl;

n is 0 to 3;

m is 0 to 3;

$R_1$ is $C_{1-10}$ alkyl, $C_{2-10}$alkenyl, $C_{2-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with 1 to 3 substituents independently selected from halo, cyano, hydroxy, oxo, $C_{1-3}$alkyl, and $C_{1-3}$alkoxy;

or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated$C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated$C_{1-4}$alkylthio, halo, cyano, and hydroxy, or $R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyano, and hydroxy;

each $R_2$ is independently selected from the group consisting of halo, hydroxy, cyano, $C_{1-4}$ alkoxy, halogenated $C_{1-4}$alkoxy, $C_{1-4}$ alkyl, halogenated$C_{1-4}$ alkyl, and —C(O)H;

each $R_3$ is independently selected from the group consisting of $C_{1-4}$ alkyl, $C_{1-4}$ alkoxy, halo, cyano, and hydroxy;

$R_4$ is $C_{1-10}$ alkyl, halogenated $C_{1-10}$alkyl, or phenyl$C_{1-3}$ alkyl, wherein said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated$C_{1-4}$ alkoxy, $C_{3-8}$ cycloalkyl, cyano, tert-butyldimethylsilyloxy, heterocyclyl optionally substituted with 1 or 2 $C_{1-3}$alkyl groups, and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$alkyl;

and enantiomers, diastereomers, tautomers, solvates, or pharmaceutically acceptable salts thereof.

Particularly, the present invention features a compound of Formula (Ia) wherein X is O.

Particularly, the present invention features a compound of Formula (Ia) wherein m is 0.

Particularly, the present invention features a compound of Formula (Ia) wherein n is 1 or 2.

Particularly, the present invention features a compound of Formula (Ia) wherein L is a covalent bond.

Particularly, the present invention features a compound of Formula (Ia) wherein Q is phenyl.

Particularly, the present invention features a compound of Formula (Ia) wherein Q is thienyl or pyridinyl.

Particularly, the present invention features a compound of Formula (Ia) wherein $R_1$ is phenyl substituted with $C_{1-4}$ alkyl, halogenated $C_{1-4}$alkyl, $C_{1-4}$ alkoxy, halogenated$C_{1-4}$alkoxy, halo, cyano, or hydroxy.

Particularly, the present invention features a compound of Formula (Ia) wherein $R_1$ is phenyl substituted with halogenated $C_{1-4}$alkyl or halogenated$C_{1-4}$alkoxy, preferably $R_1$ is phenyl substituted with —$OCF_2CF_2H$, —$CF_3$, or —$OCF_3$.

Particularly, the present invention features a compound of Formula (Ia) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, hydroxy, halogenated $C_{1-4}$alkylthio, or an optionally substituted five membered heterocyclyl ring fused to the phenyl ring forming a bicyclic ring system.

Particularly, the present invention features a compound of Formula (Ia) wherein $R_1$ is $C_{1-6}$ alkyl substituted with hydroxy, $C_{1-4}$alkoxy, oxo, halo, or cyano.

Particularly, the present invention features a compound of Formula (Ia) wherein $R_1$ is furanyl or thienyl optionally substituted with $C_{1-3}$alkyl, $C_{1-3}$alkoxy, hydroxy, or cyano.

Particularly, the present invention features a compound of Formula (Ia) wherein n is 1 and $R_2$ is halo, halogenated $C_{1-4}$alkyl, or halogenated 4alkoxy, preferably $R_2$ is —$OCF_2CF_2H$ or —$OCF_3$.

Particularly, the present invention features a compound of Formula (Ia) wherein n is 1, 2, or 3 and each $R_2$ is independently selected from halo, halogenated $C_{1-4}$alkyl, and halogenated $C_{1-4}$alkoxy; preferably $R_2$ is —$OCF_2CF_2H$, —$OCF_3$ or F.

Particularly, the present invention features a compound of Formula (Ia) wherein n is 1 and $R_2$ is halogenated $C_{1-4}$alkoxy, preferably $R_2$ is —$OCF_2CF_2H$.

Particularly, the present invention features a compound of Formula (Ia) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

Particularly, the present invention features a compound of Formula (Ia) wherein $R_4$ is $C_{1-5}$ alkyl substituted with —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$alkyl.

Particularly, the present invention features a compound of Formula (Ia) wherein $R_4$ is halogenated$C_{1-4}$ alkyl substituted with oxo, hydroxy, $C_{1-4}$alkoxy, or cyano; preferably $R_4$ is fluorinated$C_{1-3}$ alkyl substituted with hydroxy.

Particularly, the present invention features a compound of Formula (Ia) wherein $R_4$ is phenyl$C_{1-3}$ alkyl wherein the phenyl group is substituted with hydroxy, $C_{1-4}$alkoxy, cyano, or halogenated$C_{1-4}$ alkoxy, preferably $R_4$ is phenyl$C_{1-3}$ alkyl wherein the phenyl group is substituted with halogenated$C_{1-4}$ alkoxy.

In particular, the present invention is directed to a compound of Formula (Ia) wherein X is O;

Q is phenyl;

m is 0;

n is 1 or 2;

L is a covalent bond;

$R_1$ is phenyl optionally substituted with $C_{1-4}$ alkyl, halogenated$C_{1-4}$alkyl, $C_{1-4}$alkoxy, halogenated$C_{1-4}$ alkoxy, or cyano;

Each $R_2$ is independently selected from halo, hydroxy, cyano, $C_{1-4}$ alkoxy, halogenated$C_{1-4}$ alkoxy, $C_{1-4}$alkyl, halogenated$C_{1-4}$alkyl, and —C(O)H; and $R_4$ is $C_{1-5}$ alkyl substituted with 1 to 2 members independently selected from hydroxy, $C_{1-4}$alkoxy, oxo, halogenated$C_{1-4}$alkoxy, $C_{3-8}$cycloalkyl, cyano; or $R_4$ is halogenated$C_{1-4}$ alkyl substituted with hydroxy, $C_{1-4}$alkoxy, oxo, or cyano.

In particular, the present invention is directed to a compound of Formula (Ia) wherein X is O;

m is 0; and

L is a covalent bond.

In particular, the present invention is directed to a compound of Formula (Ia) as shown above, wherein (n) is 1; (m) is 0; and the Q-$R_2$ group is

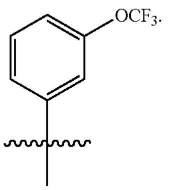

In particular, the present invention is directed to a compound of Formula (Ia) as shown above, wherein (m) is 0; and $R_1$ is

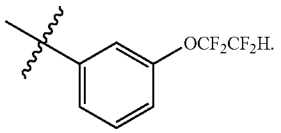

In particular, the present invention is directed to a compound of Formula (Ia) as shown above wherein (m) is 0, and $R_4$ is

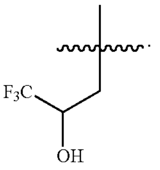

In particular, the present invention is directed to a compound of Formula (Ia) wherein X is O;

Q is phenyl;

m is 0;

n is 1 or 2;

L is a covalent bond;

$R_1$ is $C_{1-5}$alkyl substituted with oxo, hydroxy or $C_{1-3}$alkoxy; thienyl optionally substituted with $C_{1-3}$alkyl or $C_{1-3}$alkoxy; furanyl; or phenyl optionally substituted with —$OCF_2CF_2H$, —$CF_3$, —F, —$OCH_3$, —Cl, or —$OCF_3$;

Each $R_2$ is independently selected from —$OCF_3$, —$CF_3$, —F; and $R_4$ is $C_{1-6}$alkyl optionally substituted with 1 to 2 members independently selected from —OH and —$OCH_3$; or $R_4$ is halogenated$C_{1-4}$ alkyl substituted with hydroxy, $C_{1-4}$alkoxy, oxo, or cyano.

In particular, the present invention is directed to a compound of Formula (Ia) wherein X is O;

Q is thienyl or pyridinyl;

m is 0;

n is 0;

L is a covalent bond;

$R_1$ is phenyl optionally substituted with $C_{1-4}$ alkyl, halogenated$C_{1-4}$alkyl, $C_{1-4}$alkoxy, halogenated$C_{1-4}$ alkoxy, halo, or cyano; and $R_4$ is $C_{1-5}$ alkyl substituted with 1 to 2 members independently selected from hydroxy, $C_{1-4}$alkoxy, oxo, halogenated$C_{1-4}$alkoxy, heterocyclyl, $C_{3-8}$cycloalkyl, and cyano; or $R_4$ is halogenated$C_{1-4}$ alkyl substituted with hydroxy, $C_{1-4}$alkoxy, oxo, or cyano.

In particular, the present invention is directed to a compound of Formula (Ia) as shown above wherein:

(a) X is O;

(b) X is S;

(c) $R_1$ is $C_{1-6}$alkyl substituted with hydroxy, oxo, or $C_{1-3}$alkoxy;

(d) $R_1$ is thienyl optionally substituted with $C_{1-3}$alkyl or $C_{1-3}$alkoxy;

(e) $R_1$ is phenyl optionally substituted with 1 or 2 members selected from $R_a$ and $R_b$, wherein $R_a$ and $R_b$ are independently selected from the group consisting of $C_{1-4}$ alkyl, halogenated$C_{1-4}$ alkyl, $C_{1-4}$ alkoxy, halogenated $C_{1-4}$ alkoxy, phenyl$C_{1-3}$alkoxy, —S—$CF_3$, halo, cyano, and hydroxy, or $R_a$ and $R_b$ together with the carbon atoms they are attached to form 5- or 6-membered heterocyclyl fused to the phenyl ring; preferably $R_1$ is phenyl,

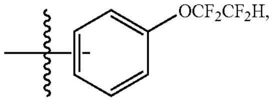 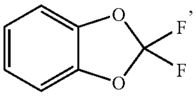,

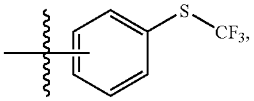 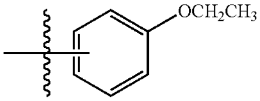,

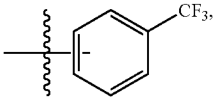 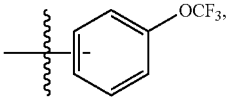

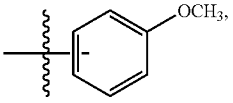

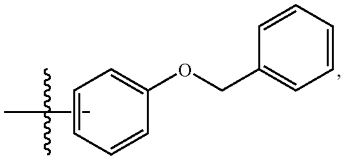,

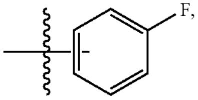 or 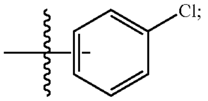;

(f) $R_1$ is optionally substituted 5- or 6-membered heteroaryl, preferably,

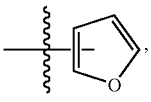, 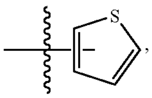, 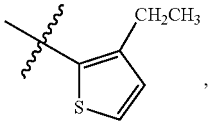,

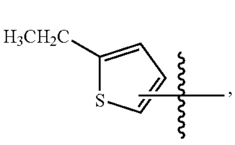, 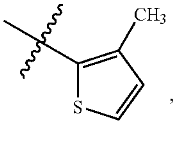,

-continued

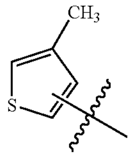 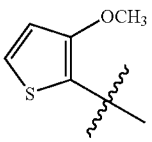 or 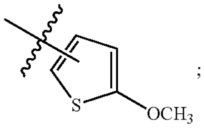 ;

(g) L is a covalent bond;

(h) Q is phenyl;

(i) Q is thienyl, oxazolyl, thiazolyl, isoxazolyl, pyridinyl, and pyridazinyl; and more preferably thienyl and pyridinyl;

(j) each $R_2$ is independently selected from halo, hydroxy, cyano, $C_{1-4}$ alkoxy, halogenated$C_{1-4}$ alkoxy, $C_{1-4}$alkyl, halogenated$C_{1-4}$alkyl, and —C(O)H; preferably —$CH_3$, —$CH_2CH_3$, —C(O)H, —O—$CH_3$, —O—$CF_3$, —O—$CH(CH_3)_2$, —$CH(CH_3)_2$, CN, OH, F, Cl, and —$CF_3$; more preferably —O—$CF_3$, F, and —$CF_3$;

(k) n is 1, 2, or 3;

(l) m is 0;

(m) $R_4$ is —C(O)O—$C_{1-4}$alkyl, preferably —C(O)O—$CH_3$ or —C(O)O—$CH_2CH_3$;

(n) $R_4$ is $C_{1-5}$ alkyl optionally substituted with 1 or 2 members independently selected from oxo, hydroxy, $C_{1-4}$ alkoxy, $C_{3-5}$ cycloalkyl, CN, heterocyclyl, and —$NR_cR_d$, wherein $R_c$ and $R_d$ are independently selected from H, —$S(O)_2$—$C_{1-4}$alkyl, $C_{1-3}$ alkyl, —C(O)—$C_{1-3}$ alkyl, and —C(O)O—$C_{1-3}$ alkyl, (o) $R_4$ is $C_{1-5}$ alkyl optionally substituted with 1 or 2 members independently selected from oxo, hydroxy, —$NH_2$, —$N(CH_3)_2$, —O—$CH_3$, —O—$CH_2CH_3$,

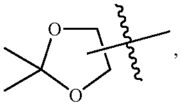, 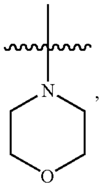, 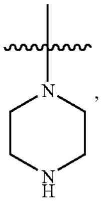, 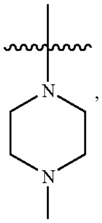,

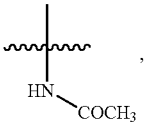, 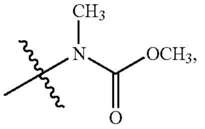 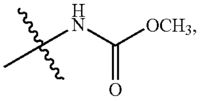

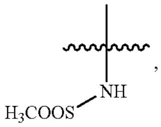, and 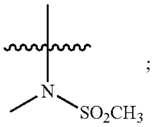 ;

(p) $R_4$ is halogenated $C_{1-4}$ alkyl optionally substituted with oxo, hydroxy, $C_{1-4}$ alkoxy, or cyano; preferably $R_4$ is fluorinated$C_{1-3}$alkyl substituted with hydroxy; more preferably $R_4$ is

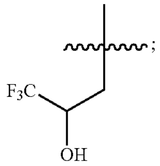

and enantiomers, diastereomers, tautomers, solvates, or pharmaceutically acceptable salts thereof; or any possible combinations of examples (a)-(p) above.

More particularly, the present invention is directed to a compound of Formula (Ia) as shown above wherein:

m is 0;

n is 1, 2, or 3;

$R_1$ is —$CH_2$—CH=$CH_2$, —$CH_2CH_2CH_2OH$, —$CH_2CH_2CH_2$—O—$CH_3$, or —$CH_2$—C(O)—$C(CH_3)_3$, Ph,

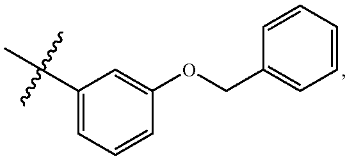,

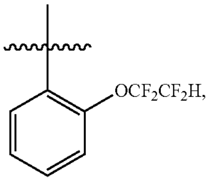 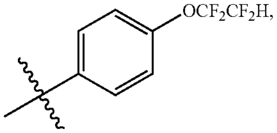

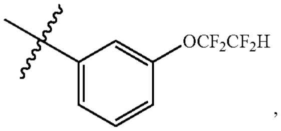, 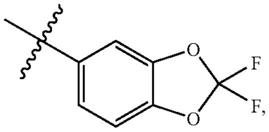

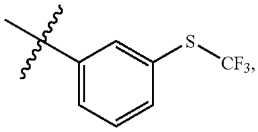 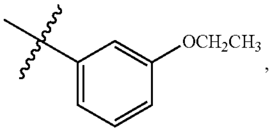,

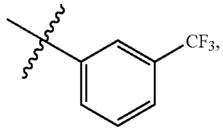 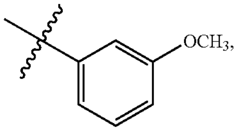

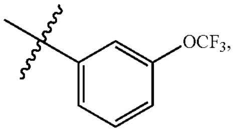 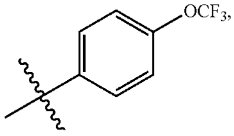

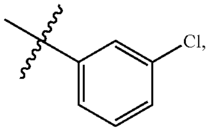 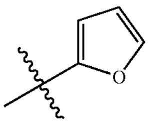,

-continued

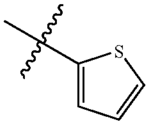, 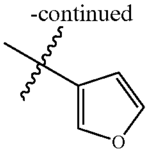, 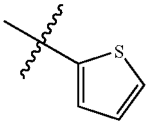,

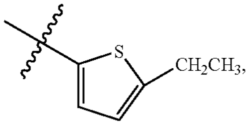 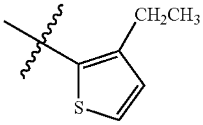,

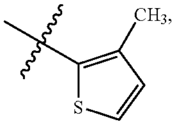 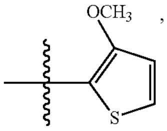, or

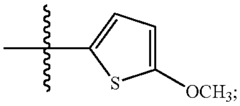

Each $R_2$ is independently selected from —O—$CF_3$, F, or —$CF_3$; and $R_4$ is —C(O)O—$CH_3$, —C(O)O—$CH_2CH_3$, or $C_{1-5}$ alkyl optionally substituted with 1-2 members independently selected from oxo, hydroxy, $NH_2$, —N$(CH_3)_2$, —O—$CH_3$,

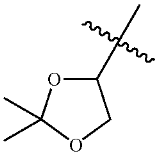, 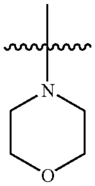, 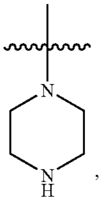,

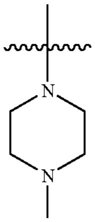, 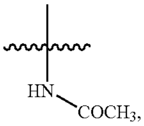 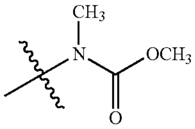,

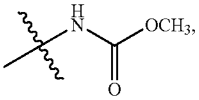 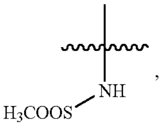, and

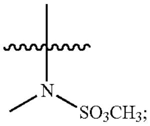 or $R_4$ is 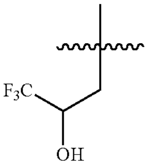.

In particular, the present invention is further directed to a compound of Formula (Ia) wherein (a) X is O;

(b) m is 0;

(c) n is 1, 2, or 3;

(d) m and n are both 0;

(e) m is 0 and n is 1;

(f) m is 0 and n is 2;

(g) L is a bond;

(h) L is O;

(i) $R_1$ is

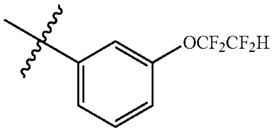 or 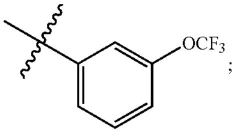;

(j) $R_1$ is

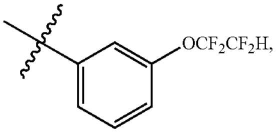 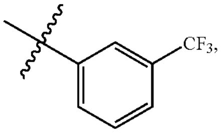 or

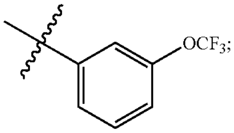

(k) $R_1$ is

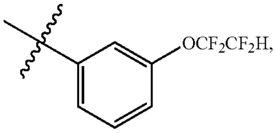

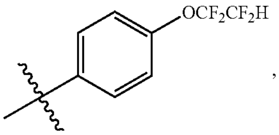, or 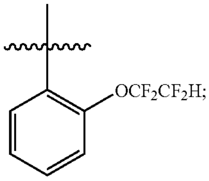

(l) $R_1$ is

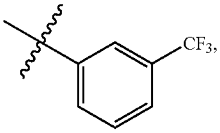 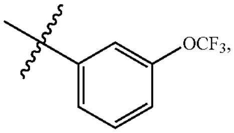 or

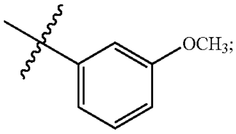

(m) $R_1$ is

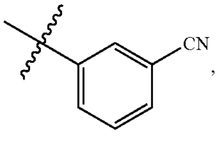, or 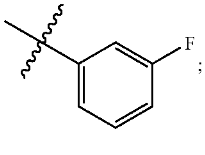;

(n) $R_1$ is —$CH_2CH_3$,

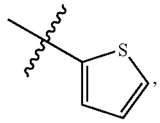, or phenyl;

(o) $R_1$ is —$CH_2CH_2CH_2OH$;

(p) $R_1$ is

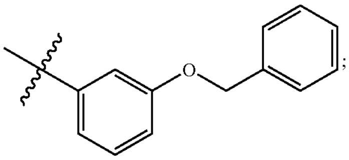;

(q) $R_1$ is

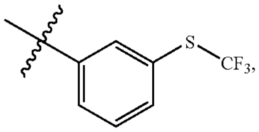, 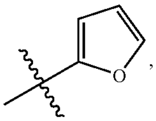, 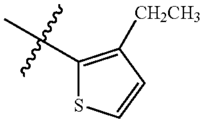, 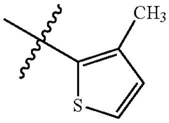, or 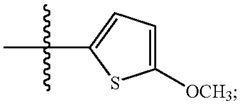;

(r) Q is phenyl or naphthalenyl;

(s) Q is phenyl;

(t) Q is a selected from the group consisting of thienyl, thiazolyl, oxazolyl, isoxazolyl, pyridinyl, and pyridizinyl;

(u) Q is

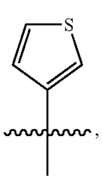, or 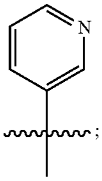;

(v) n is 1 and Q is

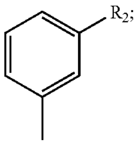

(w) n is 1 and Q is

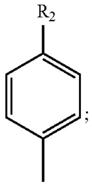;

(x) n is 2 and Q is

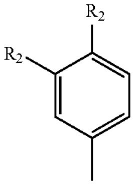 or 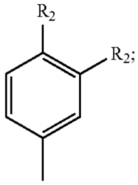

(y) n is 2 and Q is

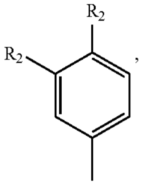, 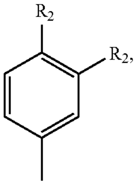, or 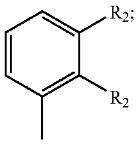

(z) n is 3 and Q is

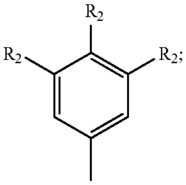

(aa) $R_2$ is —O—$CF_3$;

(bb) $R_2$ is —$CF_3$ (cc) $R_2$ is F;

(dd) $R_2$ is —$CH_3$, —$CH_2CH_3$, or —$CH(CH_3)_2$;

(ee) $R_2$ is —C(O)H, CN, OH, (ff) $R_2$ is —O—$CH(CH_3)_2$, F, Cl, or —$CF_3$;

(gg) $R_2$ is —O—$CH_3$, —O—$CF_3$, or —O—$CH(CH_3)_2$;

(hh) $R_4$ is $C_{1-5}$alkyl substituted with 1 or 2 members independently selected from oxo, hydroxy, —O—$CH_3$, and —O—$CH_2CH_3$ (ii) $R_4$ is $C_{1-5}$alkyl substituted with substituted heterocyclyl selected from

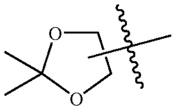 or 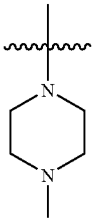 ;

(jj) $R_4$ is $C_{1-5}$alkyl substituted with

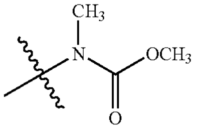 or 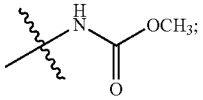

(kk) $R_4$ is halogenated$C_{1-4}$ alkyl substituted with oxo, hydroxy, or —O—$CH_3$;

(ll) $R_4$ is —$CH_2CH(OH)CF_3$;

(mm) $R_4$ is —$CH_2CH_3$, or —$CH_2CH_2$ $CH_3$;

(nn) $R_4$ is —$CH_2CH(OH)CH_2C_1$ or $R_4$ is —$CH_2CH(OH)CF_3$;

(oo) $R_4$ is —$CH_2CH(OH)CH(CH_3)_2$ or $R_4$ is —$CH_2CH(OH)CH_2OCH_3$;

(pp) m is 0, n is 1, and L is a bond;

(qq) m is 0, n is 2, and L is a bond;

(rr) m is 0, n is 3, and L is a bond (ss) m is 0, n is 1, L is a bond, and $R_1$ is

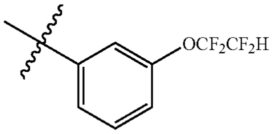 or

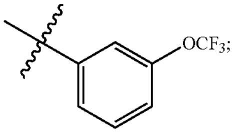

(tt) m is 0, n is 1, Lisa bond, Q is phenyl, and $R_1$ is

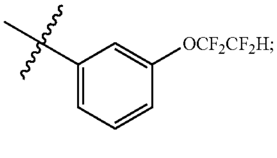

(uu) m is 0, n is 1, L is a bond, $R_1$ is

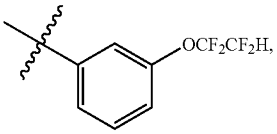

and Q is

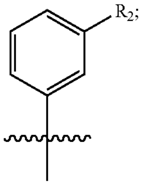

(vv) m is 0, n is 1, L is a bond, $R_1$ is

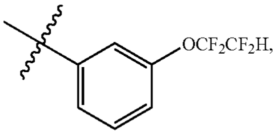

and the Q-$R_2$ group is

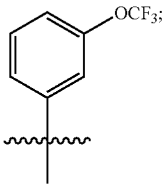

(ww) m is 0, n is 1, 2, or 3, L is a bond, Q is phenyl, and $R_1$ is

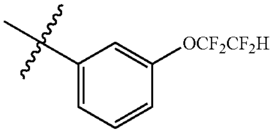 or

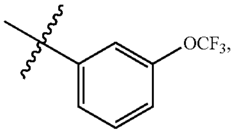

and each $R_2$ is independently selected from F, —$CF_3$, and —O—$CF_3$;

(xx) m is 0, n is 2 or 3, L is a bond, Q is

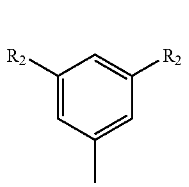

or

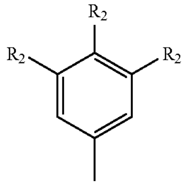

and each $R_2$ is independently selected from —O—$CF_3$, —$CF_3$, or F;

(yy) m is 0, n is 1, L is a bond, Q is

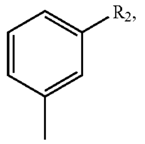

and $R_2$ is —$CH_3$, —$CH_2CH_3$, —$CH(CH_3)_2$, —C(O)H, CN, OH, —O—$CH(CH_3)_2$, F, Cl, —$CF_3$, —O—$CH_3$, —O—$CF_3$, or —O—$CH(CH_3)_2$; or enantiomers, diastereomers, tautomers, solvates, or pharmaceutically acceptable salts thereof; or any possible combinations of (a)-(yy) above.

In another aspect, the present invention is further directed to a compound of Formula (Ib):

Formula (Ib)

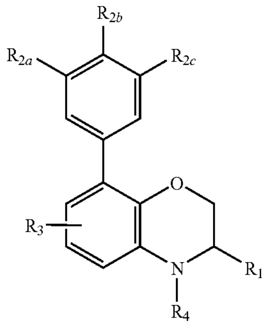

wherein:

$R_1$ is $C_{1-10}$ alkyl, $C_{2-10}$alkenyl, $C_{2-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with halo, cyano, or hydroxy, oxo, $C_{1-3}$alkyl, or $C_{1-3}$alkoxy;

or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated$C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated$C_{1-4}$alkylthio, halo, cyano, and hydroxy, or $R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyano, and hydroxy;

each of $R_{2a}$, $R_{2b}$, and $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated$C_{1-4}$ alkyl, and —C(O)H;

$R_3$ is absent or selected from the group consisting of $C_{1-4}$ alkyl, $C_{1-4}$ alkoxy, halo, cyano, and hydroxy;

$R_4$ is $C_{1-10}$ alkyl, halogenated $C_{1-10}$alkyl, or phenyl$C_{1-3}$ alkyl, wherein Said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated$C_{1-4}$ alkoxy, $C_{3-8}$ cycloalkyl, cyano, heterocyclyl, and —$NR_c R_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$alkyl;

and enantiomers, diastereomers, tautomers, solvates, or pharmaceutically acceptable salts thereof.

Particularly, the present invention features a compound of Formula (Ib) wherein $R_1$ is phenyl substituted with $C_{1-4}$ alkyl, halogenated $C_{1-4}$alkyl, $C_{1-4}$ alkoxy, halogenated$C_{1-4}$alkoxy, halo, cyano, or hydroxy.

Particularly, the present invention features a compound of Formula (Ib) wherein $R_1$ is phenyl substituted with halogenated $C_{1-4}$alkyl or halogenated$C_{1-4}$alkoxy, preferably $R_1$ is phenyl substituted with —$OCF_2CF_2H$, —$CF_3$, or —$OCF_3$.

Particularly, the present invention features a compound of Formula (Ib) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, hydroxy, halogenated $C_{1-4}$alkylthio, or an optionally substituted five membered heterocyclyl ring fused to the phenyl ring forming a bicyclic ring system.

Particularly, the present invention features a compound of Formula (Ib) wherein $R_1$ is $C_{1-6}$ alkyl substituted with hydroxy, $C_{1-3}$alkoxy, oxo, halo, or cyano.

Particularly, the present invention features a compound of Formula (Ib) wherein $R_1$ is furanyl or thienyl optionally substituted with $C_{1-3}$alkyl, $C_{1-3}$alkoxy, hydroxy, or cyano.

Particularly, the present invention features a compound of Formula (Ib) wherein $R_{2a}$ and $R_{2b}$ are both absent and $R_{2c}$ is selected from halo, halogenated $C_{1-4}$alkyl, and halogenated $C_{1-4}$alkoxy, preferably $R_2$, is —$OCF_2CF_2H$ or —$OCF_3$.

Particularly, the present invention features a compound of Formula (Ib) wherein $R_{2a}$, $R_{2b}$, and $R_{2c}$ are each independently absent or selected from halo, halogenated $C_{1-4}$alkyl, and halogenated $C_{1-4}$alkoxy, preferably $R_{2a}$, $R_{2b}$, and $R_{2c}$ are independently absent, —$OCF_2CF_2H$, —$OCF_3$ or F.

Particularly, the present invention features a compound of Formula (Ib) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

Particularly, the present invention features a compound of Formula (Ib) wherein $R_4$ is $C_{1-5}$ alkyl substituted with —$NR_c R_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$alkyl.

Particularly, the present invention features a compound of Formula (Ib) wherein $R_4$ is halogenated$C_{1-4}$ alkyl substituted with oxo, hydroxy, $C_{1-4}$alkoxy, or cyano; preferably $R_4$ is fluorinated$C_{1-3}$ alkyl substituted with hydroxy.

Particularly, the present invention features a compound of Formula (Ib) wherein $R_4$ is phenyl$C_{1-3}$ alkyl wherein the phenyl group is substituted with hydroxy, $C_{1-4}$alkoxy, cyano, or halogenated$C_{1-4}$ alkoxy, preferably $R_4$ is phenyl$C_{1-3}$ alkyl wherein the phenyl group is substituted with halogenated$C_{1-4}$ alkoxy.

In particular, the present invention is directed to a compound of Formula (Ib) wherein $R_1$ is phenyl optionally substituted with $C_{1-4}$ alkyl, halogenated$C_{1-4}$alkyl, $C_{1-4}$alkoxy, halogenated$C_{1-4}$ alkoxy, or cyano;

Each $R_{2a}$, $R_{2b}$, and $R_{2c}$ is independently absent or selected from halo, hydroxy, cyano, $C_{1-4}$ alkoxy, halogenated$C_{1-4}$ alkoxy, $C_{1-4}$alkyl, halogenated$C_{1-4}$alkyl, and —C(O)H; and $R_4$ is $C_{1-5}$ alkyl substituted with 1 to 2 members independently selected from hydroxy, $C_{1-4}$alkoxy, oxo, halogenated$C_{1-4}$alkoxy, $C_{3-8}$cycloalkyl, cyano; or $R_4$ is halogenated$C_{1-4}$ alkyl substituted with hydroxy, $C_{1-4}$alkoxy, oxo, or cyano.

In particular, the present invention is directed to a compound of Formula (Ib) as shown above wherein:

(a) $R_1$ is $C_{1-6}$alkyl substituted with hydroxy, oxo, or $C_{1-3}$alkoxy;

(b) $R_1$ is thienyl optionally substituted with $C_{1-3}$alkyl or $C_{1-3}$alkoxy;

(c) $R_1$ is phenyl optionally substituted with 1 or 2 members selected from $R_a$ and $R_b$, wherein $R_a$ and $R_b$ are independently selected from the group consisting of $C_{1-4}$ alkyl, halogenated$C_{1-4}$ alkyl, $C_{1-4}$ alkoxy, halogenated $C_{1-4}$ alkoxy, phenyl$C_{1-3}$alkoxy, —S—$CF_3$, halo, cyano, and hydroxy, or $R_a$ and $R_b$ together with the carbon atoms they are attached to form 5- or 6-membered heterocyclyl fused to the phenyl ring;

(d) $R_1$ is phenyl,

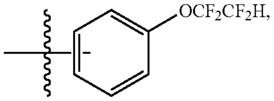 , 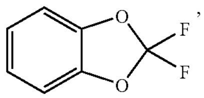 ,

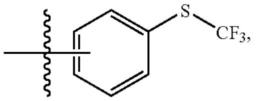 , 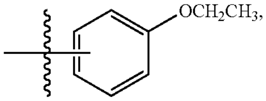 ,

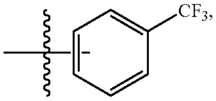 , 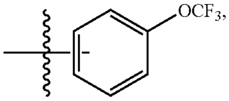 ,

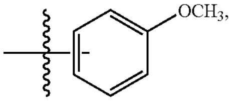 ,

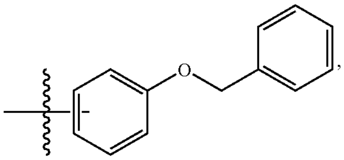 ,

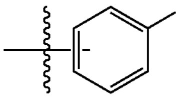 , or 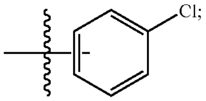 ;

(e) $R_1$ is an optionally substituted 5- or 6-membered heteroaryl, preferably,

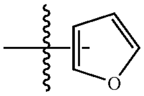 , 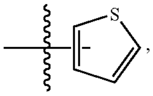 , 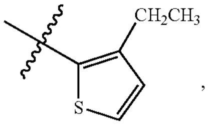 ,

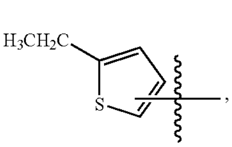 , 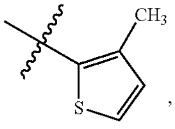 , 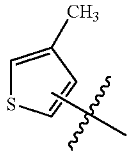

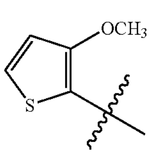 or 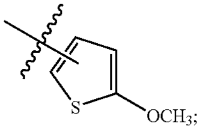 ;

(f) $R_{2a}$, $R_{2b}$, and $R_{2c}$ are each independently absent or selected from halo, hydroxy, cyano, $C_{1-4}$ alkoxy, halogenated$C_{1-4}$ alkoxy, halogenated$C_{1-4}$alkyl, and —C(O)H; preferably absent or selected from —$CH_3$, —$CH_2CH_3$, —C(O)H, —O—$CH_3$, —O—$CF_3$, —O—$CH(CH_3)_2$, —$CH(CH_3)_2$, CN, OH, F, Cl, and —$CF_3$; more preferably absent or selected from —O—$CF_3$, F, and —$CF_3$;

(g) $R_4$ is —C(O)O—$C_{1-4}$alkyl, preferably —C(O)O—$CH_3$ or —C(O)O—$CH_2CH_3$;

(h) $R_4$ is $C_{1-5}$ alkyl optionally substituted with 1 or 2 members independently selected from oxo, hydroxy, alkoxy, $C_{3-5}$ cycloalkyl, CN, heterocyclyl, and —$NR_cR_d$, wherein $R_c$ and $R_d$ are independently selected from H, —$S(O)_2$—$C_{1-4}$alkyl, $C_{1-3}$ alkyl, —C(O)—$C_{1-3}$ alkyl, and —C(O)O—$C_{1-3}$ alkyl, (i) $R_4$ is $C_{1-5}$ alkyl optionally substituted with 1 or 2 members independently selected from oxo, hydroxy, —$NH_2$, —$N(CH_3)_2$, —O—$CH_3$, —O—$CH_2CH_3$,

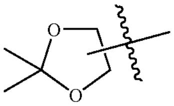 , 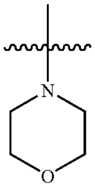 , 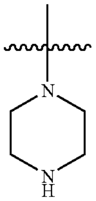 , 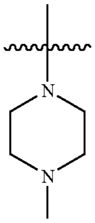 ,

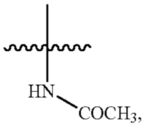 , 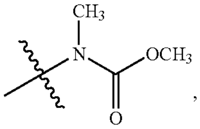 , 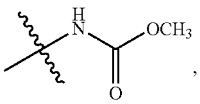 ,

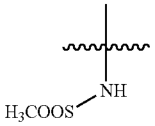 , and 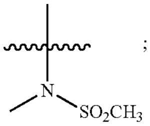 ;

(j) $R_4$ is halogenated $C_{1-4}$ alkyl optionally substituted with oxo, hydroxy, $C_{1-4}$ alkoxy, or cyano; preferably $R_4$ is fluorinated$C_{1-3}$alkyl substituted with hydroxy; more preferably $R_4$ is

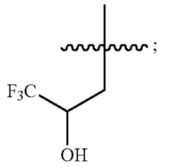

and enantiomers, diastereomers, tautomers, solvates, or pharmaceutically acceptable salts thereof; or any possible combinations of examples (a)-(j) above In another aspect, the present invention is further directed to a compound of Formula (Ic):

Formula (Ic)

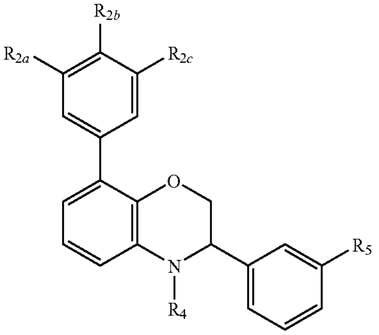

wherein:

each $R_{2a}$, $R_{2b}$, and $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated$C_{1-4}$ alkyl, and —C(O)H;

$R_4$ is $C_{1-10}$ alkyl, halogenated $C_{1-10}$alkyl, or phenyl$C_{1-3}$ alkyl, wherein Said $C_{1-10}$ alkyl, halogenated $C_{1-10}$alkyl, or phenyl$C_{1-3}$alkyl is optionally substituted with 1-3 members independently selected from the group consisting of halo, oxo, hydroxy, $C_{1-4}$ alkoxy, $C_{3-8}$ cycloalkyl, cyano, heterocyclyl, heteroaryl, tert-butyldimethylsilyloxy, and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and $SO_2C_{1-3}$alkyl;

$R_5$ is selected from the group consisting of $C_{1-4}$ alkyl, halogenated$C_{1-4}$alkyl, $C_{1-4}$ alkoxy, halogenated $C_{1-4}$ alkoxy, $C_{1-4}$ alkylthio, halo, cyano, and hydroxy;

and enantiomers, diastereomers, tautomers, solvates, or pharmaceutically acceptable salts thereof.

In particular, the present invention is directed to a compound of Formula (Ic) wherein $R_{2a}$ is absent, halo, or halogenated$C_{1-3}$alkyl; preferably $R_{2a}$ is absent, F, or $CF_3$, more preferably $R_{2a}$ is absent.

In particular, the present invention is directed to a compound of Formula (Ic) wherein $R_{2b}$ is absent or halo; preferably $R_{2b}$ is absent or F; more preferably $R_{2b}$ is absent.

In particular, the present invention is directed to a compound of Formula (Ic) wherein $R_{2c}$ is halo, hydroxy, cyano, $C_{1-4}$ alkoxy, halogenated $C_{1-4}$alkoxy, $C_{1-4}$ alkyl, or halogenated$C_{1-4}$ alkyl; preferably $R_{2c}$ is halo, halogenated$C_{1-4}$alkyl or halogenated $C_{1-4}$alkoxy; more preferably, $R_{2c}$ is —$CF_3$, —$OCF_3$ or F.

In particular, the present invention is directed to a compound of Formula (Ic) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

Particularly, the present invention features a compound of Formula (Ic) wherein $R_4$ is $C_{1-5}$ alkyl substituted with —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —$SO_2C_{1-3}$alkyl.

Particularly, the present invention features a compound of Formula (Ic) wherein $R_4$ is halogenated$C_{1-4}$ alkyl substituted with oxo, hydroxy, $C_{1-4}$alkoxy, or cyano; preferably $R_4$ is fluorinated$C_{1-3}$ alkyl substituted with hydroxy.

Particularly, the present invention features a compound of Formula (Ic) wherein $R_4$ is phenyl$C_{1-3}$ alkyl wherein the phenyl group is substituted with hydroxy, $C_{1-4}$alkoxy, cyano, or halogenated$C_{1-4}$ alkoxy, preferably phenyl$C_{1-3}$ alkyl wherein the phenyl group is substituted with halogenated$C_{1-4}$ alkoxy.

In particular, the present invention is directed to a compound of Formula (Ic) wherein $R_4$ is halogenated$C_{1-4}$ alkyl substituted with oxo, hydroxy, $C_{1-4}$alkoxy, or cyano; preferably $R_4$ is fluorinated$C_{1-3}$ alkyl substituted with hydroxy; more $R_4$ is preferably

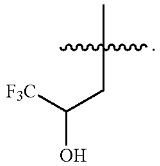

In particular, the present invention is directed to a compound of Formula (Ic) wherein $R_5$ is halogenated$C_{1-4}$alkyl, halogenated $C_{1-4}$ alkoxy, or halo; preferably $R_5$ is —$CF_3$, —$OCF_3$ or —$OCF_2CF_2H$, more preferably $R_5$ is —$OCF_3$ or —$OCF_2CF_2H$.

In particular, the present invention is directed to a compound selected from the group consisting of:

1,1,1-Trifluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol;

4H-1,4-Benzoxazine-4-ethanol, 2,3-dihydro-3-[3-(1,1,2,2-tetrafluoroethoxy)phenyl]-8-[3-(trifluoromethoxy)phenyl]-a-(trifluoromethyl)-, (3S,αS)—;

4H-1,4-Benzoxazine-4-ethanol, 2,3-dihydro-3-[3-(1,1,2,2-tetrafluoroethoxy)phenyl]-8-[3-(trifluoromethoxy)phenyl]-a-(trifluoromethyl)-, (3S,αR)—;

4H-1,4-Benzoxazine-4-ethanol, 2,3-dihydro-3-[3-(1,1,2,2-tetrafluoroethoxy)phenyl]-8-[3-(trifluoromethoxy)phenyl]-a-(trifluoromethyl)-, (3R,αS)—;

3-[3,8-Bis-(3-trifluoromethoxy-phenyl)-2,3-dihydro-benzo[1,4]oxazin-4-yl]-1,1,1-trifluoro-propan-2-ol;

4H-1,4-Benzoxazine-4-ethanol, 2,3-dihydro-3,8-bis[3-(trifluoromethoxy)phenyl]-a-(trifluoromethyl)-, (3S,αS)—;

4H-1,4-Benzoxazine-4-ethanol, 2,3-dihydro-3,8-bis[3-(trifluoromethoxy)phenyl]-a-(trifluoromethyl)-, (3S,αR)—;

3-[3-(3-Benzyl-phenyl)-8-(3-trifluoromethoxy-phenyl)-2,3-dihydro-benzo[1,4]oxazin-4-yl]-1,1,1-trifluoro-propan-2-ol;

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-ol;

1,1,1-Trifluoro-3-[8-(3-trifluoromethoxy-phenyl)-3-(3-trifluoromethylsulfanylmethyl-phenyl)-2,3-dihydro-benzo[1,4]oxazin-4-yl]-propan-2-ol;

1,1,1-Trifluoro-3-[8-(3-trifluoromethoxy-phenyl)-3-(3-trifluoromethylsulfanyl-phenyl)-2,3-dihydro-benzo[1,4]oxazin-4-yl]-propan-2-ol;

3-[3-(3-Ethoxy-phenyl)-8-(3-trifluoromethoxy-phenyl)-2,3-dihydro-benzo[1,4]oxazin-4-yl]-1,1,1-trifluoro-propan-2-ol;

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-one;

3-[3-(1,1,2,2-Tetrafluoro-ethoxyl)phenyl]-8-(3-trifluoromethoxy-phenyl)-2,3-dihydro-benzo[1,4]oxazine-4-carboxylic acid methyl ester;

3-[3-(1,1,2,2-Tetrafluoro-ethoxy)-phenyl]-8-(3-trifluoromethoxy-phenyl)-2,3-dihydro-benzo[1,4]oxazine-4-carboxylic acid ethyl ester;

4-[2-(tert-Butyl-dimethyl-silanyloxy)-ethyl]-3-[3-(1,1,2,2-tetrafluoro-ethoxy)-phenyl]-8-(3-trifluoromethoxy-phenyl)-3,4-dihydro-2H-benzo[1,4]oxazine;

2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethanol;

4-(2-Methoxy-ethyl)-3-[3-(1,1,2,2-tetrafluoro-ethoxy)-phenyl]-8-(3-trifluoromethoxy-phenyl)-3,4-dihydro-2H-benzo[1,4]oxazine;

4-[3-(tert-Butyl-dimethyl-silanyloxy)-propyl]-3-[3-(1,1,2,2-tetrafluoro-ethoxy)-phenyl]-8-(3-trifluoromethoxy-phenyl)-3,4-dihydro-2H-benzo[1,4]oxazine;

3-[3-[3-(1,1,2,2-Tetrafluoro-ethoxy)-phenyl]-8-(3-trifluoromethoxy-phenyl)-2,3-dihydro-benzo[1,4]oxazin-4-yl]-propan-1-ol;

4-(3-Methoxy-propyl)-3-[3-(1,1,2,2-tetrafluoro-ethoxy)-phenyl]-8-(3-trifluoromethoxy-phenyl)-3,4-dihydro-2H-benzo[1,4]oxazine;

Dimethyl-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-amine;

4-(2-piperazin-1-yl-ethyl)-3-[3-(1,1,2,2-tetrafluoro-ethoxy)-phenyl]-8-(3-trifluoromethoxy-phenyl)-3,4-dihydro-2H-benzo[1,4]oxazine;

4-(2-Morpholin-4-yl-ethyl)-3-[3-(1,1,2,2-tetrafluoro-ethoxy)-phenyl]-8-(3-trifluoromethoxy-phenyl)-3,4-dihydro-2H-benzo[1,4]oxazine;

4-[2-(4-Methyl-piperazin-1-yl)-ethyl]-3-[3-(1,1,2,2-tetrafluoro-ethoxy)-phenyl]-8-(3-trifluoromethoxy-phenyl)-3,4-dihydro-2H-benzo[1,4]oxazine;

4-Methyl-3-[3-(1,1,2,2-tetrafluoro-ethoxy)-phenyl]-8-(3-trifluoromethoxy-phenyl)-3,4-dihydro-2H-benzo[1,4]oxazine;

4-Ethyl-3-[3-(1,1,2,2-tetrafluoro-ethoxy)-phenyl]-8-(3-trifluoromethoxy-phenyl)-3,4-dihydro-2H-benzo[1,4]oxazine;

4-Propyl-3-[3-(1,1,2,2-tetrafluoro-ethoxy)-phenyl]-8-(3-trifluoromethoxy-phenyl)-3,4-dihydro-2H-benzo[1,4]oxazine;

4H-1,4-Benzoxazine-4-ethanol, 2,3-dihydro-α-methyl-3-[3-(1,1,2,2-tetrafluoroethoxy)phenyl]-8-[3-(trifluoromethoxy)phenyl]-(3S,αR)—;

4H-1,4-Benzoxazine-4-ethanol, 2,3-dihydro-a-methyl-3-[3-(1,1,2,2-tetrafluoroethoxy)phenyl]-8-[3-(trifluoromethoxy)phenyl]-, (3S,αS)—;

2-Propanone, 3-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-1,1,1-trifluoro-;

2-Propanone, 1-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-;

2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethylamine;

N-{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-acetamide;

{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-carbamic acid methyl ester;

Methyl-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-carbamic acid methyl ester;

N-{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-methanesulfonamide;

N-Methyl-N-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-methanesulfonamide;

2H-1,4-Benzoxazine, 4-[[(4S)-2,2-dimethyl-1,3-dioxolan-4-yl]methyl]-3,4-dihydro-3-[3-(1,1,2,2-tetrafluoroethoxy)phenyl]-8-[3-(trifluoromethoxy)phenyl]-, (3S)—;

2H-1,4-Benzoxazine, 4-[[(4S)-2,2-dimethyl-1,3-dioxolan-4-yl]methyl]-3,4-dihydro-3-[3-(1,1,2,2-tetrafluoroethoxy)phenyl]-8-[3-(trifluoromethoxy)phenyl]-, (3R)—;

1,2-Propanediol, 3-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-, (2S)—;

1,2-Propanediol, 3-[(3R)-2,3-dihydro-3-[3-(1,1,2,2-tetrafluoroethoxy)phenyl]-8-[3-(trifluoromethoxy)phenyl]-4H-1,4-benzoxazin-4-yl]-, (2S)—;

2-Methyl-1-[3-[3-[1,1,2,2-tetrafluoro-ethoxy)-phenyl]-8-(3-trifluoromethoxy-phenyl)-2,3-dihydro-benzo[1,4]oxazin-4-yl]-propan-2-ol;

3-[3-Allyl-8-(3-trifluoromethoxy-phenyl)-2,3-dihydro-benzo[1,4]oxazin-4-yl]-1,1,1-trifluoro-propan-2-ol;

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol;

1,1,1-Trifluoro-3-[3-(3-methoxy-propyl)-8-(3-trifluoromethoxy-phenyl)-2,3-dihydro-benzo[1,4]oxazin-4-yl]-propan-2-ol;

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol;

1,1,1-Trifluoro-3-[3-(3-methoxy-propyl)-8-(3-trifluoromethoxy-phenyl)-2,3-dihydro-benzo[1,4]oxazin-4-yl]-propan-2-ol;

3,3-Dimethyl-1-[4-(3,3,3-trifluoro-2-hydroxy-propyl)-8-(3-trifluoromethoxy-phenyl)-3,4-dihydro-2H-benzo[1,4]oxazin-3-yl]-butan-2-one;

3-[3-(5-Ethyl-thiophen-2-yl)-8-(3-trifluoromethoxy-phenyl)-2,3-dihydro-benzo[1,4]oxazin-4-yl]-1,1,1-trifluoro-propan-2-ol;

1,1,1-Trifluoro-3-[3-(3-methoxy-thiophen-2-yl)-8-(3-trifluoromethoxy-phenyl)-2,3-dihydro-benzo[1,4]oxazin-4-yl]-propan-2-ol;

1,1,1-Trifluoro-3-[3-(5-methoxy-thiophen-2-yl)-8-(3-trifluoromethoxy-phenyl)-2,3-dihydro-benzo[1,4]oxazin-4-yl]-propan-2-ol;

3-{8-(3,5-Difluoro-phenyl)-3-[3-(1,1,2,2-tetrafluoro-ethoxy)-phenyl]-2,3-dihydro-benzo[1,4]oxazin-4-yl}-1,1,1-trifluoro-propan-2-ol;

1,1,1-Trifluoro-3-{8-(3-fluoro-phenyl)-3-[3-(1,1,2,2-tetrafluoro-ethoxy)-phenyl]-2,3-dihydro-benzo[1,4]oxazin-4-yl}-propan-2-ol;

1-Fluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol;

1,1,1-Trifluoro-3-[8-(3-trifluoromethoxy-phenyl)-3-(3-trifluoromethyl-phenyl)-2,3-dihydro-benzo[1,4]oxazin-4-yl]-propan-2-ol;

4H-1,4-Benzoxazine-4-ethanol, 8-(3,5-difluorophenyl)-2,3-dihydro-3-[3-(1,1,2,2-tetrafluoroethoxy)phenyl]-α-(trifluoromethyl)-, (3S,αS)—;

4H-1,4-Benzoxazine-4-ethanol, 8-(3,5-difluorophenyl)-2,3-dihydro-3-[3-(1,1,2,2-tetrafluoroethoxy)phenyl]-α-(trifluoromethyl)-, (3S,αR)—;

4H-1,4-Benzoxazine-4-ethanol, 2,3-dihydro-α-fluoromethyl-3-[3-(1,1,2,2-tetrafluoroethoxy)phenyl]-8-[3-(trifluoromethoxy)phenyl]-, (3S,αR)—;

4H-1,4-Benzoxazine-4-ethanol, 2,3-dihydro-a-fluoromethyl-3-[3-(1,1,2,2-tetrafluoroethoxy)phenyl]-8-[3-(trifluoromethoxy)phenyl]-, (3S,αS)—;

4H-1,4-Benzoxazine-4-ethanol, 2,3-dihydro-3-[3-(1,1,2,2-tetrafluoroethoxy)phenyl]-8-[3,4,5-trifluoro-phenyl]-α-(trifluoromethyl)-, (3S,αS)—;

4H-1,4-Benzoxazine-4-ethanol, 2,3-dihydro-3-[3-(1,1,2,2-tetrafluoroethoxy)phenyl]-8-[3,4,5-trifluoro-phenyl]-α-(trifluoromethyl)-, (3S,αR)—;

4H-1,4-Benzoxazine-4-ethanol, 2,3-dihydro-3-[3-(1,1,2,2-tetrafluoroethoxy)phenyl]-8-[3,5-bis(trifluoromethyl)phenyl]-α-(trifluoromethyl)-, (3S,αS)—;

4H-1,4-Benzoxazine-4-ethanol, 2,3-dihydro-3-[3-(1,1,2,2-tetrafluoroethoxy)phenyl]-8-[3,5-bis(trifluoromethyl)phenyl]-α-(trifluoromethyl)-, (3S,αR)—;

4H-1,4-Benzoxazine-4-ethanol, 2,3-dihydro-3-[3-(trifluoromethoxy)phenyl]-8-[3,5-(difluoro)phenyl]-α-(trifluoromethyl)-, (3S,αS)—;

4H-1,4-Benzoxazine-4-ethanol, 2,3-dihydro-3-[3-(trifluoromethoxy)phenyl]-8-[3,5-(difluoro)phenyl]-α-(trifluoromethyl)-, (3S,αR)—;

4H-1,4-Benzoxazine-4-ethanol, 2,3-dihydro-3-[3-(trifluoromethoxy)phenyl]-8-[3,4,5-(trifluoro)phenyl]-α-(trifluoromethyl)-, (3S,αS)—;

4H-1,4-Benzoxazine-4-ethanol, 2,3-dihydro-3-[3-(trifluoromethoxy)phenyl]-8-[3,4,5-(trifluoro)phenyl]-α-(trifluoromethyl)-, (3S,αR)—;

3-Methyl-1-[3-[3-(1,1,2,2-tetrafluoro-ethoxy)-phenyl]-8-(3-trifluoromethoxy-phenyl)-2,3-dihydro-benzo[1,4]oxazin-4-yl]-butan-2-ol;

1,1,1-Trifluoro-3-[3-(3-methyl-thiophen-2-yl)-8-(3-trifluoromethoxy-phenyl)-2,3-dihydro-benzo[1,4]oxazin-4-yl]-propan-2-ol;

3-[3-(3-Ethyl-thiophen-2-yl)-8-(3-trifluoromethoxy-phenyl)-2,3-dihydro-benzo[1,4]oxazin-4-yl]-1,1,1-trifluoro-propan-2-ol;

1,1,1-Trifluoro-3-[3-furan-2-yl-8-(3-trifluoromethoxy-phenyl)-2,3-dihydro-benzo[1,4]oxazin-4-yl]-propan-2-ol;

1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol;

1,1,1-Trifluoro-3-[3-phenyl-8-(3-trifluoromethoxy-phenyl)-2,3-dihydro-benzo[1,4]oxazin-4-yl]-propan-2-ol;

1,1,1-Trifluoro-3-[3-(4-trifluoromethoxy-phenyl)-8-(3-trifluoromethoxy-phenyl)-2,3-dihydro-benzo[1,4]oxazin-4-yl]-propan-2-ol;

1,1,1-Trifluoro-3-[3-(3-methoxy-phenyl)-8-(3-trifluoromethoxy-phenyl)-2,3-dihydro-benzo[1,4]oxazin-4-yl]-propan-2-ol;

3-[3-(3-Chloro-phenyl)-8-(3-trifluoromethoxy-phenyl)-2,3-dihydro-benzo[1,4]oxazin-4-yl]-1,1,1-trifluoro-propan-2-ol;

1,1,1-Trifluoro-3-[3-thiophen-2-yl-8-(3-trifluoromethoxy-phenyl)-2,3-dihydro-benzo[1,4]oxazin-4-yl]-propan-2-ol;

1,1,1-Trifluoro-3-[3-furan-3-yl-8-(3-trifluoromethoxy-phenyl)-2,3-dihydro-benzo[1,4]oxazin-4-yl]-propan-2-ol;

1,1,1-Trifluoro-3-[3-[3-(1,1,2,2-tetrafluoro-ethoxy)-phenyl]-8-(3-trifluoromethoxy-phenyl)-2,3-dihydro-benzo[1,4]thiazin-4-yl]-propan-2-ol; and enantiomers, diastereomers, tautomers, solvates, or pharmaceutically acceptable salts thereof.

In particular, the present invention is directed to a compound of Formula (I), (Ia), (Ib) or (Ic) selected from the compounds shown in Table 1 below and enantiomers, diastereomers, tautomers, solvates, or pharmaceutically acceptable salts thereof.

More particularly, the present invention is directed to a compound selected from:

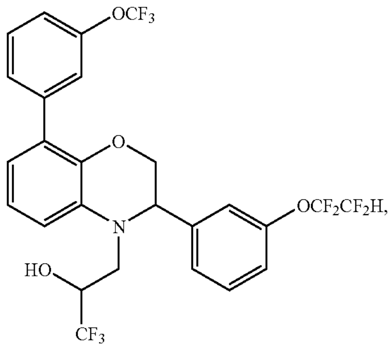

,

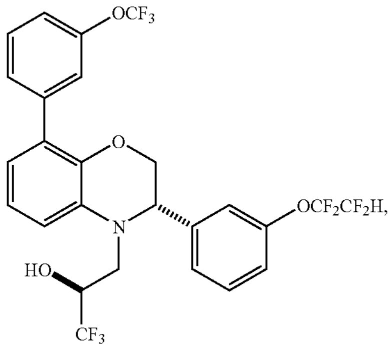

,

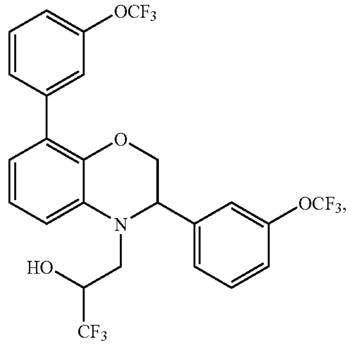

,

-continued
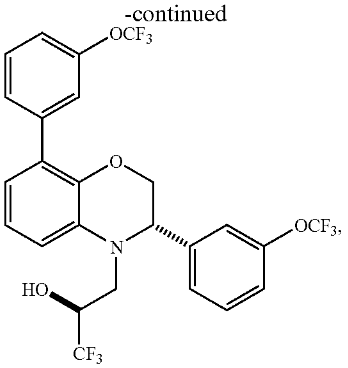
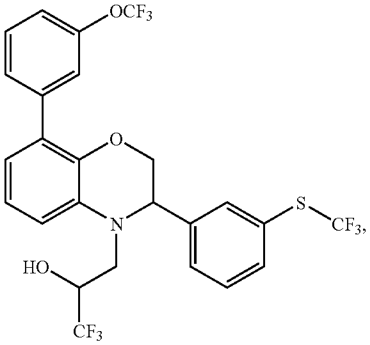
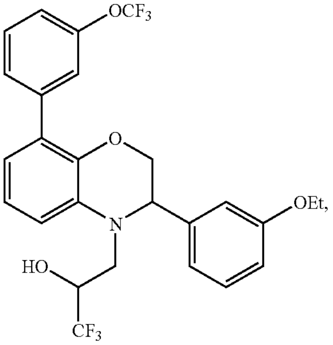
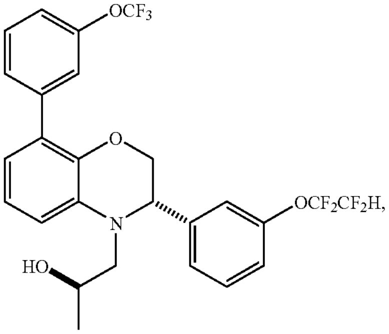
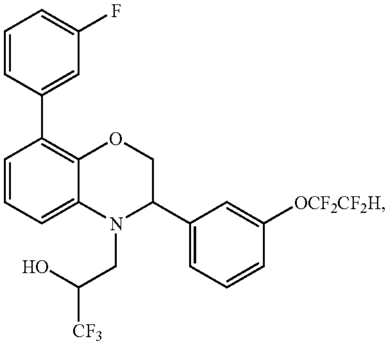
-continued
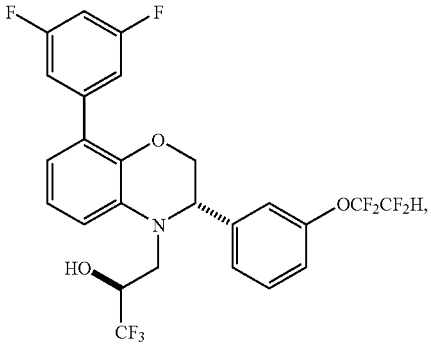
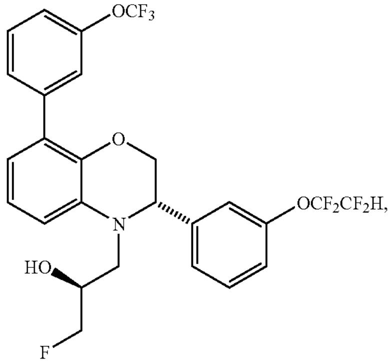
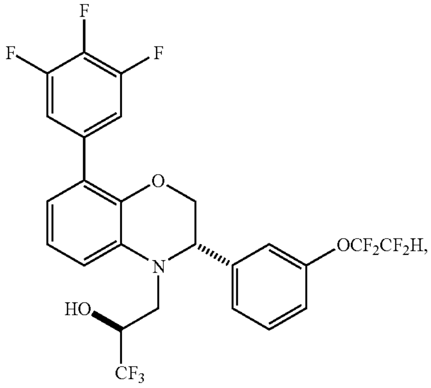
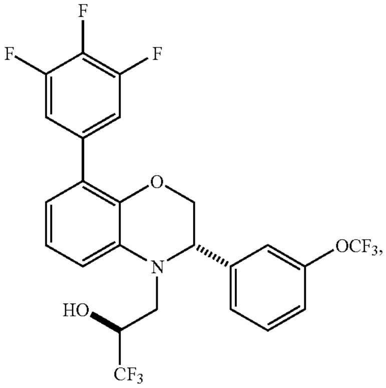
and -continued

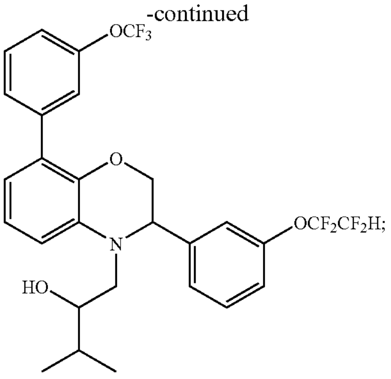

and enantiomers, diastereomers, tautomers, solvates, or pharmaceutically acceptable salts thereof.

In particular, the present invention is directed to a compound of the formula:

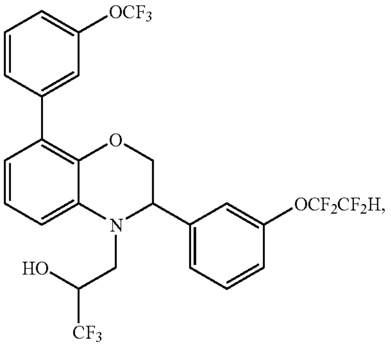

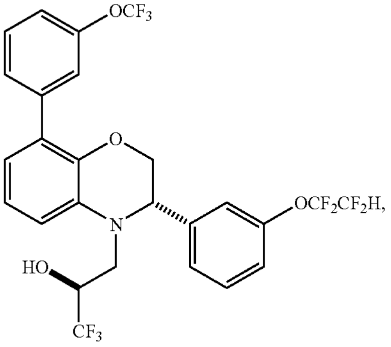

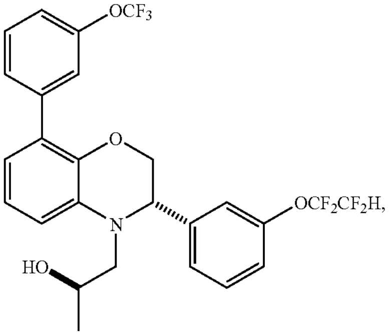

-continued

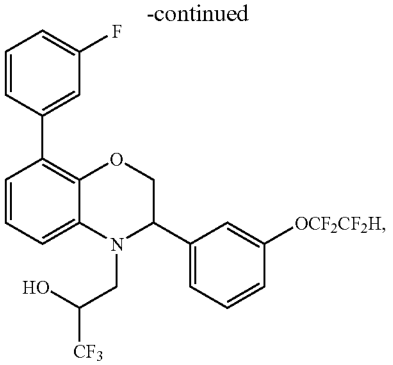

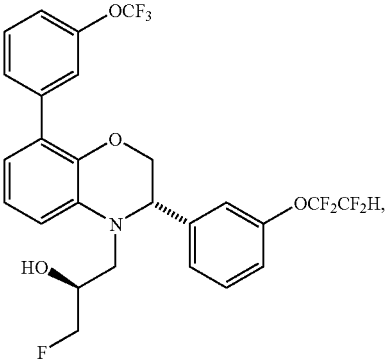

or

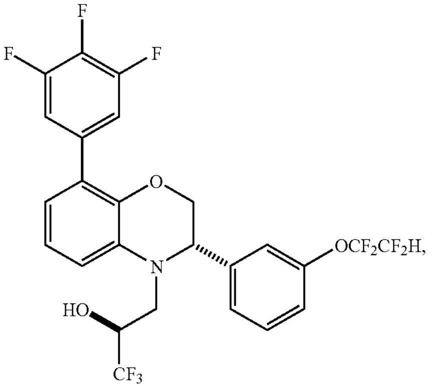

or enantiomers, diastereomers, tautomers, solvates, or pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts" (*Ref. International J. Pharm.,* 1986, 33, 201-217*; J. Pharm. Sci.,* 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Representative hydroxy group prodrug forms include, but are not limited to, $C_{1-4}$alkylethers, substituted $C_{1-4}$alkylethers, and $C_{1-4}$alkyl esters.

Another embodiment of the present invention is a composition comprising the dextrorotatory enantiomer of a compound of the present invention, wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of the present invention wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

In another aspect, the present invention is directed to pharmaceutical compositions containing one or more compounds, salts or solvates of the present invention as described herein admixed with a pharmaceutically acceptable carrier, excipient or diluent, wherein the compositions can be used to treat a condition directly or indirectly mediated by CETP.

Even though the compounds of the present invention (including their enantiomers, diastereomers, tautomers, pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of the present invention and one or more pharmaceutically acceptable carriers, excipients or diluents.

By way of example, in the pharmaceutical compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions may be administered in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

The instant pharmaceutical composition will generally contain a per dosage unit (e.g., tablet, capsule, powder, injection, teaspoonful and the like) from about 0.001 to about 50 mg/kg. In one embodiment, the instant pharmaceutical composition contains a per dosage unit of from about 0.01 to about 20 mg/kg of compound, and preferably from about 0.05 to about 10 mg/kg. Methods are known in the art for determining therapeutically effective doses for the instant pharmaceutical composition. The therapeutically effective amount for administering the pharmaceutical composition to a human, for example, can be determined by persons skilled in the art by the use of established animal models.

A therapeutically effective amount for use of the instant compound of a pharmaceutical composition thereof comprises a dose range of from about 0.01 mg to about 1,000 mg, preferably from about 10 to about 800 mg, in particular from about 25 mg to about 750 mg, or more particularly, a dose range of from about 50 mg to about 400 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the subject to be treated. In certain embodiments, an effective amount of the drug may be supplied at a dosage level of from about 0.01 mg/kg to about 100 mg/kg of body weight per day, or any range therein. Preferably, the range is from about 0.5 to about 50.0 mg/kg of body weight per day, or any range therein. More preferably, from about 1.0 to about 5.0 mg/kg of body weight per day, or any range therein. The compounds may be administered on a regimen of 1 to 4 times per day.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of the present invention may be administered in any of the foregoing compositions and dosage regimens or by means of those compositions and dosage regimens established in the art whenever use of the compounds of the invention as CETP inhibitors is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiments, the present invention is further directed to a process for preparation of the compounds of the present invention.

As inhibitors of CETP, the compounds of the present invention are useful in methods for treating, preventing, or inhibiting the progression of, a disease or condition in a mammal which disease or condition is affected by the inhibition of CETP. Such methods comprise administering to a mammal in need of such treatment or prevention a therapeutically effective amount of a compound of the present invention, or a pharmaceutically acceptable salt or solvate thereof as described herein.

The present invention is also directed to a method of treating or preventing a disease or condition in a subject, particularly a mammal including human, which disease or condition is affected by the modulation of CETP. Therefore, in yet another aspect, the present invention is directed to a method of treating or preventing a disease or condition in a subject which disease or condition is affected by the modulation of CETP, which method comprises administering to a subject in need of such treatment or prevention a therapeutically effective amount of a compound of the present invention, pharmaceutically acceptable salt or solvate thereof as described herein.

In a further aspect, the present invention is directed to a method of increasing HDL-C (HDL cholesterol) in a subject, which method comprises administering to a subject in need thereof a therapeutically effective amount of a compound of the present invention, pharmaceutically acceptable salt or solvate thereof as described herein.

In a further aspect, the present invention is directed to a method of increasing the ratio of HDL-C/total cholesterol in a subject, which method comprises administering to a subject in need thereof a therapeutically effective amount of a compound of the present invention, pharmaceutically acceptable salt or solvate thereof as described herein.

In a further aspect, the present invention is directed to a method of increasing the ratio of HDL-C/LDL-C in a subject, which method comprises administering to a subject in need thereof a therapeutically effective amount of a compound of the present invention, pharmaceutically acceptable salt or solvate thereof as described herein.

In a further aspect, the present invention is directed to a method of lowering either or both of LDL-C (LDL-cholesterol) and non-HDL-C cholesterol in a subject, which method comprises administering to a subject in need thereof a therapeutically effective amount of a compound of the present invention, pharmaceutically acceptable salt or solvate thereof as described herein.

Examples of the disease or condition intended to be within the scope of the present invention include, but are not limited to, atherosclerosis, peripheral vascular disease, dyslipidemia (including hypertriglyceridemia, hypercholesterolemia, mixed hyperlipidemia, and hypo-HDL-cholesterolemia), hyper-LDL-cholesterolemia hyperbetaliproteinemia, hypoalphalipoproteinemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and Metabolic Syndrome.

Preferably the compounds of the present invention are useful for the treatment of dyslipidemia (including hypertriglyceridemia, hypercholesterolemia, mixed hyperlipidemia, and hypo-HDL-cholesterolemia) and atherosclerosis.

While the present invention comprises compositions comprising one or more of the compounds of the present invention, the present invention also comprises compositions comprising intermediates used in the manufacture of compounds of the present invention.

The compounds of the present invention, pharmaceutically acceptable salts or solvates thereof can also be useful in combination therapy with one or more additional compounds, said additional compound being, for example, an HMG-CoA reductase inhibitor, an microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor, a bile acid sequestrant, and/or an “antihypertensive agent” (examples of an antihypertensive agent include, a calcium channel blocker, an ACE inhibitor, an A-II (Angiotensin-II receptor) antagonist, a diuretic, a beta-adrenergic receptor blocker, an alpha-adrenergic receptor blocker, or a vasodilator).

The term “jointly effective amount” as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term “jointly effective amount” refers to that amount of each active compound or pharmaceutical agent, alone or in combination, that treats or inhibits in a subject the onset or progression of a disease or condition as being sought by a researcher, veterinarian, medical doctor or other clinician. Thus in another aspect, the present invention provides combinations of two or more drugs wherein, for example, (a) each drug is administered in an independently therapeutically or prophylactically effective amount; (b) at least one drug in the combination administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

In certain embodiments, this invention provides a method for treating or preventing in a subject one or more diseases or conditions as described herein, said method comprising (a) administering to said subject a jointly effective amount of a compound of Formula (I), (Ia), (Ib), or (Ic) or an enantiomer, diastereomer, tautomer, or pharmaceutically acceptable salt thereof as described herein; and (b) administering to said subject a jointly effective amount of an HMG-CoA reductase inhibitor, an microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor, a bile acid sequestrant, or an antihypertensive agent.

said co-administration being in any order and the combined jointly effective amounts providing the desired therapeutic or prophylactic effect.

In certain embodiments, this invention provides a method for treating or preventing in a subject one or more diseases or conditions as described herein, said method comprising (a) administering to said subject a jointly effective amount of a compound of Formula (I), (Ia), (Ib) or (Ic) or an enantiomer, diastereomer, tautomer, or pharmaceutically acceptable salt thereof as described herein; and (b) administering to said subject a jointly effective amount of an HMG-CoA reductase inhibitor, said co-administration being in any order and the combined jointly effective amounts providing the desired therapeutic or prophylactic effect.

Such administration encompasses co-administration of these therapeutic agents in a substantially simultaneous manner, such as in a single capsule having a fixed ratio of active ingredients or in multiple, separate capsules for each agent. In addition, such administration also encompasses use of each type of therapeutic agent in a sequential manner.

The HMG-CoA reductase inhibitor for use in the present invention may be any HMG-CoA reductase inhibitor which is preferably capable of lower plasma concentrations of low-density lipoprotein, total cholesterol, or both. In a preferred aspect, the HMG-CoA reductase inhibitor is from a class of therapeutics commonly called statins. Examples of HMG-CoA reductase inhibitors that may be used include but are not limited to lovastatin (Mevacor®), simvastatin (Zocor®), pravastatin (Pravachol®), lactones of pravastatin, fluvastatin (Lescol®), lactones of fluvastatin, atorvastatin (Lipitor®), lactones of atorvastatin, cerivastatin (also known as rivastatin and Baychol®), lactones of cerivastatin, rosuvastatin (Crestor®), lactones of rosuvastatin, itavastatin, nisvastatin, visastatin, atavastatin, bervastatin, compactin, dihydrocompactin, dalvastatin, fluindostatin, pitivastatin, mevastatin, and velostatin (also referred to as synvinolin), and pharmaceutically acceptable forms thereof. Preferably the HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof.

In one embodiment the present invention provides a combination therapy comprising the use of a first amount of a compound of Formula (I), (Ia), (Ib) or (Ic) or an enantiomer, diastereomer, tautomer, or pharmaceutically acceptable salt thereof as described herein and a second amount of an HMG CoA reductase inhibitor compound useful in the prophylaxis or treatment of hyperlipidemia, atherosclerosis, or hypercholesterolemia, wherein said first and second amounts together comprise an anti-hyperlipidemic condition effective amount, an anti-atherosclerotic condition effective amount, or an anti-hypercholesterolemic condition effective amount of the compounds.

General Synthetic Methods

Representative compounds of the present invention can be synthesized in accordance with the general synthetic method described below as well as the illustrative examples that follow. Since the schemes are an illustration, the invention should not be construed as being limited by the chemical reactions and conditions expressed. The preparation of the various starting materials used in the schemes is well within the skill of persons versed in the art.

General Scheme 1

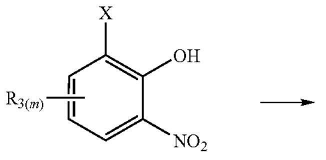

GA1

X = Br, I

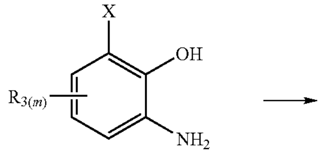

GA2

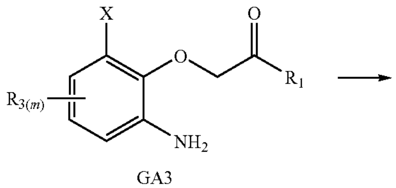

GA3

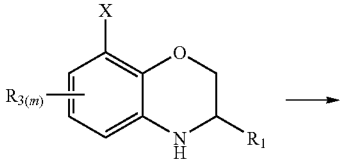

GA4

-continued

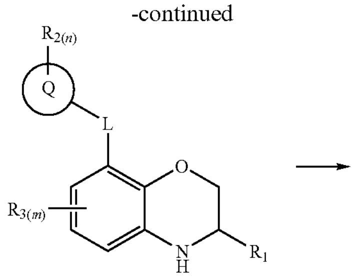

GA5

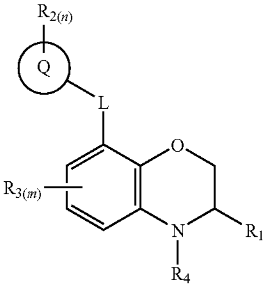

Id

In accordance with General Scheme 1, wherein $R_3$ is $C_{1-4}$ alkyl, $C_{1-4}$ alkoxy, halo, or cyano, and $R_1$, $R_2$, $R_4$, m, n, L, and Q are as described herein, reduction of GA1 gives GA2. O-alkylation of GA2 with alpha-halo-ketone gives GA3. Reductive amination of GA3 gives GA4. Transition metal-catalyzed cross-coupling of GA4 gives GA5. Alkylation of GA5 with various electrophile gives compounds of Formula (Id). When $R_3$ is OH, one can first protect the OH of GA1 as OTBS-GA1, then follow the same sequences described above in General Scheme 1 to give compounds of Formula (II),

II

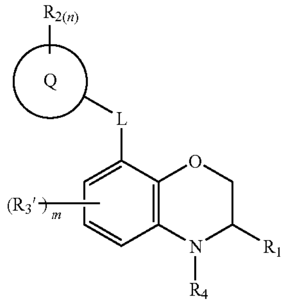

wherein $R_3$' is OTBS and $R_1$, $R_2$, $R_4$, m, n, L, and Q are as described herein, followed by removal of the TBS protection group to give compounds of Formula (Ie):

Ie

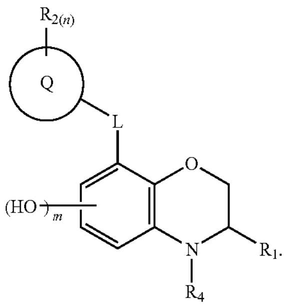

General Scheme 2 (Method B)

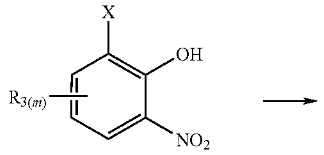

GA1

X = Br, I

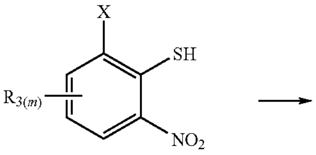

GB2

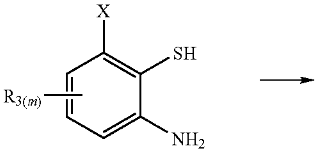

GB3

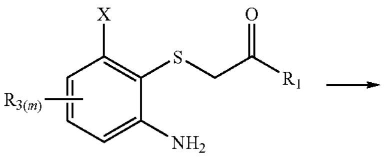

GB4

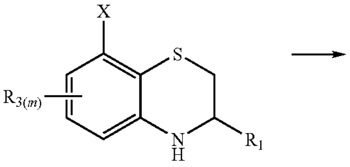

GB5

-continued

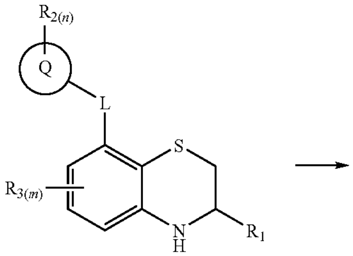

GB6

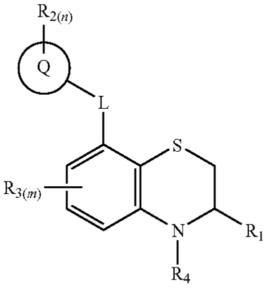

If

In accordance with General Scheme 2, wherein $R_3$ is $C_{1-4}$ alkyl, $C_{1-4}$ alkoxy, halo, or cyano, and $R_1$, $R_2$, $R_4$, m, n, L, and Q are as described herein, reaction of GA1 with $(CH_3)_2NC$-sCl followed by treatment with KOH gives GB2. Reduction of GB2 gives GB3. S-alkylation of GB3 with alpha-halo-ketone gives GB4. Reductive amination of GB4 gives GB5. Transition metal-catalyzed cross-coupling of GB5 gives GB6. Alkylation of GB6 with various electrophile gives compounds of Formula (If). When $R_3$ is OH, one can first protect the OH of GA1 as OTBS-GA1, then followed the same sequences as just described above to give compounds of Formula (II),

II

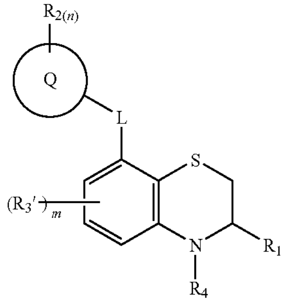

wherein $R_3$' is OTBS and $R_1$, $R_2$, $R_4$, m, n, L, and Q are as described herein, followed by removal of the TBS protection group to give compounds of Formula (Ig):

Ig

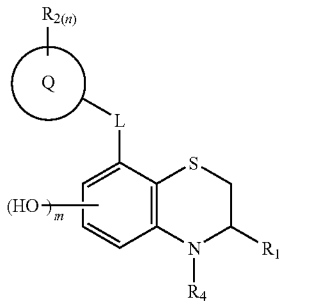

Compounds of the present invention that are chiral may be separated into their enantiomers by chromatography on a chiral stationary phase. Alternatively, the basic compounds of the present invention may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

Abbreviations

Ac=$CH_3C(O)$—
Aq=aqueous
Cpd, Cmpd=compound
con=concentration
DCE=dichloroethane
DCM=dichloromethane
DIEA=diisopropylethyl amine
DMF=N,N-dimethylformamide
DMSO=dimethylsulfoxide
DPPF=diphenylphosphinoferrocene
Et=ethyl
EtOAc=ethyl acetate
h or hr=hour(s)
HATU=N-[(dimethylamino)(3H-1,2,3-triazolo(4,5-b)pyridine-3-yloxy)methylene]-N-methylmethanaminium hexafluorophosphate
HDL=High Density Lipoprotein
HDL-C=high density lipoprotein cholesterol
IDL=Intermediate Density Lipoprotein
LAH=lithium aluminum hydride
LDL=Low Density Lipoprotein
LDL-C=Low Density Lipoprotein cholesterol
$LiN(TMS)_2$=Lithium bis(trimethylsilyl)amide
Me=methyl
min=minute(s)
NBS=N-bromosuccinimide
Ph=phenyl
PPA=polyphosphoric acid
psi=pascal per square inch
Rf=retention time
t-Boc=tert-butoxycarbonyl
TBSO=tert-butyldimethylsilyloxy
t-Bu=tert-butyl
TEA=triethylamine
TFA=trifluoroacetic acid
THF=tetrahydrofuran
TLC=(thin layer chromatography)
TMS=trimethylsilyl
TMSOTf=trimethylsilyl triflate
Tol=toluene
VLDL=Very Low Density Lipoprotein
$Yb(OTf)_3$=Ytterbium tristriflate

EXAMPLES

Example 1

Cmpd 1

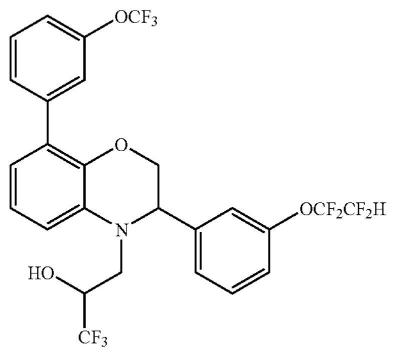

(Higher Rf Cmpd)

1,1,1-Trifluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Scheme A1

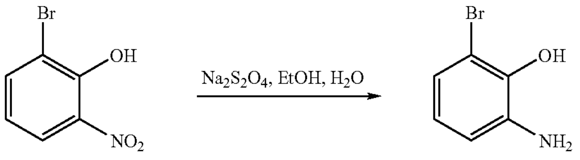

A1a, 73%

-continued

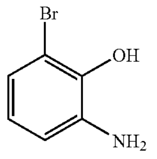

Ala

2-Amino-6-bromo-phenol

To a mixture of 2-bromo-6-nitro-phenol (15.0 g, 68.8 mmol) in EtOH (200 mL) at 60° C. was added a warm solution of $Na_2S_2O_4$ (50.0 g, 287 mmol) in water (180 mL) dropwise. Upon the addition of $Na_2S_2O_4$ solution the reaction mixture turned to deep orange. After addition of about half of the $Na_2S_2O_4$ solution, the deep orange changed to light yellow. The reaction mixture was allowed to cool to room temperature and EtOH was removed in vacuo. The residue was filtered, and the solid was washed with water and dried under vacuum. The filtrate was extracted with $CH_2Cl_2$. The combined organic layers were dried ($Na_2SO_4$) and concentrated. The solids were combined to give 11.1 g (86%) of Ala as a white crystalline material: $^1H$ NMR (300 MHz, $CDCl_3$) δ 6.87-6.83 (m, 1H), 6.66-6.63 (m, 2H), 5.39 (brs, 1H), 3.85 (brs, 2H); MS (ES) m/z: 188 ($M+H^+$).

Scheme A2

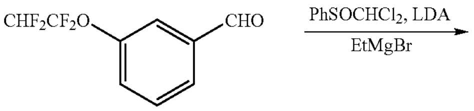

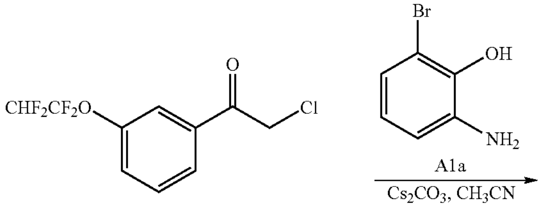

A2a, 49%

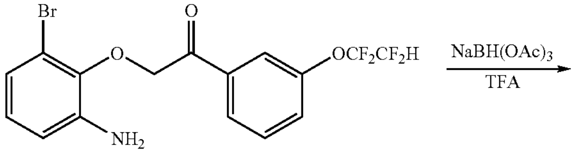

A2b, 67%

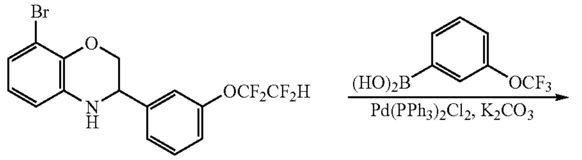

A2c, 100%

-continued

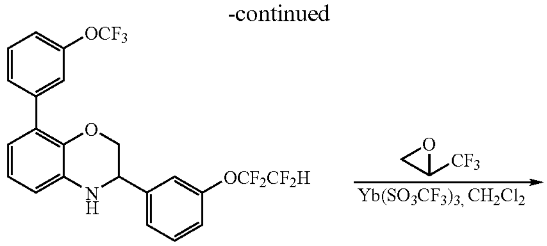

A2d, 87%

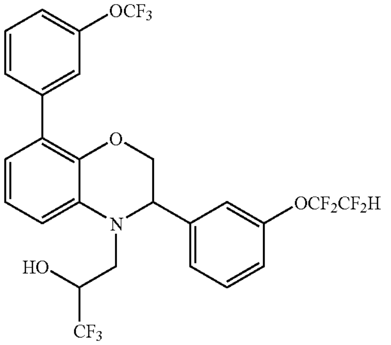

+

Cmpd 1, 17%
Higher Rf Cmpd

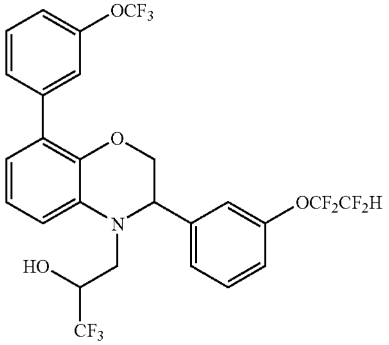

Cmpd 2, 26%
Lower Rf Cmpd

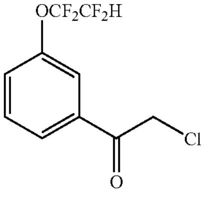

A2a

2-Chloro-1-[3-(1,1,2,2-tetrafluoro-ethoxy)-phenyl] ethanone

To a solution of dichlorophenylmethyl sulfoxide (5.94 g, 28.4 mmol; K. C. Tin & T. Dust, *Tetra. Lett.* 1970, 4643) in THF (100 mL) at −78° C. was added LDA (1.8 M in THF, 20.5 mL, 36.9 mmol). The reaction mixture was stirred at −78° C. for 15 min and then was added 3-(1,1,2,2-tetrafluoro-ethoxy)-benzaldehyde (6.94 g, 31.3 mmol). After stirring at −78° C. for 45 min, EtMgBr (1.0 M solution in $^t$BuOMe, 60 mL, 60 mmol) was added. The reaction mixture was stirred at −78° C. for another 40 min, quenched with $NH_4Cl$ aqueous solution and acidified with 1 N HCl. The organic layer was separated and the aqueous layer was extracted with $CH_2Cl_2$. The combined organic phases were dried ($Na_2SO_4$), concentrated and purified by column chromatography to give 4.13 g (49%) of A2a as a yellow oil: $^1$H NMR (300 MHz, $CDCl_3$) δ 7.89 (dd, J=7.6, 2.6 Hz, 1H), 7.81 (s, 1H), 7.58-7.46 (m, 2H), 5.95 (tt, J=53.0, 2.7 Hz, 1H), 4.68 (s, 2H); MS (ES) m/z: 293 ($M+Na^+$).

A2b

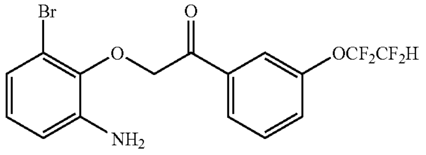

2-(2-Amino-6-bromo-phenoxy)-1-[3-(1,1,2,2-tetrafluoro-ethoxy)-phenyl]-ethanone

A mixture of A1a (2.59 g, 13.8 mmol), A2a (4.10 g, 15.2 mmol) and $Cs_2CO_3$ (4.49 g, 13.8 mmol) in $CH_3CN$ (40 mL) was stirred at room temperature for 2.5 h. The solid was filtered and washed with THF and $CH_2Cl_2$. The filtrate was concentrated and purified by column chromatography to give 3.87 g (67%) of A2b as a brownish oil: $^1$H NMR (300 MHz, $CDCl_3$) δ 7.84 (s, 1H), 7.76 (d, J=7.8 Hz, 1H), 7.51 (t, J=8.0 Hz, 1H), 7.41-7.36 (m, 3H), 6.93 (t, J=7.9 Hz, 1H), 5.95 (mt, J=53.0 Hz, 1H), 5.17 (s, 2H); MS (ES) m/z: 404 ($M-H_2O$).

A2c

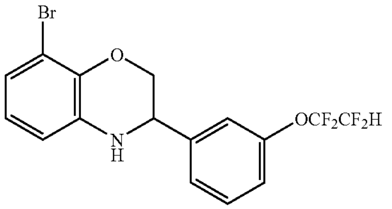

8-Bromo-3-[3-(1,1,2,2-tetrafluoro-ethoxy)-phenyl]-3,4-dihydro-2H-benzo[1,4]oxazine To a mixture of A2b (2.77 g, 6.56 mmol) and $NaB(OAc)_3H$ (2.78 g, 13.1 mmol) in 1,2-dichloroethane (40 mL) was added trifluoroacetic acid (0.500 mL, 6.5 mmol). After stirring at room temperature for 45 min, $NaHCO_3$ saturated solution was added and the aqueous layer was extracted with $CH_2Cl_2$. The combined organic phases were dried ($Na_2SO_4$), concentrated and purified by column chromatography to get 2.67 g (100%) of A2c as a yellow oil: $^1$H NMR (300 MHz, $CDCl_3$) δ 7.42 (t, J=8.2 Hz, 1H), 7.31 (d, J=7.7 Hz, 1H), 7.26 (s, 1H), 7.22 (d, J=8.1 Hz, 1H), 6.96 (d, J=7.8 Hz, 1H), 6.72-6.62 (m, 2H), 5.92 (bt, J=45.8 Hz, 1H), 4.55 (bd, J=8.5 Hz, 1H), 4.42 (bd, J=10.7 Hz, 1H), 4.12 (brs, 1H), 4.07-4.02 (m, 1H); MS (ES) m/z: 406 ($M+H^+$).

A2d

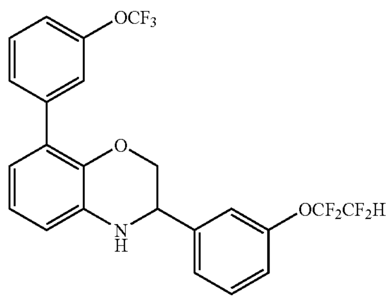

3-[3-(1,1,2,2-Tetrafluoro-ethoxyl)-phenyl]-8-(3-trifluoromethoxy-phenyl)-3,4-dihydro-2H-benzo[1,4]oxazine A mixture of A2c (2.00 g, 4.93 mmol), 3-trifluoromethoxy-benzene boronic acid (2.03 g, 9.85 mmol) and 2 N $K_2CO_3$ (7.4 mL, 14.8 mmol) in 1,4-dioxane (50 mL) was purged with $N_2$ for 15 min, and $PdCl_2(PPh_3)_2$ (210 mg, 0.299 mmol) was added. The reaction mixture was purged with $N_2$ for another 10 min and heated at 95° C. for 20 h. After cooling to room temperature, $NH_4Cl$ aqueous solution was added and the mixture was extracted with $CH_2Cl_2$. The combined organic layers were dried ($Na_2SO_4$), concentrated and purified by column chromatography to give 2.09 g (87%) of A2d as a clear oil: $^1$H NMR (300 MHz, $CDCl_3$) δ 7.49-7.14 (m, 8H), 6.89 (t, J=7.7 Hz, 1H), 6.78-6.70 (m, 2H), 5.91 (tt, J=53.1, 2.8 Hz, 1H), 4.58 (dd, J=8.2, 2.7 Hz, 1H), 4.32 (dd, J=10.6, 1.9 Hz, 1H), 4.14 (brs, 1H), 3.99 (dd, J=10.6, 6.4 Hz, 1H); MS (ES) m/z: 488 ($M+H^+$).

Cmpd 1

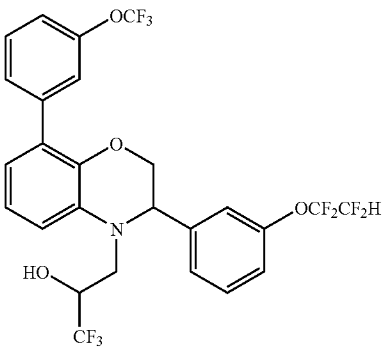

Higher Rf Cmpd 1,1,1-Trifluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol A mixture of A2d (38 mg, 0.078 mmol), 2-trifluoromethyl-oxirane (44 mg, 0.39 mmol) and $Yb(SO_3CF_3)_3$ (5 mg, 0.008 mmol) in $CH_2Cl_2$ (0.35 mL) was heated at 50° C. for 18 h in a sealed tube. After cooling to room temperature, the crude mixture was purified by thin layer chromatography (20% EtOAc in hexane) to give 8 mg (17%) higher Rf compound 1 as a clear oil: $^1$H NMR (300 MHz, $CDCl_3$) δ 7.44-7.35 (m, 4H), 7.22-7.12 (m, 4H), 7.01 (t, J=7.9 Hz, 1H), 6.81-6.76 (m, 2H), 5.89 (tt, J=53.1, 2.7 Hz, 1H), 4.86 (t, J=3.8 Hz, 1H), 4.40

(m, 1H), 4.27 (dd, J=11.0, 3.2 Hz, 1H), 4.17 (dd, J=11.0, 4.7 Hz, 1H), 3.82 (d, J=15.6 Hz, 1H), 3.32 (dd, J=15.7, 9.6 Hz, 1H), 2.47 (brs, 1H); MS (ES) m/z: 600 (M−H+).

Example 2

Cmpd 2

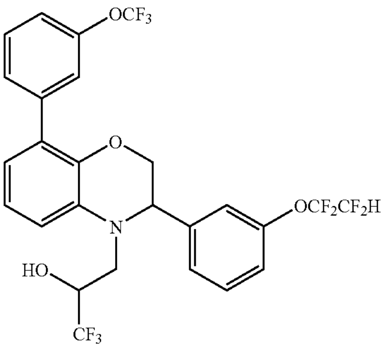

Lower Rf Cmpd 1,1,1-Trifluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Compound 2 was isolated as a lower Rf compound (26%, clear oil) in the same reaction of synthesizing compound 1: $^1$H NMR (300 MHz, $CDCl_3$) δ 7.45-7.34 (m, 4H), 7.19-7.14 (m, 3H), 7.09 (s, 1H), 7.02 (t, J=7.9 Hz, 1H), 6.89 (d, J=7.3 Hz, 1H), 6.78 (d, J=7.6 Hz, 1H), 5.88 (tt, J=53.1, 2.7 Hz, 1H), 4.55 (t, J=2.9 Hz, 1H), 4.34-4.20 (m, 3H), 3.70 (dd, J=15.7, 6.5 Hz, 1H), 3.56 (dd, J=15.7, 5.2 Hz, 1H), 2.30 (brs, 1H); MS (ES) m/z: 600 (M+H+).

Example 3

Cmpd 3

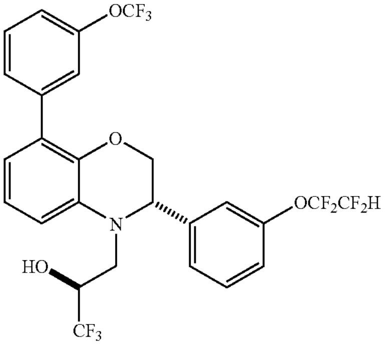

4H-1,4-Benzoxazine-4-ethanol, 2,3-dihydro-3-[3-(1,1,2,2-tetrafluoroethoxy)phenyl]-8-[3-(trifluoromethoxy)phenyl]-α-(trifluoromethyl)-, (3S,αS)—

Scheme C1

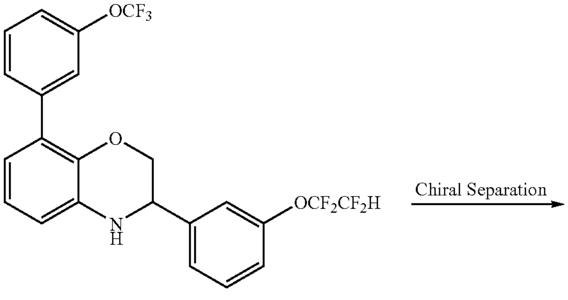

A2d

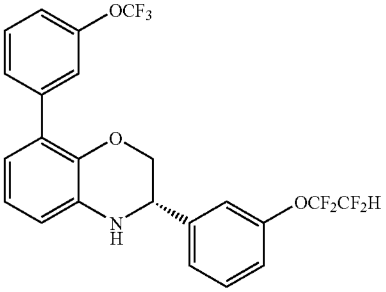

C1a

+

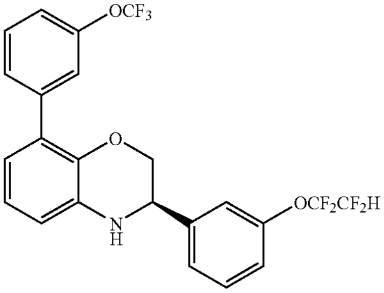

C1b

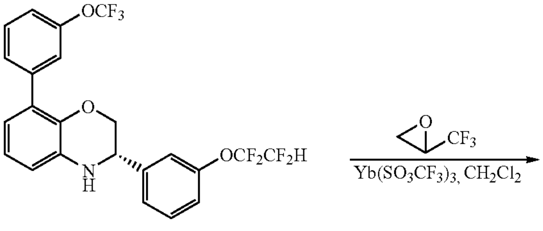

C1a

-continued

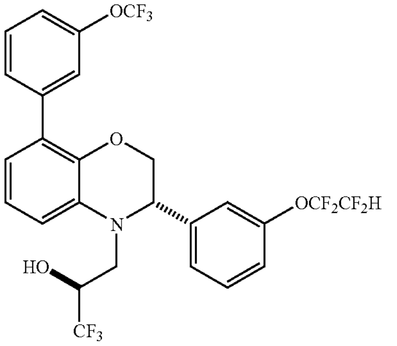

+

Cmpd 3

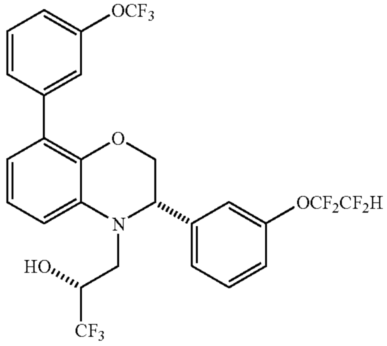

Cmpd 4

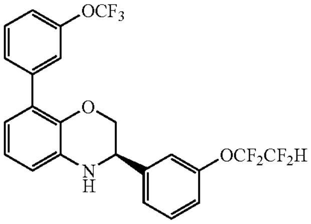

C1b

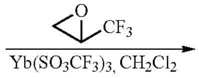

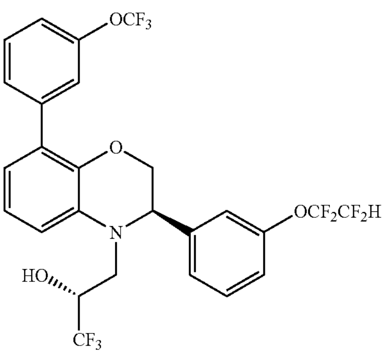

+

Cmpd 5

-continued

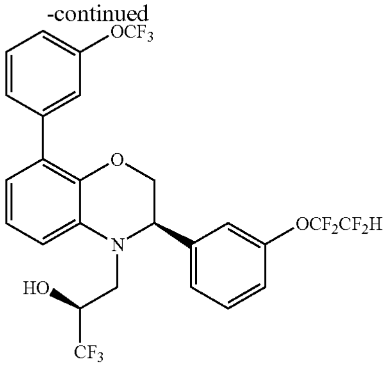

Cmpd 6

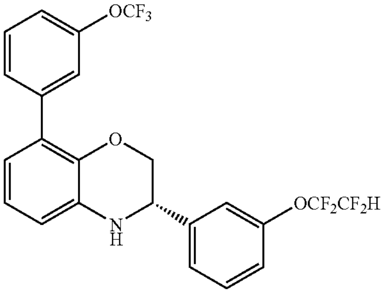

C1a 2H-1,4-Benzoxazine, 3,4-dihydro-3-[3-(1,1,2,2-tetrafluoroethoxy)phenyl]-8-[3-(trifluoromethoxy)phenyl]-, (3S)—

The racemic mixture A2d (1.5 g) was separated by chiral HPLC (column: Chiralcel OJ; eluent: isocratic mixture of 90% heptane and 10% ethanol) to give enantiomers C1a (first off HPLC, 0.63 g) and C1b (second off HPLC, 0.54 g). Spectrums of C1a are as follows: $[\alpha]^{20}_{D}$ +34.4° (c=1, $CHCl_3$); 1H NMR (300 MHz, $CDCl_3$) δ 7.49-7.11 (m, 8H), 6.90 (t, J=7.7 Hz, 1H), 6.78-6.71 (m, 2H), 5.91 (tt, J=53.1, 2.6 Hz, 1H), 4.58 (dd, J=8.3, 2.6 Hz, 1H), 4.31 (dd, J=10.6, 2.3 Hz, 1H), 4.15 (brs, 1H), 3.99 (dd, J=10.6, 8.4 Hz, 1H); MS (ES) m/z: 488 ($M+H^+$).

C1b

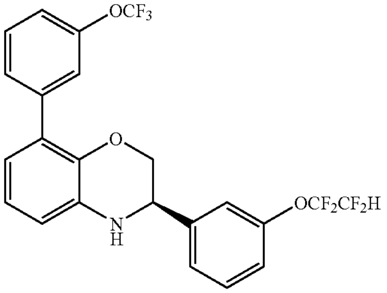

2H-1,4-Benzoxazine, 3,4-dihydro-3-[3-(1,1,2,2-tetrafluoroethoxy)phenyl]-8-[3-(trifluoromethoxy)phenyl]-, (3R)—

Spectrums of C1b are as following: $[\alpha]^{20}_{D}$ −35.7° (c=1, $CHCl_3$); $^1H$ NMR (300 MHz, $CDCl_3$) δ 7.50-7.12 (m, 8H), 6.90 (t, J=7.7 Hz, 1H), 6.79-6.70 (m, 2H), 5.90 (tt, J=53.1, 2.8 Hz, 1H), 4.59 (dd, J=8.2, 2.7 Hz, 1H), 4.31 (dd, J=10.6, 1.9 Hz, 1H), 4.15 (brs, 1H), 3.99 (dd, J=10.6, 6.4 Hz, 1H); MS (ES) m/z: 488 (M+H$^+$).

Cmpd 3

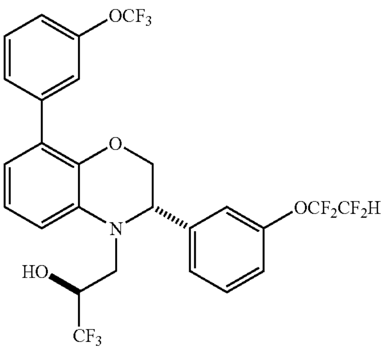

4H-1,4-Benzoxazine-4-ethanol, 2,3-dihydro-3-[3-(1,1,2,2-tetrafluoroethoxy)phenyl]-8-[3-(trifluoromethoxy)phenyl]-α-(trifluoromethyl)-, (3S,αS)—

Replacing A2d with C1a and following the same procedure as in the preparation of compound 1 and 2 gave compound 3 and 4. Spectrums of compound 3 are as follows: $[\alpha]^{20}_D$ −69.6° (c=(1, $CHCl_3$); $^1$H NMR (300 MHz, $CDCl_3$) δ 7.44-7.35 (m, 4H), 7.22-7.12 (m, 4H), 7.01 (t, J=7.9 Hz, 1H), 6.81-6.77 (m, 2H), 5.90 (tt, J=53.1, 2.7 Hz, 1H), 4.87 (t, J=3.8 Hz, 1H), 4.40 (m, 1H), 4.28 (dd, J=11.0, 3.2 Hz, 1H), 4.18 (dd, J=11.0, 4.7 Hz, 1H), 3.82 (d, J=15.6 Hz, 1H), 3.34 (dd, J=15.7, 9.6 Hz, 1H), 2.50 (brs, 1H); MS (ES) m/z: 600 (M+H$^+$). Anal. Calcd. For $C_{26}H_{19}F_{10}NO_4$: C, 52.10; H, 3.19; N, 2.34. Found: C, 51.95; H, 2.82; N, 2.34.

Example 4

Cmpd 4

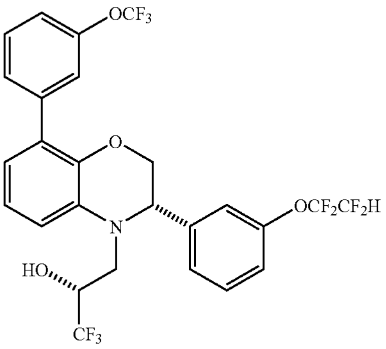

4H-1,4-Benzoxazine-4-ethanol, 2,3-dihydro-3-[3-(1,1,2,2-tetrafluoroethoxy)phenyl]-8-[3-(trifluoromethoxy)phenyl]-α-(trifluoromethyl)-, (3S,αR)—

Spectrums of compound 4 are as following: $[\alpha]^{20}_D$ −80.8° (c=1, $CHCl_3$); $^1$H NMR (300 MHz, $CDCl_3$) δ 7.42-7.32 (m, 4H), 7.19-7.10 (m, 3H), 7.09 (s, 1H), 7.02 (t, J=7.9 Hz, 1H), 6.89 (d, J=8.1 Hz, 1H), 6.79 (d, J=7.6 Hz, 1H), 5.87 (tt, J=53.1, 2.6 Hz, 1H), 4.54 (s, 1H), 4.36-4.20 (m, 3H), 3.70 (dd, J=15.8, 6.5 Hz, 1H), 3.56 (dd, J=15.7, 5.2 Hz, 1H), 2.30 (brs, 1H); MS (ES) m/z: 600 (M+H$^+$).

Example 5

Cmpd 5

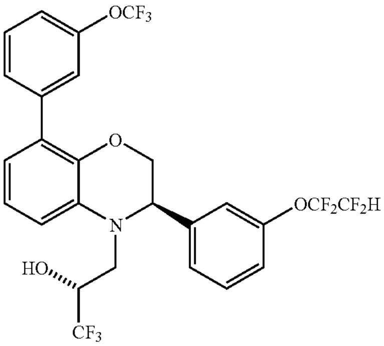

4H-1,4-Benzoxazine-4-ethanol, 2,3-dihydro-3-[3-(1,1,2,2-tetrafluoroethoxy)phenyl]-8-[3-(trifluoromethoxy)phenyl]-α-(trifluoromethyl)-, (3R,αR)—

Replacing A2d with C1b and following the same procedure as in the preparation of compound 1 and 2 gave compound 5 and 6. Spectrums of compound 5 are as following: $[\alpha]^{20}_D$ +68.4° (c=1, $CHCl_3$); $^1$H NMR (300 MHz, $CDCl_3$) δ 7.44-7.35 (m, 4H), 7.22-7.12 (m, 4H), 7.01 (t, J=7.9 Hz, 1H), 6.81-6.77 (m, 2H), 5.90 (tt, J=53.1, 2.7 Hz, 1H), 4.87 (t, J=3.8 Hz, 1H), 4.40 (m, 1H), 4.28 (dd, J=11.0, 3.2 Hz, 1H), 4.18 (dd, J=11.0, 4.7 Hz, 1H), 3.82 (d, J=15.6 Hz, 1H), 3.34 (dd, J=15.7, 9.6 Hz, 1H), 2.50 (brs, 1H); MS (ES) m/z: 600 (M+H$^+$).

Example 6

Cmpd 6

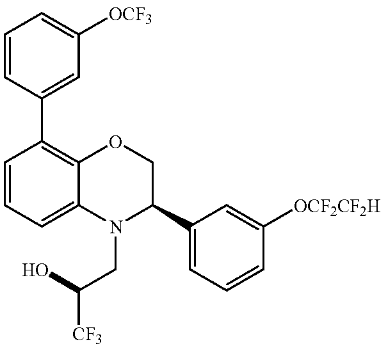

4H-1,4-Benzoxazine-4-ethanol, 2,3-dihydro-3-[3-(1,1,2,2-tetrafluoroethoxy)phenyl]-8-[3-(trifluoromethoxy)phenyl]-α-(trifluoromethyl)-, (3R,αS)—

Spectrums of compound 6 are as following: $[\alpha]^{20}_D$ +71° (c=0.33, $CHCl_3$); $^1$H NMR (300 MHz, $CDCl_3$) δ 7.42-7.32 (m, 4H), 7.19-7.10 (m, 3H), 7.09 (s, 1H), 7.02 (t, J=7.9 Hz, 1H), 6.89 (d, J=8.1 Hz, 1H), 6.79 (d, J=7.6 Hz, 1H), 5.87 (tt, J=53.1, 2.6 Hz, 1H), 4.54 (s, 1H), 4.36-4.20 (m, 3H), 3.70 (dd, J=15.8, 6.5 Hz, 1H), 3.56 (dd, J=15.7, 5.2 Hz, 1H), 2.30 (brs, 1H); MS (ES) m/z: 600 (M+H$^+$).

Scheme C2

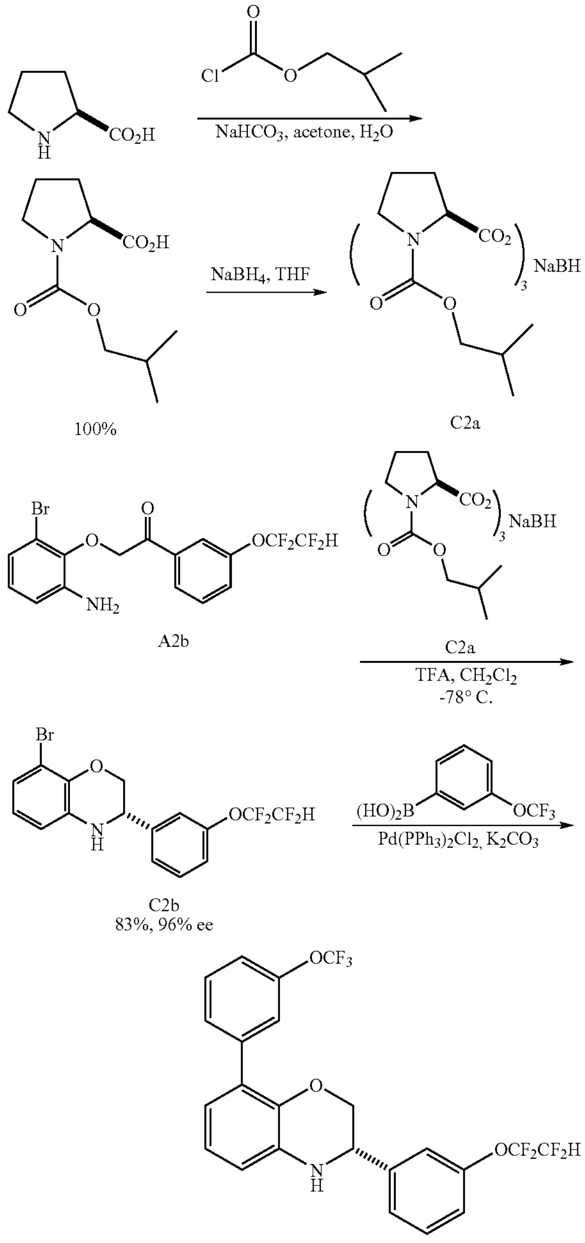

100%
C2a
A2b
C2a
C2b
83%, 96% ee
C1a, 89%

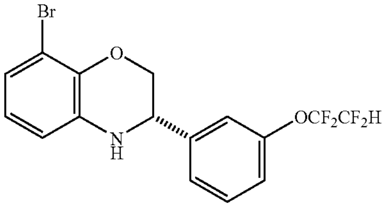

C2b 2H-1,4-Benzoxazine, 3,4-dihydro-3-[3-(1,1,2,2-tetrafluoroethoxy)phenyl]-8-bromo-, (3S)—

To a solution of C2a (6.94 g, 10.2 mmol; S. Atarashi, H. Tsurumi, T. Fujiwara and I. Hayakawa, *J. Heterocyclic Chem.* 1991, 28, 329) in dichloromethane (25 mL) at −78° C. was added a solution of A2b (2.06 g, 4.88 mmol) in $CH_2Cl_2$ (11 mL) followed by TFA (0.37 mL, 4.88 mmol). After stirring at −78° C. for 2 h, $NaHCO_3$ saturated solution was added and the aqueous layer was extracted with $CH_2Cl_2$. The combined organic phases were dried ($Na_2SO_4$), concentrated and purified by column chromatography to get 1.7 g (86%) of C2b as a yellow oil: $[\alpha]^{20}_D$ +66.0° (c=1, $CHCl_3$); $^1H$ NMR (300 MHz, $CDCl_3$) δ 7.42 (t, J=8.2 Hz, 1H), 7.31 (d, J=7.7 Hz, 1H), 7.26 (s, 1H), 7.22 (d, J=8.1 Hz, 1H), 6.96 (d, J=7.8 Hz, 1H), 6.72-6.62 (m, 2H), 5.92 (bt, J=45.8 Hz, 1H), 4.55 (bd, J=8.5 Hz, 1H), 4.42 (bd, J=10.7 Hz, 1H), 4.12 (brs, 1H), 4.07-4.02 (m, 1H); MS (ES) m/z: 406 (M+H$^+$).

C1a

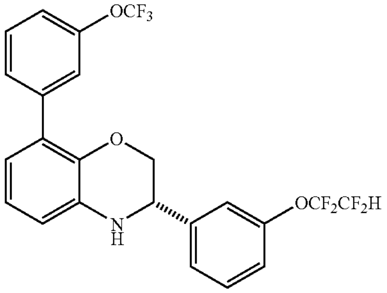

2H-1,4-Benzoxazine, 3,4-dihydro-3-[3-(1,1,2,2-tetrafluoroethoxy)phenyl]-8-[3-(trifluoromethoxy)phenyl]-, (3S)—

Replacing A2c with C2b and following the same procedure as in the preparation of compound A2d gave compound Cl a (89%): $[\alpha]^{20}_D$ +33.5° (c=1, $CHCl_3$); $^1H$ NMR (300 MHz, $CDCl_3$) δ 7.49-7.14 (m, 8H), 6.89 (t, J=7.7 Hz, 1H), 6.78-6.70 (m, 2H), 5.91 (tt, J=53.1, 2.8 Hz, 1H), 4.58 (dd, J=8.2, 2.7 Hz, 1H), 4.32 (dd, J=10.6, 1.9 Hz, 1H), 4.14 (brs, 1H), 3.99 (dd, J=10.6, 6.4 Hz, 1H); MS (ES) m/z: 488 (M+H$^+$).

Example 7

Cmpd 7

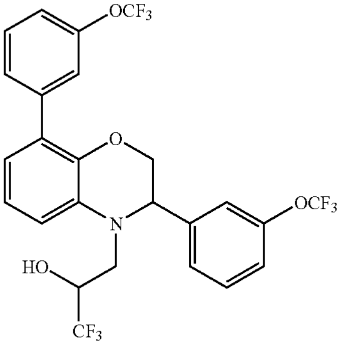

Higher Rf Cmpd

3-[3,8-Bis-(3-trifluoromethoxy-phenyl)-2,3-dihydro-benzo[1,4]oxazin-4-yl]-1,1,1-trifluoro-propan-2-ol Scheme D

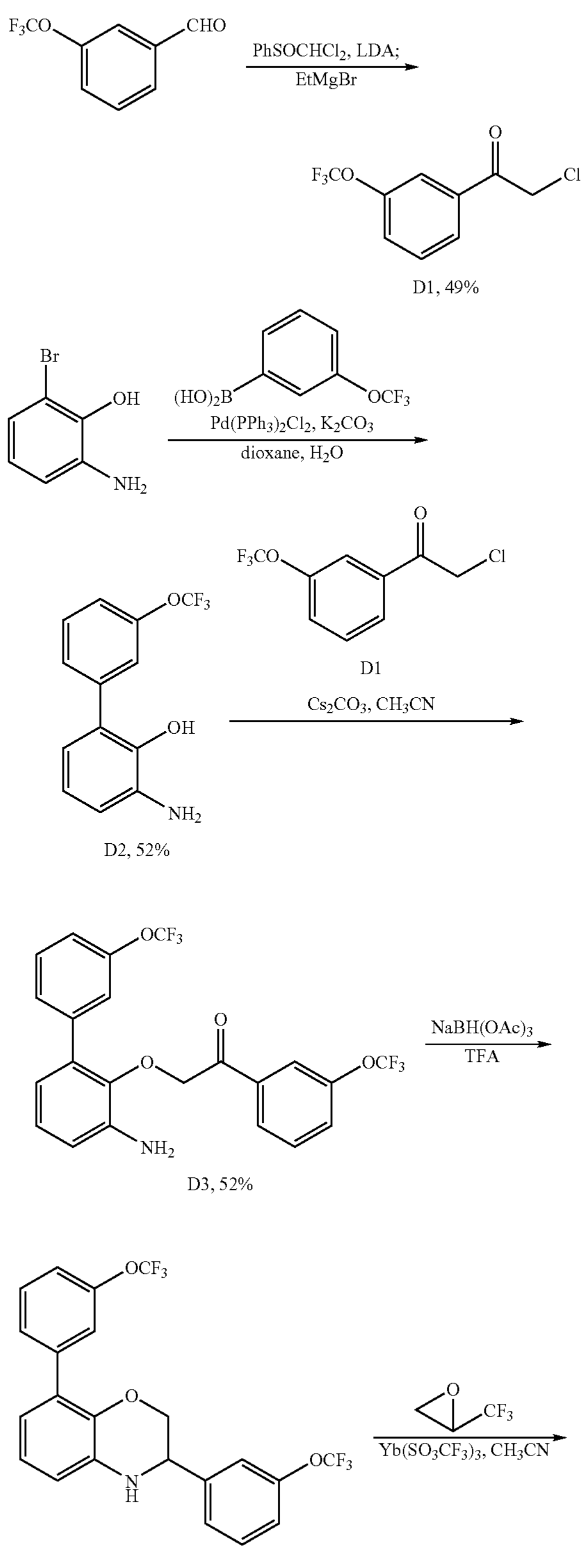

-continued

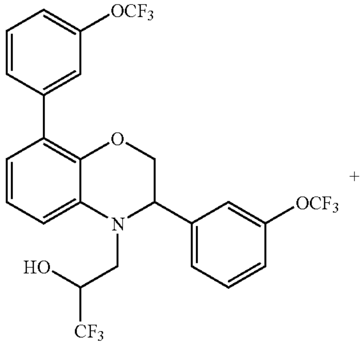

Cmpd 7, 34%
Higher Rf Cmpd

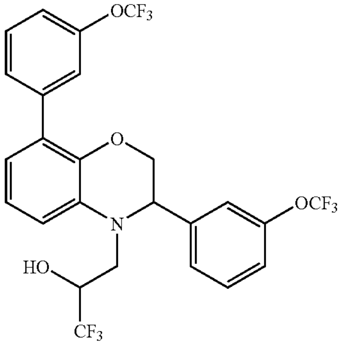

Cmpd 8, 41%
Lower Rf Cmpd

D1

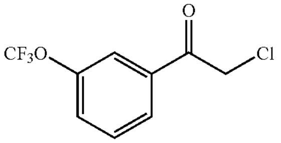

2-Chloro-1-(3-trifluoromethoxy-phenyl)-ethanone

Replacing 3-(1,1,2,2-tetrafluoro-ethoxy)-benzaldehyde with 3-trifluoro-methoxy-benzaldehyde and following the same procedure as in the preparation of compound A2a gave compound D1 (49%): $^{1}H$ NMR (300 MHz, $CDCl_3$) δ 7.89 (d, J=7.6 Hz, 1H), 7.82 (s, 1H), 7.60-7.46 (m, 2H), 4.68 (s, 2H).

D2

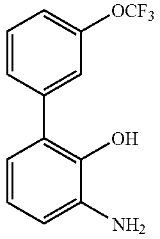

3-Amino-3'-trifluoromethoxy-biphenyl-2-ol

A mixture of 2-amino-6-bromo-phenol (255 mg, 1.36 mmol), m-trifluoromethoxy-phenyl boronic acid (560 mg, 2.72 mmol), $K_2CO_3$ (2.0 M, 2.0 mL, 4.0 mmol) in 1,4-dioxane (8 mL) was degassed under $N_2$ for 10 min, and $PdCl_2$ $(PPh_3)_2$ (95 mg, 0.14 mmol) was added. The mixture was purged with $N_2$ for another 10 min then heated at 100° C. for 17 h. After cooling to room temperature, the organic layer was separated and the aqueous layer was extracted with $CH_2Cl_2$. The combined organic layers were dried ($Na_2SO_4$), concentrated and purified by column chromatography to give 191 mg (52%) of D2 as a yellow oil: $^1$H NMR (300 MHz, $CDCl_3$) δ 7.54-7.40 (m, 2H), 7.35 (s, 1H), 7.24 (m, 1H), 6.88-6.77 (m, 2H), 6.70-6.62 (m, 1H), 5.20 (brs, 1H), 3.78 (brs, 2H); MS (ES) m/z: 270 (M+H$^+$).

D3

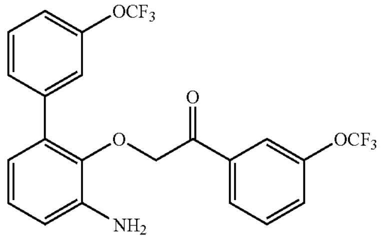

2-(3-Amino-3'-trifluoromethoxy-biphenyl-2-yloxy)-1-(3-trifluoromethoxy-phenyl)-ethanone To a solution of phenol (145 mg, 0.539 mmol), acyl chloride (141 mg, 0.591 mmol) and DMF (1.5 mL) was added $K_2CO_3$ (82 mg, 0.59 mmol). After stirring at room temperature for 2 h, the reaction mixture was partitioned between $Et_2O$ and water. The organic layer was washed with water and the aqueous layer was back extracted with $Et_2O$. The combined organic extracts were dried ($Na_2SO_4$), concentrated and purified by column chromatography to give 100 mg (39%) of D3 as a yellow oil: $^1$H NMR (300 MHz, $CDCl_3$) δ 7.87 (s, 1H), 7.79 (d, J=7.9 Hz, 1H), 7.55-7.30 (m, 7H), 7.28-7.19 (m, 1H), 7.13 (t, J=7.8 Hz, 1H), 5.03 (s, 2H); MS (ES) m/z: 454 (M−$H_2O$+H$^+$).

D4

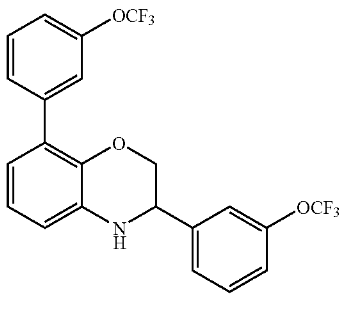

3,8-Bis-(3-trifluoromethoxy-phenyl)-3,4-dihydro-2H-benzo[1,4]oxazine

Replacing A2b with D3 and following the same procedure as in the preparation of compound A2c gave compound D4 (88%): $^1$H NMR (300 MHz, $CDCl_3$) δ 7.50-7.12 (m, 8H), 6.90 (t, J=7.7 Hz, 1H), 6.79-6.70 (m, 2H), 4.57 (bd, J=8.2 Hz, 1H), 4.32 (m, 1H), 4.13 (brs, 1H), 3.98 (dd, J=10.7, 8.3 Hz, 1H); MS (ES) m/z: 456 (M+H$^+$).

Cmpd 7

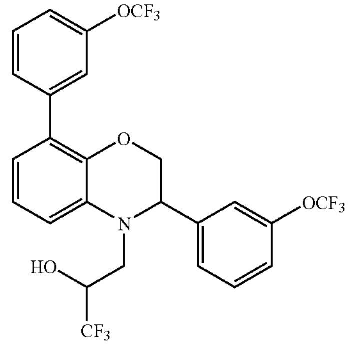

Higher Rf Cmpd

3-[3,8-Bis-(3-trifluoromethoxy-phenyl)-2,3-dihydro-benzo[1,4]oxazin-4-yl]-1,1,1-trifluoro-propan-2-ol Replacing A2d with D4 and following the same procedure as in the preparation of compound 1 and 2 gave higher Rf compound 7 (34%) and Lower Rf compound 8 (eluent: 20% EtOAc in hexane). Spectrums of compound 7 are as follows: $^1$H NMR (300 MHz, $CDCl_3$) δ 7.42-7.34 (m, 4H), 7.22-7.10 (m, 4H), 7.01 (t, J=7.9 Hz, 1H), 6.81-6.76 (m, 2H), 4.87 (t, J=3.8 Hz, 1H), 4.41 (m, 1H), 4.27 (dd, J=11.0, 3.1 Hz, 1H), 4.16 (dd, J=11.0, 4.6 Hz, 1H), 3.83 (d, J=15.6 Hz, 1H), 3.31 (dd, J=15.7, 9.6 Hz, 1H), 2.46 (d, J=3.5 Hz, 1H); MS (ES) m/z: 568 (M+H$^+$).

Example 8

Cmpd 8

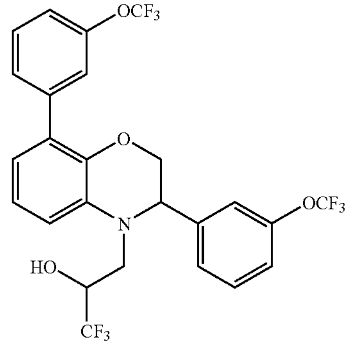

Lower Rf Cmpd

3-[3,8-Bis-(3-trifluoromethoxy-phenyl)-2,3-dihydro-benzo[1,4]oxazin-4-yl]-1,1,1-trifluoro-propan-2-ol Spectrums of compound 8 (41%) are as follows: $^1$H NMR (300 MHz, $CDCl_3$) δ 7.40-7.31 (m, 4H), 7.20-6.99 (m, 5H), 6.89 (d, J=8.2 Hz, 1H), 6.78 (d, J=7.6 Hz, 1H), 4.55 (t, J=2.9

Hz, 1H), 4.36-4.20 (m, 3H), 3.70 (dd, J=15.7, 6.5 Hz, 1H), 3.55 (dd, J=15.7, 5.2 Hz, 1H), 2.29 (brs, 1H); MS (ES) m/z: 568 (M+H+).
Example 9
Cmpd 9
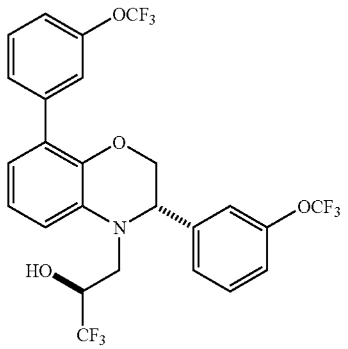
4H-1,4-Benzoxazine-4-ethanol, 2,3-dihydro-3,8-bis [3-(trifluoromethoxy)phenyl]-α-(trifluoromethyl)-, (3S,αS)—
Scheme E
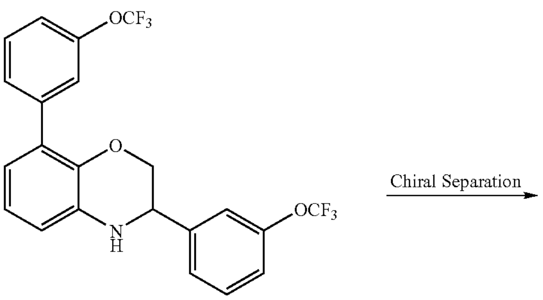
D4
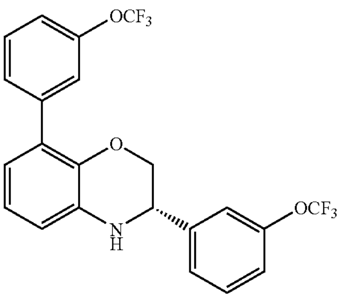
+
E1
-continued
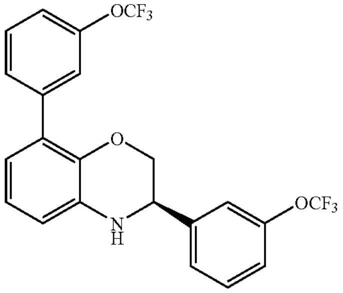
E2
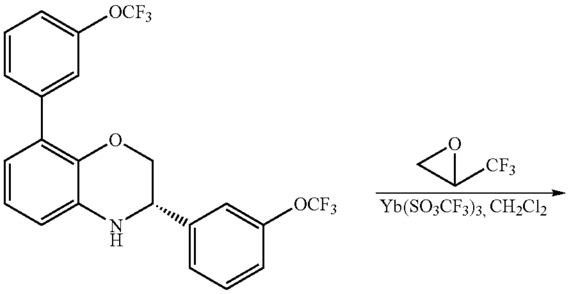
E1
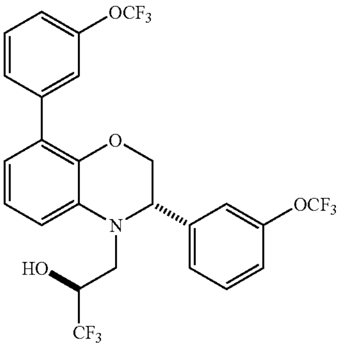
+
Cmpd 9
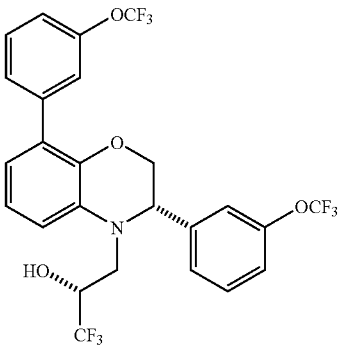
Cmpd 10

-continued

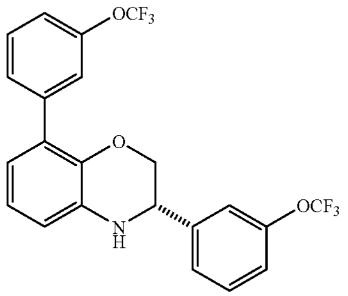

E1

2H-1,4-Benzoxazine, 3,4-dihydro-3,8-bis[3-(trifluoromethoxy)phenyl]-, (3S)—

The racemic mixture D4 was separated by chiral HPLC (column: Chiralcel OJ; eluent: isocratic mixture of 90% heptane and 10% ethanol) to give enantiomers E1 (first off HPLC column) and E2 (second off HPLC column). Spectrums of E1 are as following: $[\alpha]^{20}_D$ +33.4° (c=1, $CHCl_3$); $^1H$ NMR (300 MHz, $CDCl_3$) δ 7.50-7.12 (m, 8H), 6.90 (t, J=7.7 Hz, 1H), 6.79-6.70 (m, 2H), 4.57 (bd, J=8.2 Hz, 1H), 4.32 (m, 1H), 4.13 (brs, 1H), 3.98 (dd, J=10.7, 8.3 Hz, 1H); MS (ES) m/z: 456 ($M+H^+$).

E2

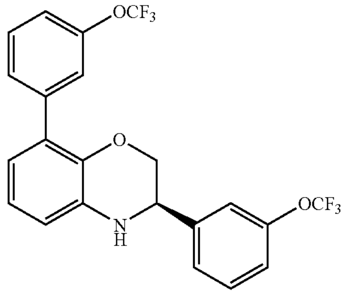

2H-1,4-Benzoxazine, 3,4-dihydro-3,8-bis[3-(trifluoromethoxy)phenyl]-, (3R)—

Spectrums of E2 are as following: $[\alpha]^{20}_D$ −29.0° (c=1, $CHCl_3$); $^1H$ NMR (300 MHz, $CDCl_3$) δ 7.50-7.12 (m, 8H), 6.90 (t, J=7.7 Hz, 1H), 6.79-6.70 (m, 2H), 4.57 (bd, J=8.2 Hz, 1H), 4.32 (m, 1H), 4.13 (brs, 1H), 3.98 (dd, J=10.7, 8.3 Hz, 1H); MS (ES) m/z: 456 ($M+H^+$).

Cmpd 9

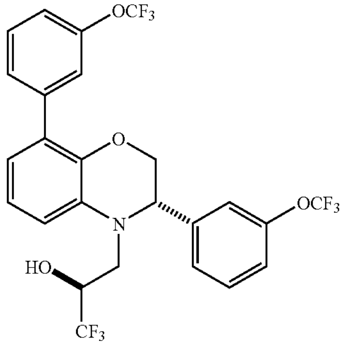

4H-1,4-Benzoxazine-4-ethanol, 2,3-dihydro-3,8-bis[3-(trifluoromethoxy)phenyl]-α-(trifluoromethyl)-, (3S,αS)—

Replacing A2d with E1 and following the same procedure as in the preparation of compound 1 and 2 gave compound 9 and 10. Spectrums of compound 9 are as following: $^1H$ NMR (300 MHz, $CDCl_3$) δ 7.42-7.34 (m, 4H), 7.22-7.10 (m, 4H), 7.01 (t, J=7.9 Hz, 1H), 6.81-6.76 (m, 2H), 4.87 (t, J=3.8 Hz, 1H), 4.41 (m, 1H), 4.27 (dd, J=11.0, 3.1 Hz, 1H), 4.16 (dd, J=11.0, 4.6 Hz, 1H), 3.83 (d, J=15.6 Hz, 1H), 3.31 (dd, J=15.7, 9.6 Hz, 1H), 2.46 (d, J=3.5 Hz, 1H); MS (ES) m/z: 568 ($M+H^+$). Anal. Calcd. For $C_{25}H_{18}F_9NO_4$: C, 52.92; H, 3.20; N, 2.47. Found: C, 52.79; H, 3.00; N, 2.43.

Example 10

Cmpd 10

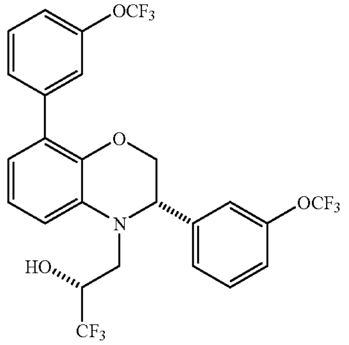

4H-1,4-Benzoxazine-4-ethanol, 2,3-dihydro-3,8-bis[3-(trifluoromethoxy)phenyl]-α-(trifluoromethyl)-, (3S,αR)—

Spectrums of compound 10 are as following: $^1H$ NMR (300 MHz, $CDCl_3$) δ 7.40-7.31 (m, 4H), 7.20-6.99 (m, 5H), 6.89 (d, J=8.2 Hz, 1H), 6.78 (d, J=7.6 Hz, 1H), 4.55 (t, J=2.9

Hz, 1H), 4.36-4.20 (m, 3H), 3.70 (dd, J=15.7, 6.5 Hz, 1H), 3.55 (dd, J=15.7, 5.2 Hz, 1H), 2.29 (brs, 1H); MS (ES) m/z: 568 (M+H+).

Example 11

Cmpd 11

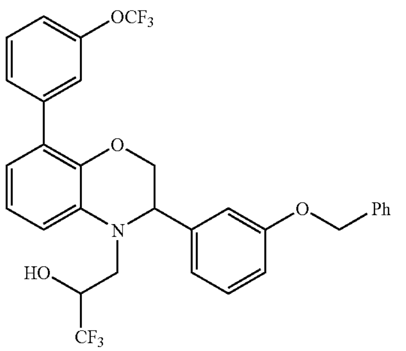

Higher Rf Cmpd

3-[3-(3-Benzyl-phenyl)-8-(3-trifluoromethoxy-phenyl)-2,3-dihydro-benzo[1,4]oxazin-4-yl]-1,1,1-trifluoro-propan-2-ol Scheme F

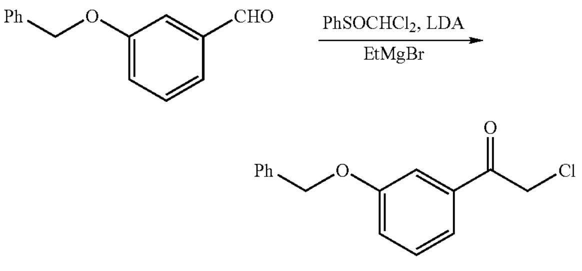

F1, 36%

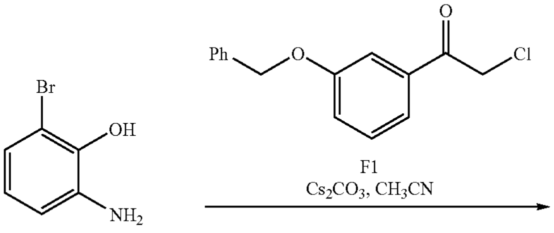

D2

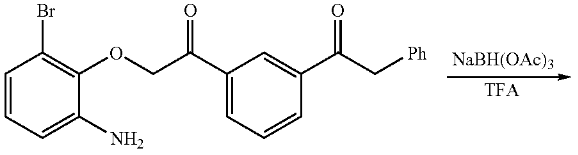

F2, 70%

-continued

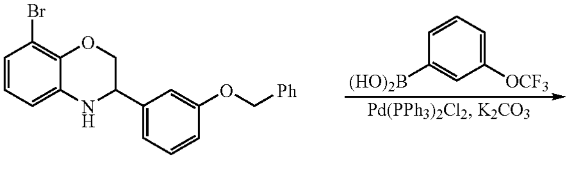

F3, 80%

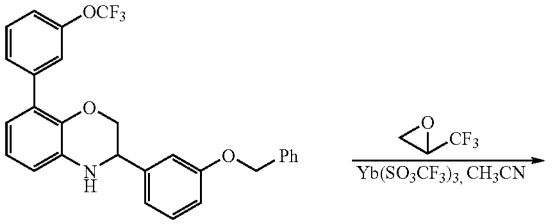

F4, 89%

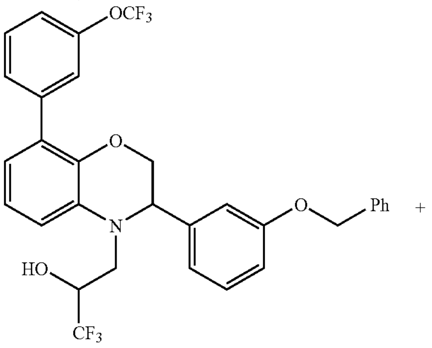

Cmpd 11, 45%
Higher Rf Cmpd

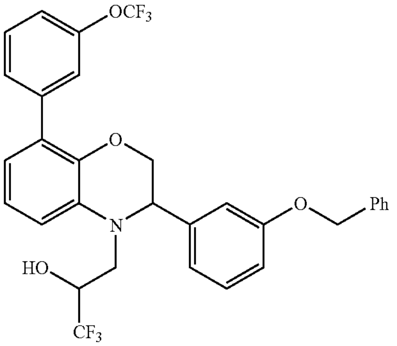

Cmpd 12, 45%
Lower Rf Cmpd

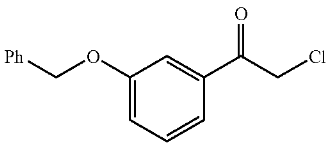

F1

1-(3-Benzyl-phenyl)-2-chloro-ethanone

Replacing 3-(1,1,2,2-tetrafluoro-ethoxy)-benzaldehyde with 3-benzyl-benzaldehyde and following the same procedure as in the preparation of compound A2a gave compound F1 (36%): $^{1}$H NMR (300 MHz, $CDCl_3$) δ 7.60-7.50 (m, 2H), 7.48-7.32 (m, 6H), 7.25-7.20 (m, 1H), 5.12 (s, 2H), 4.68 (s, 2H).

F2

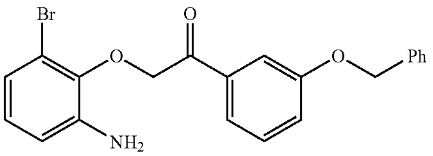

2-(2-Amino-6-bromo-phenoxy)-1-(3-benzyloxy-phenyl)-ethanone

Replacing A2a with F1 and following the same procedure as in the preparation of compound A2b gave compound F2 (70%): $^1$H NMR (300 MHz, $CDCl_3$) δ 7.63 (s, 1H), 7.50-7.32 (m, 9H), 7.13 (bd, J=7.6 Hz, 1H), 6.91 (t, J=7.9 Hz, 1H), 5.15 (s, 4H); MS (ES) m/z: 394 (M−$H_2O$).

F3

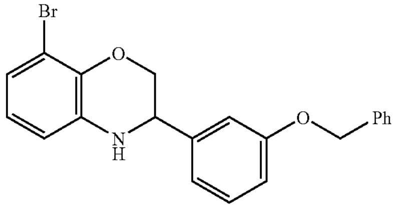

3-(3-Benzyloxy-phenyl)-8-bromo-3,4-dihydro-2H-benzo[1,4]oxazine

Replacing A2b with F2 and following the same procedure as in the preparation of compound A2c gave compound F3 (80%): $^1$H NMR (300 MHz, $CDCl_3$) δ 7.45-7.22 (m, 6H), 7.02-6.89 (m, 4H), 6.66 (t, J=7.8 Hz, 1H), 6.59 (d, J=8.0 Hz, 1H), 5.06 (s, 2H), 4.47 (bd, J=7.7 Hz, 1H), 4.41 (bd, J=10.6 Hz, 1H), 4.07-3.99 (m, 2H); MS (ES) m/z: 398 (M+2).

F4

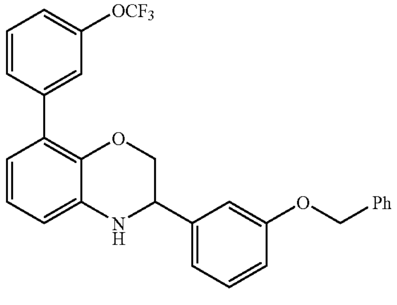

3-(3-Benzyloxy-phenyl)-8-(3-trifluoromethoxy-phenyl)-3,4-dihydro-2H-benzo[1,4]oxazine Replacing A2c with F3 and following the same procedure as in the preparation of compound A2d gave compound F4 (89%): $^1$H NMR (300 MHz, $CDCl_3$) δ 7.50-7.28 (m, 9H), 7.16 (d, J=8.1 Hz, 1H), 7.05 (s, 1H), 6.99 (d, J=7.7 Hz, 1H), 6.95 (dd, J=8.2, 2.5 Hz, 1H), 6.88 (t, J=7.7 Hz, 1H), 6.74 (d, J=7.6 Hz, 1H), 6.70 (d, J=7.8 Hz, 1H), 5.07 (s, 2H), 4.52 (dd, J=8.5, 2.6 Hz, 1H), 4.30 (dd, J=10.6, 2.4 Hz, 1H), 4.11 (brs, 1H), 3.98 (dd, J=10.3, 8.9 Hz, 1H); MS (ES) m/z: 478 (M+H$^+$).

Cmpd 11

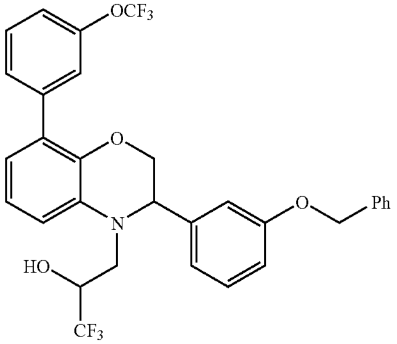

Higher Rf Cmpd

3-[3-(3-Benzyloxy-phenyl)-8-(3-trifluoromethoxy-phenyl)-2,3-dihydro-benzo[1,4]oxazin-4-yl]-1,1,1-trifluoro-propan-2-ol Replacing A2d with F4 and following the same procedure as in the preparation of compound 1 and 2 gave higher Rf compound 11 (45%) and lower Rf compound 12 (solvent for column: 20% EtOAc in hexane). Spectrums of compound 11 are as following: $^1$H NMR (300 MHz, $CDCl_3$) δ 7.45-7.28 (m, 9H), 7.14 (d, J=7.8 Hz, 1H), 7.02-6.83 (m, 4H), 6.76 (m, 2H), 5.06 (d, J=11.9 Hz, 1H), 5.00 (d, J=11.9 Hz, 1H), 4.75 (t, J=4.1 Hz, 1H), 4.30-4.20 (m, 2H), 4.18-4.10 (m, 1H), 3.70 (d, J=15.5, 1H), 3.31 (dd, J=15.7, 9.6 Hz, 1H), 2.38 (brs, 1H); MS (ES) m/z: 590 (M+H$^+$).

Example 12

Cmpd 12

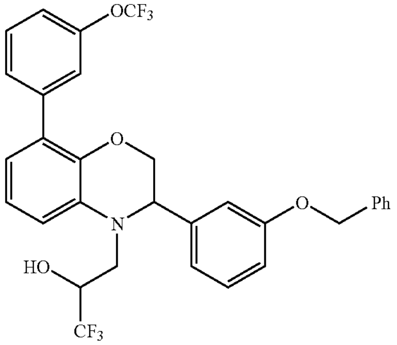

Lower Rf Cmpd

3-[3-(3-Benzyl-phenyl)-8-(3-trifluoromethoxy-phenyl)-2,3-dihydro-benzo[1,4]oxazin-4-yl]-1,1,1-trifluoro-propan-2-ol Spectrums of compound 12 (45%) are as following: $^1$H NMR (300 MHz, $CDCl_3$) δ 7.45-7.23 (m, 10H), 7.14 (d, J=7.9 Hz, 1H), 7.01 (t, J=7.9 Hz, 1H), 6.92 (d, J=8.2 Hz, 1H), 6.80 (m, 3H), 5.04 (d, J=11.9 Hz, 1H), 4.96 (d, J=12.0 Hz, 1H), 4.45 (t, J=3.0 Hz, 1H), 4.22 (d, J=3.1 Hz, 2H), 4.12 (m, 1H), 3.57 (m, 2H), 2.10 (brs, 1H); MS (ES) m/z: 590 (M+H$^+$).

Example 13

Cmpd 13

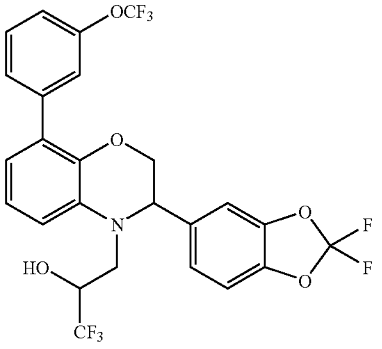

Higher Rf Cmpd

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-ol Scheme G

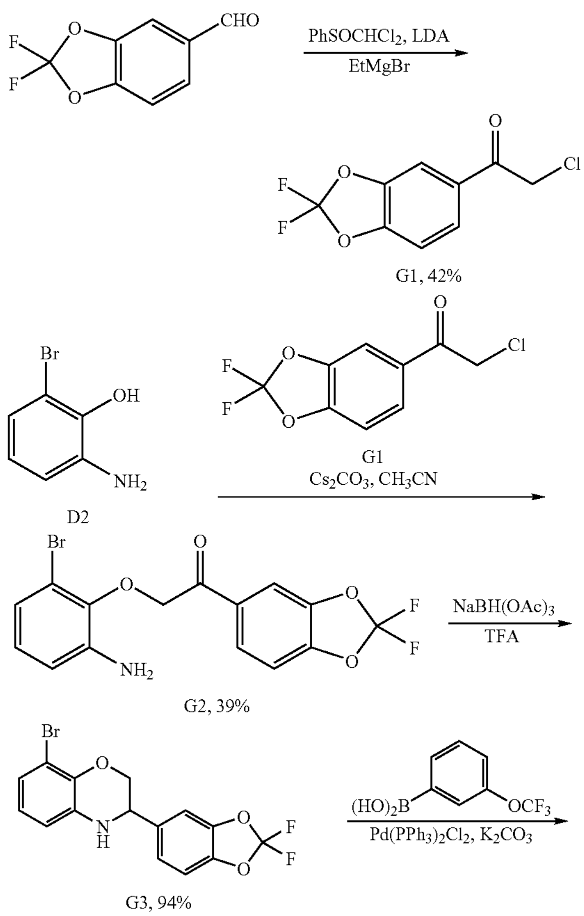

-continued

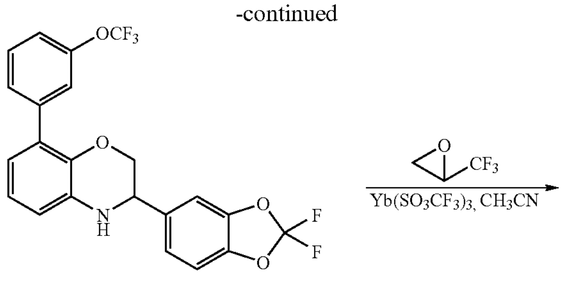

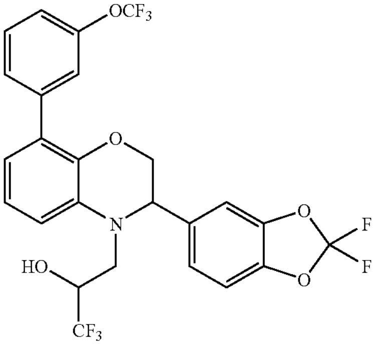

Cmpd 13, 38%
Higher Rf Cmpd

+

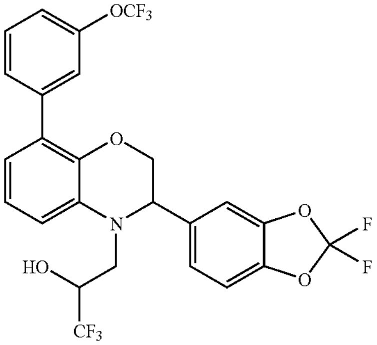

Cmpd 14, 38%
Lower Rf Cmpd

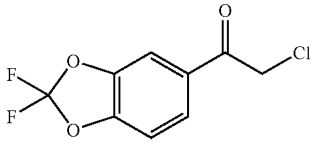

G1

2-Chloro-1-(2,2-difluoro-benzo[1,3]dioxol-5-yl)-ethanone

Replacing 3-(1,1,2,2-tetrafluoro-ethoxy)-benzaldehyde with 2,2-difluoro-indan-5-carbaldehyde and following the same procedure as in the preparation of compound A2a gave compound G1 (42%): $^1$H NMR (300 MHz, $CDCl_3$) δ 7.78 (d, J=8.4 Hz, 1H), 7.71 (d, J=3.2 Hz, 1H), 7.18 (d, J=8.4 Hz, 1H), 4.63 (s, 2H).

G2

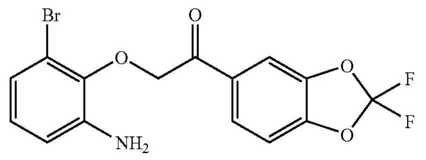

2-(2-Amino-6-bromo-phenoxy)-1-(2,2-difluoro-benzo[1,3]dioxol-5-yl)-ethanone

Replacing A2a with G1 and following the same procedure as in the preparation of compound A2b gave compound G2 (39%): $^{1}H$ NMR (300 MHz, $CDCl_3$) δ 7.83 (s, 1H), 7.54 (d, J=8.4 Hz, 1H), 7.39-7.34 (m, 2H), 7.15 (d, J=8.4 Hz, 1H), 6.92 (d, J=7.9 Hz, 1H), 5.14 (s, 2H); MS (ES) m/z: 368 ($M-H_2O$).

G3

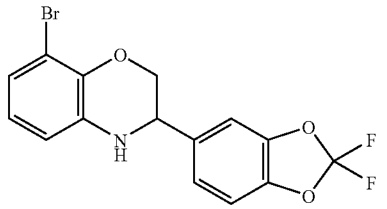

8-Bromo-3-(2,2-difluoro-benzo[1,3]dioxol-5-yl)-3,4-dihydro-2H-benzo[1,4]oxazine

Replacing A2b with G2 and following the same procedure as in the preparation of compound A2c gave compound G3 (94%): $^{1}H$ NMR (300 MHz, $CDCl_3$) δ 7.13-7.04 (m, 3H), 6.94 (d, J=7.9 Hz, 1H), 6.68 (t, J=7.9 Hz, 1H), 6.61 (d, J=8.0 Hz, 1H), 4.50 (dd, J=8.1, 2.3 Hz, 1H), 4.36 (bd, J=10.8 Hz, 1H), 4.08 (brs, 1H), 3.99 (dd, J=10.7, 8.4 Hz, 1H); MS (ES) m/z: 370 (M).

G4

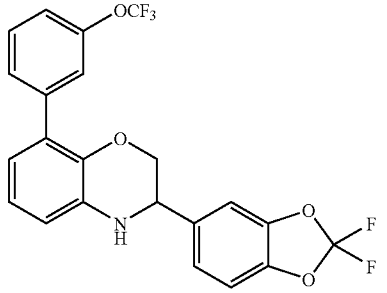

3-(2,2-Difluoro-benzo[1,3]dioxol-5-yl)-8-(3-trifluoromethoxy-phenyl)-3,4-dihydro-2H-benzo[1,4]oxazine Replacing A2c with G3 and following the same procedure as in the preparation of compound A2d gave compound G4 (96%): $^{1}H$ NMR (300 MHz, $CDCl_3$) δ 7.50-7.39 (m, 3H), 7.20-7.10 (m, 3H), 7.06 (d, J=8.2 Hz, 1H), 6.89 (t, J=7.8 Hz, 1H), 6.77 (d, J=7.6 Hz, 1H), 6.71 (d, J=7.8 Hz, 1H), 4.55 (bd, J=5.7 Hz, 1H), 4.28 (dd, J=10.7, 2.1 Hz, 1H), 4.11 (brs, 1H), 3.95 (dd, J=10.6, 8.3 Hz, 1H); MS (ES) m/z: 452 ($M+H^+$).

Cmpd 13

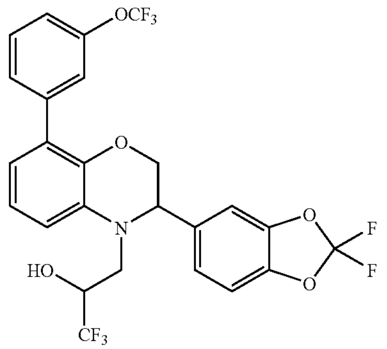

Higher Rf Cmpd

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-ol Replacing A2d with G4 and following the same procedure as in the preparation of compound 1 and 2 gave compound 13 and 14 (38%). Spectrums of compound 13 are as following: $^{1}H$ NMR (300 MHz, $CDCl_3$) δ 7.42-7.32 (m, 3H), 7.14 (d, J=7.6 Hz, 1H), 7.05-6.85 (m, 5H), 6.78 (d, J=7.6 Hz, 1H), 4.52 (t, J=2.8 Hz, 1H), 4.25-4.13 (m, 3H), 3.69 (dd, J=15.7, 6.5 Hz, 1H), 3.53 (dd, J=15.8, 5.2 Hz, 1H), 2.40 (brs, 1H); MS (ES) m/z: 564 ($M+H^+$).

Example 14

Cmpd 14

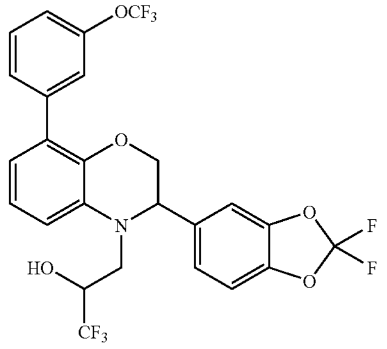

Lower Rf Cmpd

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-ol Spectrums of compound 14 (38%) are as following: $^{1}H$ NMR (300 MHz, $CDCl_3$) δ 7.45-7.34 (m, 3H), 7.15 (d, J=7.4 Hz, 1H), 7.07-6.96 (m, 4H), 6.80-6.72 (m, 2H), 4.85 (t, J=3.8 Hz, 1H), 4.44 (bm, 1H), 4.25 (dd, J=10.9, 3.1 Hz, 1H), 4.12

(dd, J=11.0, 4.6 Hz, 1H), 3.82 (d, J=15.6 Hz, 1H), 3.30 (dd, J=15.7, 9.7 Hz, 1H), 2.48 (d, J=3.1 Hz, 1H); MS (ES) m/z: 564 ($M+H^+$).

Example 15

Comp 15

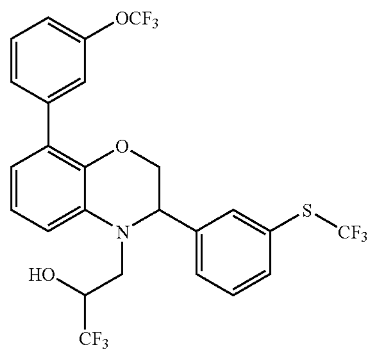

Higher Rf Cmpd 1,1,1-Trifluoro-3-[8-(3-trifluoromethoxy-phenyl)-3-(3-trifluoromethylsulfanylmethyl-phenyl)-2,3-dihydro-benzo[1,4]oxazin-4-yl]propan-2-ol Scheme H

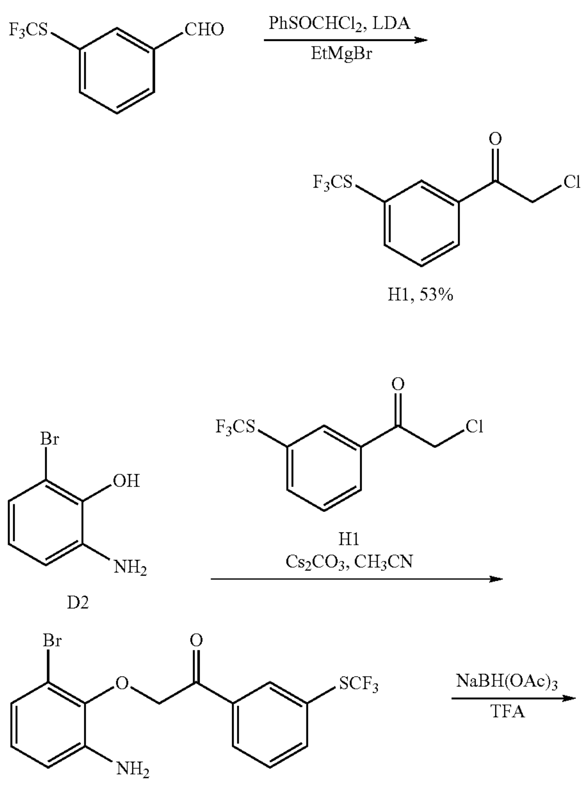

H1, 53%
H1
D2
H2, 60%

-continued

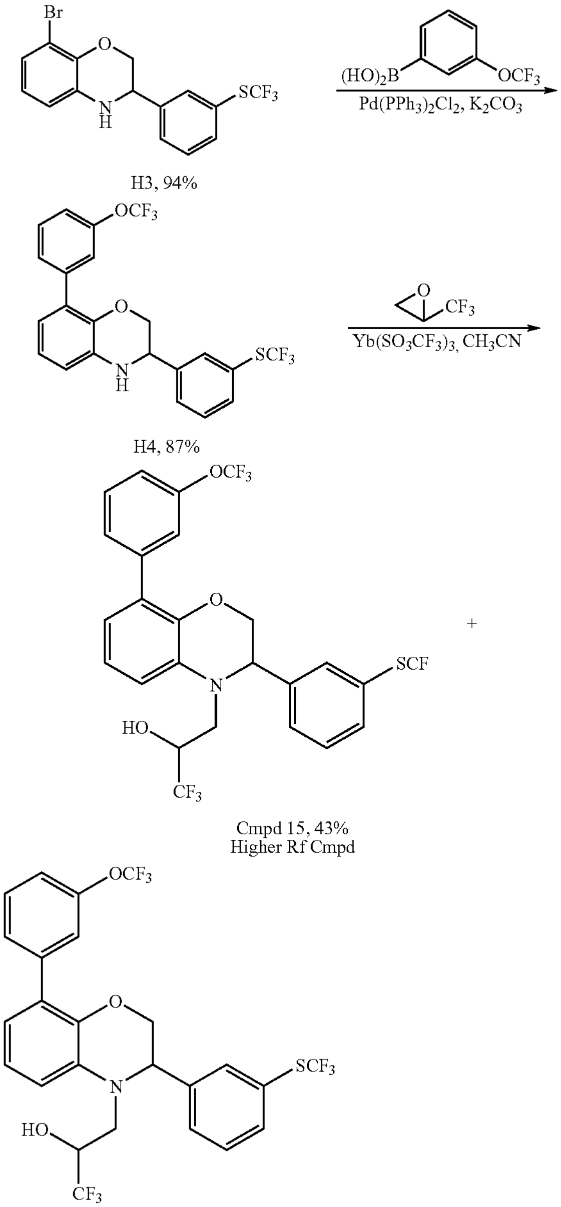

H3, 94%
H4, 87%
Cmpd 15, 43%
Higher Rf Cmpd
+
Cmpd 16, 40%
Lower Rf Cmpd

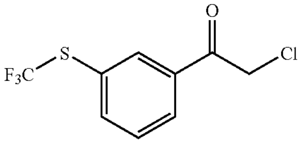

H1

2-Chloro-1-(3-trifluoromethylsulfanyl-phenyl)-ethanone

Replacing 3-(1,1,2,2-tetrafluoro-ethoxy)-benzaldehyde with 3-trifluoromethylsulfanyl-benzaldehyde and following the same procedure as in the preparation of compound A2a gave compound H1 (53%): $^1H$ NMR (300 MHz, $CDCl_3$) δ 8.24 (s, 1H), 8.08 (m, 1H), 7.91 (d, J=7.8 Hz, 1H), 7.59 (t, J=7.8 Hz, 1H), 4.69 (s, 2H).

H2

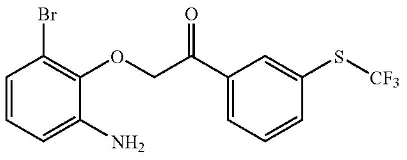

2-(2-Amino-6-bromo-phenoxy)-1-(3-trifluoromethylsulfanyl-phenyl)-ethanone

Replacing A2a with H1 and following the same procedure as in the preparation of compound A2b gave compound H2 (60%): $^1$H NMR (300 MHz, $CDCl_3$) δ 8.22 (s, 1H), 8.01 (d, J=7.9 Hz, 1H), 7.80 (t, J=7.8 Hz, 1H), 7.56 (t, J=7.8 Hz, 1H), 7.39 (m, 2H), 6.93 (t, J=7.9 Hz, 1H), 5.18 (s, 2H); MS (ES) m/z: 388 (M−$H_2O$).

H3

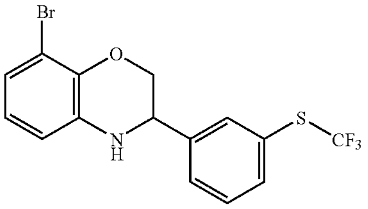

8-Bromo-3-(3-trifluoromethylsulfanyl-phenyl)-3,4-dihydro-2H-benzo[1,4]oxazine

Replacing A2b with H2 and following the same procedure as in the preparation of compound A2c gave compound H3 (94%): $^1$H NMR (300 MHz, $CDCl_3$) δ 7.70-7.61 (m, 2H), 7.55-7.41 (m, 2H), 6.96 (dd, J=7.7, 1.7 Hz, 1H), 6.72-6.60 (m, 2H), 4.56 (bd, J=8.3 Hz, 1H), 4.44-4.38 (m, 1H), 4.12 (brs, 1H), 4.05 (dd, J=10.8, 2.5 Hz, 1H); MS (ES) m/z: 390 (M), 392 (M+2).

H4

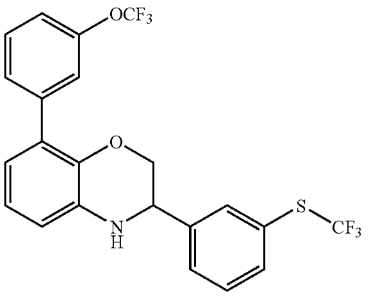

8-(3-Trifluoromethoxy-phenyl)-3-(3-trifluoromethylsulfanyl-phenyl)-3,4-dihydro-2H-benzo[1,4]oxazine Replacing A2c with H3 and following the same procedure as in the preparation of compound A2d gave compound H4 (87%): $^1$H NMR (300 MHz, $CDCl_3$) δ 7.70 (s, 1H), 7.64 (d, J=7.5 Hz, 1H), 7.54 (d, J=7.7 Hz, 1H), 7.50-7.39 (m, 4H), 7.16 (d, J=8.1 Hz, 1H), 6.89 (t, J=7.7 Hz, 1H), 6.80-6.71 (m, 2H), 4.60 (bd, J=6.5 Hz, 1H), 4.31 (d, J=10.7 Hz, 1H), 4.15 (s, 1H), 4.00 (dd, J=10.7, 8.3 Hz, 1H); MS (ES) m/z: 472 (M+H$^+$).

Cmpd 15

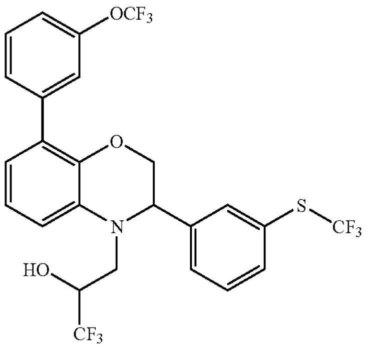

Higher Rf Cmpd 1,1,1-Trifluoro-3-[8-(3-trifluoromethoxy-phenyl)-3-(3-trifluoromethylsulfanyl-phenyl)-2,3-dihydro-benzo[1,4]oxazin-4-yl]-propan-2-ol Replacing A2d with H4 and following the same procedure as in the preparation of compound 1 and 2 gave higher Rf compound 15 (43%) and lower Rf compound 16 (solvent for column: 20% EtOAc in hexane). Spectrums of compound 15 are as following: $^1$H NMR (300 MHz, $CDCl_3$) δ 7.61 (d, J=6.9 Hz, 1H), 7.56 (s, 1H), 7.45-7.33 (m, 5H), 7.14 (d, J=7.1 Hz, 1H), 7.02 (t, J=7.9 Hz, 1H), 6.81-6.76 (m, 2H), 4.88 (t, J=3.8 Hz, 1H), 4.41 (m, 1H), 4.27 (dd, J=11.0, 3.2 Hz, 1H), 4.17 (t, J=11.0, 4.6 Hz, 1H), 3.83 (t, J=15.7 Hz, 1H), 3.31 (dd, J=15.7, 9.6 Hz, 1H), 2.49 (brs, 1H); MS (ES) m/z: 584 (M+H$^+$).

Example 16

Cmpd 16

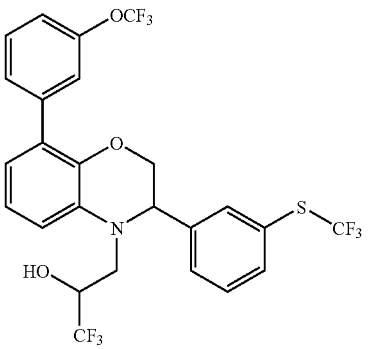

Lower Rf Cmpd 1,1,1-Trifluoro-3-[8-(3-trifluoromethoxy-phenyl)-3-(3-trifluoromethylsulfanyl-phenyl)-2,3-dihydro-benzo[1,4]oxazin-4-yl]-propan-2-ol Spectrums of compound 16 (40%) are as following: $^1$H NMR (300 MHz, $CDCl_3$) δ 7.60 (d, J=7.3 Hz, 1H), 7.52 (s, 1H), 7.44-7.31 (m, 5H), 7.14 (d, J=7.8 Hz, 1H), 7.03 (t, J=7.9 Hz, 1H), 6.90 (d, J=8.2 Hz, 1H), 6.79 (d, J=7.6 Hz, 1H), 4.57

(s, 1H), 4.36-4.19 (m, 3H), 3.70 (dd, J=14.6, 6.2 Hz, 1H), 3.55 (dd, J=15.7, 5.2 Hz, 1H), 2.30 (brs, 1H); MS (ES) m/z: 584 (M+H+).

Example 17

Cmpd 17

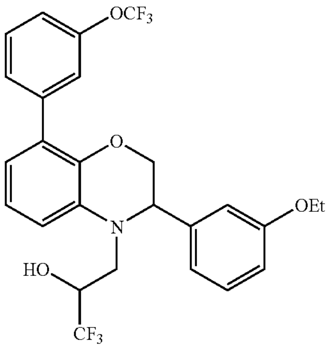

Higher Rf Cmpd

3-[3-(3-Ethoxy-phenyl)-8-(3-trifluoromethoxy-phenyl)-2,3-dihydro-benzo[1,4]oxazin-4-yl]-1,1,1-trifluoro-propan-2-ol Scheme I

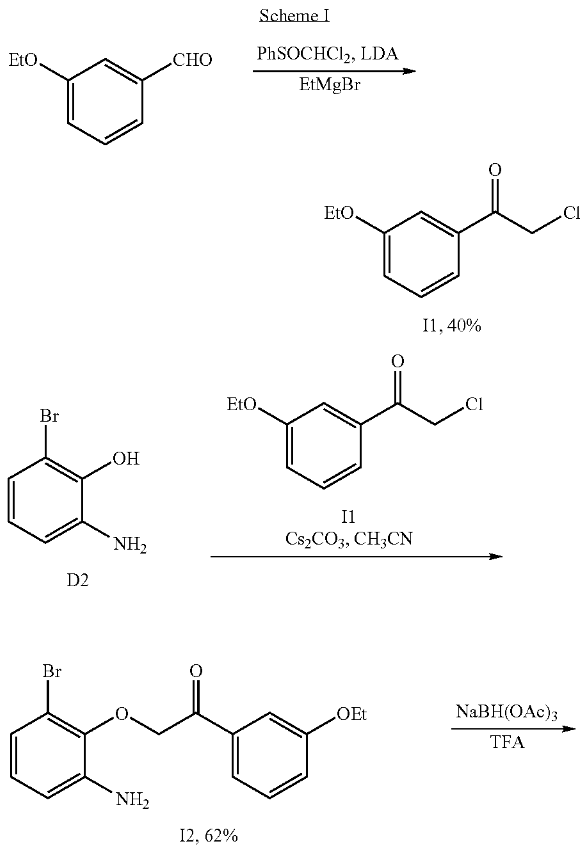

-continued

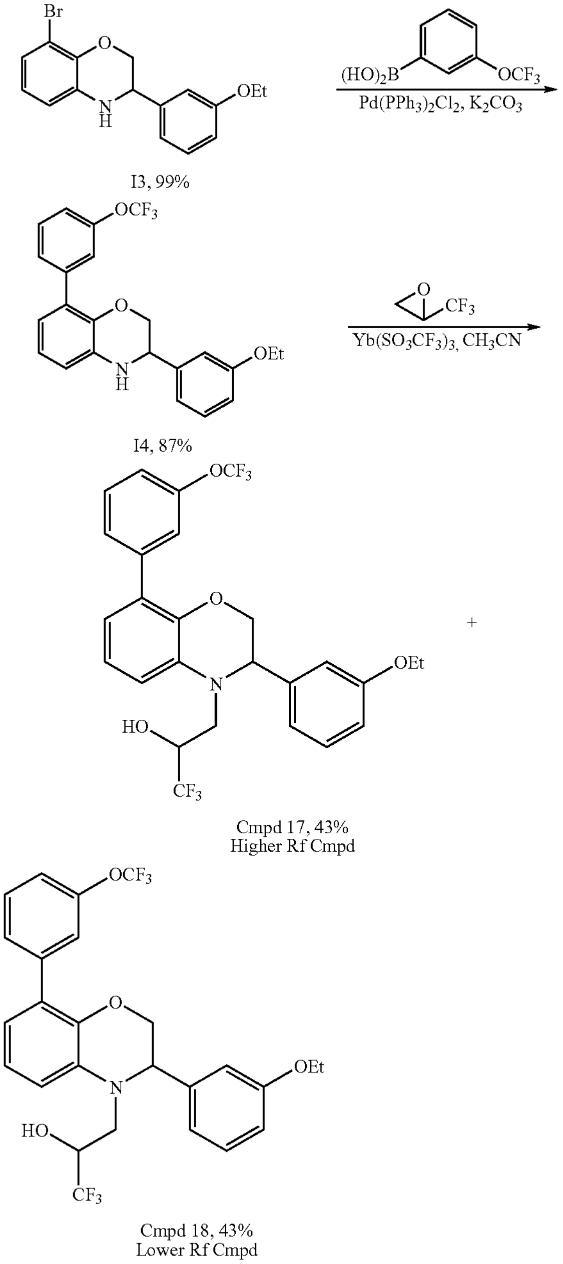

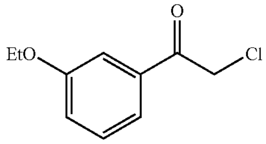

I1

2-Chloro-1-(3-ethoxy-phenyl)ethanone

Replacing 3-(1,1,2,2-tetrafluoro-ethoxy)-benzaldehyde with 3-ethoxy-benzaldehyde and following the same procedure as in the preparation of compound A2a gave compound I1 (40%): $^1H$ NMR (300 MHz, $CDCl_3$) δ 7.47 (m, 2H), 7.39 (t, J=7.9 Hz, 1H), 7.14 (m, 1H), 4.70 (s, 2H), 4.09 (q, J=7.0 Hz, 2H), 1.44 (t, J=7.0 Hz, 3H).

I2

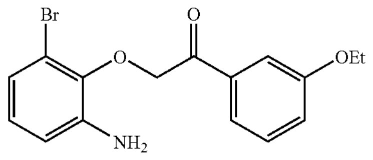

2-(2-Amino-6-bromo-phenoxy)-1-(3-ethoxy-phenyl)-ethanone

Replacing A2a with 11 and following the same procedure as in the preparation of compound A2b gave compound 12 (62%): $^1$H NMR (300 MHz, $CDCl_3$) δ 7.53 (s, 1H), 7.40-7.33 (m, 4H), 7.07-7.03 (m, 1H), 6.91 (t, J=8.0 Hz, 1H), 5.16 (s, 2H), 4.12 (q, J=7.0 Hz, 2H), 1.45 (t, J=7.0 Hz, 3H); MS (ES) m/z: 332 (M−$H_2O$).

I3

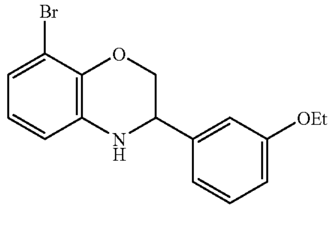

8-Bromo-3-(3-ethoxy-phenyl)-3,4-dihydro-2H-benzo[1,4]oxazine

Replacing A2b with 12 and following the same procedure as in the preparation of compound A2c gave compound 13 (99%): $^1$H NMR (300 MHz, $CDCl_3$) δ 7.29 (t, J=8.0 Hz, 1H), 6.98-6.84 (m, 4H), 6.67 (t, J=7.9 Hz, 1H), 6.61 (d, J=7.9 Hz, 1H), 4.48 (bd, J=8.7 Hz, 1H), 4.43-4.39 (m, 1H), 4.09-3.99 (m, 4H), 1.42 (t, J=7.0 Hz, 3H); MS (ES) m/z: 334 (M), 336 (M+2).

I4

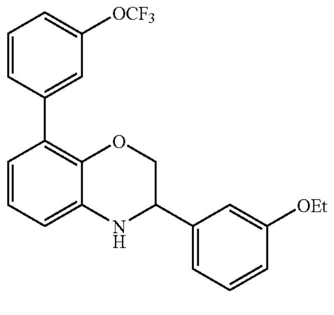

3-(3-Ethoxy-phenyl)-8-(3-trifluoromethoxy-phenyl)-3,4-dihydro-2H-benzo[1,4]oxazine Replacing A2c with 13 and following the same procedure as in the preparation of compound A2d gave compound 14 (87%): $^1$H NMR (300 MHz, $CDCl_3$) δ 7.51-7.38 (m, 3H), 7.28 (t, J=8.1 Hz, 1H), 7.15 (d, J=8.1 Hz, 1H), 6.98-6.95 (m, 2H), 6.95-6.84 (m, 2H), 6.76-6.67 (m, 2H), 4.51 (dd, J=8.5, 2.5 Hz, 1H), 4.31 (d, J=10.5 Hz, 1H), 4.11-3.92 (m, 4H), 1.41 (t, J=7.0 Hz, 3H); MS (ES) m/z: 416 (M+H$^+$).

Cmpd 17

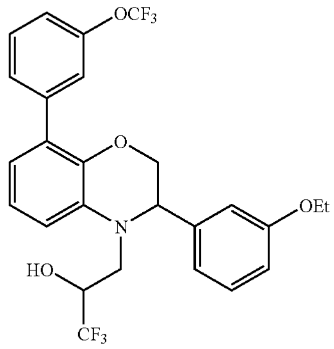

Higher Rf Cmpd

3-[3-(3-Ethoxy-phenyl)-8-(3-trifluoromethoxy-phenyl)-2,3-dihydro-benzo[1,4]oxazin-4-yl]-1,1,1-trifluoro-propan-2-ol Replacing A2d with 14 and following the same procedure as in the preparation of compound 1 and 2 gave compound higher Rf compound 17 (43%) and lower Rf compound 18 (solvent for column: 20% EtOAc in hexane). Spectrums of compound 17 are as following: $^1$H NMR (300 MHz, $CDCl_3$) δ 7.47-7.36 (m, 3H), 7.29-7.22 (m, 1H), 7.15 (d, J=8.1 Hz, 1H), 6.99 (t, J=7.9 Hz, 1H), 6.88-6.75 (m, 5H), 4.77 (dd, J=5.2, 3.3 Hz, 1H), 4.34 (t, J=7.4 Hz, 1H), 4.26 (dd, J=10.9, 3.2 Hz, 1H), 4.15 (dd, J=10.9, 5.4 Hz, 1H), 4.00 (q, J=7.0 Hz, 2H), 3.78 (d, J=5.7 Hz, 1H), 3.37 (dd, J=15.7, 9.7 Hz, 1H), 2.49 (s, 1H), 1.39 (t, J=7.0 Hz, 3H); MS (ES) m/z: 528 (M+H$^+$).

Example 18

Cmpd 18

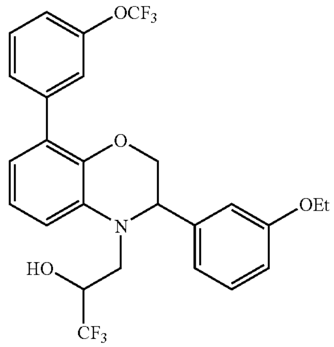

Lower Rf Cmpd

3-[3-(3-Ethoxy-phenyl)-8-(3-trifluoromethoxy-phenyl-2,3-dihydro-benzo[1,4]oxazin-4-yl]-1,1,1-trifluoro-propan-2-ol Spectrums of compound 18 (43%) are as following: $^1$H NMR (300 MHz, $CDCl_3$) δ 7.45-7.34 (m, 3H), 7.25 (t, J=7.9 Hz, 1H), 7.13 (d, J=7.9 Hz, 1H), 7.00 (t, J=7.9 Hz, 1H), 6.90-6.75 (m, 5H), 4.47 (t, J=3.3 Hz, 1H), 4.32-4.20 (m, 3H), 3.98 (q, J=7.0 Hz, 2H), 3.69-3.58 (m, 2H), 2.23 (brs, 1H), 1.38 (t, J=7.0 Hz, 3H); MS (ES) m/z: 528 (M+H$^+$).

Example 19

Cmpd 19

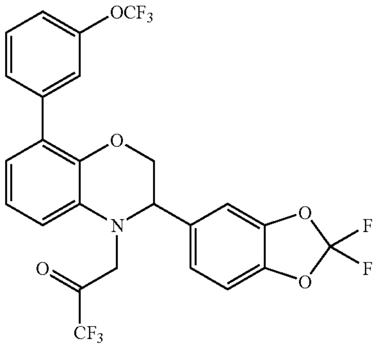

3-[3-(2,2-Difluoro-benzo[1,3]dioxol-5-yl)-8-(3-trifluoromethoxy-phenyl)-2,3-dihydro-benzo[1,4]oxazin-4-yl]-1,1,1-trifluoro-propan-2-one Scheme J

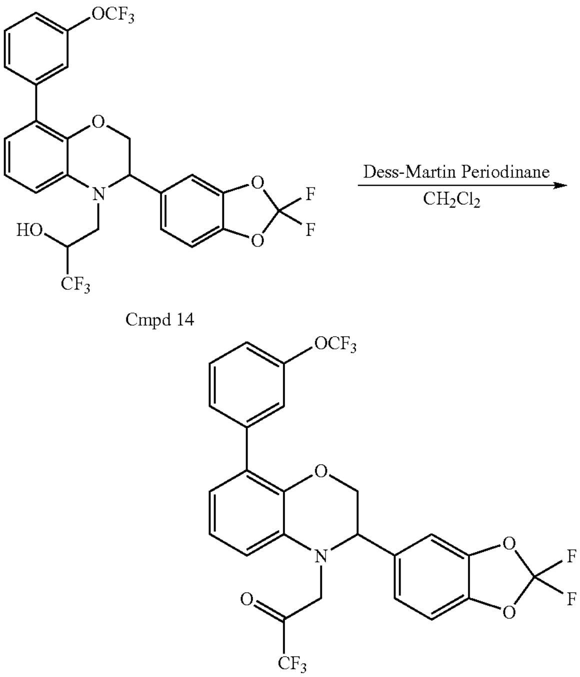

Cmpd 14

Cmpd 19

To a solution of compound 14 (25 mg, 0.044 mmol) in $CH_2Cl_2$ (1 mL) at 4° C. was added Dess-Martin periodinane (28 mg, 0.066 mmol). After stirring at 4° C. for 2 h, $Na_2S_2O_3$ and $NaHCO_3$ aqueous solution were added and the solution was stirred vigorously for ~15 min. The mixture was extracted with $CH_2Cl_2$ and the combined organic extracts were dried ($Na_2SO_4$) and concentrated to give compound 19 as an oil: $^1$H NMR (300 MHz, $CDCl_3$) δ 7.47-7.38 (m, 3H), 7.17 (d, J=7.9 Hz, 1H), 7.09-6.92 (m, 4H), 6.82 (d, J=7.7 Hz, 1H), 6.49 (d, J=8.1 Hz, 1H), 4.65 (d, J=19.6 Hz, 1H), 4.58 (d, J=5.9 Hz, 1H), 4.30 (dd, J=11.0, 3.2 Hz, 1H), 4.17-4.10 (m, 2H); MS (ES) m/z: 581 (M+K$^+$).

Example 20

Cmpd 20

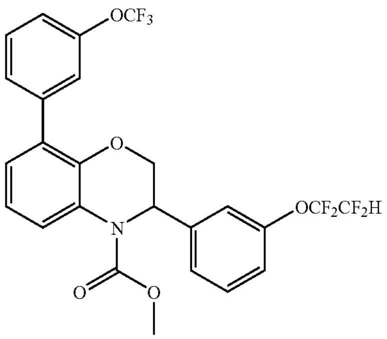

3-[3-(1,1,2,2-Tetrafluoro-ethoxy)-phenyl]-8-(3-trifluoromethoxy-phenyl)-2,3-dihydro-benzo[1,4]oxazine-4-carboxylic acid methyl ester Scheme K

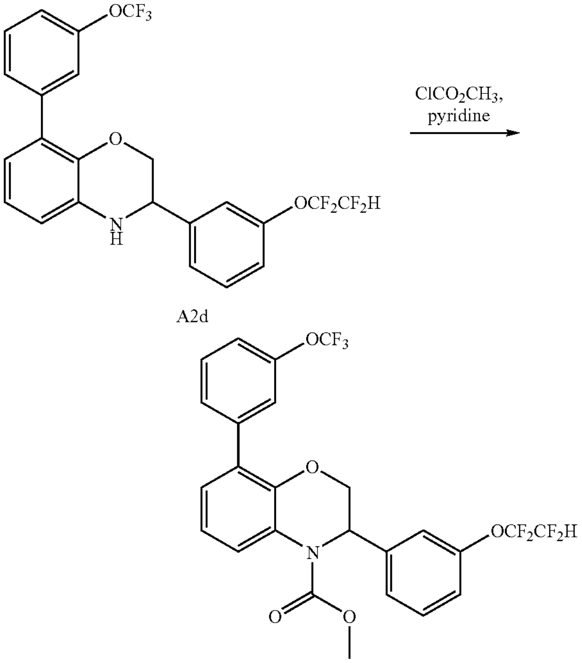

A2d

Cmpd 20, 25%

A mixture of A2d (40 mg, 0.082 mmol), pyridine (0.040 mL, 0.50 mmol) and methyl chloroformate (0.026 mL, 0.34 mmol)) in $CH_2Cl_2$ (1 mL) was stirred at room temperature for 24 h. The mixture was concentrated and purified by column chromatography to afford 11 mg (25%) of compound 20 as an oil: $^1$H NMR (300 MHz, $CDCl_3$) δ 7.93 (t, J=3.9 Hz, 1H), 7.40-7.09 (m, 8H), 7.01 (m, 2H), 5.86 (tt, J=53.1, 2.8 Hz, 1H), 5.72 (m, 1H), 4.62 (dd, J=11.4, 2.4 Hz, 1H), 4.39 (dd, J=11.4, 3.3 Hz, 1H), 3.85 (s, 3H); MS (ES) m/z: 546 (M+H$^+$).

Example 21

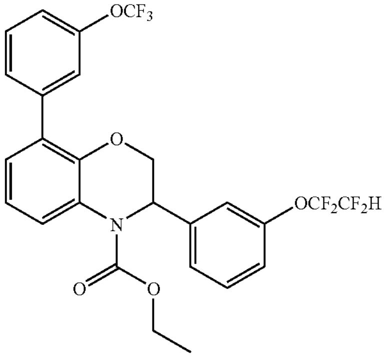

Cmpd 21

3-[3-(1,1,2,2-Tetrafluoro-ethoxy)-phenyl]-8-(3-trifluoromethoxy-phenyl)-2,3-dihydro-benzo[1,4]oxazine-4-carboxylic acid ethyl ester Scheme L

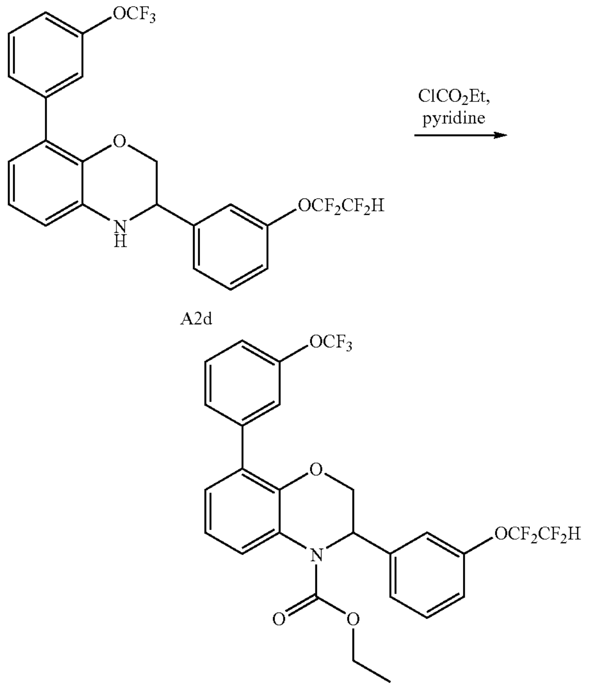

A2d

Cmpd 21, 76%

Replacing methyl chloroformate with ethyl chloroformate and following the same procedure as in the preparation of compound 20 gave compound 21 (76%): $^1$H NMR (300 MHz, $CDCl_3$) δ 7.99 (t, J=4.9 Hz, 1H), 7.42-7.09 (m, 8H), 7.02 (s, 1H), 7.00 (s, 1H), 5.86 (tt, J=53.1, 2.8 Hz, 1H), 5.71 (m, 1H), 4.59 (dd, J=11.4, 2.5 Hz, 1H), 4.38 (dd, J=11.4, 3.4 Hz, 1H), 4.37-4.24 (m, 2H), 1.30 (t, J=7.1 Hz, 3H); MS (ES) m/z: 560 (M+H$^+$).

Example 22

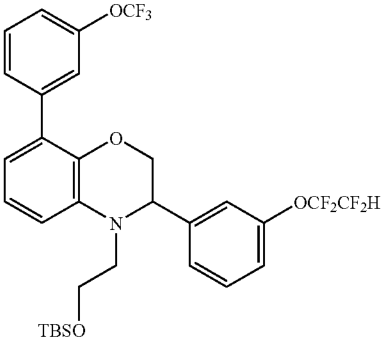

Compound 22

4-[2-(tert-Butyl-dimethyl-silanyloxy)-ethyl]-3-[3-(1,1,2,2-tetrafluoro-ethoxy)-phenyl]-8-(3-trifluoromethoxy-phenyl)-3,4-dihydro-2H-benzo[1,4]oxazine Scheme M

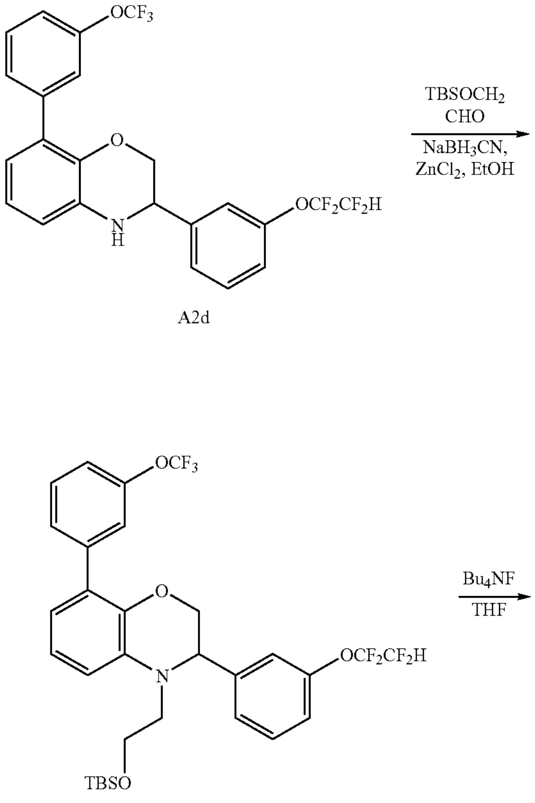

A2d

Cmpd 22, 33%

-continued

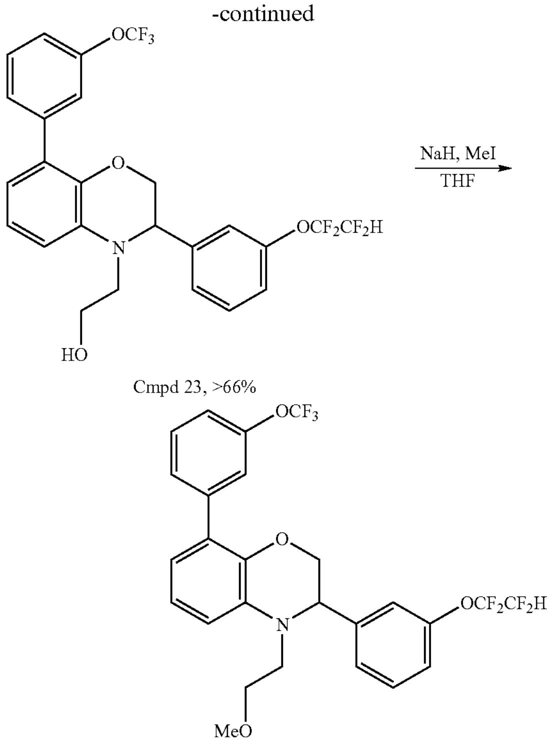

Cmpd 22

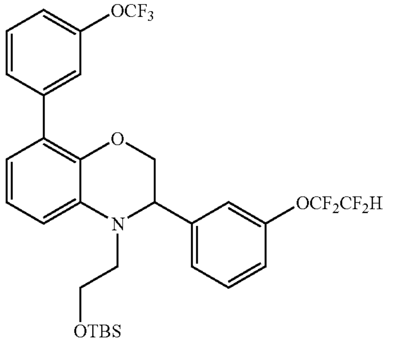

4-[2-(tert-Butyl-dimethyl-silanyloxy)-ethyl]-3-[3-(1,1,2,2-tetrafluoro-ethoxy)-phenyl]-8-(3-trifluoromethoxy-phenyl)-3,4-dihydro-2H-benzo[1,4]oxazine A mixture of A2d (50 mg, 0.10 mmol), $TBSOCH_2CHO$ (54 mg, 0.31 mmol), molecular sieves (3 Å, 0.62 g) in EtOH (1.2 mL) was heated at 65° C. for 1 h and cooled to room temperature.

A mixture of $NaBH_3CN$ (26 mg, 0.41 mmol), $ZnCl_2$ (0.5 M in THF, 0.41 mL, 0.20 mmol) and EtOH (0.5 mL) was stirred at room temperature for 1 h and then was added to the above mixture. The resulting reaction mixture was stirred at room temperature overnight and filtered. The filtrate was concentrated and partitioned between $CH_2Cl_2$ and water. The organic layer was dried ($Na_2SO_4$), concentrated and purified by column chromatography to afford 22 mg (33%) of compound 22: $^1H$ NMR (400 MHz, $CDCl_3$) δ 7.46-7.32 (m, 4H), 7.21-7.10 (m, 4H), 6.98 (t, J=7.9 Hz, 1H), 6.85 (d, J=8.2 Hz, 1H), 6.70 (d, J=7.6 Hz, 1H), 5.89 (bt, J=53.1 Hz, 1H), 4.73 (t, J=3.7 Hz, 1H), 4.21 (dd, J=10.9, 3.2 Hz, 1H), 4.14 (dd, J=10.9, 4.4 Hz, 1H), 3.93-3.85 (m, 1H), 3.70-3.51 (m, 2H), 3.32-3.23 (m, 1H), 0.87 (s, 9H), 0.00 (s, 6H); MS (ES) m/z: 646 (M+H$^+$).

Example 23

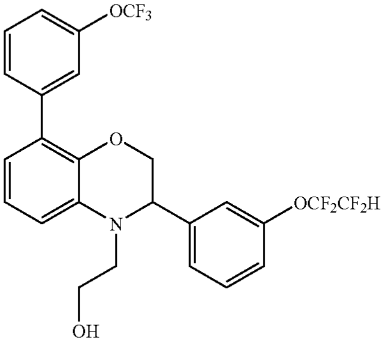

Cmpd 23

2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethanol To a solution of compound 22 (160 mg, 0.248 mmol) in THF (2 mL) was added $Bu_4NF$ (1.0 M in THF, 0.3 mL, 0.3 mmol). After stirring at room temperature for 30 min, the reaction mixture was concentrated and purified by column chromatography to afford 87 mg (>66%) of compound 23: $^1H$ NMR (400 MHz, $CDCl_3$) δ 7.45-7.32 (m, 4H), 7.21-7.10 (m, 4H), 6.98 (t, J=7.9 Hz, 1H), 6.88 (d, J=7.8 Hz, 1H), 6.73 (d, J=7.6 Hz, 1H), 5.88 (tt, J=53.1, 2.7 Hz, 1H), 4.67 (t, J=3.5 Hz, 1H), 4.26 (dd, J=10.9, 3.1 Hz, 1H), 4.18 (dd, J=10.9, 4.1 Hz, 1H), 3.92-3.83 (m, 1H), 3.79-3.71 (m, 1H), 3.60 (dt, J=15.2, 5.0 Hz, 1H), 3.41-3.31 (m, 1H), 1.26 (t, J=7.1 Hz, 1H); MS (ES) m/z: 532 (M+H$^+$).

Example 24

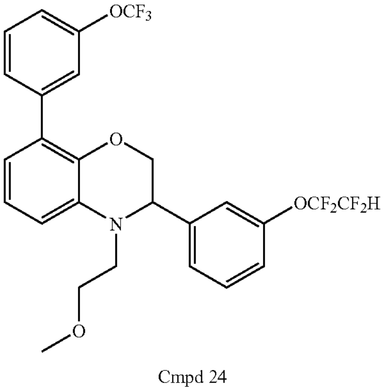

Cmpd 24

4-(2-Methoxy-ethyl)-3-[3-(1,1,2,2-tetrafluoro-ethoxy)-phenyl]-8-(3-trifluoromethoxy-phenyl)-3,4-dihydro-2H-benzo[1,4]oxazine To a solution of compound 23 (11 mg, 0.021 mmol) in THF (0.6 mL) was added NaH (60% in mineral oil, much excess amount) followed by MeI (much excess amount). The reaction mixture was stirred at room temperature for 5 h and then partitioned between $CH_2Cl_2$ and water. The organic layer was dried ($Na_2SO_4$), concentrated and purified by column chromatography to afford 13 mg (100%) of compound 24 as a clear oil: $^1$H NMR (400 MHz, $CDCl_3$) δ 7.44-7.31 (m, 4H), 7.20-7.10 (m, 4H), 6.98 (t, J=7.9 Hz, 1H), 6.84 (d, J=8.2 Hz, 1H), 6.71 (d, J=7.6 Hz, 1H), 5.88 (tt, J=53.1, 2.7 Hz, 1H), 4.69 (t, J=3.5 Hz, 1H), 4.21 (dd, J=10.8, 3.1 Hz, 1H), 4.15 (dd, J=10.8, 4.2 Hz, 1H), 3.70-3.56 (m, 2H), 3.49-3.41 (m, 1H), 3.39-3.31 (m, 1H), 3.29 (s, 3H); MS (ES) m/z: 546 (M+H$^+$).

Example 25

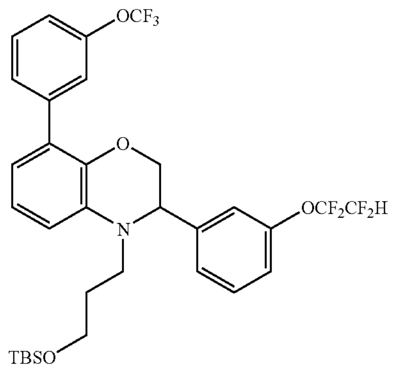

Cmpd 25

4-[3-(tert-Butyl-dimethyl-silanyloxy)-propyl]-3-[3-(1,1,2,2-tetrafluoro-ethoxy)-phenyl]-8-(3-trifluoromethoxy-phenyl)-3,4-dihydro-2H-benzo[1,4]oxazine Scheme N

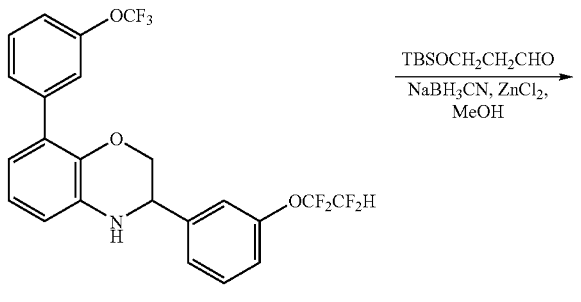

A2d

-continued

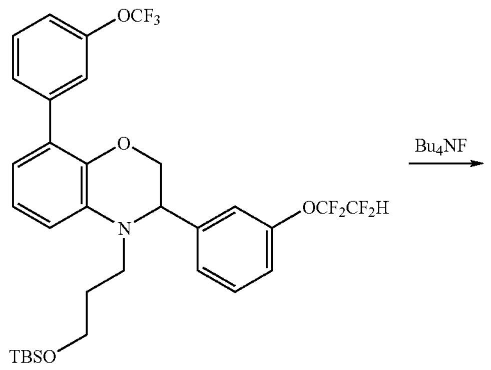

Cmpd 25, 22%

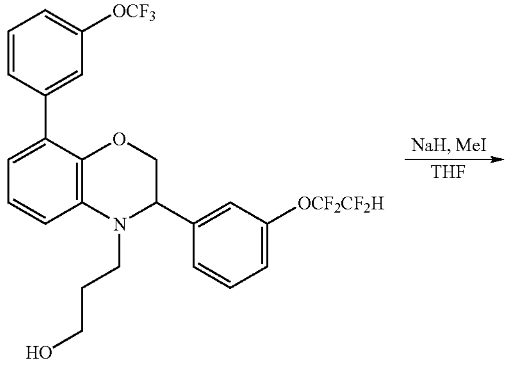

Cmpd 26

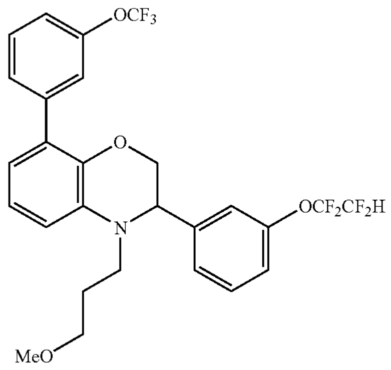

Cmpd 27

Cmpd 25

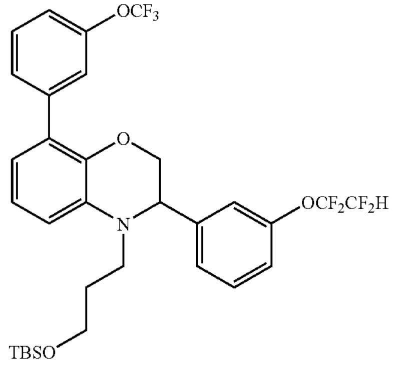

4-[3-(tert-Butyl-dimethyl-silanyloxy)-propyl]-3-[3-(1,1,2,2-tetrafluoro-ethoxy)-phenyl]-8-(3-trifluoromethoxy-phenyl)-3,4-dihydro-2H-benzo[1,4]oxazine Replacing $TBSOCH_2CHO$ with $TBSOCH_2CH_2CHO$ and following the same procedure as in the preparation of compound 22 gave compound 25 (22%): $^1H$ NMR (300 MHz, $CDCl_3$) δ 7.43-7.30 (m, 4H), 7.19-7.09 (m, 4H), 7.00-6.87 (m, 2H), 6.67 (d, J=7.4 Hz, 1H), 6.70 (d, J=7.5 Hz, 1H), 5.86 (bt, J=53.1 Hz, 1H), 4.54 (t, J=3.6 Hz, 1H), 4.23-4.10 (m, 2H), 3.60 (t, J=5.7 Hz, 2H), 3.58-3.44 (m, 1H), 3.30-3.18 (m, 1H), 1.83-1.65 (m, 2H), 0.86 (s, 9H), 0.00 (s, 6H); MS (ES) m/z: 660 ($M+H^+$).

Example 26

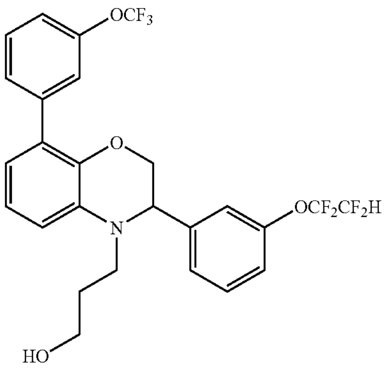

Cmpd 26

3-[3-[3-(1,1,2,2-Tetrafluoro-ethoxy)-phenyl]-8-(3-trifluoromethoxy-phenyl)-2,3-dihydro-benzo[1,4]oxazin-4-yl]-propan-1-ol Replacing 22 with 25 and following the same procedure as in the preparation of compound 23 gave compound 26: $^1H$ NMR (300 MHz, $CDCl_3$) δ 7.45-7.31 (m, 4H), 7.21-7.10 (m, 4H), 6.99 (t, J=7.8 Hz, 1H), 6.88 (d, J=7.6 Hz, 1H), 6.70 (d, J=7.5 Hz, 1H), 5.88 (tt, J=53.1, 2.8 Hz, 1H), 4.56 (t, J=3.6 Hz, 1H), 4.22 (dd, J=10.8, 3.3 Hz, 1H), 4.16 (dd, J=11.0, 4.2 Hz, 1H), 3.68 (t, J=5.9 Hz, 2H), 3.63-3.51 (m, 1H), 3.31-3.19 (m, 1H), 1.95-1.72 (m, 2H), 1.36 (brs, 1H); MS (ES) m/z: 546 ($M+H^+$).

Example 27

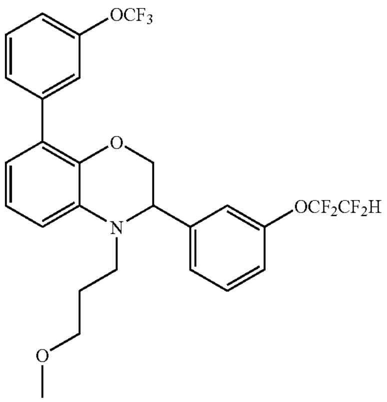

Cmpd 27

4-(3-Methoxy-propyl)-3-[3-(1,1,2,2-tetrafluoro-ethoxy)-phenyl]-8-(3-trifluoromethoxy-phenyl)-3,4-dihydro-2H-benzo[1,4]oxazine Replacing 23 with 26 and following the same procedure as in the preparation of compound 24 gave compound 27: $^1H$ NMR (400 MHz, $CDCl_3$) δ 7.46-7.31 (m, 4H), 7.21-7.10 (m, 4H), 6.99 (t, J=8.0 Hz, 1H), 6.86 (d, J=8.2 Hz, 1H), 6.69 (d, J=7.6 Hz, 1H), 5.88 (tt, J=53.1, 2.6 Hz, 1H), 4.52 (t, J=3.5 Hz, 1H), 4.21 (dd, J=10.9, 3.1 Hz, 1H), 4.16 (dd, J=10.8, 4.1 Hz, 1H), 3.59-3.50 (m, 1H), 3.41-3.32 (m, 2H), 3.30 (s, 3H), 3.28-3.18 (m, 1H), 1.89-1.79 (m, 2H); MS (ES) m/z: 560 ($M+H^+$).

Example 28

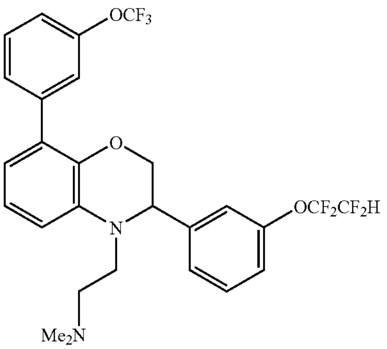

Cmpd 28

Dimethyl-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-amine Scheme O

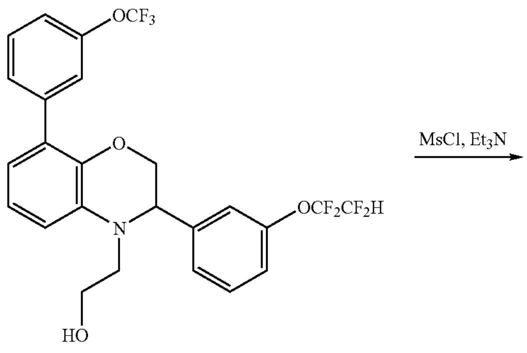

Cmpd

-continued

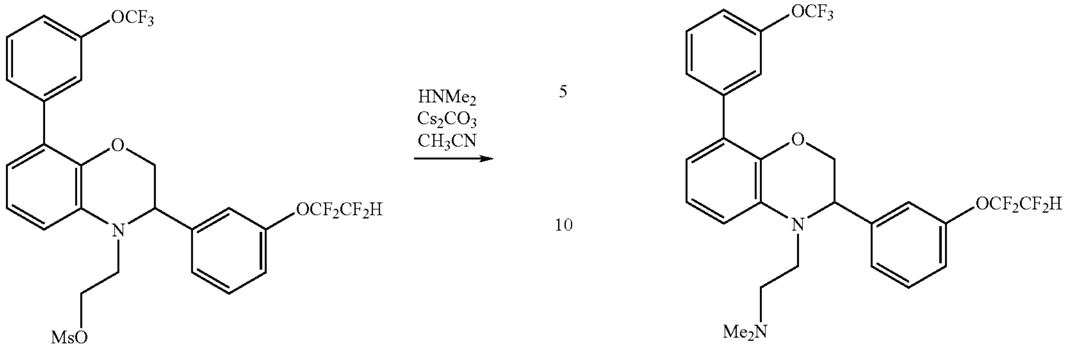

01, 100%

Cmpd 28

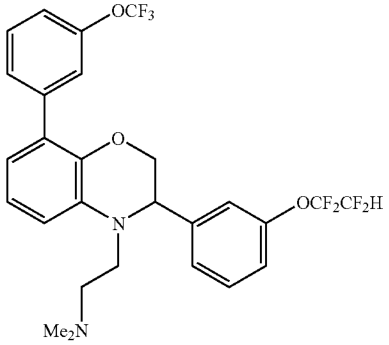

Cmpd 28, 38%

O1

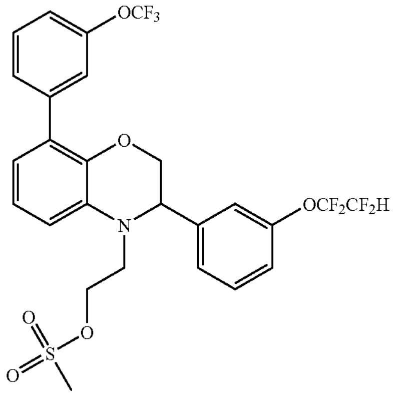

Methanesulfonic acid 2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl ester To a solution of 23 (87 mg, 0.16 mmol) and $Et_3N$ (0.046 mL, 0.33 mmol) in $CH_2Cl_2$ (2 mL) at 0° C. was added methanesulfonyl chloride (0.019 mL, 0.25 mmol). The cooling bath was removed and the solution was stirred at room temperature for 3 h. The reaction mixture was concentrated and purified by column chromatography to give 97 mg (100%) of compound O1 as a clear oil: $^1H$ NMR (400 MHz, $CDCl_3$) δ 7.43-7.33 (m, 4H), 7.22-7.11 (m, 4H), 7.01 (t, J=7.9 Hz, 1H), 6.82 (d, J=8.1 Hz, 1H), 6.77 (d, J=7.6 Hz, 1H), 5.89 (tt, J=53.1, 2.8 Hz, 1H), 4.64 (t, J=3.8 Hz, 1H), 4.48-4.38 (m, 1H), 4.31-4.21 (m, 2H), 4.16 (dd, J=11.1, 4.6 Hz, 1H), 3.79 (dt, J=15.8, 5.2 Hz, 1H), 3.59-3.50 (m, 1H), 2.91 (s, 3H); MS (ES) m/z: 610 ($M+H^+$).

Dimethyl-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-amine A mixture of O1 (20 mg, 0.033 mmol), $HNMe_2$.HCl (67 mg, 0.82 mmol), $Cs_2CO_3$ (24 mg, 0.074 mmol) and $Et_3N$ (0.14 mL, 1.01 mmol) in $CH_3CN$ (1 mL) was heated in a sealed tube at 70° C. for 2 days. After cooling to room temperature, the reaction mixture was concentrated and partitioned between $CH_2Cl_2$ and water. The organic layer was dried ($Na_2SO_4$), concentrated and purified by column chromatography to give 7 mg (38%) of compound 28 as a yellow oil: $^1H$ NMR (300 MHz, $CDCl_3$) δ 7.48-7.31 (m, 4H), 7.22-7.10 (m, 4H), 6.99 (t, J=7.9 Hz, 1H), 6.84 (d, J=7.7 Hz, 1H), 6.71 (d, J=7.5 Hz, 1H), 5.88 (bt, J=53.1 Hz, 1H), 4.62 (t, J=3.8 Hz, 1H), 4.20 (dd, J=10.8, 3.2 Hz, 1H), 4.14 (dd, J=10.9, 4.6 Hz, 1H), 3.59-3.45 (m, 1H), 3.30-3.18 (m, 1H), 2.62-2.50 (m, 1H), 2.45-2.32 (m, 1H), 2.20 (s, 6H); MS (ES) m/z: 559 ($M+H^+$).

Example 29

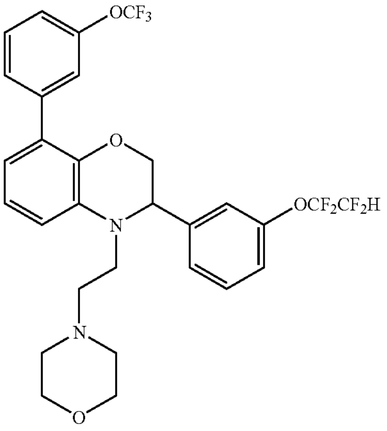

Cmpd 29

4-(2-Morpholin-4-yl-ethyl)-3-[3-(1,1,2,2-tetrafluoro-ethoxy)-phenyl]-8-(3-trifluoromethoxy-phenyl)-3,4-dihydro-2H-benzo[1,4]oxazine Scheme P

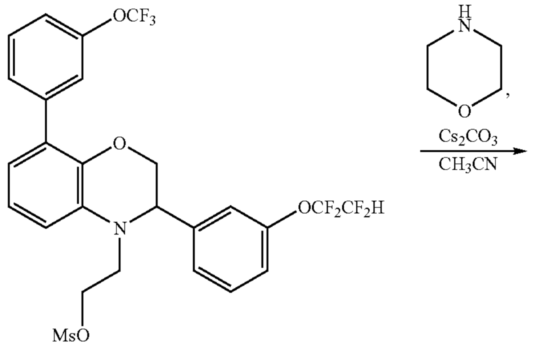

O1

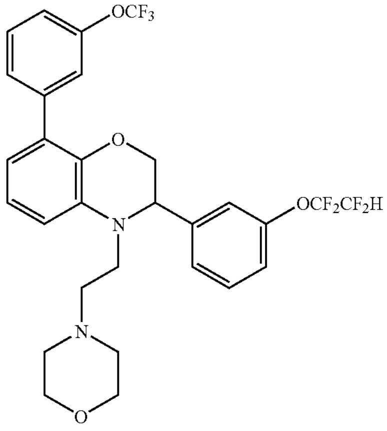

Cmpd 29, 18%

A mixture of O1 (17 mg, 0.028 mmol), morpholine (0.07 mL, 0.080 mmol) and $Cs_2CO_3$ (11 mg, 0.034 mmol) in $CH_3CN$ (1 mL) was heated in a sealed tube at 65° C. overnight. After cooling to room temperature, the reaction mixture was concentrated and partitioned between $CH_2Cl_2$ and water. The organic layer was dried ($Na_2SO_4$), concentrated and purified by column chromatography to give 3 mg (18%) of compound 29: $^1H$ NMR (400 MHz, $CDCl_3$) δ 7.46-7.35 (m, 4H), 7.21-7.11 (m, 4H), 6.99 (t, J=7.9 Hz, 1H), 6.84 (d, J=8.0 Hz, 1H), 6.71 (d, J=7.6 Hz, 1H), 5.89 (tt, J=53.1, 2.7 Hz, 1H), 4.66 (t, J=3.9 Hz, 1H), 4.21 (dd, J=10.8, 3.3 Hz, 1H), 4.14 (dd, J=10.9, 4.8 Hz, 1H), 3.67 (t, J=4.6 Hz, 4H), 3.59-3.49 (m, 1H), 3.31-3.21 (m, 1H), 2.18-2.58 (m, 1H), 2.50-2.35 (m, 5H); MS (ES) m/z: 601 ($M+H^+$).

Example 30

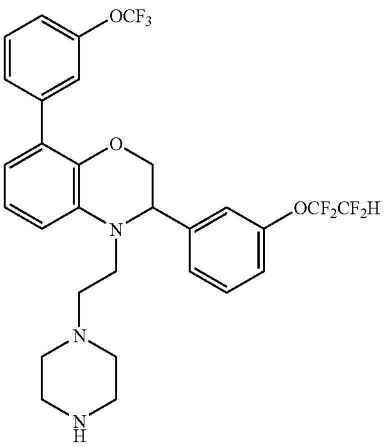

Cmpd 30

4-(2-piperazin-1-yl-ethyl)-3-[3-(1,1,2,2-tetrafluoro-ethoxy)-phenyl]-8-(3-trifluoromethoxy-phenyl)-3,4-dihydro-2H-benzo[1,4]oxazine Scheme Q

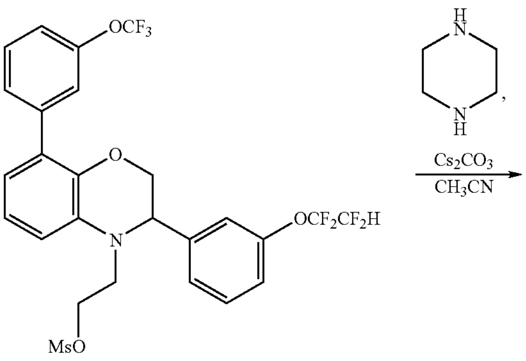

O1

-continued

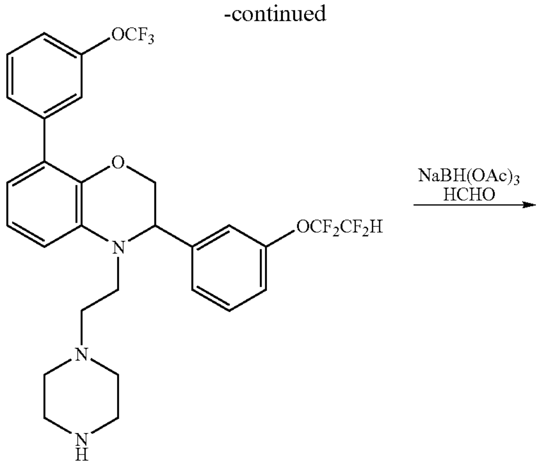

Cmpd 30, 41%

4-(2-piperazin-1-yl-ethyl)-3-[3-(1,1,2,2-tetrafluoro-ethoxy)-phenyl]-8-(3-trifluoromethoxy-phenyl)-3,4-dihydro-2H-benzo[1,4]oxazine Replacing morpholine with piperazine and following the same procedure as in the preparation of compound 29 gave compound 30 (oil, 41%): $^1$H NMR (300 MHz, $CDCl_3$) δ 7.47-7.31 (m, 4H), 7.21-7.10 (m, 4H), 6.98 (t, J=7.9 Hz, 1H), 6.84 (d, J=8.2 Hz, 1H), 6.70 (d, J=7.6 Hz, 1H), 5.89 (tt, J=53.1, 2.7 Hz, 1H), 4.65 (t, J=3.7 Hz, 1H), 4.25-4.09 (m, 2H), 3.60-3.49 (m, 1H), 3.32-3.20 (m, 1H), 2.69-2.58 (m, 1H), 2.51-2.29 (m, 5H), 1.44-1.21 (m, 4H); MS (ES) m/z: 600 (M+H$^+$).

Example 31

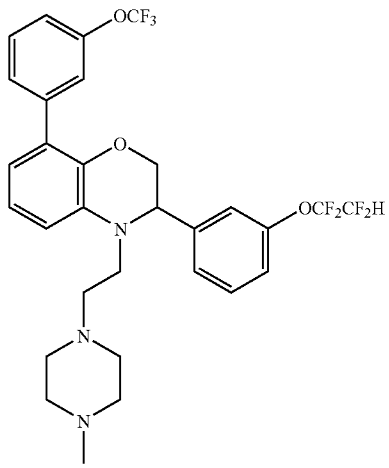

Cmpd 31, 37%

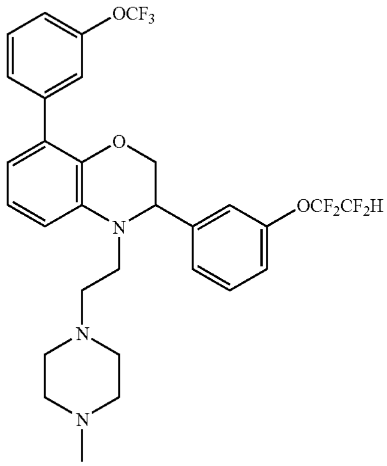

Cmpd 31

Cmpd 30

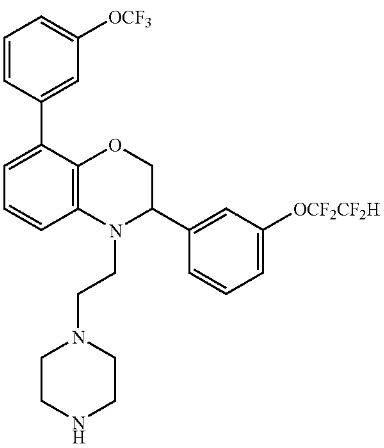

4-[2-(4-Methyl-piperazin-1-yl)-ethyl]-3-[3-(1,1,2,2-tetrafluoro-ethoxy)-phenyl]-8-(3-trifluoromethoxy-phenyl)-3,4-dihydro-2H-benzo[1,4]oxazine A mixture of 30 (8 mg, 0.013 mmol) and HCHO (37% in water, 13 mg, 0.13 mmol) in $CH_2Cl_2$ was stirred at room temperature for 30 min. $NaB(OAc)_3H$ (14 mg, 0.066 mmol) was added and the reaction mixture was stirred at room temperature for 1 h. $NaHCO_3$ saturated solution was added and the aqueous layer was extracted with $CH_2Cl_2$. The combined organic phases were dried ($Na_2SO_4$), concentrated and purified by column chromatography to get 3 mg (37%) of compound 31 as a yellow oil: $^1$H NMR (300 MHz, $CDCl_3$) δ 7.48-7.22 (m, 4H), 7.22-7.10 (m, 4H), 6.98 (t, J=7.8 Hz, 1H), 6.84 (d, J=8.0 Hz, 1H), 6.70 (d, J=7.0 Hz, 1H), 5.89 (tt, J=53.1, 2.6 Hz, 1H), 4.65 (t, J=3.6 Hz, 1H), 4.20 (dd, J=10.9, 3.2 Hz, 1H), 4.13 (dd, J=10.9, 4.6 Hz, 1H), 3.60-3.48 (m, 1H), 3.31-3.19 (m, 1H), 2.20-2.59 (m, 1H), 2.44 (m, 5H), 2.28 (s, 3H), 1.82 (s, 4H); MS (ES) m/z: 614 ($M+H^+$).

Example 32

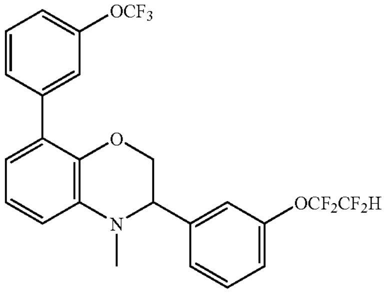

Cmpd 32

4-Methyl-3-[3-(1,1,2,2-tetrafluoro-ethoxy)-phenyl]-8-(3-trifluoromethoxy-phenyl)-3,4-dihydro-2H-benzo[1,4]oxazine Scheme R

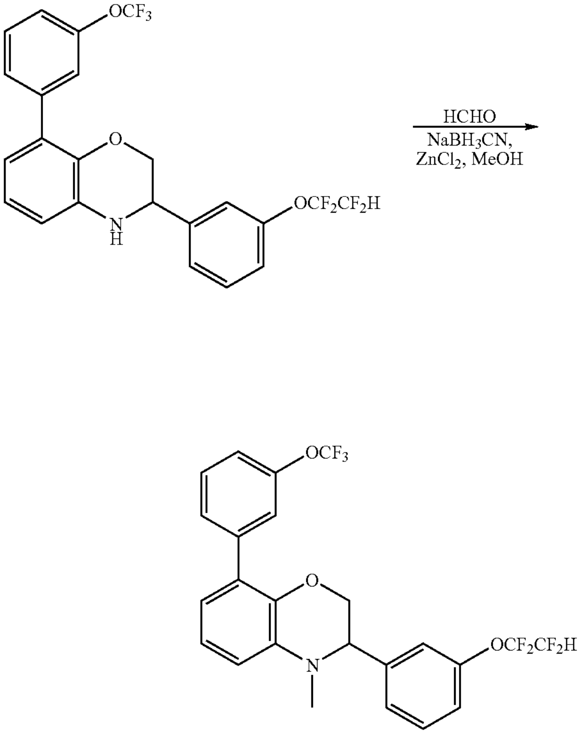

Cmpd 32, 55%

Replacing $TBSOCH_2CHO$ with HCHO and following the same procedure as in the preparation of compound 22 gave compound 32 (55%): $^1$H NMR (300 MHz, $CDCl_3$) δ 7.48-7.32 (m, 4H), 7.23-7.11 (m, 4H), 7.00 (t, J=7.9 Hz, 1H), 6.83 (d, J=8.1 Hz, 1H), 6.74 (d, J=7.6 Hz, 1H), 5.89 (tt, J=53.1, 2.8 Hz, 1H), 4.39 (dd, J=5.7, 3.1 Hz, 1H), 4.26 (dd, J=11.0, 3.2 Hz, 1H), 4.10 (dd, J=10.9, 5.8 Hz, 1H), 2.85 (s, 3H); MS (ES) m/z: 502 ($M+H^+$).

Example 33

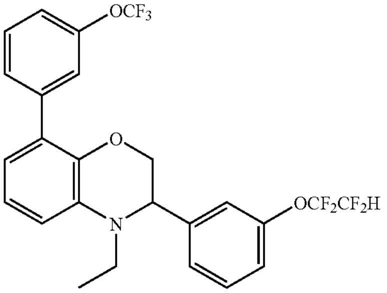

Cmpd 33

4-Ethyl-3-[3-(1,1,2,2-tetrafluoro-ethoxy)-phenyl]-8-(3-trifluoromethoxy-phenyl)-3,4-dihydro-2H-benzo[1,4]oxazine Scheme S

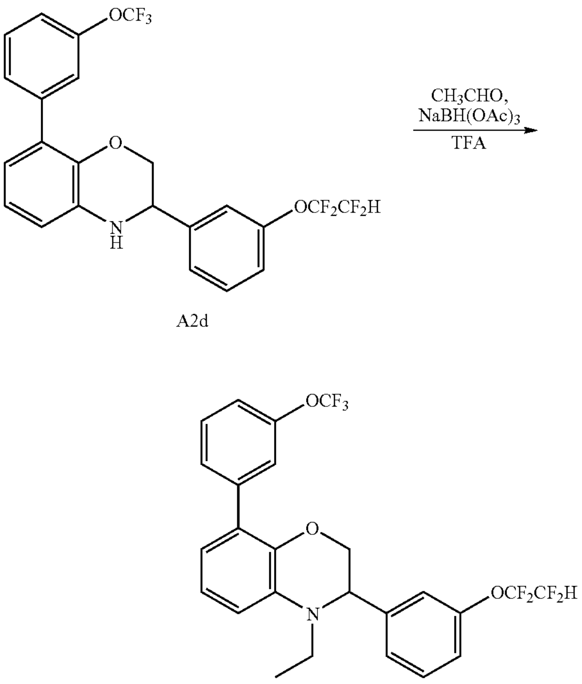

Cmpd 33, 79%

Replacing A2b with A2d, adding $CH_3CHO$ and following the same procedure as in the preparation of compound A2c gave compound 33 (clear oil, 79%): $^1$H NMR (300 MHz, $CDCl_3$) δ 7.46-7.33 (m, 4H), 7.25-7.11 (m, 4H), 6.99 (t, J=7.9 Hz, 1H), 6.85 (d, J=7.4 Hz, 1H), 6.70 (d, J=7.6 Hz, 1H), 5.88 (tt, J=53.1, 2.8 Hz, 1H), 4.51 (t, J=4.1 Hz, 1H), 4.21-4.11 (m, 2H), 3.59-3.48 (m, 1H), 3.20-3.10 (m, 1H), 1.11 (t, J=7.1 Hz, 3H); MS (ES) m/z: 516 (M+H$^+$).

Example 34

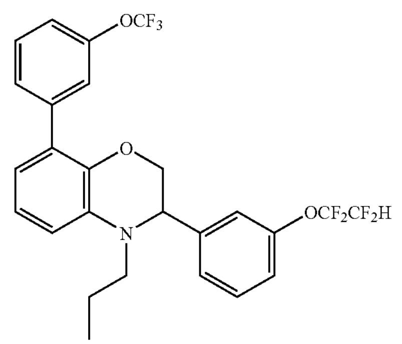

Cmpd 34

4-Propyl-3-[3-(1,1,2,2-tetrafluoro-ethoxy)-phenyl]-8-(3-trifluoromethoxy-phenyl)-3,4-dihydro-2H-benzo[1,4]oxazine Scheme T

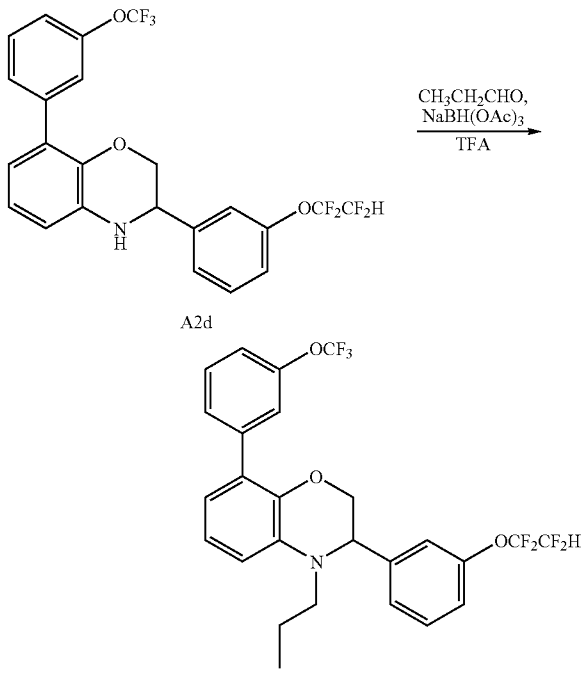

A2d

Cmpd 34, 92%

Replacing $CH_3CHO$ with $CH_3CH_2CHO$ and following the same procedure as in the preparation of compound 33 gave compound 34 (clear oil, 92%): $^1$H NMR (300 MHz, $CDCl_3$) δ 7.45-7.31 (m, 4H), 7.21-7.09 (m, 4H), 6.98 (t, J=7.9 Hz, 1H), 6.80 (d, J=8.2 Hz, 1H), 6.68 (d, J=7.6 Hz, 1H), 5.88 (tt, J=53.1, 2.8 Hz, 1H), 4.53 (t, J=3.7 Hz, 1H), 4.20 (dd, J=10.9, 3.3 Hz, 1H), 4.15 (dd, J=10.8, 4.3 Hz, 1H), 3.46-3.33 (m, 1H), 3.08-2.93 (m, 1H), 1.70-1.52 (m, 2H), 0.89 (t, J=7.4 Hz, 3H); MS (ES) m/z: 530 (M+H$^+$).

Example 35

Cmpd 35

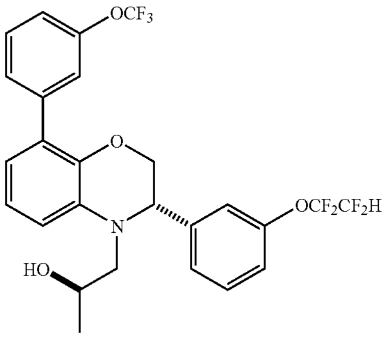

4H-1,4-Benzoxazine-4-ethanol, 2,3-dihydro-α-methyl-3-[3-(1,1,2,2-tetrafluoroethoxy)phenyl]-8-[3-(trifluoromethoxy)phenyl]-, (3S,αR)—

Scheme U

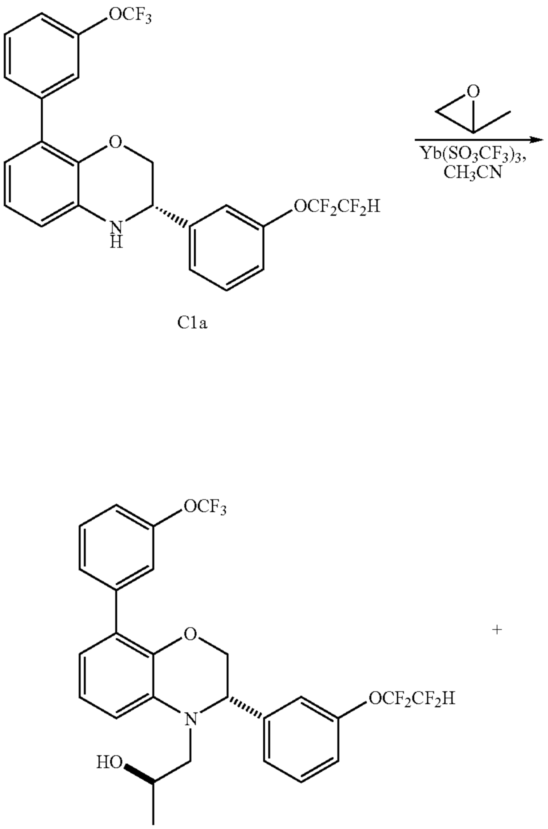

C1a

Cmpd 35

-continued

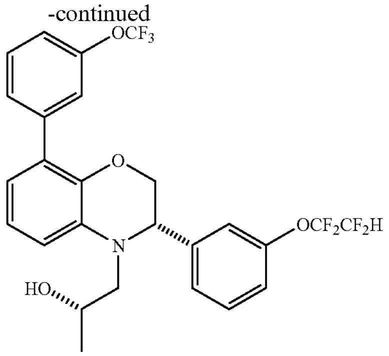

Cmpd 36

Cmpd 35

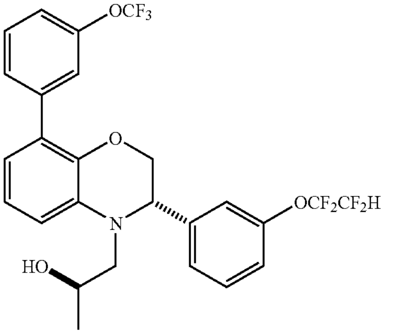

4H-1,4-Benzoxazine-4-ethanol, 2,3-dihydro-α-methyl-3-[3-(1,1,2,2-tetrafluoroethoxy)phenyl]-8-[3-(trifluoromethoxy)phenyl]-, (3S,αR)—

Replacing 2-trifluoromethyl-oxirane with 2-methyl-oxirane and following the same procedure as in the preparation of compound 3 and 4 gave compound 35 and 36. The spectrums of compound 35 are as following: $^1$H NMR (400 MHz, $CDCl_3$) δ 7.44-7.32 (m, 4H), 7.19-7.09 (m, 4H), 6.98 (t, J=7.9 Hz, 1H), 6.82 (d, J=7.4 Hz, 1H), 6.73 (d, J=7.6 Hz, 1H), 5.88 (tt, J=53.1, 2.7 Hz, 1H), 4.77 (t, J=3.1 Hz, 1H), 4.30 (dd, J=10.9, 3.0 Hz, 1H), 4.32-4.17 (m, 2H), 3.46 (dd, J=15.2, 2.4 Hz, 1H), 3.05 (dd, J=15.2, 9.7 Hz, 1H), 1.82 (brs, 1H), 1.18 (d, J=6.3 Hz, 3H); MS (ES) m/z: 546 (M+H$^+$).

Example 36

Cmpd 36

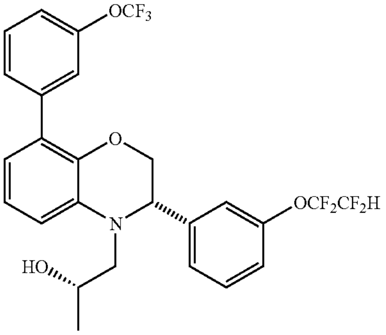

4H-1,4-Benzoxazine-4-ethanol, 2,3-dihydro-α-methyl-3-[3-(1,1,2,2-tetrafluoroethoxy)phenyl]-8-[3-(trifluoromethoxy)phenyl]-, (3S,αS)—

The spectrums of compound 36 are as following: $^1$H NMR (400 MHz, $CDCl_3$) δ 7.42-7.30 (m, 4H), 7.19-7.08 (m, 4H), 7.01-6.91 (m, 2H), 6.73 (d, J=7.3 Hz, 1H), 5.87 (tt, J=53.1, 2.6 Hz, 1H), 4.61 (d, J=2.4 Hz, 1H), 4.29 (dd, J=10.8, 2.8 Hz, 1H), 4.24 (dd, J=10.8, 2.7 Hz, 1H), 4.20-4.12 (m, 1H), 3.49 (dd, J=15.0, 7.6 Hz, 1H), 3.15 (dd, J=15.1, 4.8 Hz, 1H), 1.67 (brs, 1H), 1.24 (d, J=6.2 Hz, 3H); MS (ES) m/z: 546 (M+H$^+$).

Example 37

Cmpd 37

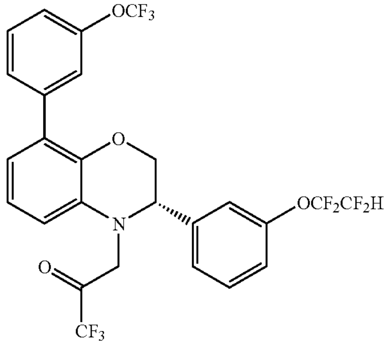

2-Propanone, 3-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-1,1,1-trifluoro- Scheme V

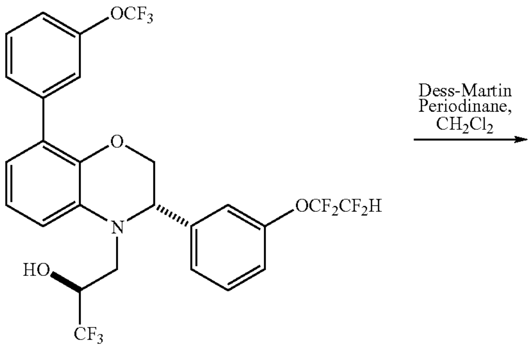

Cmpd 3

-continued

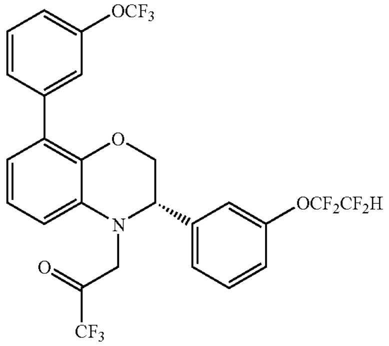

Cmpd 37, 71%

To a solution of compound 3 (27 mg, 0.045 mmol) in $CH_2Cl_2$ (1.5 mL) at 4° C. was added Dess-Martin periodinane (30 mg, 0.071 mmol). After stirring at 4° C. for 30 min and then room temperature for another 30 min, $Na_2S_2O_3$ and $NaHCO_3$ aqueous solution were added and the solution was stirred vigorously for ~5 min. The solution was extracted with $CH_2Cl_2$ and the combined organic extracts were dried ($Na_2SO_4$), concentrated and purified by column chromatography to give a mixture of 39 and hydrate. The mixture was treated with 2 M HCl/$Et_2O$ in $CH_2Cl_2$ (2 mL) for 3 h, washed with water, dried ($Na_2SO_4$) and concentrated to afford pure compound 37 (19 mg, 71%): $^1H$ NMR (300 MHz, $CDCl_3$) δ 7.49-7.37 (m, 4H), 7.29-7.09 (m, 4H), 6.95 (t, J=7.9 Hz, 1H), 6.81 (d, J=7.6 Hz, 1H), 6.49 (d, J=7.9 Hz, 1H), 5.89 (bt, J=53.0 Hz, 1H), 4.70-4.59 (m, 2H), 4.32 (dd, J=11.1, 3.1 Hz, 1H), 4.20-4.08 (m, 2H); MS (ES) m/z: 616 ($M+H_2O+H^+$).

Example 38

Cmpd 38

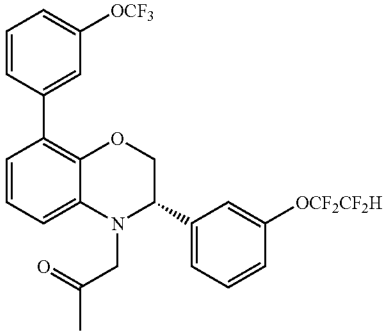

2-Propanone, 1-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-

Scheme W

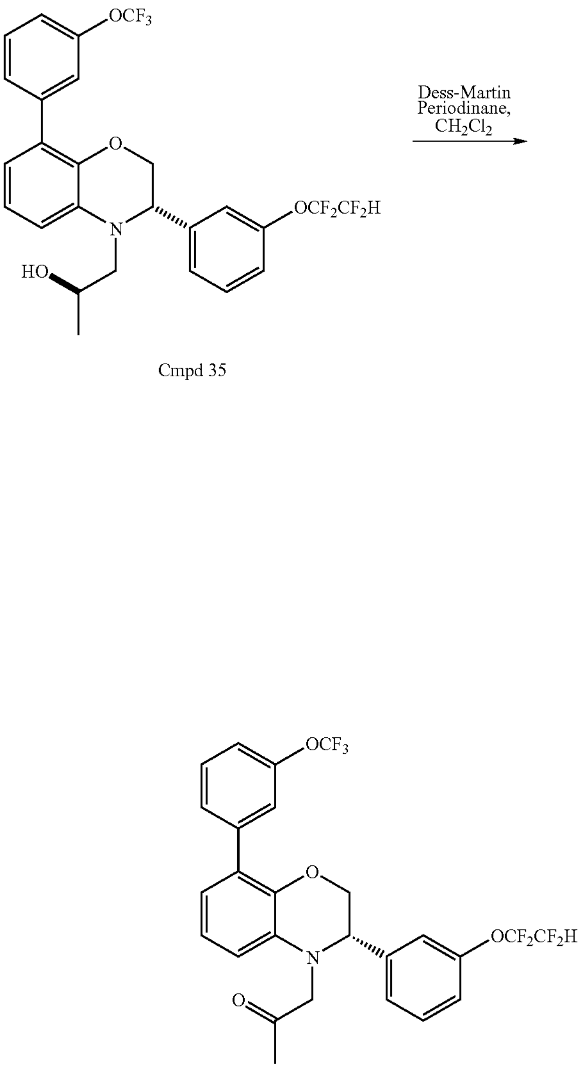

Cmpd 35

Cmpd 38

To a solution of compound 35 (36 mg, 0.066 mmol) in $CH_2Cl_2$ (1.5 mL) at 4° C. was added Dess-Martin periodinane (56 mg, 0.13 mmol). After stirring at 4° C. for 45 min, $Na_2S_2O_3$ and $NaHCO_3$ aqueous solution were added and the solution was stirred vigorously for ~10 min. The solution was extracted with $CH_2Cl_2$ and the combined organic extracts were dried ($Na_2SO_4$), concentrated and purified by column chromatography to give compound 38 (10 mg, 28%): $^1H$ NMR (400 MHz, $CDCl_3$) δ 7.47-7.36 (m, 4H), 7.23-7.12 (m, 4H), 6.93 (t, J=7.9 Hz, 1H), 6.75 (d, J=7.7 Hz, 1H), 6.48 (d, J=8.1 Hz, 1H), 5.89 (tt, J=53.1, 2.8 Hz, 1H), 4.61 (dd, J=5.3, 3.3 Hz, 1H), 4.31 (dd, J=11.0, 3.3 Hz, 1H), 4.21 (d, J=18.7 Hz, 1H), 4.17 (dd, J=11.0, 5.5 Hz, 1H), 3.74 (d, J=8.7 Hz, 1H), 2.13 (s, 3H); MS (ES) m/z: 544 (M+H$^+$).

Example 39

Cmpd 39

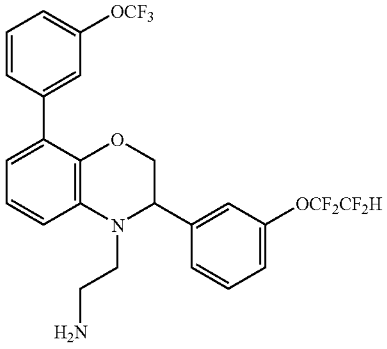

2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethylamine Scheme X

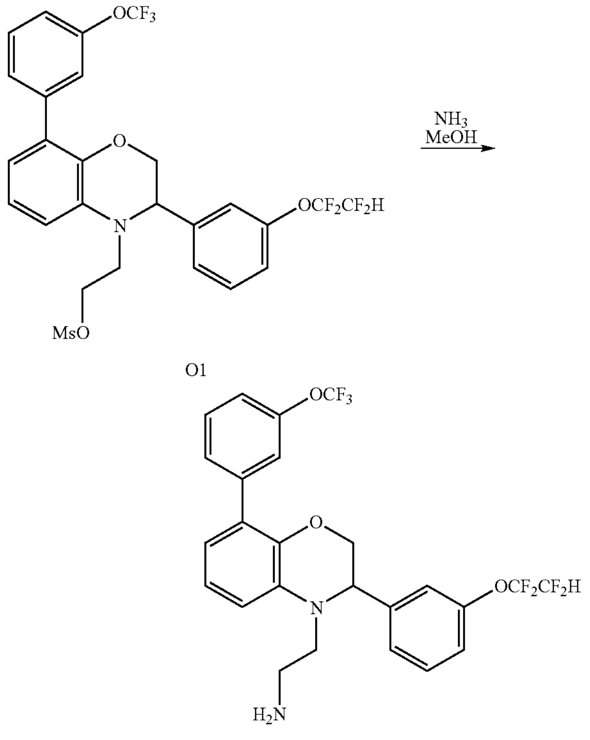

A mixture of O1 (33 mg, 0.054 mmol) and $NH_3$ (2 M in MeOH, 2 mL, 4 mmol) in a sealed tube was heated at 70° C. for 23 h. After cooling to room temperature, the reaction mixture was concentrated and partitioned between $CH_2Cl_2$ and saturated $NaHCO_3$ solution. The organic layer was dried ($Na_2SO_4$) and concentrated to give 30 mg (100%) of compound 39: $^1$H NMR (300 MHz, $CDCl_3$) δ 7.46-7.32 (m, 4H), 7.21-7.10 (m, 4H), 6.98 (t, J=7.9 Hz, 1H), 6.87 (d, J=7.3 Hz, 1H), 6.71 (d, J=7.5 Hz, 1H), 5.88 (tt, J=53.1, 2.8 Hz, 1H), 4.61 (t, J=3.3 Hz, 1H), 4.24 (dd, J=10.8, 3.1 Hz, 1H), 4.17 (dd, J=10.8, 4.1 Hz, 1H), 3.57-3.42 (m, 1H), 3.29-3.15 (m, 1H), 3.05-2.80 (m, 2H); MS (ES) m/z: 531 (M+H$^+$).

Example 40

Cmpd 40

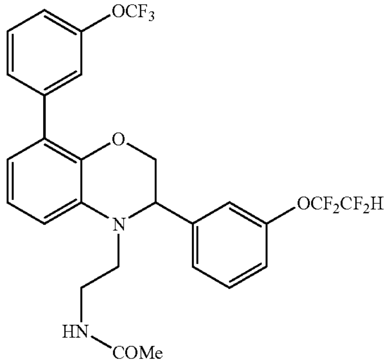

N-{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-acetamide Scheme Y

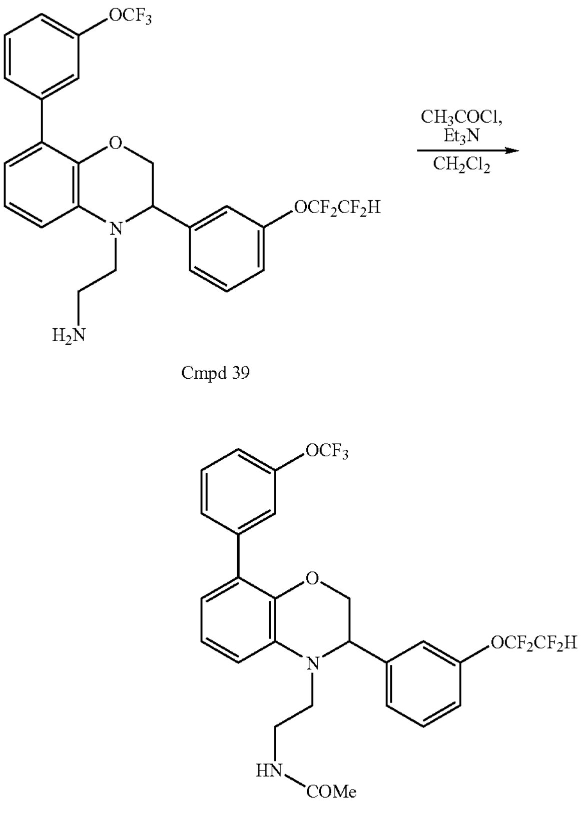

A mixture of compound 39 (11 mg, 0.021 mmol), acetyl chloride (1 drop) and $Et_3N$ (0.016 mL, 0.11 mmol) in $CH_2Cl_2$ (1 mL) was heated for 24 h and concentrated. The residue was purified by column chromatography to give 7 mg (59%) of compound 40: $^1H$ NMR (300 MHz, $CDCl_3$) δ 7.45-7.32 (m, 4H), 7.21-7.10 (m, 4H), 7.05-6.95 (m, 2H), 6.73 (dd, J=6.9, 2.2 Hz, 1H), 5.89 (tt, J=53.1, 2.8 Hz, 1H), 5.46 (brs, 1H), 4.54 (t, J=3.6 Hz, 1H), 4.23-4.11 (m, 2H), 3.58-3.35 (m, 4H), 1.86 (m, 3H); MS (ES) m/z: 573 ($M+H^+$).

Example 41

Cmpd 41

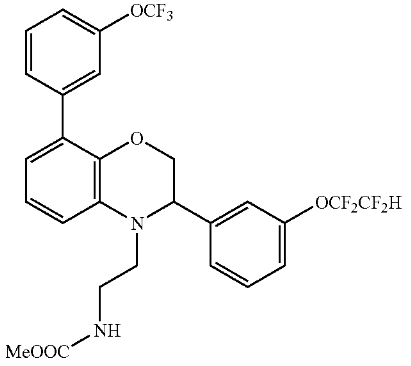

{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-carbamic acid methyl ester Scheme Z

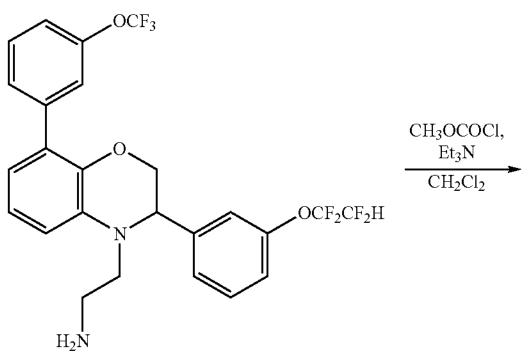

Cmpd 39

-continued

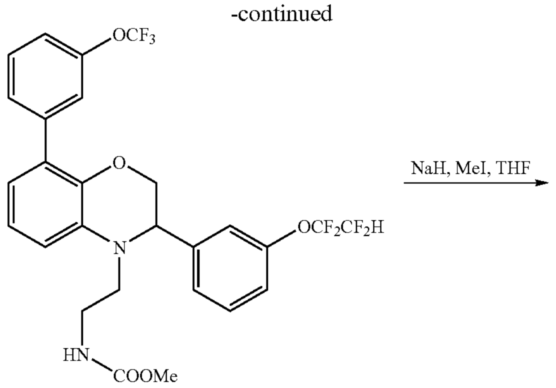

Cmpd 41, 59%

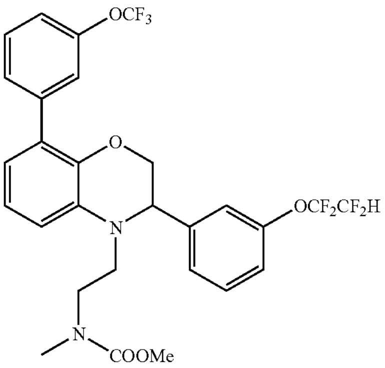

Cmpd 42

Cmpd 41

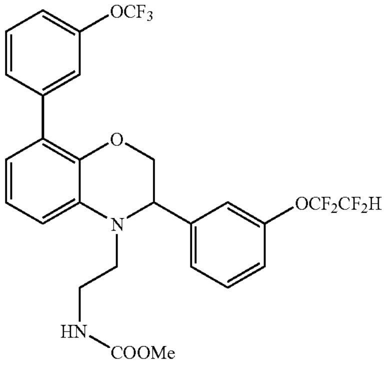

{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-carbamic acid methyl ester Replacing acetyl chloride with methyl chloroformate and following the same procedure as in the preparation of compound 40 gave compound 41: $^1H$ NMR (400 MHz, $CDCl_3$) δ 7.44-7.31 (m, 4H), 7.20-7.10 (m, 4H), 7.04-6.93 (m, 2H), 6.73 (d, J=7.7 Hz, 1H), 5.89 (tt, J=53.0, 2.6 Hz, 1H), 4.71 (brs, 1H), 4.55 (t, J=3.6 Hz, 1H), 4.22 (dd, J=11.0, 3.1 Hz, 1H), 4.16 (dd, J=11.0, 4.0 Hz, 1H), 3.65 (s, 3H), 3.59-3.49 (m, 1H), 3.34 (m, 3H); MS (ES) m/z: 589 (M+H$^+$).

Example 42

Cmpd 42

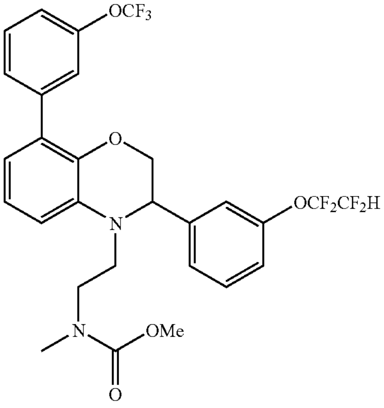

Methyl-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-carbamic acid methyl ester Replacing 23 with 41 and following the same procedure as in the preparation of compound 24 gave compound 42: $^1$H NMR (400 MHz, $CDCl_3$) δ 7.46-7.32 (m, 4H), 7.23-7.11 (m, 4H), 7.05-6.99 (m, 2H), 6.73 (m, 1H), 5.92 (bt, J=52.9 Hz, 1H), 4.56 (d, J=25.0 Hz, 1H), 4.24-4.10 (m, 2H), 3.65 (s, 3H), 3.55-3.20 (m, 4H), 2.88 (s, 3H); MS (ES) m/z: 603 (M+H$^+$).

Example 43

Cmpd 43

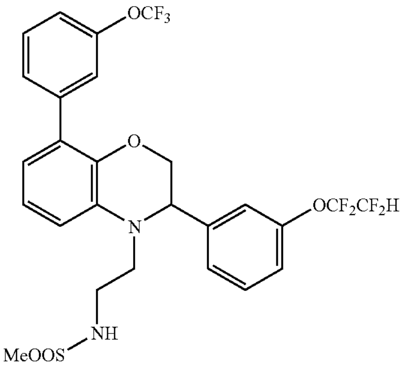

N-{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-methanesulfonamide Scheme AA

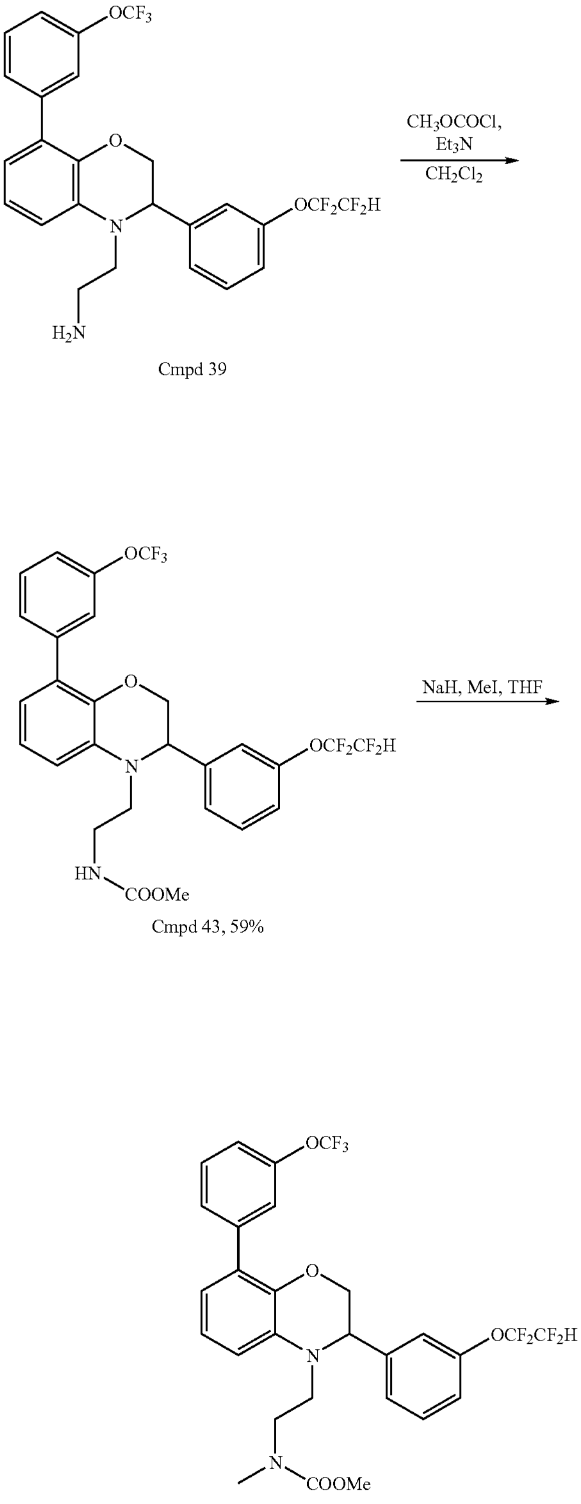

Cmpd 39

Cmpd 43, 59%

Cmpd 44

-continued

Cmpd 43

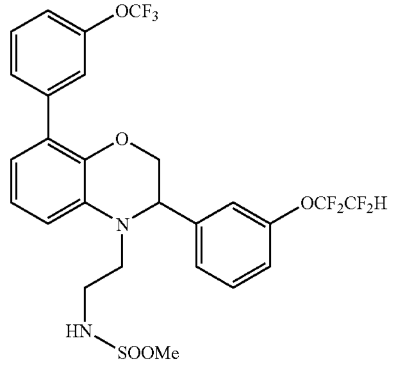

N-{2-[3-[3-(1,1,2,2-Tetrafluoro-ethoxy)-phenyl]-8-(3-trifluoromethoxy-phenyl)-2,3-dihydro-benzo[1,4]oxazin-4-yl]-ethyl}-methanesulfonamide Replacing 23 with 39 and following the same procedure as in the preparation of compound O1 gave compound 43: $^1$H NMR (400 MHz, $CDCl_3$) δ 7.42-7.35 (m, 4H), 7.21-7.10 (m, 4H), 7.01 (t, J=7.9 Hz, 1H), 6.88 (d, J=8.2 Hz, 1H), 6.76 (d, J=7.6 Hz, 1H), 5.89 (tt, J=53.1, 2.8 Hz, 1H), 4.59 (t, J=3.6 Hz, 1H), 4.35 (t, J=6.4 Hz, 1H), 4.26 (dd, J=11.0, 3.2 Hz, 1H), 4.17 (dd, J=11.0, 4.3 Hz, 1H), 3.66-3.57 (m, 1H), 3.49-3.19 (m, 3H), 2.89 (s, 3H); MS (ES) m/z: 609 (M+H$^+$).

Example 44

Cmpd 44

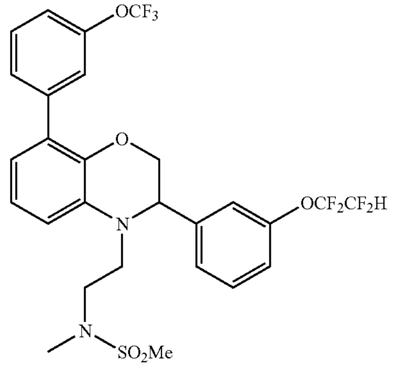

N-Methyl-N-{2-[3-[3-(1,1,2,2-tetrafluoro-ethoxy)-phenyl]-8-(3-trifluoromethoxy-phenyl)-2,3-dihydro-benzo[1,4]oxazin-4-yl]-ethyl}-methanesulfonamide Replacing 23 with 39 and following the same procedure as in the preparation of compound 24 gave compound 44: $^1$H NMR (400 MHz, $CDCl_3$) δ 7.45-7.35 (m, 4H), 7.26-7.11 (m, 4H), 7.01 (t, J=8.0 Hz, 1H), 6.88 (d, J=7.0 Hz, 1H), 6.74 (d, J=7.6 Hz, 1H), 5.90 (tt, J=53.1, 2.8 Hz, 1H), 4.62 (t, J=3.9 Hz, 1H), 4.24 (dd, J=11.0, 3.2 Hz, 1H), 4.16 (dd, J=11.0, 4.7 Hz, 1H), 3.68-3.58 (m, 1H), 3.44-3.32 (m, 2H), 3.19-3.09 (m, 1H), 2.80 (s, 3H), 2.76 (s, 3H); MS (ES) m/z: 623 (M+H$^+$).

Example 45

Cmpd 45

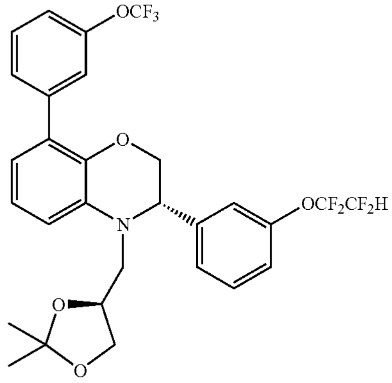

2H-1,4-Benzoxazine, 4-[[(4S)-2,2-dimethyl-1,3-dioxolan-4-yl]methyl]-3,4-dihydro-3-[3-(1,1,2,2-tetrafluoroethoxy)phenyl]-8-[3-(trifluoromethoxy)phenyl]-, (3S)—

Scheme BB

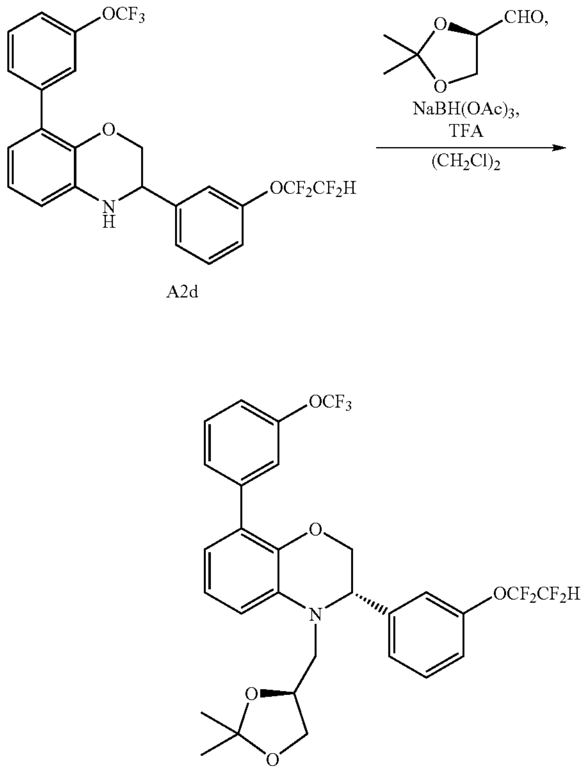

A2d

Cmpd 45

+

-continued

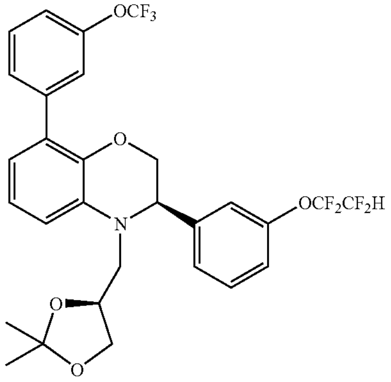

Cmpd 46

Cmpd 45

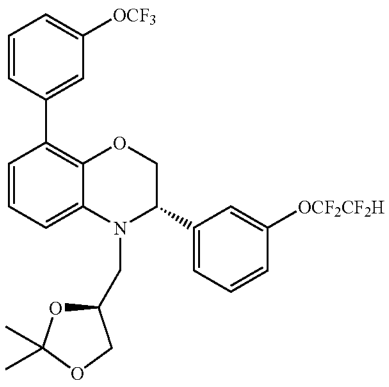

2H-1,4-Benzoxazine, 4-[[(4S)-2,2-dimethyl-1,3-dioxolan-4-yl]methyl]-3,4-dihydro-3-[3-(1,1,2,2-tetrafluoroethoxy)phenyl]-8-[3-(trifluoromethoxy)phenyl]-, (3S)—

Replacing $CH_3CHO$ with (R)-(+)-2,2-dimethyl-[1,3]dioxolane-4-carbaldehyde and following the same procedure as in the preparation of compound 33 gave compound 45 and 46. The spectrums of compound 45 are as following: $^1$H NMR (300 MHz, $CDCl_3$) δ 7.47-7.31 (m, 4H), 7.21-7.11 (m, 4H), 6.98 (t, J=7.9 Hz, 1H), 6.81 (d, J=7.6 Hz, 1H), 6.72 (d, J=7.6 Hz, 1H), 5.88 (tt, J=53.2, 2.8 Hz, 1H), 4.83 (t, J=3.8 Hz, 1H), 4.50-4.41 (m, 1H), 4.24 (dd, J=10.8, 3.2 Hz, 1H), 4.14 (dd, J=10.9, 4.5 Hz, 1H), 3.97 (dd, J=8.3, 6.4 Hz, 1H), 3.58 (dd, J=15.5, 3.1 Hz, 1H), 3.47 (dd, J=8.3, 6.6 Hz, 1H), 3.22 (dd, J=15.5, 8.1 Hz, 1H), 1.38 (s, 3H), 1.31 (s, 3H); MS (ES) m/z: 602 (M+H$^+$).

Example 46

Cmpd 46

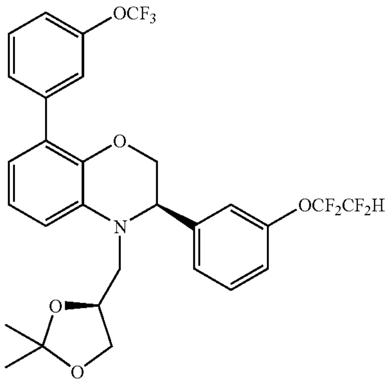

2H-1,4-Benzoxazine, 4-[[(4S)-2,2-dimethyl-1,3-dioxolan-4-yl]methyl]-3,4-dihydro-3-[3-(1,1,2,2-tetrafluoroethoxy)phenyl]-8-[3-(trifluoromethoxy)phenyl]-, (3R)—

The spectrums of compound 46 are as following: $^1$H NMR (300 MHz, $CDCl_3$) δ 7.42-7.31 (m, 4H), 7.19-7.10 (m, 3H), 7.07 (s, 1H), 6.99 (t, J=7.9 Hz, 1H), 6.84 (d, J=7.7 Hz, 1H), 6.72 (d, J=7.3 Hz, 1H), 5.87 (bt, J=53.1 Hz, 1H), 4.65 (t, J=2.9 Hz, 1H), 4.38-4.27 (m, 2H), 4.21 (dd, J=10.9, 3.1 Hz, 1H), 4.06 (dd, J=8.1, 6.1 Hz, 1H), 3.70 (t, J=7.5 Hz, 1H), 3.62 (dd, J=15.3, 4.6 Hz, 1H), 3.31 (dd, J=15.4, 5.9 Hz, 1H), 1.40 (s, 3H), 1.33 (s, 3H); MS (ES) m/z: 602 (M+H$^+$).

Example 47

Cmpd 47

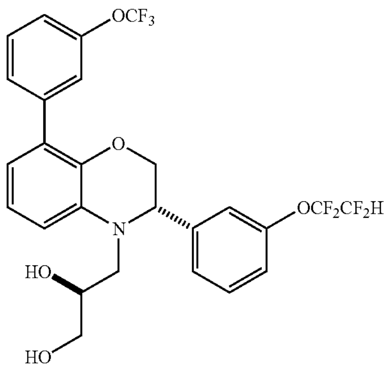

1,2-Propanediol, 3-[(3S)-2,3-dihydro-3-[3-(1,1,2,2-tetrafluoroethoxy)phenyl]-8-[3-(trifluoromethoxy)phenyl]-4H-1,4-benzoxazin-4-yl]-, (2S)—

Scheme CC

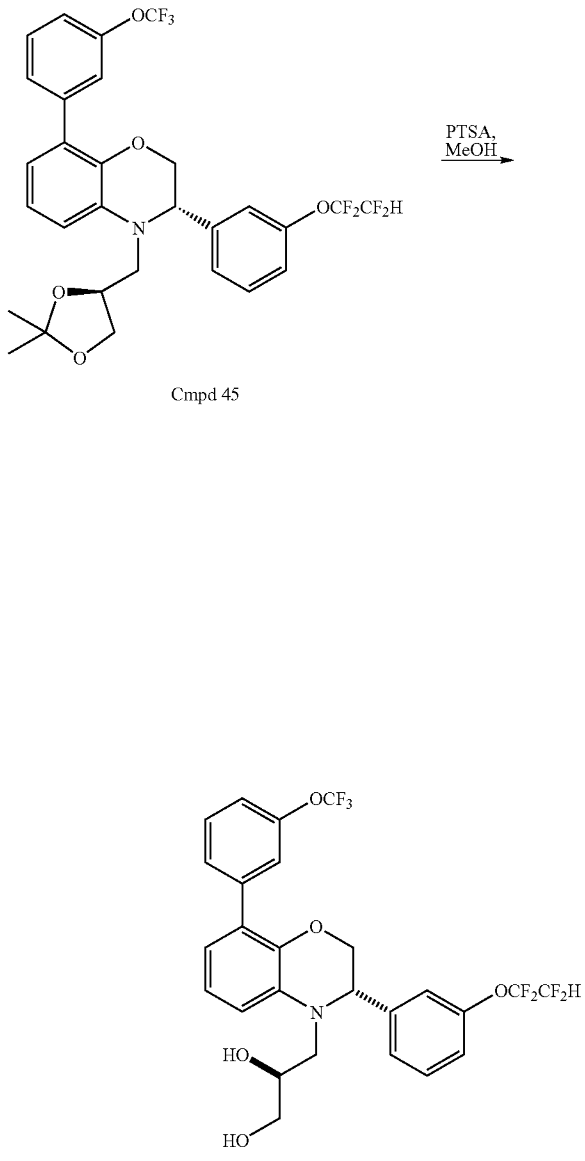

Cmpd 45

Cmpd 47

A mixture of compound 45 (5 mg) and PTSA (11 mg) in MeOH (1 mL) was stirred for 1 h and concentrated. The residue was purified by PLC (50% EtOAc in hexane) to give compound 47: $^1$H NMR (400 MHz, $CDCl_3$) δ 7.44-7.32 (m, 4H), 7.20-7.10 (m, 4H), 6.98 (t, J=7.9 Hz, 1H), 6.85 (d, J=8.2 Hz, 1H), 6.74 (d, J=7.6 Hz, 1H), 5.88 (tt, J=53.1, 2.8 Hz, 1H), 4.77 (t, J=3.4 Hz, 1H), 4.29 (dd, J=10.9, 3.1 Hz, 1H), 4.20 (dd, J=10.9, 4.0 Hz, 1H), 4.10 (m, 1H), 3.70 (d, J=10.8 Hz, 1H), 3.56-3.48 (m, 2H), 3.22 (dd, J=15.3, 9.1 Hz, 1H), 2.27 (brs, 1H), 1.78 (brs, 1H); MS (ES) m/z: 562 (M+H$^+$).

Example 48

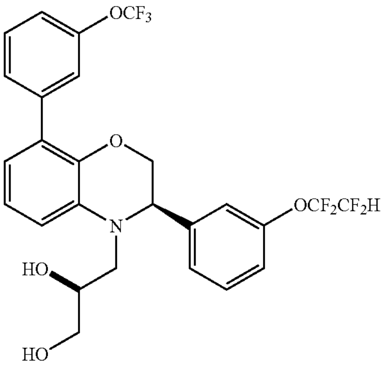

Cmpd 48

1,2-Propanediol, 3-[(3R)-2,3-dihydro-3-[3-(1,1,2,2-tetrafluoroethoxy)phenyl]-8-[3-(trifluoromethoxy)phenyl]-4H-1,4-benzoxazin-4-yl]-, (2S)—

Scheme DD

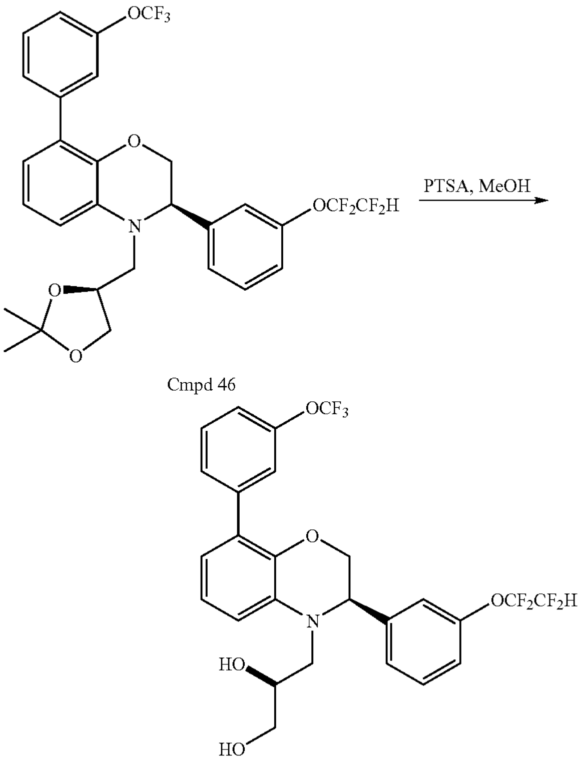

Cmpd 46

Cmpd 48

Replacing 45 with 46 and following the same procedure as in the preparation of compound 47 gave compound 48: $^1$H NMR (400 MHz, $CDCl_3$) δ 7.42-7.31 (m, 4H), 7.19-7.08 (m, 4H), 7.00 (t, J=7.9 Hz, 1H), 6.92 (d, J=7.2 Hz, 1H), 6.73 (d, J=6.1 Hz, 1H), 5.88 (bt, J=53.2 Hz, 1H), 4.63 (t, J=3.0 Hz, 1H), 4.28 (dd, J=10.7, 3.0 Hz, 1H), 4.23 (dd, J=10.8, 3.1 Hz, 1H), 4.08 (m, 1H), 3.79 (d, J=14.4 Hz, 1H), 3.63-3.53 (m, 2H), 3.30 (dd, J=15.1, 6.8 Hz, 1H), 2.08 (brs, 1H), 1.84 (brs, 1H); MS (ES) m/z: 562 (M+H⁺).

Example 49

Cmpd 49

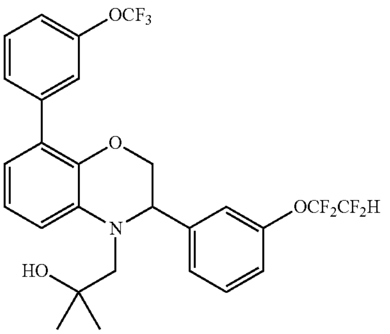

2-Methyl-1-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Scheme EE

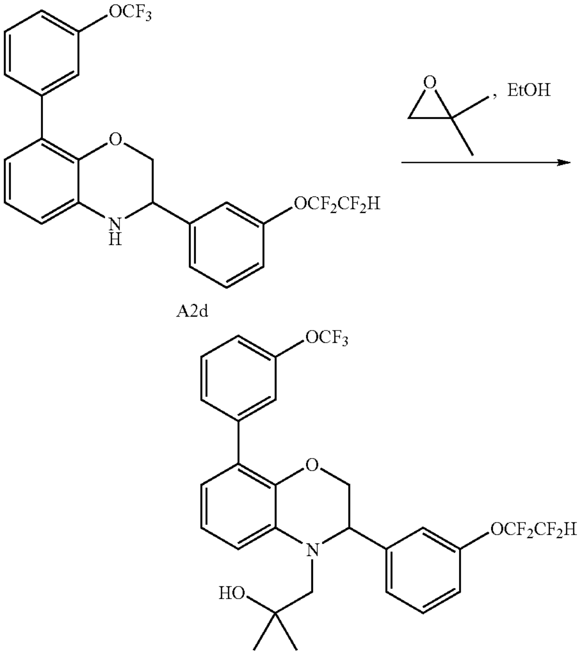

A2d

Cmpd 49, 19%

A mixture of compound A2d (23 mg, 0.047 mmol) and 2,2-dimethyl-oxirane (0.1 mL, 1.13 mmol) in EtOH (0.2 mL) in a sealed tube was heated at 110° C. for 5 d. After cooling to room temperature, the mixture was concentrated and purified by column chromatography to give 5 mg (19%) of compound 49 as an oil: $^1$H NMR (300 MHz, $CDCl_3$) δ 7.40-7.29 (m, 4H), 7.15-6.92 (m, 6H), 6.71 (d, J=7.2 Hz, 1H), 5.86 (bt, J=53.1 Hz, 1H), 4.82 (m, 1H), 4.38 (dd, J=10.7, 2.5 Hz, 1H), 4.32 (d, J=19.0, 2.4 Hz, 1H), 3.52 (d, J=15.3 Hz, 1H), 3.16 (d, J=15.4 Hz, 1H), 1.32 (s, 3H), 1.30 (s, 3H); MS (ES) m/z: 560 (M+H⁺).

Example 50

Cmpd 50

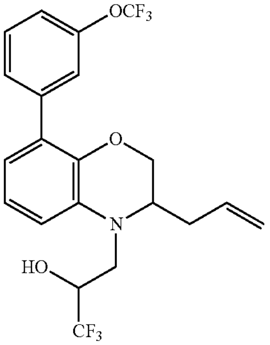

(Higher Rf Cmpd)

3-[3-Allyl-8-(3-trifluoromethoxy-phenyl)-2,3-dihydro-benzo[1,4]oxazin-4-yl]-1,1,1-trifluoro-propan-2-ol Scheme FF

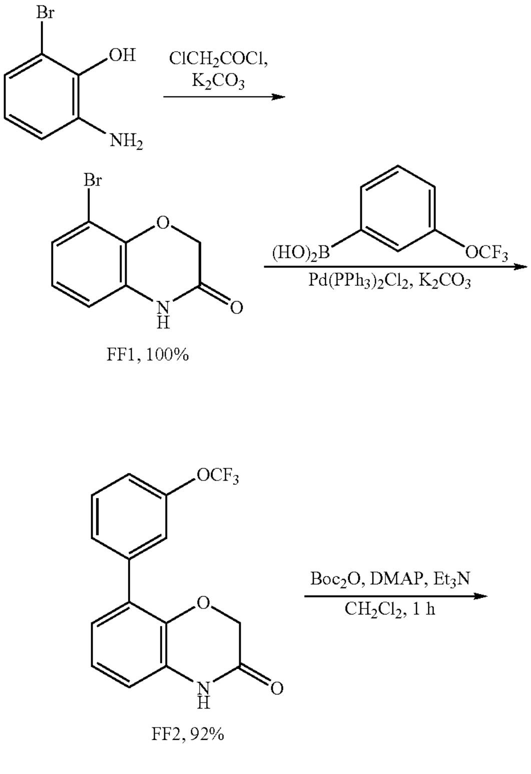

FF1, 100%

FF2, 92%

-continued

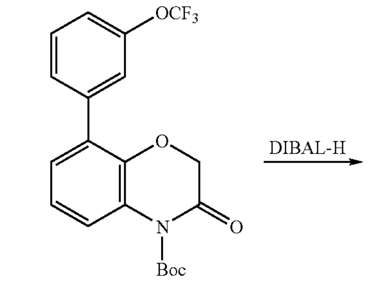

FF3, 94%

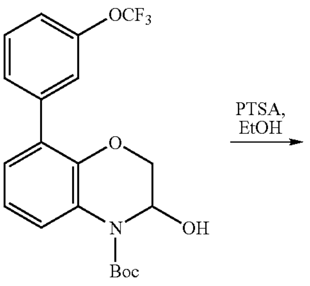

FF4, 92%

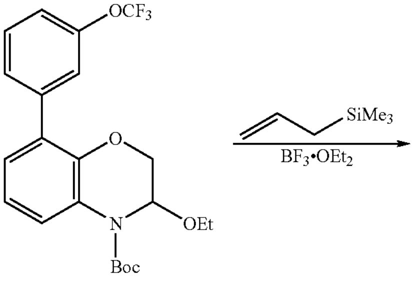

FF5, 94%

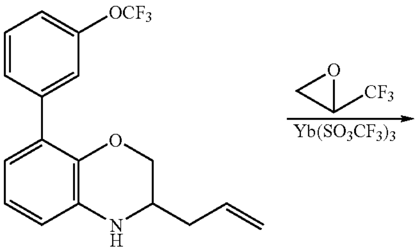

FF6, 72%

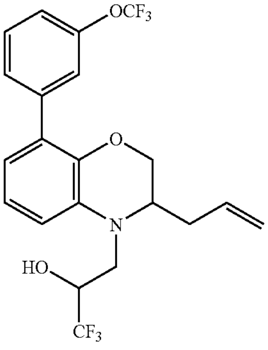

+

Cmpd 50, 41%
Higher Rf Cmpd

-continued

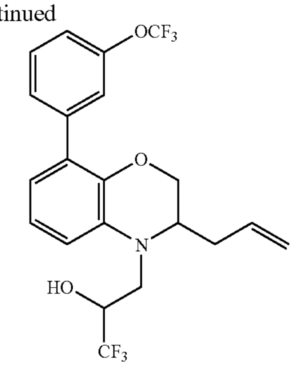

Cmpd 51, 48%
Lower Rf Cmpd

FF1

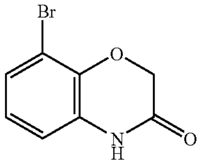

8-Bromo-4H-benzo[1,4]oxazin-3-one

To a solution of A1a (1.30 g, 6.91 mmol) in 2-butanone (35 mL) was added a solution of $K_2CO_3$ (3.34 g, 24.2 mmol) in water (5 mL) followed by chloro acetyl chloride (0.8 mL, 10 mmol). After stirring at room temperature for 2 h and then 80° C. for another 2 h, the mixture was cooled down and was let standing at room temperature overnight. The precipitated crystals were filtered, washed with $Et_2O$ and dried under vacuum to give 1.58 g (100%) of compound FF1 as a pink crystal: $^1H$ NMR (400 MHz, $CDCl_3$) δ 8.21 (brs, 1H), 7.22 (m, 1H), 6.85 (t, J=8.0 Hz, 1H), 6.76 (d, J=7.9 Hz, 1H), 4.73 (s, 2H).

FF2

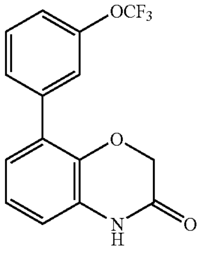

8-(3-Trifluoromethoxy-phenyl)-4H-benzo[1,4]oxazin-3-one

Replacing A2c with FF1 and following the same procedure as in the preparation of A2d gave compound FF1 (92%): $^1H$ NMR (300 MHz, $CDCl_3$) δ 8.91 (brs, 1H), 7.49-7.39 (m, 3H), 7.09-7.03 (m, 2H), 6.87 (dd, J=5.8, 3.6 Hz, 1H), 4.63 (s, 2H); MS (ES) m/z: 332 (M+$Na^+$).

FF3

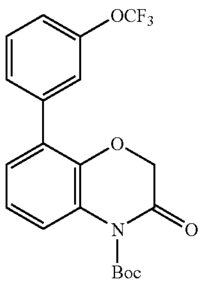

3-Oxo-8-(3-trifluoromethoxy-phenyl)-2,3-dihydro-benzo[1,4]oxazine-4-carboxylic acid tert-butyl ester To a solution of FF2 (3.27 g, 10.6 mmol) and $Boc_2O$ (3.50 g, 16.1 mmol) in $CH_2Cl_2$ (60 mL) was added DMAP (0.25 g, 2.05 mmol) and $Et_3N$ (2.3 mL, 16.5 mmol). After stirring for 1 h, the mixture was concentrated and purified by column chromatography to give 4.05 g (94%) of compound FF3 as a yellow oil: $^1$H NMR (300 MHz, $CDCl_3$) δ 7.45-7.43 (m, 2H), 7.37 (s, 3H), 7.26-7.11 (m, 4H), 4.53 (s, 2H), 1.63 (s, 9H); MS (ES) m/z: 432 ($M+Na^+$).

FF4

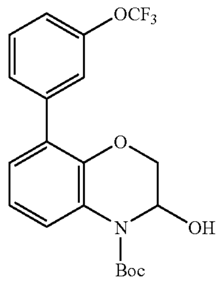

3-Hydroxy-8-(3-trifluoromethoxy-phenyl)-2,3-dihydro-benzo[1,4]oxazine-4-carboxylic acid tert-butyl ester To a solution of FF3 (3.20 g, 7.8 mmol) in THF (35 mL) at −78° C. was added DIBAL (1.0 M in hexane, 14 mL, 14 mmol). After stirring at −78° C. for 30 min, the reaction was quenched with saturated $NH_4Cl$ followed by potassium sodium tartrate (aq). The reaction mixture was allowed to warm to room temperature, the organic layer was separated, and the aqueous layer was extracted with $CH_2Cl_2$. The combined organic extracts were dried ($Na_2SO_4$) and concentrated to give 2.96 g (92%) of compound FF4 as a yellow oil: $^1$H NMR (300 MHz, $CDCl_3$) δ 7.91-7.88 (m, 1H), 7.44-7.38 (m, 3H), 7.18 (d, J=7.5 Hz, 1H), 7.04-7.01 (m, 2H), 5.93 (m, 1H), 4.11-4.09 (m, 2H), 3.45 (d, J=4.9 Hz, 1H), 1.59 (s, 9H); MS (ES) m/z: 434 ($M+Na^+$).

FF5

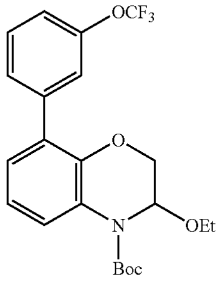

3-Ethoxy-8-(3-trifluoromethoxy-phenyl)-2,3-dihydro-benzo[1,4]oxazine-4-carboxylic acid tert-butyl ester A mixture of compound FF4 (2.95 g, 7.18 mmol) and PTSA (0.71 g, 3.2 mmol) in EtOH (40 mL) was stirred for 22 h and concentrated. The residue was purified by column chromatography to give 2.97 g (94%) of compound FF5 as an oil: $^1$H NMR (300 MHz, $CDCl_3$) δ 7.73 (m, 1H), 7.49-7.36 (m, 3H), 7.16 (m, 1H), 7.04 (d, J=7.6 Hz, 1H), 6.96 (t, J=7.9 Hz, 1H), 5.78 (s, 1H), 4.41 (d, J=11.2 Hz, 1H), 4.14 (dd, J=11.2, 2.2 Hz, 1H), 3.63 (q, J=7.2 Hz, 2H), 1.57 (s, 9H), 1.17 (t, J=7.1 Hz, 3H); MS (ES) m/z: 462 ($M+Na^+$).

FF6

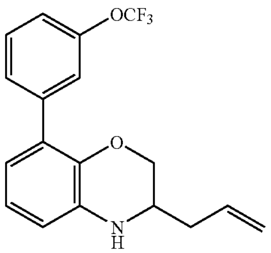

3-Allyl-8-(3-trifluoromethoxy-phenyl)-3,4-dihydro-2H-benzo[1,4]oxazine

To a solution of FF5 (86 mg, 0.20 mmol) and allyltrimethylsilane (156 mL, 0.98 mmol) in $CH_2Cl_2$ (2.5 mL) at 4° C. was added $BF_3.OEt_2$ (0.075 mL, 0.59 mmol). The reaction mixture was allowed to warm to room temperature and stirred for 2.5 h. More allyltrimethylsilane (0.080 mL, 0.49 mmol) and $BF_3.OEt_2$ (0.050 mL, 0.39 mmol) were added and the reaction mixture was stirred for another 1 h. Saturated $NaHCO_3$ was added to quench the reaction and the resulting mixture was extracted with $CH_2Cl_2$ The combined organic extracts were dried ($Na_2SO_4$), concentrated and purified to give 47 mg (72%) of compound FF6 as a clear oil: $^1$H NMR (300 MHz, $CDCl_3$) δ 7.50-7.35 (m, 3H), 7.15 (d, J=8.2 Hz, 1H), 6.83 (t, J=7.7 Hz, 1H), 6.69 (d, J=7.6 Hz, 1H), 6.61 (d, J=7.6 Hz, 1H), 5.91-5.75 (m, 1H), 5.20 (d, J=12.2 Hz, 2H), 4.25 (dd, J=10.5, 2.8 Hz, 1H), 3.91 (brs, 1H), 3.87 (dd, J=10.5, 7.6 Hz, 1H), 3.49-3.43 (m, 1H), 2.40-2.28 (m, 1H), 2.26-2.11 (m, 1H); MS (ES) m/z: 336 ($M+H^+$).

Cmpd 50

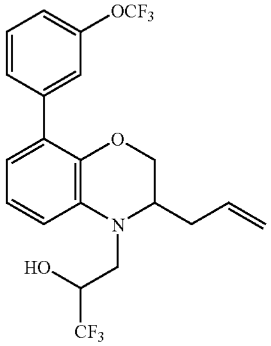

3-[3-Allyl-8-(3-trifluoromethoxy-phenyl)-2,3-dihydro-benzo[1,4]oxazin-4-yl]-1,1,1-trifluoro-propan-2-ol Replacing A2d with FF6 and following the same procedure as in the preparation of compound 1 and 2 gave higher Rf compound 50 (41%) and lower Rf compound 51 (solvent for column: 20% EtOAc in hexane). Spectrums of compound 50 are as following: $^1$H NMR (300 MHz, $CDCl_3$) δ 7.49-7.38 (m, 3H), 7.17 (d, J=7.8 Hz, 1H), 6.94 (t, J=7.9 Hz, 1H), 6.76 (d, J=7.6 Hz, 1H), 6.70 (d, J=8.1 Hz, 1H), 5.92-5.78 (m, 1H), 5.17 (s, 1H), 5.12 (d, J=5.3 Hz, 1H), 4.36 (m, 1H), 4.22 (dd, J=10.7, 1.7 Hz, 1H), 3.99 (dd, J=10.7, 2.4 Hz, 1H), 3.75 (dd, J=15.1, 2.0 Hz, 1H), 3.49-3.36 (m, 2H), 2.62 (d, J=3.2 Hz, 1H), 2.36 (m, 2H); MS (ES) m/z: 448 (M+H$^+$).

Example 51

Cmpd 51

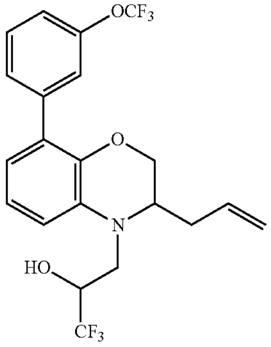

(Lower Rf Cmpd)

3-[3-Allyl-8-(3-trifluoromethoxy-phenyl)-2,3-dihydro-benzo[1,4]oxazin-4-yl]-1,1,1-trifluoro-propan-2-ol Spectrums of compound 51 (48%) are as following: $^1$H NMR (300 MHz, $CDCl_3$) δ 7.49-7.38 (m, 3H), 7.16 (d, J=7.8 Hz, 1H), 6.94 (t, J=7.9 Hz, 1H), 6.80-6.71 (m, 2H), 5.91-5.78 (m, 1H), 5.14 (d, J=12.1 Hz, 2H), 4.29 (m, 1H), 4.23 (dd, J=10.7, 1.6 Hz, 1H), 3.94 (dd, J=10.6, 2.2 Hz, 1H), 3.70-3.53 (m, 2H), 3.31 (dd, J=10.6, 8.2 Hz, 1H), 2.64 (d, J=4.2 Hz, 1H), 2.50-2.31 (m, 2H); MS (ES) m/z: 448 (M+H$^+$).

Example 52

Cmpd 52

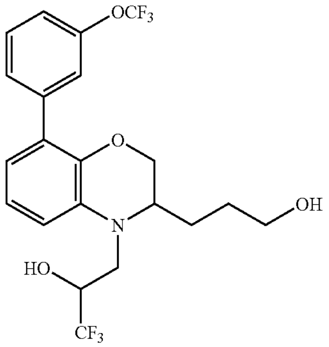

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol Scheme GG

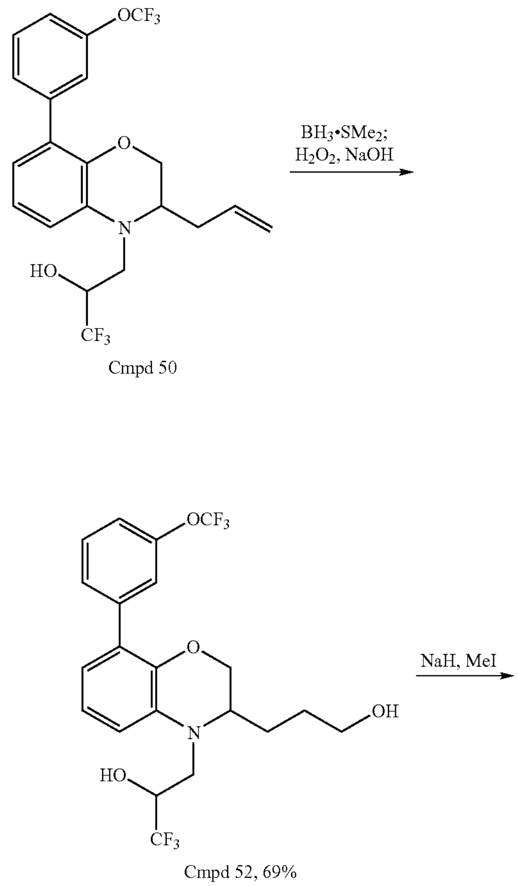

-continued

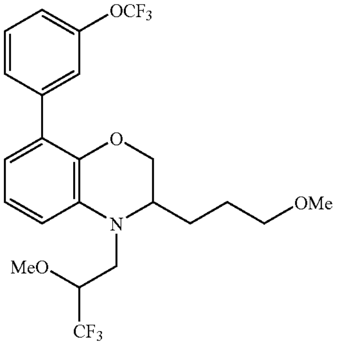

Cmpd 53, 94%

Cmpd 52

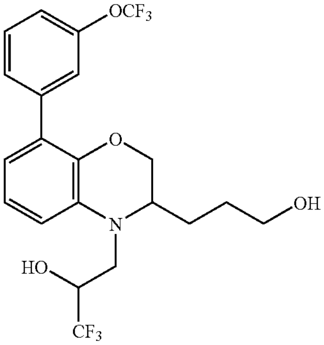

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol To a solution of 50 (18 mg, 0.040 mmol) in THF (1 mL) at 4° C. was added $BH_3.SMe_2$ (2 M in THF, 0.050 mL, 0.10 mmol). The reaction mixture was stirred at 4° C. for 10 min and then at room temperature for 2 h. MeOH were added to quench the reaction and then 1.0 M NaOH (0.3 mL) and 30% $H_2O_2$ (0.1 mL) were added. After stirring for 1 h, the mixture was partitioned between $CH_2Cl_2$ and brine. The organic layer was dried ($Na_2SO_4$), concentrated and purified by column chromatography to give 13 mg (69%) of compound 52 as a clear oil: $^1$H NMR (300 MHz, $CDCl_3$) δ 7.49-7.38 (m, 3H), 7.16 (d, J=7.7 Hz, 1H), 6.93 (t, J=7.9 Hz, 1H), 6.73 (bt, J=8.2 Hz, 2H), 4.36 (m, 1H), 4.20 (d, J=10.7 Hz, 1H), 4.02 (dd, J=10.7, 2.4 Hz, 1H), 3.78 (d, J=15.1 Hz, 1H), 3.66 (m, 2H), 3.44-3.35 (m, 2H), 3.02 (m, 1H), 1.71-1.62 (m, 5H); MS (ES) m/z: 466 (M+H$^+$).

Example 53

Cmpd 53

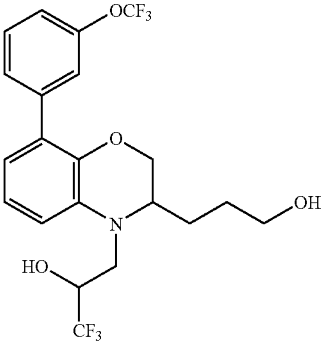

1,1,1-Trifluoro-3-[3-(3-methoxy-propyl)-8-(3-trifluoromethoxy-phenyl)-2,3-dihydro-benzo[1,4]oxazin-4-yl]-]propan-2-ol Replacing compound 26 with 52 and following the same procedure as in the preparation of compound 27 gave compound 53 (94%): $^1$H NMR (400 MHz, $CDCl_3$) δ 7.47 (d, J=7.7 Hz, 1H), 7.43-7.38 (m, 2H), 7.16 (d, J=8.0 Hz, 1H), 6.93 (t, J=7.9 Hz, 1H), 6.69 (d, J=7.6 Hz, 1H), 6.61 (d, J=7.8 Hz, 1H), 4.21 (d, J=10.6 Hz, 1H), 3.97-3.89 (m, 2H), 3.80 (d, J=15.5 Hz, 1H), 3.54 (s, 3H), 3.39-3.32 (m, 6H), 1.68-1.56 (m, 5H); MS (ES) m/z: 494 (M+H$^+$).

Example 54

Cmpd 54

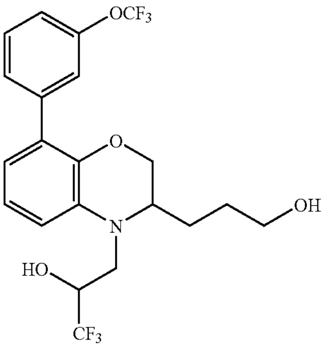

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol Scheme GG

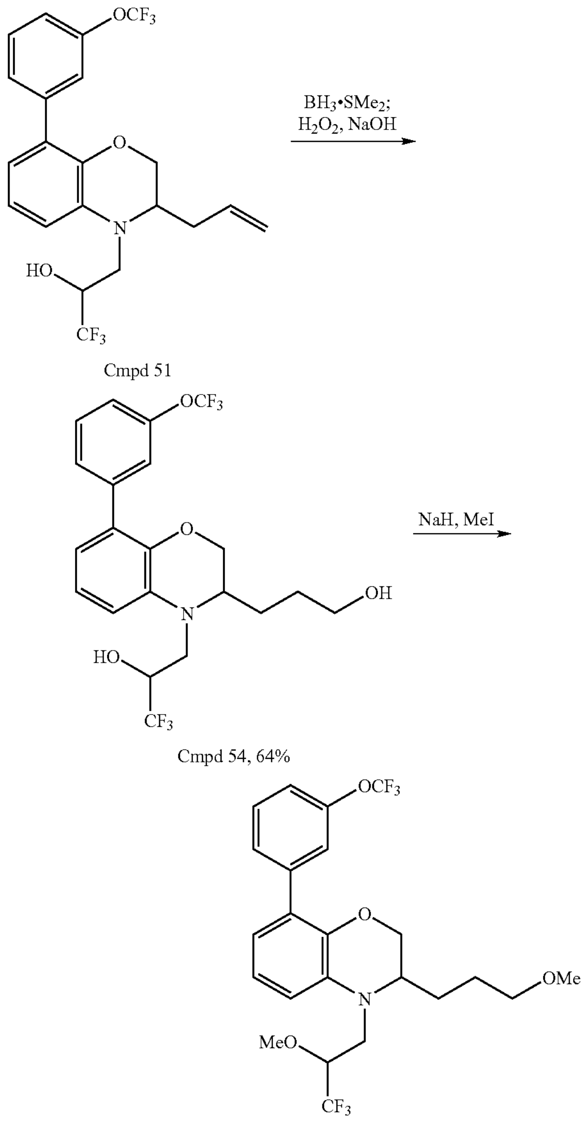

Cmpd 54

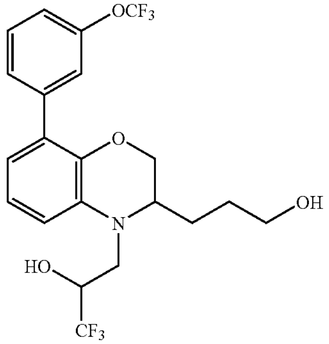

3-[4-(3,3,3-Trifluoro-2-hydroxy-propyl)-8-(3-trifluoromethoxy-phenyl)-3,4-dihydro-2H-benzo[1,4]oxazin-3-yl]-propan-1-ol Replacing compound 50 with 51 and following the same procedure as in the preparation of compound 52 gave compound 54 (64%): $^1$H NMR (300 MHz, $CDCl_3$) δ 7.49-7.38 (m, 3H), 7.16 (d, J=7.6 Hz, 1H), 6.93 (t, J=7.9 Hz, 1H), 6.74 (bt, J=7.4 Hz, 2H), 4.30 (m, 1H), 4.20 (d, J=9.7 Hz, 1H), 3.95 (dd, J=10.8, 2.3 Hz, 1H), 3.78-3.44 (m, 5H), 3.34 (m, 1H), 1.89-1.59 (m, 5H); MS (ES) m/z: 466 ($M+H^+$).

Example 55

Cmpd 55

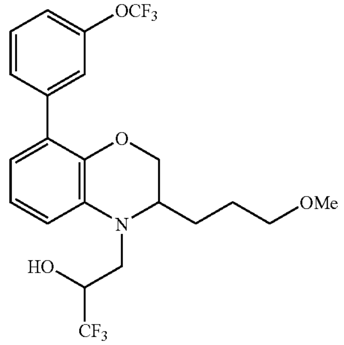

1,1,1-Trifluoro-3-[3-(3-methoxy-propyl)-8-(3-trifluoromethoxy-phenyl-2,3-dihydro-benzo[1,4]oxazin-4-yl]-propan-2-ol Replacing compound 26 with 54 and following the same procedure as in the preparation of compound 27 gave compound 55 (63%): $^1$H NMR (400 MHz, $CDCl_3$) δ 7.47-7.45 (m, 1H), 7.42-7.38 (m, 2H), 7.16 (d, J=8.0 Hz, 1H), 6.93 (t, J=7.9 Hz, 1H), 6.71-6.66 (m, 2H), 4.20 (d, J=10.7 Hz, 1H), 3.93 (d, J=10.7 Hz, 1H), 3.79 (m, 1H), 3.61-3.57 (m, 5H), 3.39 (m, 2H), 3.32 (s, 3H), 1.73-1.58 (m, 5H); MS (ES) m/z: 494 ($M+H^+$).

Example 56

Cmpd 56

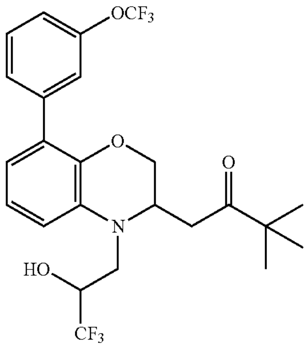

(Higher Rf Cmpd)

3,3-Dimethyl-1-[4-(3,3,3-trifluoro-2-hydroxy-propyl)-8-(3-trifluoromethoxy-phenyl)-3,4-dihydro-2H-benzo[1,4]oxazin-3-yl]-butan-2-one Scheme HH

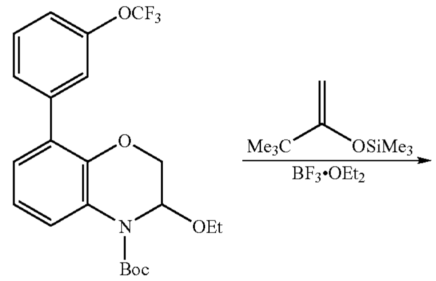

FF5

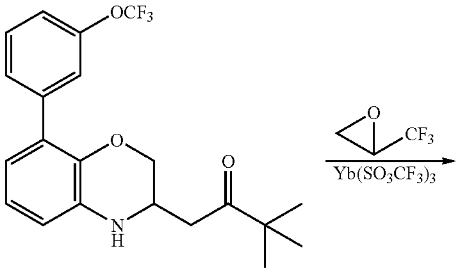

HH1, 50%

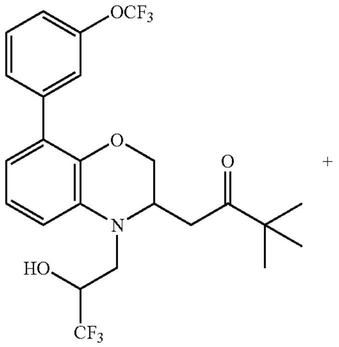

Cmpd 56, 43%
Higher Rf Cmpd

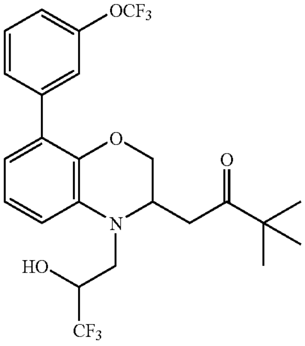

Cmpd 57, 48%
Lower Rf Cmpd

-continued

HH1

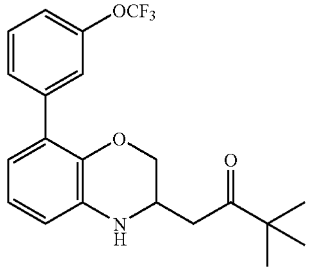

3,3-Dimethyl-1-[8-(3-trifluoromethoxy-phenyl)-3,4-dihydro-2H-benzo[1,4]oxazin-3-yl]-butan-2-one Replacing allyl trimethylsilane with (1-tert-butyl-vinyloxy)-trimethyl-silane and following the same procedure as in the preparation of FF6 gave compound HH1 (50%): $^1$H NMR (300 MHz, $CDCl_3$) δ 7.41-7.30 (m, 3H), 7.08 (d, J=7.9 Hz, 1H), 6.76 (t, J=7.7 Hz, 1H), 6.61 (d, J=7.6 Hz, 1H), 6.52 (d, J=7.8 Hz, 1H), 4.47 (brs, 1H), 4.11 (dd, J=10.5, 2.4 Hz, 1H), 3.92-3.79 (m, 2H), 2.66 (d, J=6.1 Hz, 2H), 1.08 (s, 9H); MS (ES) m/z: 394 (M+H$^+$).

Cmpd 56

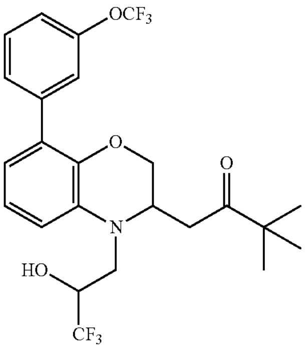

Higher Rf Cmpd 3,3-Dimethyl-1-[4-(3,3,3-trifluoro-2-hydroxy-propyl)-8-(3-trifluoromethoxy-phenyl)-3,4-dihydro-2H-benzo[1,4]oxazin-3-yl]-butan-2-one Replacing A2d with HH1 and following the same procedure as in the preparation of compound 1 and 2 gave higher Rf compound 56 (43%, eluent for column: 20% EtOAc in hexane) and lower Rf compound 57 (48%). Spectrums of compound 56 are as following: $^1$H NMR (300 MHz, $CDCl_3$) δ 7.45-7.40 (m, 3H), 7.19 (m, 1H), 6.96 (t, J=7.8 Hz, 1H), 6.84-6.77 (m, 2H), 4.42 (m, 1H), 4.12 (d, J=10.6 Hz, 1H), 4.05-3.91 (m, 2H), 3.61 (dd, J=15.1, 2.5 Hz, 1H), 3.43 (dd, J=15.0, 9.5 Hz, 1H), 3.12 (brs, 1H), 2.84 (dd, J=17.7, 7.4 Hz, 1H), 2.68 (dd, J=17.7, 5.8 Hz, 1H), 1.09 (s, 9H); MS (ES) m/z: 506 (M+H$^+$).

Example 57

Cmpd 57

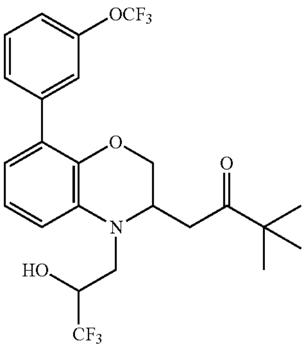

Lower Rf Cmpd 3,3-Dimethyl-1-[4-(3,3,3-trifluoro-2-hydroxy-propyl)-8-(3-trifluoromethoxy-phenyl)-3,4-dihydro-2H-benzo[1,4]oxazin-3-yl]-butan-2-one Spectrums of compound 57 are as following: $^1$H NMR (300 MHz, $CDCl_3$) δ 7.47-7.39 (m, 3H), 7.19 (d, J=6.8 Hz, 1H), 6.97 (t, J=7.8 Hz, 1H), 6.85 (d, J=7.6 Hz, 1H), 6.78 (d, J=8.2 Hz, 1H), 4.36 (brs, 1H), 4.14-4.02 (m, 2H), 4.00-3.88 (m, 2H), 3.66 (dd, J=15.1, 3.7 Hz, 1H), 3.40 (dd, J=15.3, 7.6 Hz, 1H), 2.93 (dd, J=17.9, 7.2 Hz, 1H), 2.75 (dd, J=18.0, 6.0 Hz, 1H), 1.11 (s, 9H); MS (ES) m/z: 506 (M+H$^+$).

Example 58

Cmpd 58

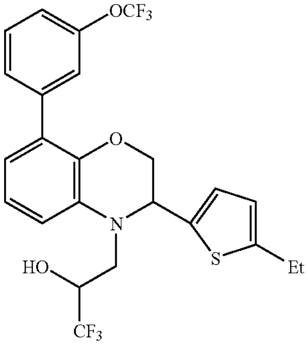

(Higher Rf Cmpd)

3-[3-(5-Ethyl-thiophen-2-yl)-8-(3-trifluoromethoxy-phenyl)-2,3-dihydro-benzo[1,4]oxazin-4-yl]-1,1,1-trifluoro-propan-2-ol Scheme II

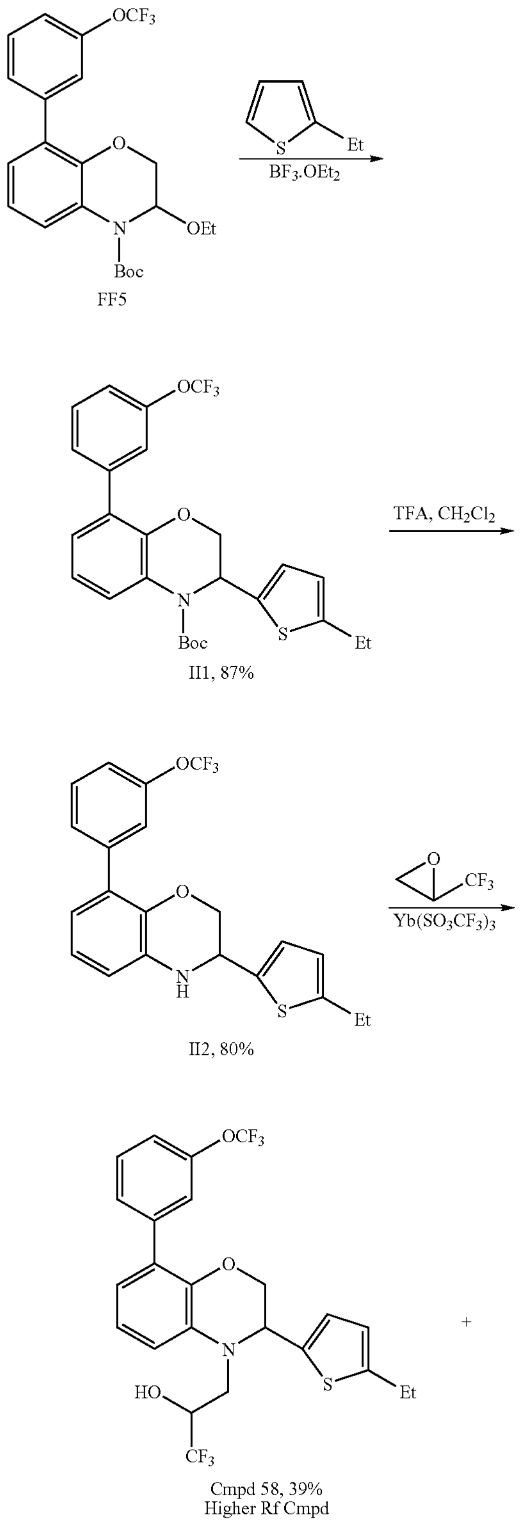

-continued

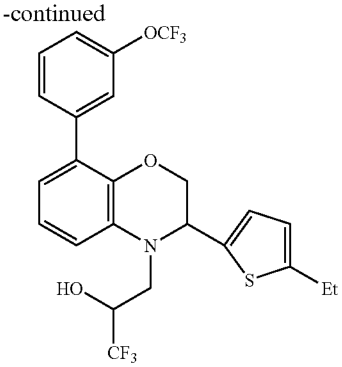

Cmpd 58, 49%
Lower Rf Cmpd

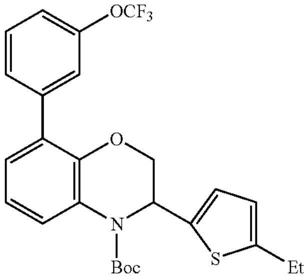

II1

3-(5-Ethyl-thiophen-2-yl)-8-(3-trifluoromethoxy-phenyl)-2,3-dihydro-benzo[1,4]oxazine-4-carboxylic acid tert-butyl ester To a solution of FF5 (75 mg, 0.17 mmol) and 2-ethyl-thiophene (100 mg, 0.89 mmol) in $CH_2Cl_2$ (2 mL) at 4° C. was added $BF_3.OEt_2$ (0.026 mL, 0.21 mmol). The reaction mixture was stirred at 4° C. for 40 min and quenched with saturated $NaHCO_3$. The solution was extracted with $CH_2Cl_2$ and the combined organic extracts were dried ($Na_2SO_4$), concentrated and purified by column chromatography to give 75 mg (87%) of compound II1 as a clear oil: $^1$H NMR (300 MHz, $CDCl_3$) δ 7.89 (d, J=7.0 Hz, 1H), 7.50-7.37 (m, 3H), 7.16 (d, J=7.4 Hz, 1H), 7.01-6.95 (m, 2H), 6.83 (d, J=3.5 Hz, 1H), 6.57 (t, J=3.5 Hz, 1H), 5.85 (s, 1H), 4.57 (dd, J=11.1, 1.7 Hz, 1H), 4.35 (dd, J=11.1, 3.2 Hz, 1H), 2.74 (q, J=7.4 Hz, 2H), 1.57 (s, 9H), 1.24 (t, J=7.5 Hz, 3H); MS (ES) m/z: 528 ($M+H^+$).

II2

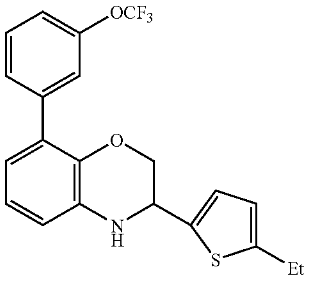

3-(5-Ethyl-thiophen-2-yl)-8-(3-trifluoromethoxy-phenyl)-3,4-dihydro-2H-benzo[1,4]oxazine A mixture of II1 (70 mg, 0.14 mmol) and TFA (0.25 mL) in $CH_2Cl_2$ (1 mL) was stirred at room temperature for 1 h and concentrated. The residue was partitioned between $NaHCO_3$ and $CH_2Cl_2$. The organic layer was dried ($Na_2SO_4$), concentrated and purified by column chromatography to give 45 mg (80%) of compound II2 as a yellow oil: $^1$H NMR (400 MHz, $CDCl_3$) δ 7.51-7.38 (m, 3H), 7.16 (d, J=8.1 Hz, 1H), 6.88-6.73 (m, 2H), 6.74 (d, J=7.6 Hz, 1H), 6.68-6.65 (m, 2H), 4.79 (dd, J=8.1, 2.9 Hz, 1H), 4.34 (dd, J=10.6, 3.0 Hz, 1H), 4.19 (brs, 1H), 4.06 (dd, J=10.5, 8.2 Hz, 1H), 2.82 (q, J=7.5 Hz, 2H), 1.30 (t, J=7.5 Hz, 3H); MS (ES) m/z: 406 ($M+H^+$).

Cmpd 58

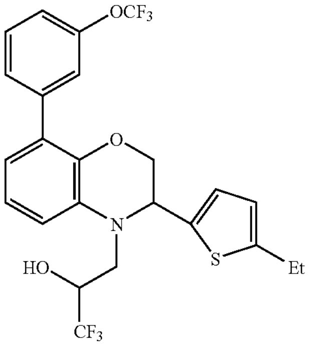

Higher Rf Cmpd

3-[3-(5-Ethyl-thiophen-2-yl)-8-(3-trifluoromethoxy-phenyl)-2,3-dihydro-benzo[1,4]oxazin-4-yl]-1,1,1-trifluoro-propan-2-ol Replacing A2d with II2 and following the same procedure as in the preparation of compound 1 and 2 gave higher Rf compound 58 (39%, solvent for column: 20% EtOAc in hexane) and lower Rf compound 59 (49%). Spectrums of compound 58 are as following: $^1$H NMR (400 MHz, $CDCl_3$) δ 7.50-7.38 (m, 3H), 7.16 (d, J=8.1 Hz, 1H), 6.97 (t, J=7.9 Hz, 1H), 6.84 (d, J=3.4 Hz, 1H), 6.78-6.74 (m, 2H), 6.65 (d, J=3.4 Hz, 1H), 4.92 (m, 1H), 4.34-4.21 (m, 3H), 3.70 (d, J=15.6 Hz, 1H), 3.50 (dd, J=15.6, 9.5 Hz, 1H), 2.80 (q, J=7.5 Hz, 2H), 2.50 (brs, 1H), 1.28 (t, J=7.6 Hz, 3H); MS (ES) m/z: 518 ($M+H^+$).

Example 59

Cmpd 59

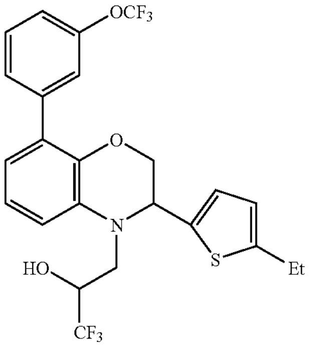

Lower Rf Cmpd

3-[3-(5-Ethyl-thiophen-2-yl)-8-(3-trifluoromethoxy-phenyl)-2,3-dihydro-benzo[1,4]oxazin-4-yl]-1,1,1-trifluoro-propan-2-ol Spectrums of compound 59 are as following: $^1$H NMR (400 MHz, $CDCl_3$) δ 7.51-7.38 (m, 3H), 7.16 (d, J=8.2 Hz, 1H), 6.98 (t, J=8.0 Hz, 1H), 6.84-6.77 (m, 3H), 6.65 (d, J=3.4 Hz, 1H), 4.67 (t, J=2.9 Hz, 1H), 4.34-4.23 (m, 3H), 3.69 (dd, J=15.6, 4.8 Hz, 1H), 3.57 (dd, J=15.5, 7.0 Hz, 1H), 2.78 (q, J=7.5 Hz, 2H), 2.34 (brs, 1H), 1.27 (t, J=7.5 Hz, 3H); MS (ES) m/z: 518 (M+H$^+$).

Example 60

Cmpd 60

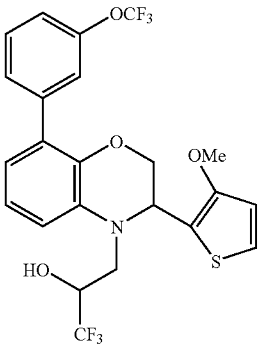

(Higher Rf Cmpd)

1,1,1-Trifluoro-3-[3-(3-methoxy-thiophen-2-yl)-8-(3-trifluoromethoxy-phenyl)-2,3-dihydro-benzo[1,4]oxazin-4-yl]-propan-2-ol Scheme JJ

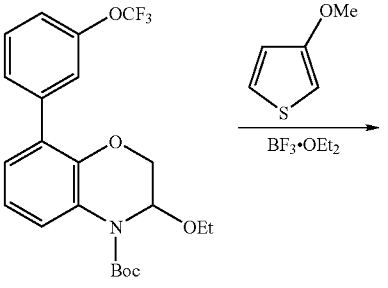

FF5

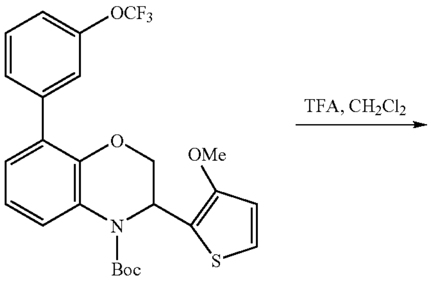

JJ1, 50%

-continued

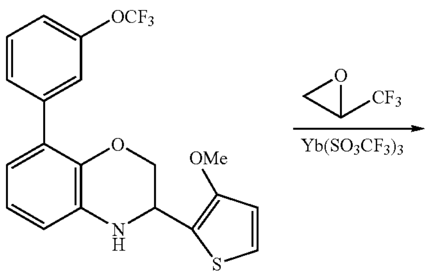

JJ2, 81%

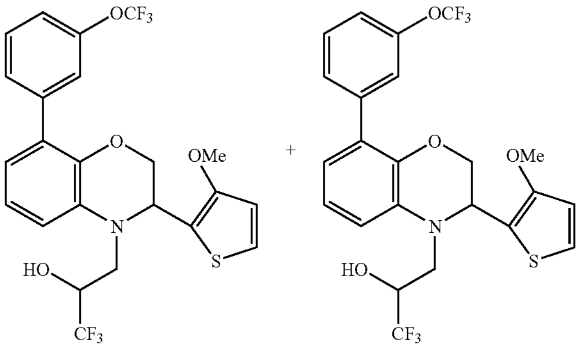

Cmpd 60, 28%
Higher Rf Cmpd

Cmpd 61, 35%
Lower Rf Cmpd

JJ1

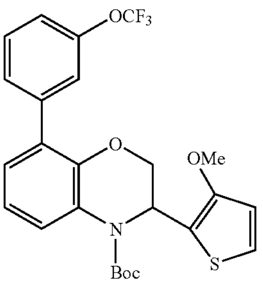

3-(3-Methoxy-thiophen-2-yl)-8-(3-trifluoromethoxy-phenyl)-2,3-dihydro-benzo[1,4]oxazine-4-carboxylic acid tert-butyl ester Replacing 2-ethyl-thiophene with 3-methoxythiophene and following the same procedure as in the preparation of compound II1 gave compound JJ1 (50%): $^1$H NMR (300 MHz, $CDCl_3$) δ 7.88 (d, J=7.9 Hz, 1H), 7.47-7.36 (m, 3H), 7.15 (d, J=8.0 Hz, 1H), 7.03-6.98 (m, 3H), 6.79 (d, J=5.4 Hz, 1H), 6.13 (t, J=2.5 Hz, 1H), 4.46 (dd, J=10.8, 2.0 Hz, 1H), 4.31 (dd, J=10.8, 2.2 Hz, 1H), 3.86 (s, 3H), 1.54 (s, 9H); MS (ES) m/z: 530 (M+Na$^+$).

JJ2

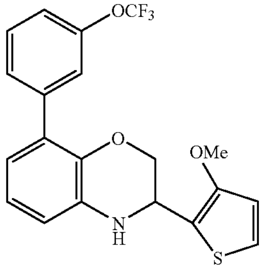

3-(3-Methoxy-thiophen-2-yl)-8-(3-trifluoromethoxy-phenyl)-3,4-dihydro-2H-benzo[1,4]oxazine Replacing II1 with JJ1 and following the same procedure as in the preparation of compound II2 gave compound JJ2 (81%): $^1$H NMR (400 MHz, $CDCl_3$) δ 7.52-7.38 (m, 3H), 7.19-7.12 (m, 2H), 6.89-6.81 (m, 2H), 6.74 (d, J=7.6 Hz, 1H), 6.66 (d, J=7.8 Hz, 1H), 4.98 (dd, J=7.7, 3.0 Hz, 1H), 4.35 (dd, J=10.5, 3.0 Hz, 1H), 4.18 (brs, 1H), 4.06 (dd, J=10.5, 7.8 Hz, 1H), 3.86 (s, 3H); MS (ES) m/z: 408 ($M+H^+$).

Cmpd 60

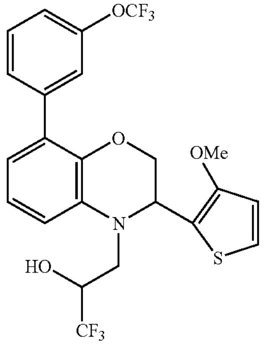

Higher Rf Cmpd 1,1,1-Trifluoro-3-[3-(3-methoxy-thiophen-2-yl)-8-(3-trifluoromethoxy-phenyl)-2,3-dihydro-benzo[1,4]oxazin-4-yl]-propan-2-ol Replacing A2d with JJ2 and following the same procedure as in the preparation of compound 1 and 2 gave higher Rf compound 60 (28%) and lower Rf compound 61 (35%, solvent for column: 20% EtOAc in hexane). Spectrums of compound 60 are as following: $^1$H NMR (300 MHz, $CDCl_3$) δ 7.52-7.38 (m, 3H), 7.21-7.12 (m, 2H), 6.96 (t, J=7.9 Hz, 1H), 6.87 (d, J=5.5 Hz, 1H), 6.76 (d, J=8.0 Hz, 2H), 5.12 (t, J=3.9 Hz, 1H), 4.29 (d, J=3.9 Hz, 2H), 4.24 (m, 1H), 3.90 (s, 3H), 3.67 (dd, J=15.6, 2.6 Hz, 1H), 3.47 (dd, J=15.6, 9.6 Hz, 1H), 2.84 (brs, 1H); MS (ES) m/z: 520 ($M+H^+$).

Example 61

Cmpd 61

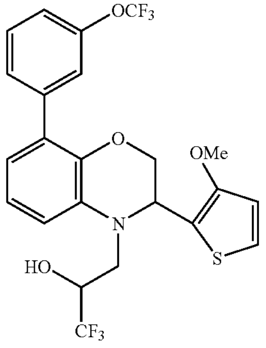

Lower Rf Cmpd 1,1,1-Trifluoro-3-[3-(3-methoxy-thiophen-2-yl)-8-(3-trifluoromethoxy-phenyl)-2,3-dihydro-benzo[1,4]oxazin-4-yl]-propan-2-ol Spectrums of compound 61 are as following: $^1$H NMR (300 MHz, $CDCl_3$) δ 7.53-7.38 (m, 3H), 7.20-7.12 (m, 2H), 6.95 (t, J=7.5 Hz, 1H), 6.86 (d, J=5.5 Hz, 1H), 6.78 (d, J=7.6 Hz, 2H), 4.93 (t, J=2.9 Hz, 1H), 4.41-4.26 (m, 3H), 3.88 (s, 3H), 3.65-3.49 (m, 2H), 2.60 (brs, 1H); MS (ES) m/z: 520 ($M+H^+$).

Example 62

Cmpd 62

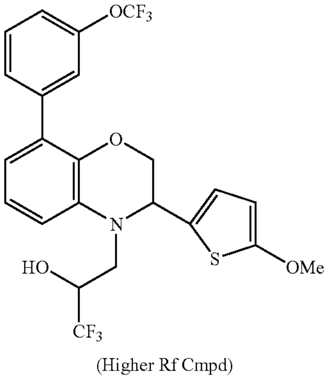

(Higher Rf Cmpd)

1,1,1-Trifluoro-3-[3-(5-methoxy-thiophen-2-yl)-8-(3-trifluoromethoxy-phenyl)-2,3-dihydro-benzo[1,4]oxazin-4-yl]-propan-2-ol Scheme KK

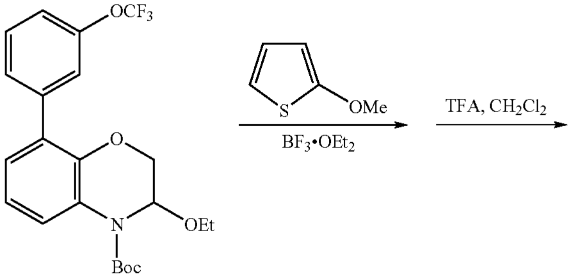

FF5

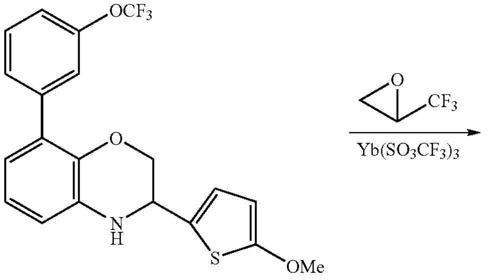

KK1

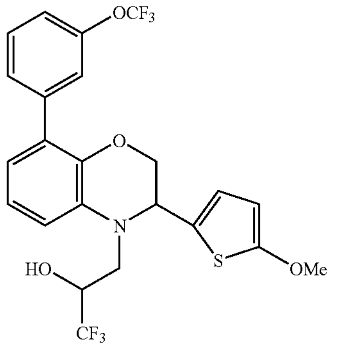

Cmpd 62
Higher Rf Cmpd

+

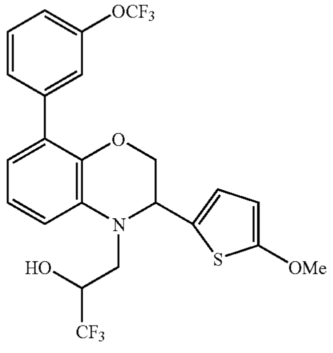

Cmpd 63
Lower Rf Cmpd

-continued

KK1

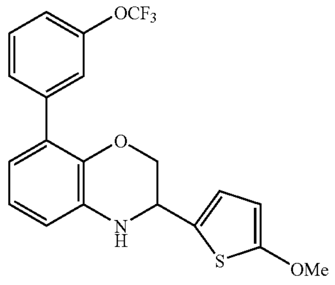

3-(5-Methoxy-thiophen-2-yl)-8-(3-trifluoromethoxy-phenyl)-3,4-dihydro-2H-benzo[1,4]oxazine Replacing 3-methoxy-thiophene with 2-methoxythiophene and following the same procedure as in the preparation of compound JJ1 gave low yield of Boc-protected intermediate (not pure).

Replacing JJ1 with the above intermediate and following the same procedure as in the preparation of compound JJ2 gave compound KK1: $^1$H NMR (300 MHz, $CDCl_3$) δ 7.52-7.38 (m, 3H), 7.17 (d, J=7.5 Hz, 1H), 6.89-6.80 (m, 2H), 6.74 (d, J=7.5 Hz, 1H), 6.66 (d, J=7.7 Hz, 1H), 6.62 (d, J=5.8 Hz, 1H), 4.75 (dd, J=8.2, 3.0 Hz, 1H), 4.31 (dd, J=10.5, 3.1 Hz, 1H), 4.11-4.03 (m, 2H), 3.95 (s, 3H); MS (ES) m/z: 408 ($M+H^+$).

Cmpd 62

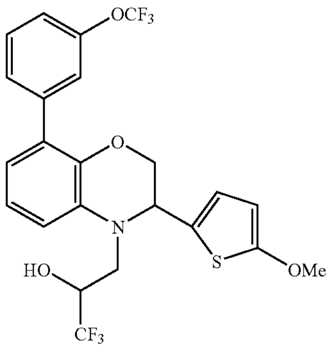

(Higher Rf Cmpd)

1,1,1-Trifluoro-3-[3-(5-methoxy-thiophen-2-yl)-8-(3-trifluoromethoxy-phenyl)-2,3-dihydro-benzo[1,4]oxazin-4-yl]-propan-2-ol Replacing A2d with KK1 and following the same procedure as in the preparation of compound 1 and 2 gave higher Rf compound 62 and lower Rf compound 63 (solvent for column: 20% EtOAc in hexane). Spectrums of compound 62 are as following: $^1$H NMR (400 MHz, $CDCl_3$) δ 7.49-7.38 (m, 3H), 7.15 (d, J=7.9 Hz, 1H), 6.96 (t, J=7.9 Hz, 1H), 6.79-6.74 (m, 2H), 6.67 (d, J=5.9 Hz, 1H), 6.59 (d, J=5.9 Hz, 1H), 4.85 (t, J=4.3 Hz, 1H), 4.25-4.15 (m, 3H), 3.95 (s, 3H), 3.66 (dd, J=15.6, 2.4 Hz, 1H), 3.41 (dd, J=15.6, 9.6 Hz, 1H), 2.60 (brs, 1H); MS (ES) m/z: 520 ($M+H^+$).

Example 63

Cmpd 63

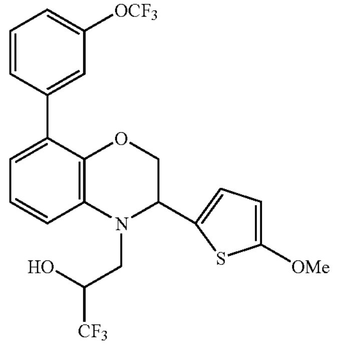

Lower Rf Cmpd 1,1,1-Trifluoro-3-[3-(5-methoxy-thiophen-2-yl)-8-(3-trifluoromethoxy-phenyl)-2,3-dihydro-benzo[1,4]oxazin-4-yl]-propan-2-ol Spectrums of compound 63 are as following: $^1$H NMR (400 MHz, $CDCl_3$) δ 7.49-7.38 (m, 3H), 7.16 (d, J=8.2 Hz, 1H), 6.97 (t, J=7.9 Hz, 1H), 6.81-6.75 (m, 2H), 6.70 (d, J=6.0 Hz, 1H), 6.60 (d, J=5.7 Hz, 1H), 4.66 (t, J=3.5 Hz, 1H), 4.34-4.22 (m, 3H), 3.96 (s, 3H), 3.57-3.55 (m, 2H), 2.37 (brs, 1H); MS (ES) m/z: 520 ($M+H^+$).

Example 64

Cmpd 64

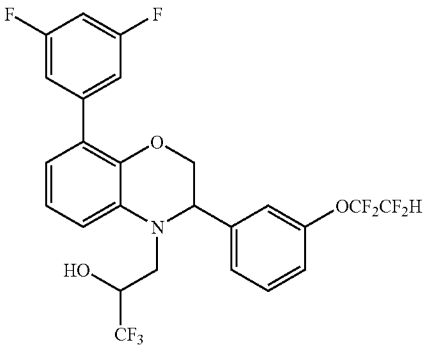

(Higher Rf Cmpd)

3-{8-(3,5-Difluoro-phenyl)-3-[3-(1,1,2,2-tetrafluoro-ethoxy)-phenyl]-2,3-dihydro-benzo[1,4]oxazin-4-yl}-1,1,1-trifluoro-propan-2-ol Scheme LL

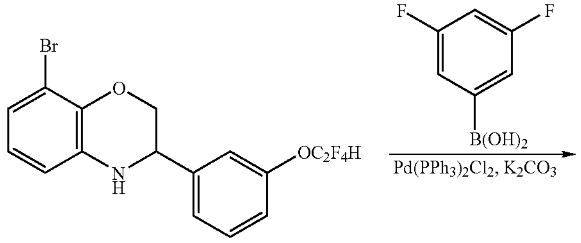

A2c

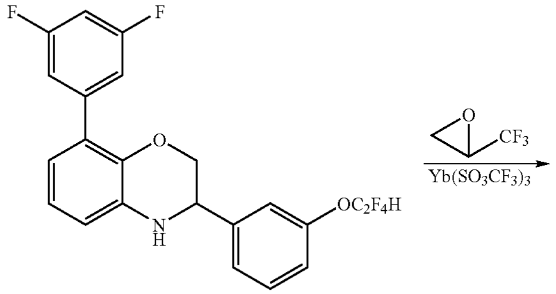

LL1, 87%

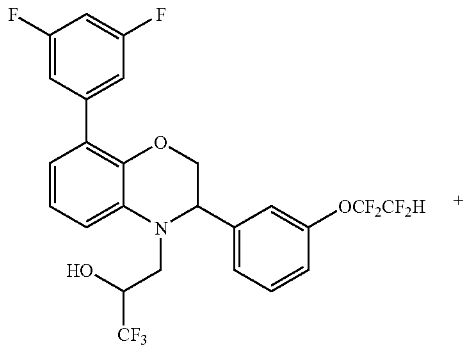

Cmpd 64, 35%
Higher Rf Cmpd

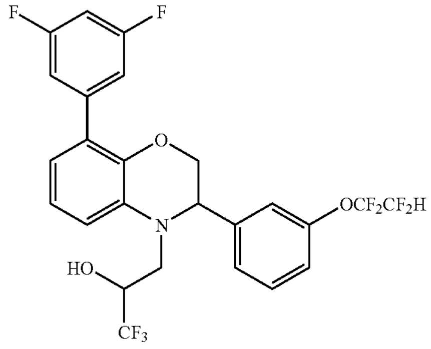

Cmpd 65, 45%
Lower Rf Cmpd

-continued

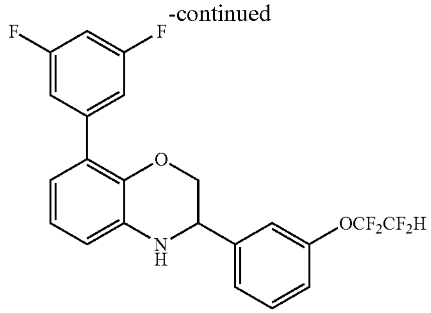

LL1

8-(3,5-Difluoro-phenyl)-3-[3-(1,1,2,2-tetrafluoro-ethoxy)-phenyl]-3,4-dihydro-2H-benzo[1,4]oxazine Replacing 3-trifluoromethoxy-benzene-boronic acid with 3,5-difluoro-benzene-boronic acid and following the same procedure as in the preparation of compound A2d gave compound LL1: $^1$H NMR (300 MHz, $CDCl_3$) δ 7.41 (t, J=7.9 Hz, 1H), 7.35-7.19 (m, 3H), 7.09 (d, J=2.2 Hz, 1H), 7.06 (d, J=2.1 Hz, 1H), 6.88 (t, J=7.7 Hz, 1H), 6.29-6.69 (m, 3H), 5.90 (tt, J=53.1, 2.7 Hz, 1H), 4.56 (dd, J=7.2, 2.5 Hz, 1H), 4.32 (d, J=8.3 Hz, 1H), 4.14 (brs, 1H), 3.98 (dd, J=10.6, 8.3 Hz, 1H); MS (ES) m/z: 440 (M+H$^+$).

Cmpd 64

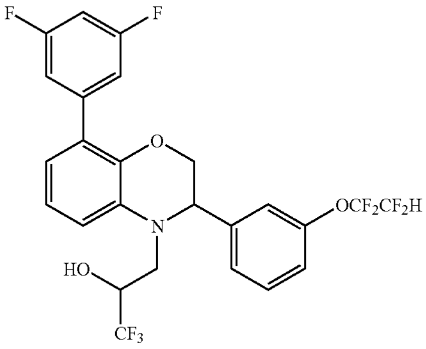

Higher Rf Cmpd

3-{8-(3,5-Difluoro-phenyl)-3-[3-(1,1,2,2-tetrafluoro-ethoxy)-phenyl]-2,3-dihydro-benzo[1,4]oxazin-4-yl}-1,1,1-trifluoro-propan-2-ol Replacing A2d with LL1 and following the same procedure as in the preparation of compound 1 and 2 gave higher Rf compound 64 and lower Rf compound 65 (solvent for column: 20% EtOAc in hexane). Spectrums of compound 64 are as following: $^1$H NMR (300 MHz, $CDCl_3$) δ 7.39 (t, J=7.9 Hz, 1H), 7.19 (s, 1H), 7.17 (s, 1H), 7.11 (s, 1H), 7.08-6.97 (m, 3H), 6.83-6.69 (m, 3H), 5.89 (tt, J=53.1, 2.8 Hz, 1H), 4.86 (t, J=3.8 Hz, 1H), 4.39 (m, 1H), 4.27 (dd, J=10.9, 3.2 Hz, 1H), 4.18 (dd, J=11.0, 5.7 Hz, 1H), 3.82 (t, J=15.5 Hz, 1H), 3.33 (dd, J=15.7, 9.6 Hz, 1H), 2.44 (d, J=3.7 Hz, 1H); MS (ES) m/z: 552 (M+H$^+$).

Example 65

Cmpd 65

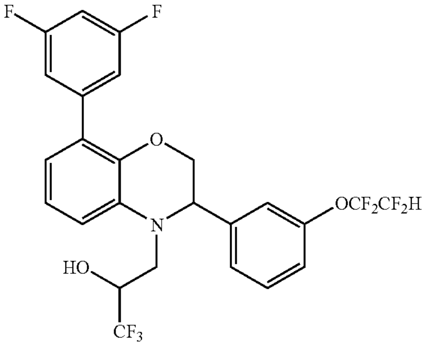

Lower Rf Cmpd

3-{8-(3,5-Difluoro-phenyl)-3-[3-(1,1,2,2-tetrafluoro-ethoxy)-phenyl]-2,3-dihydro-benzo[1,4]oxazin-4-yl}-1,1,1-trifluoro-propan-2-ol Spectrums of compound 65 are as following: $^1$H NMR (300 MHz, $CDCl_3$) δ 7.37 (t, J=7.9 Hz, 1H), 7.21-6.99 (m, 6H), 6.90 (d, J=7.3 Hz, 1H), 6.79-6.69 (m, 2H), 5.88 (tt, J=53.1, 2.8 Hz, 1H), 4.55 (t, J=2.8 Hz, 1H), 4.37-4.21 (m, 3H), 3.70 (dd, J=15.7, 6.4 Hz, 1H), 3.56 (dd, J=15.7, 5.1 Hz, 1H), 2.28 (d, J=4.5 Hz, 1H); MS (ES) m/z: 552 (M+H$^+$).

Example 66

Cmpd 66

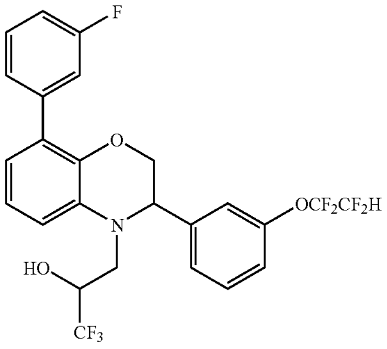

(Higher Rf Cmpd)

1,1,1-Trifluoro-3-{8-(3-fluoro-phenyl)-3-[3-(1,1,2,2-tetrafluoro-ethoxy)-phenyl]-2,3-dihydro-benzo[1,4]oxazin-4-yl}-propan-2-ol Scheme MM

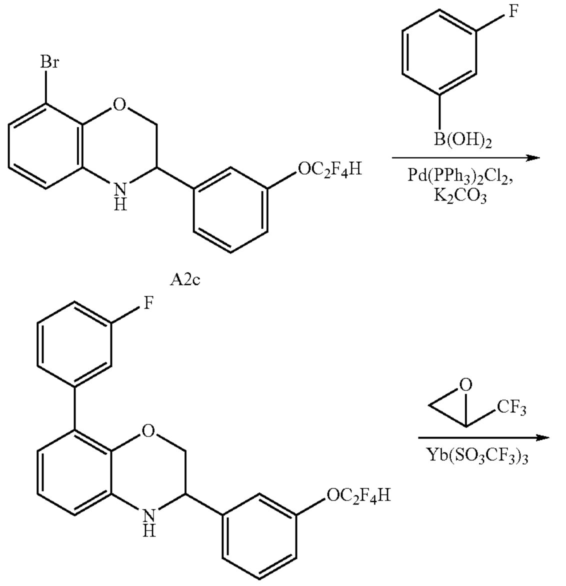

A2c

MM1, 86%

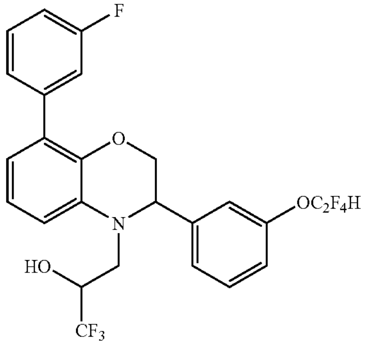

Cmpd 66, 44%
Higher Rf Cmpd

+

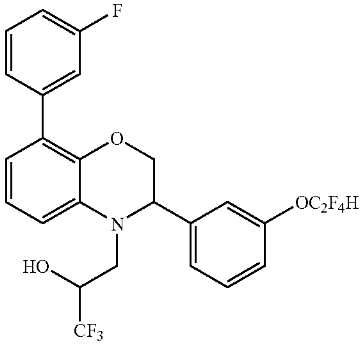

Cmpd 67, 47%
Lower Rf Cmpd

-continued

MM1

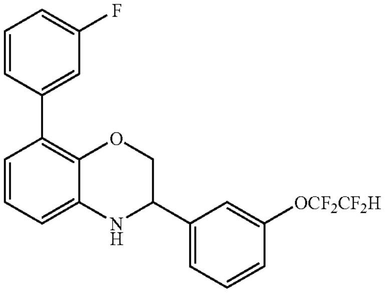

8-(3-Fluoro-phenyl)-3-[3-(1,1,2,2-tetrafluoro-ethoxy)-phenyl]-3,4-dihydro-2H-benzo[1,4]oxazine Replacing 3-trifluoromethoxy-benzene-boronic acid with 3-fluoro-benzene-boronic acid and following the same procedure as in the preparation of compound A2d gave compound MM1: $^1$H NMR (400 MHz, $CDCl_3$) δ 7.43-7.23 (m, 6H), 7.20 (d, J=8.0 Hz, 1H), 7.00 (bt, J=8.0 Hz, 1H), 6.89 (t, J=7.7 Hz, 1H), 6.77 (d, J=7.6 Hz, 1H), 6.72 (d, J=7.8 Hz, 1H), 5.91 (tt, J=53.1, 2.7 Hz, 1H), 4.58 (d, J=8.1 Hz, 1H), 4.31 (dt, J=10.7, 2.3 Hz, 1H), 4.13 (brs, 1H), 3.98 (dd, J=10.6, 8.4 Hz, 1H).

Cmpd 66

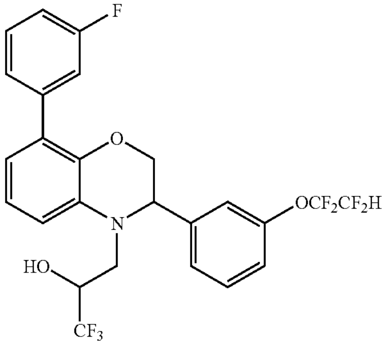

Higher Rf Cmpd 1,1,1-Trifluoro-3-{8-(3-fluoro-phenyl)-3-[3-(1,1,2,2-tetrafluoro-ethoxy)-phenyl]-2,3-dihydro-benzo[1,4]oxazin-4-yl}-propan-2-ol Replacing A2d with MM1 and following the same procedure as in the preparation of compound 1 and 2 gave compound higher Rf compound 66 and lower Rf compound 67 (solvent for column: 20% EtOAc in hexane). Spectrums of compound 66 are as following: $^1$H NMR (300 MHz, $CDCl_3$) δ 7.41-7.23 (m, 6H), 7.12 (s, 1H), 7.02-6.95 (m, 2H), 6.81-6.76 (m, 2H), 5.88 (tt, J=53.1, 2.8 Hz, 1H), 4.85 (t, J=3.8 Hz, 1H), 4.46-4.32 (m, 1H), 4.26 (dd, J=10.9, 3.2 Hz, 1H), 4.16

(dd, J=10.9, 4.7 Hz, 1H), 3.82 (d, J=15.7 Hz, 1H), 3.32 (dd, J=15.7, 9.6 Hz, 1H); MS (ES) m/z: 534 (M+H$^+$).

Example 67

Cmpd 67

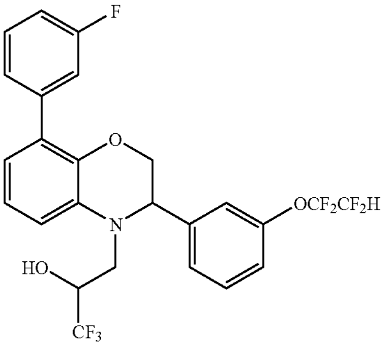

Lower Rf Cmpd 1,1,1-Trifluoro-3-{8-(3-fluoro-phenyl)-3-[3-(1,1,2,2-tetrafluoro-ethoxy)-phenyl]-2,3-dihydro-benzo[1,4]oxazin-4-yl}-propan-2-ol Spectrums of compound 67 are as following: $^1$H NMR (300 MHz, $CDCl_3$) δ 7.40-7.12 (m, 6H), 7.08 (s, 1H), 7.05-6.94 (m, 2H), 6.88 (d, J=8.0 Hz, 1H), 6.78 (d, J=7.5 Hz, 1H), 5.88 (tt, J=53.1, 2.7 Hz, 1H), 4.54 (t, J=2.8 Hz, 1H), 4.31 (dd, J=12.3, 6.4 Hz, 1H), 4.24 (d, J=3.0 Hz, 2H), 3.69 (dd, J=15.7, 6.5 Hz, 1H), 3.56 (dd, J=15.7, 5.2 Hz, 1H), 2.31 (brs, 1H); MS (ES) m/z: 534 (M+H$^+$).

Example 68

Cmpd 68

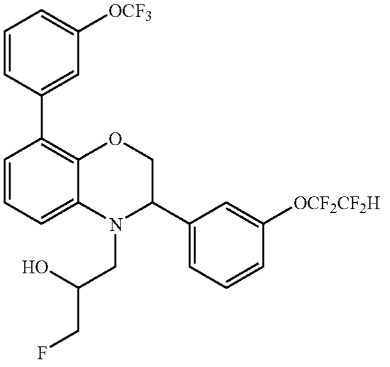

(Higher Rf Cmpd)

1-Fluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Scheme OO

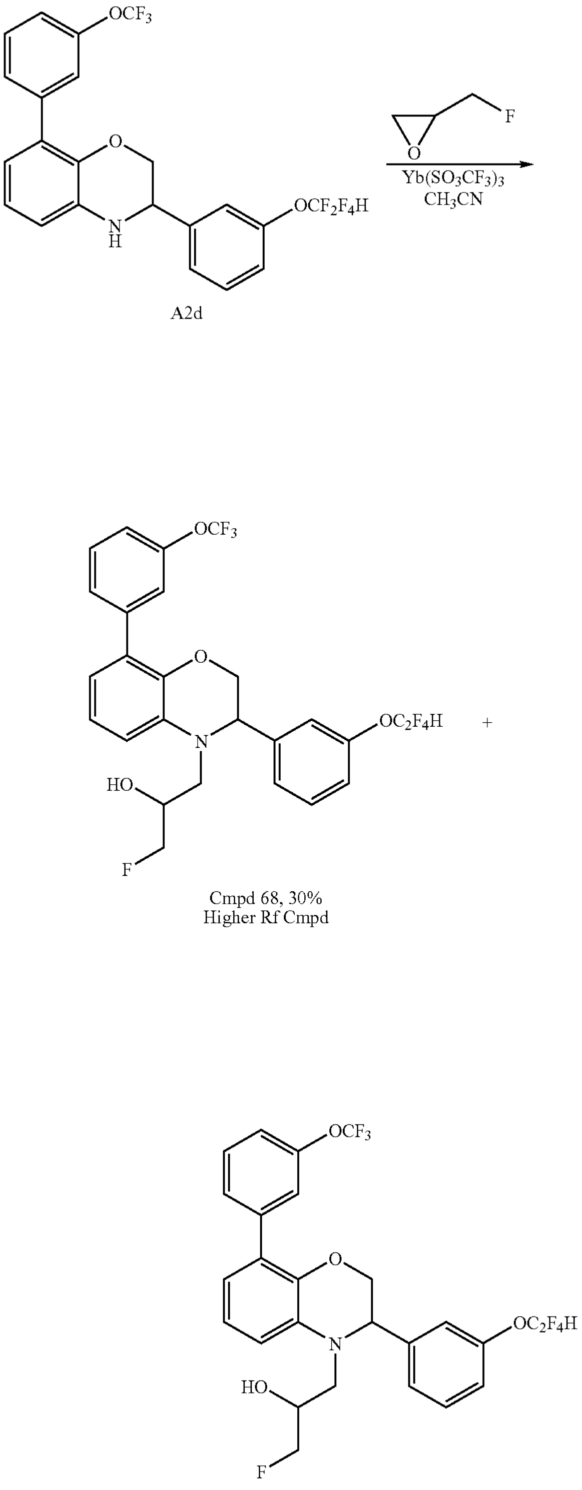

A2d

Cmpd 68, 30%
Higher Rf Cmpd

Cmpd 69, 35%
Lower Rf Cmpd

-continued

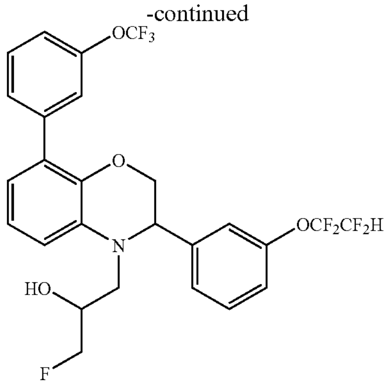

Cmpd 68
Higher Rf Cmpd

1-Fluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Replacing 2-trifluoromethyl-oxirane with 2-fluoromethyl-oxirane and following the same procedure as in the preparation of compound 1 and 2 gave higher Rf compound 68 and lower Rf compound 69 (solvent for column: 20% EtOAc in hexane). Spectrums of compound 68 are as following: $^1$H NMR (400 MHz, $CDCl_3$) δ 7.43-7.22 (m, 4H), 7.20-7.09 (m, 4H), 6.99 (t, J=7.9 Hz, 1H), 6.83 (d, J=8.2 Hz, 1H), 6.75 (d, J=7.6 Hz, 1H), 5.88 (tt, J=53.1, 2.7 Hz, 1H), 4.79 (t, J=3.3 Hz, 1H), 4.51-4.18 (m, 5H), 3.60 (dd, J=15.4, 3.0 Hz, 1H), 3.22 (dd, J=15.4, 8.8 Hz, 1H), 2.17 (brs, 1H); MS (ES) m/z: 564 $(M+H^+)$.

Example 69

Cmpd 69

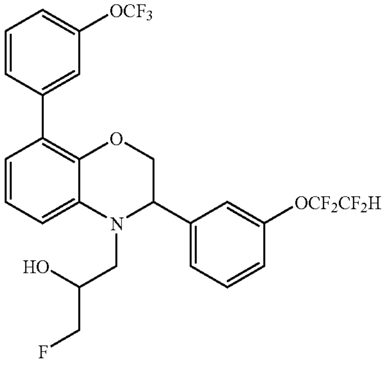

Lower Rf Cmpd

1-Fluoro-3-[3-[3-(1,1,2,2-tetrafluoro-ethoxy)-phenyl]-8-(3-trifluoromethoxy-phenyl)-2,3-dihydro-benzo[1,4]oxazin-4-yl]-propan-2-ol Spectrums of compound 69 are as following: $^1$H NMR (400 MHz, $CDCl_3$) δ 7.43-7.32 (m, 4H), 7.14 (m, 3H), 7.08 (s, 1H), 7.00 (t, J=7.9 Hz, 1H), 6.90 (d, J=8.1 Hz, 1H), 6.75 (d, J=7.6 Hz, 1H), 5.88 (tt, J=53.1, 2.6 Hz, 1H), 4.61-4.39 (m, 3H), 4.29 (dd, J=10.9, 2.9 Hz, 1H), 4.22 (dd, J=11.0, 3.2 Hz, 1H), 4.13 (m, 1H), 3.61 (dd, J=15.2, 5.8 Hz, 1H), 3.32 (dd, J=15.2, 7.3 Hz, 1H), 2.04 (brs, 1H); MS (ES) m/z: 564 $(M+H^+)$.

Example 70

Cmpd 70

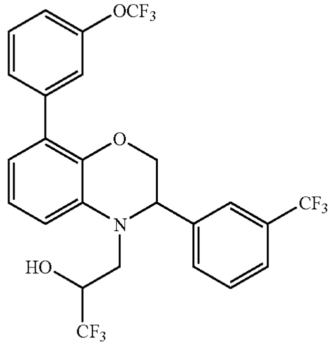

(Higher Rf Cmpd)

1,1,1-Trifluoro-3-[8-(3-trifluoromethoxy-phenyl)-3-(3-trifluoromethyl-phenyl)-2,3-dihydro-benzo[1,4]oxazin-4-yl]-propan-2-ol Scheme PP

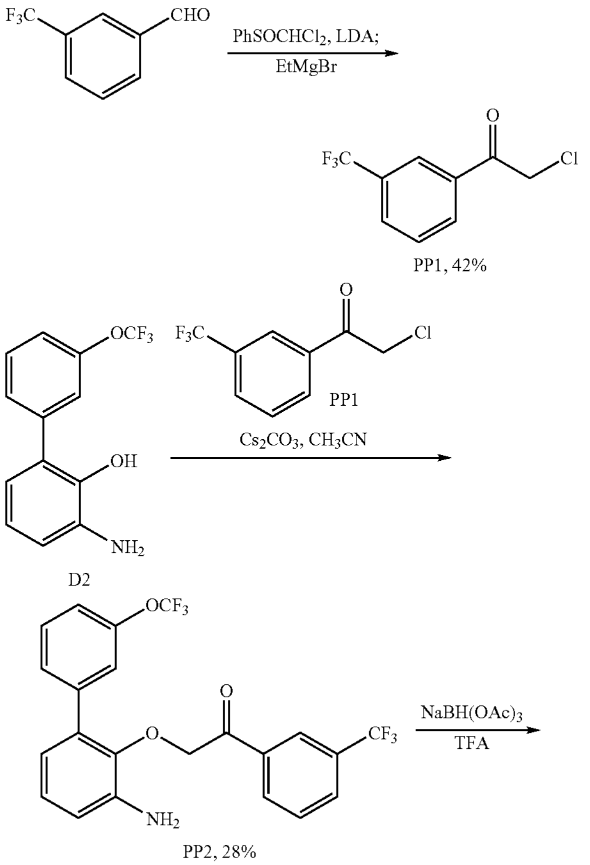

-continued

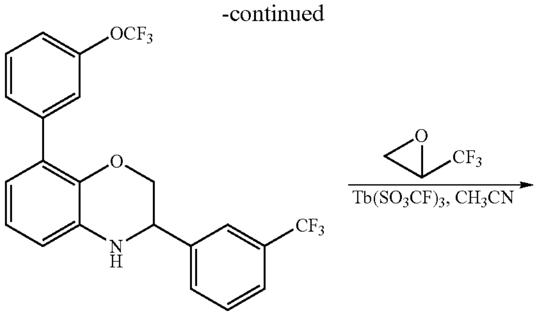

PP3, 91%

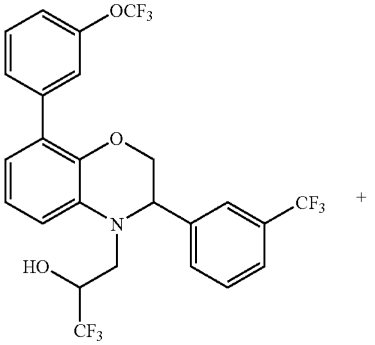

+

Cmpd 70, 34%
Higher Rf Cmpd

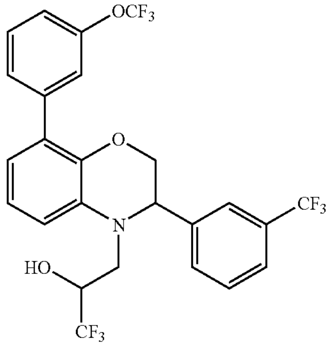

Cmpd 71, 39%
Lower Rf Cmpd

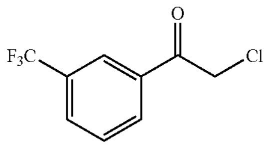

PP1

2-Chloro-1-(3-trifluoromethyl-phenyl)ethanone

Replacing 3-(1,1,2,2-tetrafluoro-ethoxy)-benzaldehyde with 3-trifluoro-benzaldehyde and following the same procedure as in the preparation of compound A2a gave compound PP1 (42%): $^1$H NMR (300 MHz, $CDCl_3$) δ 8.22 (s, 1H), 8.16 (d, J=7.8 Hz, 1H), 7.89 (d, J=7.8 Hz, 1H), 7.67 (t, J=7.9 Hz, 1H), 4.71 (s, 2H).

PP2

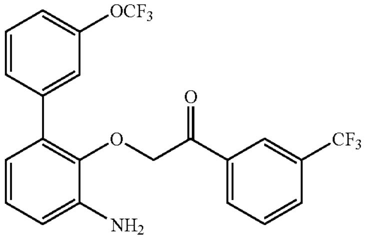

2-(3-Amino-3'-trifluoromethoxy-biphenyl-2-yloxy)-1-(3-trifluoro methyl-phenyl)-ethanone Replacing D2 with PP1 and following the same procedure as in the preparation of compound D3 gave compound PP2 (28%): $^1$H NMR (300 MHz, $CDCl_3$) δ 8.25 (s, 1H), 8.09 (d, J=8.0 Hz, 1H), 7.76 (d, J=7.8 Hz, 1H), 7.62 (t, J=7.8 Hz, 1H), 7.51-7.41 (m, 3H), 7.30-7.20 (m, 3H), 7.14 (t, J=7.7 Hz, 1H), 5.07 (s, 2H); MS (ES) m/z: 438 ($M-H_2O+H^+$).

PP3

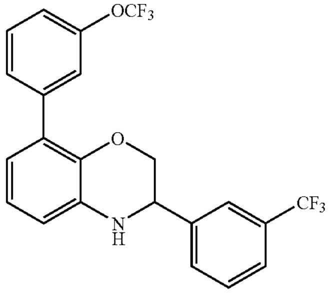

8-(3-Trifluoromethoxy-phenyl)-3-(3-trifluoromethyl-phenyl)-3,4-dihydro-2H-benzo[1,4]oxazine Replacing D3 with PP2 and following the same procedure as in the preparation of compound D4 gave compound PP3 (91%): $^1$H NMR (300 MHz, $CDCl_3$) δ 7.69 (s, 1H), 7.62 (m, 2H), 7.53-7.38 (m, 4H), 7.16 (d, J=8.1 Hz, 1H), 6.90 (t, J=7.8 Hz, 1H), 6.79-6.70 (m, 2H), 4.63 (bd, J=8.2 Hz, 1H), 4.34-4.30 (m, 1H), 4.14 (brs, 1H), 4.00 (dd, J=10.3, 8.6 Hz, 1H); MS (ES) m/z: 440 ($M+H^+$).

Cmpd 70

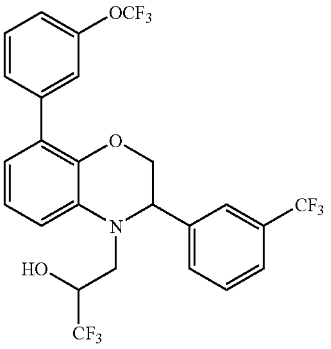

Higher Rf Cmpd 1,1,1-Trifluoro-3-[8-(3-trifluoromethoxy-phenyl)-3-(3-trifluoromethyl-phenyl)-2,3-dihydro-benzo[1,4]oxazin-4-yl]propan-2-ol Replacing A2d with PP3 and following the same procedure as in the preparation of compound 1 and 2 gave higher Rf compound 70 (34%) and lower Rf compound 71 (39%, solvent for column: 20% EtOAc in hexane). Spectrums of compound 70 are as following: $^1$H NMR (300 MHz, $CDCl_3$) δ 7.51-7.33 (m, 7H), 7.13 (d, J=7.3 Hz, 1H), 7.02 (t, J=7.9 Hz, 1H), 6.78 (m, 2H), 4.94 (t, J=3.8 Hz, 1H), 4.44 (m, 1H), 4.28 (dd, J=11.0, 3.2 Hz, 1H), 4.17 (dd, J=11.0, 4.7 Hz, 1H), 3.85 (d, J=15.7 Hz, 1H), 3.28 (dd, J=15.7, 9.6 Hz, 1H), 2.45 (d, J=3.8 Hz, 1H); MS (ES) m/z: 552 (M+H$^+$).

Example 71

Cmpd 71

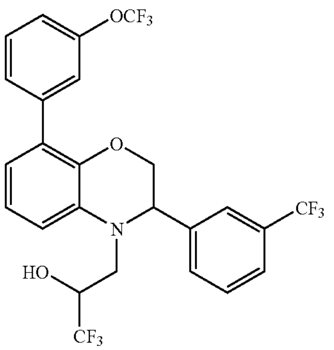

Lower Rf Cmpd 1,1,1-Trifluoro-3-[8-(3-trifluoromethoxy-phenyl)-3-(3-trifluoromethyl-phenyl)-2,3-dihydro-benzo[1,4]oxazin-4-yl]-propan-2-ol Spectrums of compound 71 are as following: $^1$H NMR (300 MHz, $CDCl_3$) δ 7.60-7.31 (m, 7H), 7.13 (m, 1H), 7.03 (t, J=7.8 Hz, 1H), 6.90 (d, J=8.2 Hz, 1H), 6.79 (d, J=7.6 Hz, 1H), 4.60 (t, J=3.0 Hz, 1H), 4.37-4.19 (m, 3H), 3.71 (dd, J=15.7, 6.5 Hz, 1H), 3.52 (dd, J=15.7, 5.2 Hz, 1H), 2.30 (brs, 1H); MS (ES) m/z: 552 (M+H$^+$).

Example 72

Cmpd 72

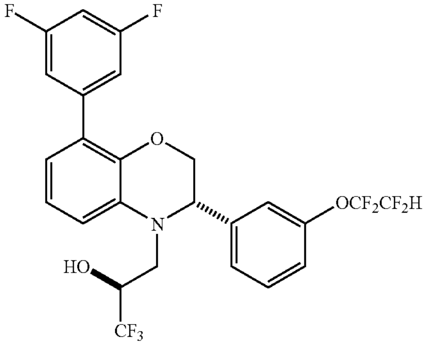

4H-1,4-Benzoxazine-4-ethanol, 8-(3,5-difluorophenyl)-2,3-dihydro-3-[3-(1,1,2,2-tetrafluoroethoxy)phenyl]-α-(trifluoromethyl)-, (3S,αS)—

Scheme QQ

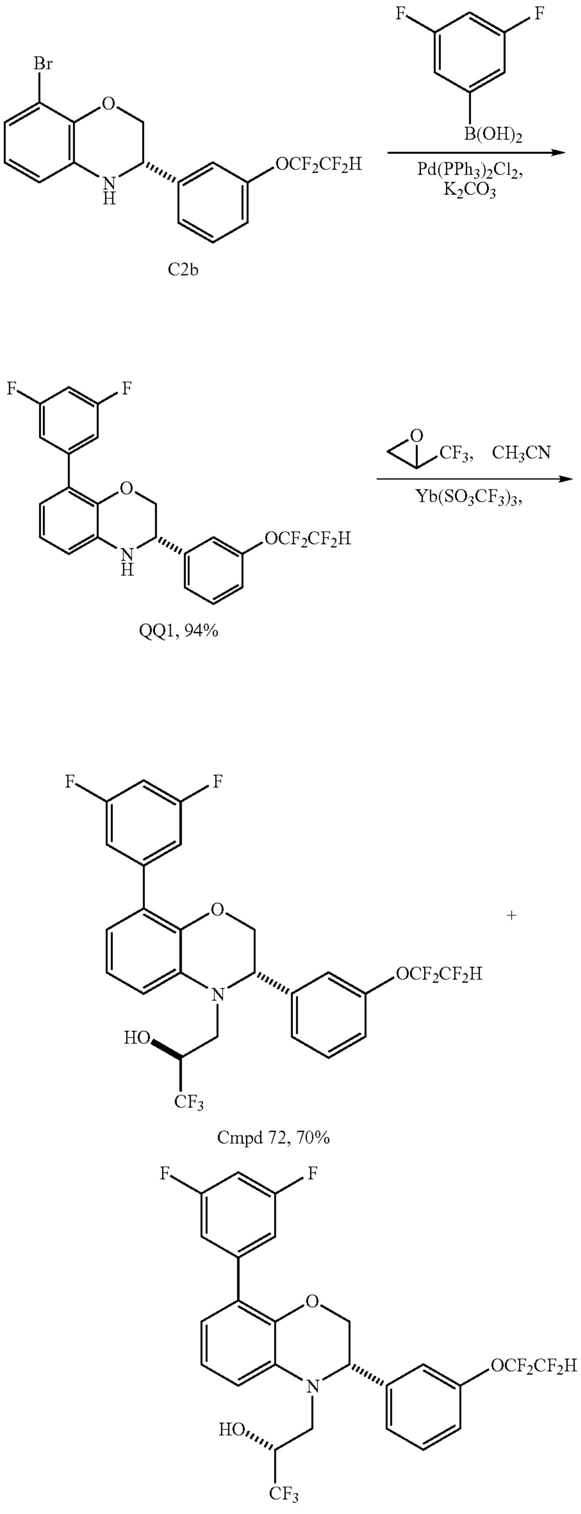

C2b

QQ1, 94%

Cmpd 72, 70%

Cmpd 73, 14%

-continued

QQ1

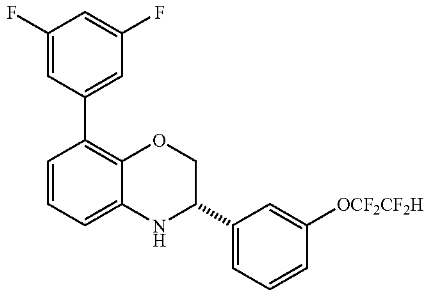

2H-1,4-Benzoxazine, 8-(3,5-difluorophenyl)-3,4-dihydro-3-[3-(1,1,2,2-tetrafluoroethoxy)phenyl]-, (3S)—

Replacing C2b with A2c and following the same procedure as in the preparation of compound LL1 gave compound QQ1: $^1$H NMR (300 MHz, $CDCl_3$) δ 7.41 (t, J=7.9 Hz, 1H), 7.35-7.19 (m, 3H), 7.09 (d, J=2.2 Hz, 1H), 7.06 (d, J=2.1 Hz, 1H), 6.88 (t, J=7.7 Hz, 1H), 6.29-6.69 (m, 3H), 5.90 (tt, J=53.1, 2.7 Hz, 1H), 4.56 (dd, J=7.2, 2.5 Hz, 1H), 4.32 (d, J=8.3 Hz, 1H), 4.14 (brs, 1H), 3.98 (dd, J=10.6, 8.3 Hz, 1H); MS (ES) m/z: 440 (M+H$^+$).

Cmpd 72

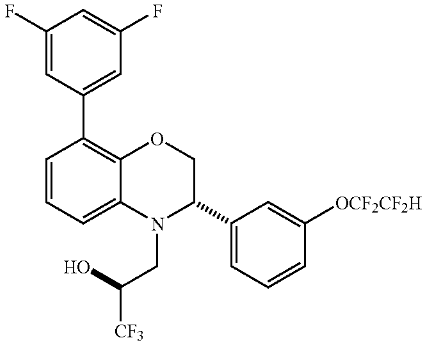

4H-1,4-Benzoxazine-4-ethanol, 8-(3,5-difluorophenyl)-2,3-dihydro-3-[3-(1,1,2,2-tetrafluoroethoxy)phenyl]-α-(trifluoromethyl)-, (3S,αS)—

Replacing A2d with QQ1 and following the same procedure as in the preparation of compound 1 and 2 gave compound 72 and 73. Spectrums of compound 72 are as following: $[\alpha]^{20}_D$ −88.8° (c=1, $CHCl_3$); $^1$H NMR (300 MHz, $CDCl_3$) δ 7.39 (t, J=7.9 Hz, 1H), 7.19 (s, 1H), 7.17 (s, 1H), 7.11 (s, 1H), 7.08-6.97 (m, 3H), 6.83-6.69 (m, 3H), 5.89 (tt, J=53.1, 2.8 Hz, 1H), 4.86 (t, J=3.8 Hz, 1H), 4.39 (m, 1H), 4.27 (dd, J=10.9, 3.2 Hz, 1H), 4.18 (dd, J=11.0, 5.7 Hz, 1H), 3.82 (t, J=15.5 Hz, 1H), 3.33 (dd, J=15.7, 9.6 Hz, 1H), 2.44 (d, J=3.7 Hz, 1H); MS (ES) m/z: 552 (M+H$^+$).

Example 73

Cmpd 73

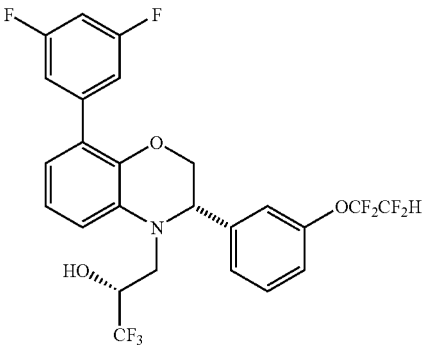

4H-1,4-Benzoxazine-4-ethanol, 8-(3,5-difluorophenyl)-2,3-dihydro-3-[3-(1,1,2,2-tetrafluoroethoxy)phenyl]-α-(trifluoromethyl)-, (3S,αR)—

Spectrums of compound 73 are as following: $^1$H NMR (300 MHz, $CDCl_3$) δ 7.37 (t, J=7.9 Hz, 1H), 7.21-6.99 (m, 6H), 6.90 (d, J=7.3 Hz, 1H), 6.79-6.69 (m, 2H), 5.88 (tt, J=53.1, 2.8 Hz, 1H), 4.55 (t, J=2.8 Hz, 1H), 4.37-4.21 (m, 3H), 3.70 (dd, J=15.7, 6.4 Hz, 1H), 3.56 (dd, J=15.7, 5.1 Hz, 1H), 2.28 (d, J=4.5 Hz, 1H); MS (ES) m/z: 552 (M+H$^+$).

Example 74

Cmpd 74

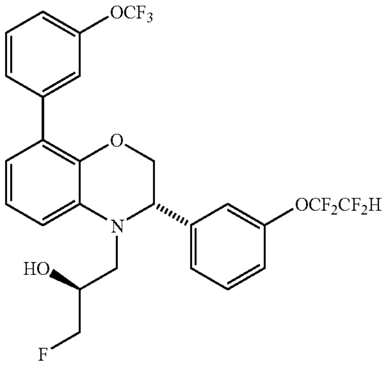

4H-1,4-Benzoxazine-4-ethanol, 2,3-dihydro-α-fluoromethyl-3-[3-(1,1,2,2-tetrafluoroethoxy)phenyl]-8-[3-(trifluoromethoxy)phenyl]-, (3S,αR)—

Scheme RR

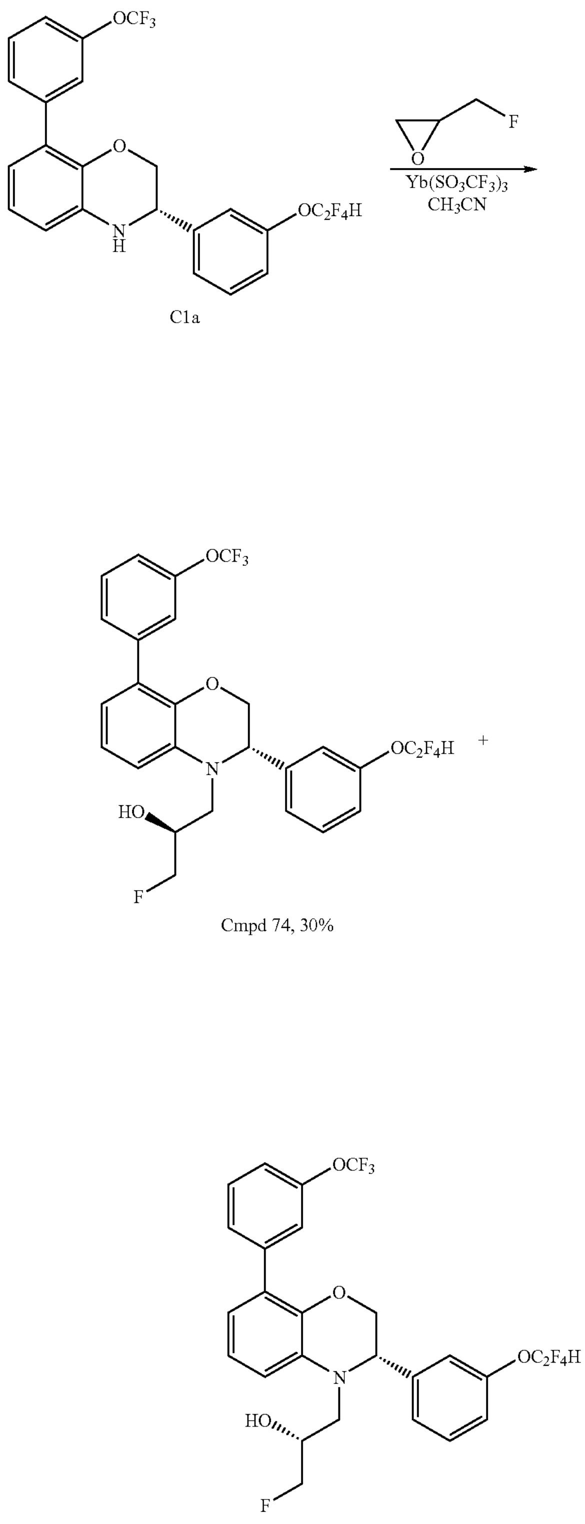

Cla

Cmpd 74, 30%

Cmpd 75, 22%

-continued

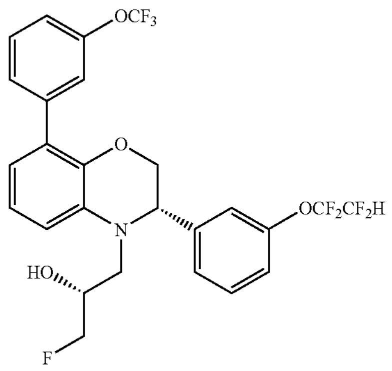

Cmpd 74

4H-1,4-Benzoxazine-4-ethanol, 2,3-dihydro-α-fluoromethyl-3-[3-(1,1,2,2-tetrafluoroethoxy)phenyl]-8-[3-(trifluoromethoxy)phenyl]-, (3S,αR)—

Replacing A2d with C1a and following the same procedure as in the preparation of compound 68 and 69 gave compound 74 (30%) and 75 (22%) (solvent for column: 25% EtOAc in hexane). Spectrums of compound 74 are as following: $[\alpha]^{20}_D$ −63.4° (c=1, $CHCl_3$); $^1H$ NMR (400 MHz, $CDCl_3$) δ 7.43-7.22 (m, 4H), 7.20-7.09 (m, 4H), 6.99 (t, J=7.9 Hz, 1H), 6.83 (d, J=8.2 Hz, 1H), 6.75 (d, J=7.6 Hz, 1H), 5.88 (tt, J=53.1, 2.7 Hz, 1H), 4.79 (t, J=3.3 Hz, 1H), 4.51-4.18 (m, 5H), 3.60 (dd, J=15.4, 3.0 Hz, 1H), 3.22 (dd, J=15.4, 8.8 Hz, 1H), 2.17 (brs, 1H); MS (ES) m/z: 564 ($M+H^+$).

Example 75

Cmpd 75

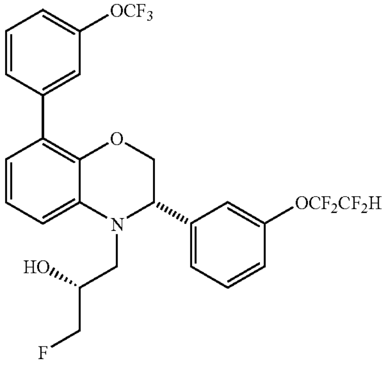

4H-1,4-Benzoxazine-4-ethanol, 2,3-dihydro-α-fluoromethyl-3-[3-(1,1,2,2-tetrafluoroethoxy)phenyl]-8-[3-(trifluoromethoxy)phenyl]-, (3S,αS)—

Spectrums of compound 75 are as following: $^1H$ NMR (400 MHz, $CDCl_3$) δ 7.43-7.32 (m, 4H), 7.14 (m, 3H), 7.08 (s, 1H), 7.00 (t, J=7.9 Hz, 1H), 6.90 (d, J=8.1 Hz, 1H), 6.75 (d, J=7.6 Hz, 1H), 5.88 (tt, J=53.1, 2.6 Hz, 1H), 4.61-4.39 (m, 3H), 4.29 (dd, J=10.9, 2.9 Hz, 1H), 4.22 (dd, J=11.0, 3.2 Hz, 1H), 4.13 (m, 1H), 3.61 (dd, J=15.2, 5.8 Hz, 1H), 3.32 (dd, J=15.2, 7.3 Hz, 1H), 2.04 (brs, 1H); MS (ES) m/z: 564 ($M+H^+$).

Example 76

Cmpd 76

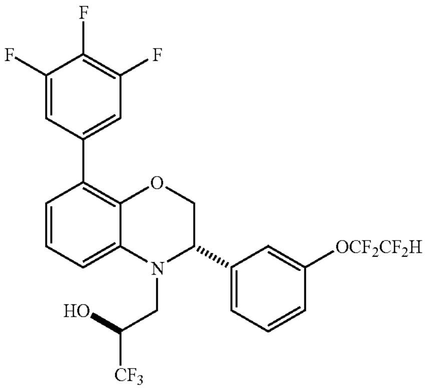

4H-1,4-Benzoxazine-4-ethanol, 2,3-dihydro-3-[3-(1,1,2,2-tetrafluoroethoxy)phenyl]-8-[3,4,5-trifluoro-phenyl]-α-(trifluoromethyl)-, (3S,αS)—

Scheme SS

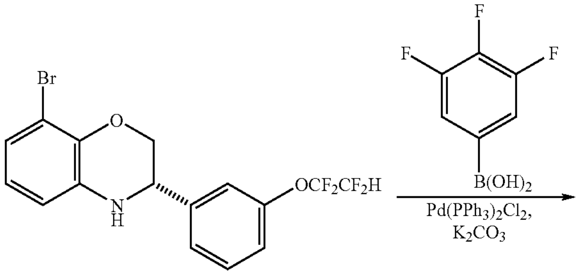

C2b

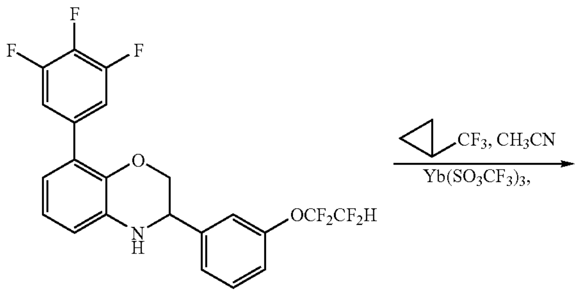

SS1, 66%

-continued

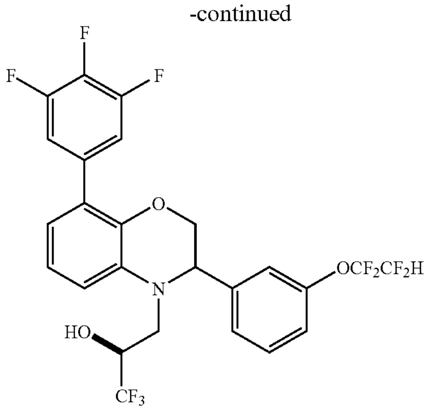

+

Cmpd 76, 67%

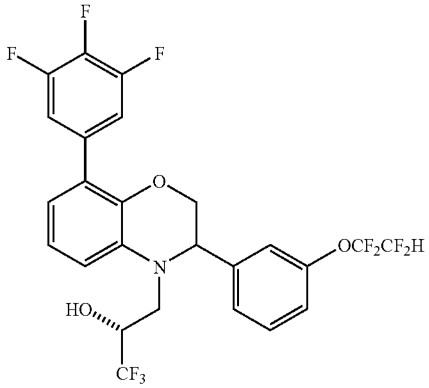

Cmpd 77, 19%

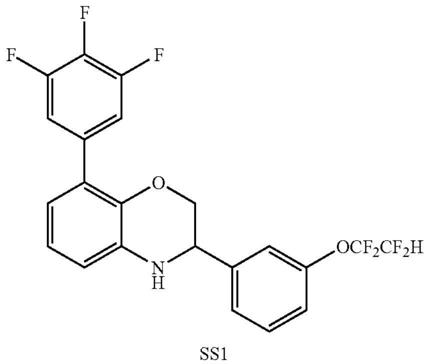

SS1

3-[3-(1,1,2,2-Tetrafluoro-ethoxy)-phenyl]-8-(3,4,5-trifluoro-phenyl)-3,4-dihydro-2H-benzo[1,4]oxazine Replacing 3,5-difluoro-benzene-boronic acid with 3,4,5-trifluoro-benzene-boronic acid and following the same procedure as in the preparation of compound QQ1 gave compound SS1: $^1H$ NMR (400 MHz, $CDCl_3$) δ 7.41 (t, J=7.9 Hz, 1H), 7.37-7.12 (m, 5H), 6.88 (t, J=7.8 Hz, 1H), 6.74-6.68 (m, 2H), 5.91 (tt, J=53.1, 2.8 Hz, 1H), 4.57 (d, J=8.2 Hz, 1H), 4.34-4.30 (m, 1H), 4.16 (s, 1H), 3.98 (dd, J=10.7, 8.3 Hz, 1H); MS (ES) m/z: 458 ($M+H^+$).

Cmpd 76

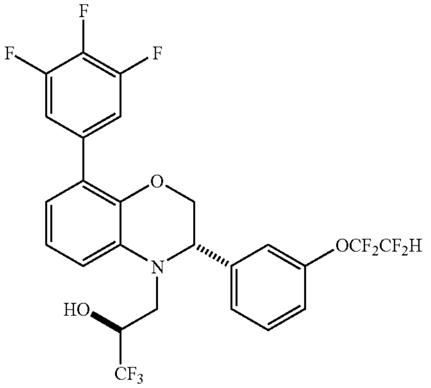

4H-1,4-Benzoxazine-4-ethanol, 2,3-dihydro-3-[3-(1,1,2,2-tetrafluoroethoxy)phenyl]-8-[3,4,5-trifluorophenyl]-α-(trifluoromethyl)-, (3S,αS)—

Replacing A2d with SS1 and following the same procedure as in the preparation of compound 1 and 2 gave compound 76 and 77. Spectrums of compound 76 are as following: $[\alpha]^{20}_D$ −79.0° (c=1, $CHCl_3$); $^1$H NMR (400 MHz, $CDCl_3$) δ 7.38 (t, J=7.9 Hz, 1H), 7.27-7.08 (m, 5H), 7.00 (t, J=7.9 Hz, 1H), 6.79 (d, J=8.2 Hz, 1H), 6.71 (d, J=7.7 Hz, 1H), 5.89 (tt, J=53.1, 2.7 Hz, 1H), 4.86 (t, J=3.8 Hz, 1H), 4.42-4.35 (m, 1H), 4.26 (dd, J=10.9, 3.2 Hz, 1H), 4.18 (dd, J=10.9, 4.6 Hz, 1H), 3.82 (d, J=15.7 Hz, 1H), 3.33 (dd, J=15.7, 9.6 Hz, 1H), 2.37 (d, J=4.6 Hz, 1H); MS (ES) m/z: 570 $(M+H^+)$.

Example 77

Cmpd 77

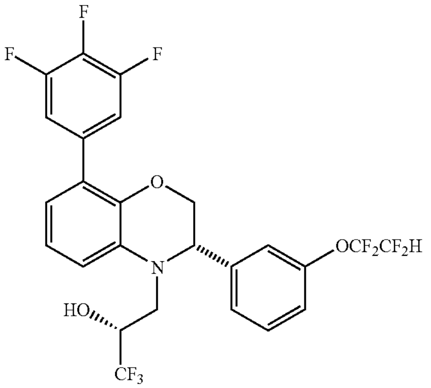

4H-1,4-Benzoxazine-4-ethanol, 2,3-dihydro-3-[3-(1,1,2,2-tetrafluoroethoxy)phenyl]-8-[3,4,5-trifluorophenyl]-α-(trifluoromethyl)-, (3S,αR)—

Spectrums of compound 77 are as following: $^1$H NMR (400 MHz, $CDCl_3$) δ 7.37 (t, J=7.9 Hz, 1H), 7.20-6.90 (m, 6H), 6.89 (d, J=8.2 Hz, 1H), 6.72 (d, J=7.6 Hz, 1H), 5.88 (tt, J=53.1, 2.8 Hz, 1H), 4.55 (t, J=3.0 Hz, 1H), 4.38-4.19 (m, 3H), 3.69 (dd, J=15.8, 6.5 Hz, 1H), 3.55 (dd, J=15.8, 5.2 Hz, 1H), 2.21 (d, J=5.0 Hz, 1H); MS (ES) m/z: 570 $(M+H^+)$.

Example 78

Cmpd 78

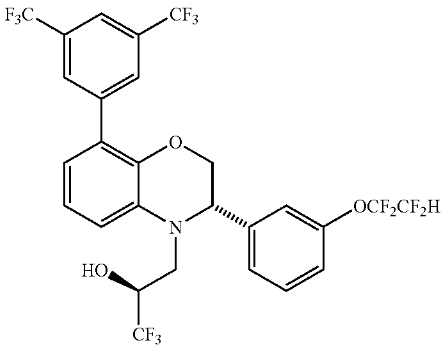

4H-1,4-Benzoxazine-4-ethanol, 2,3-dihydro-3-[3-(1,1,2,2-tetrafluoroethoxy)phenyl]-8-[3,5-bis(trifluoromethyl)phenyl]-α-(trifluoromethyl)-, (3S,αS)—

Scheme TT

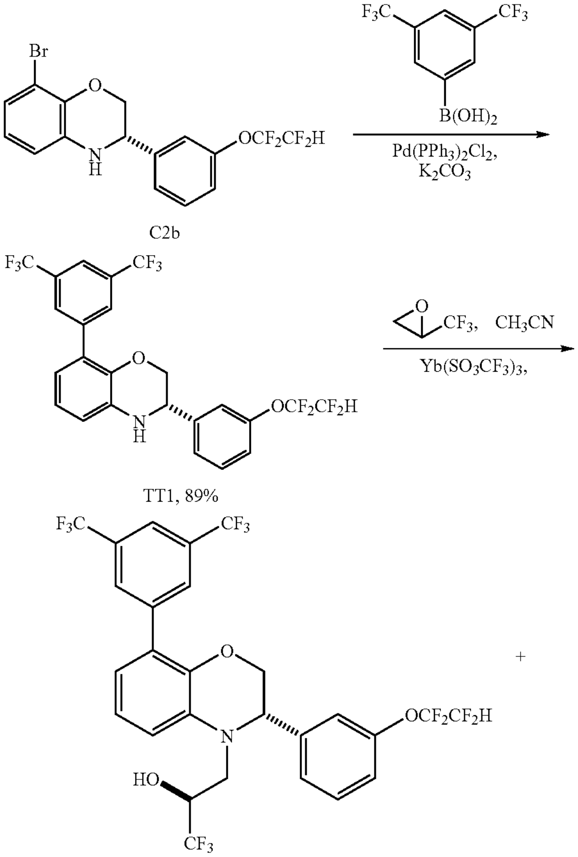

Cmpd 78, 56%

-continued

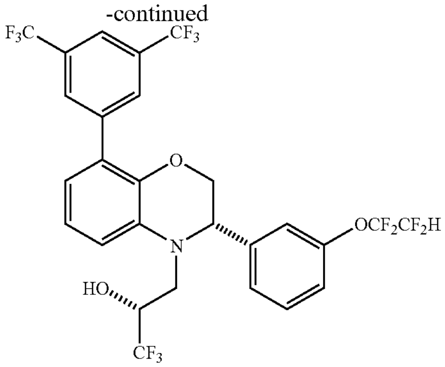

Cmpd 79, 14%

TT1

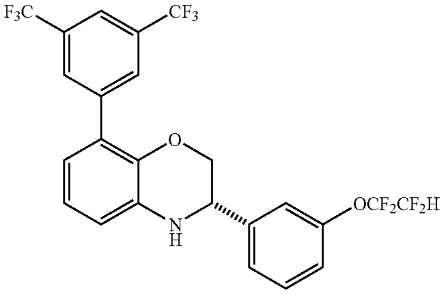

8-(3,5-Bis-trifluoromethyl-phenyl)-3-[3-(1,1,2,2-tetrafluoro-ethoxy)-phenyl]-3,4-dihydro-2H-benzo[1,4]oxazine Replacing 3,5-difluoro-benzene-boronic acid with 3,5-bis-trifluoromethyl-benzene-boronic acid and following the same procedure as in the preparation of compound QQ1 gave compound TT1: $^1H$ NMR (300 MHz, $CDCl_3$) δ 8.00 (s, 2H), 7.81 (s, 1H), 7.42 (t, J=7.8 Hz, 1H), 7.38-7.19 (m, 3H), 6.93 (t, J=8.3 Hz, 1H), 6.77 (d, J=7.7 Hz, 2H), 5.91 (tt, J=53.1, 2.8 Hz, 1H), 4.60 (d, J=8.4 Hz, 1H), 4.36-4.30 (m, 1H), 4.19 (s, 1H), 3.99 (dd, J=10.7, 8.4 Hz, 1H); MS (ES) m/z: 540 ($M+H^+$).

Cmpd 78

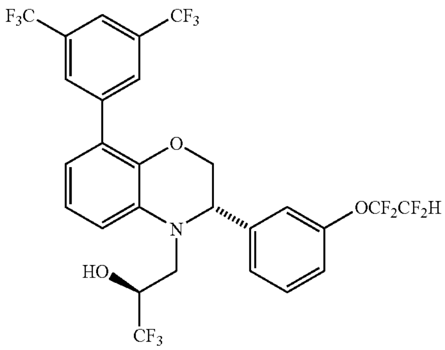

4H-1,4-Benzoxazine-4-ethanol, 2,3-dihydro-3-[3-(1,1,2,2-tetrafluoroethoxy)phenyl]-8-[3,5-bis(trifluoromethyl)phenyl]-α-(trifluoromethyl)-, (3S,αS)—

Replacing A2d with SS1 and following the same procedure as in the preparation of compound 1 and 2 gave compound 78 and 79. Spectrums of compound 78 are as following: $^1H$ NMR (400 MHz, $CDCl_3$) δ 7.93 (s, 2H), 7.80 (s, 1H), 7.39 (t, J=8.0 Hz, 1H), 7.21-7.18 (m, 2H), 7.13 (s, 1H), 7.04 (t, J=8.0 Hz, 1H), 6.84 (d, J=7.8 Hz, 1H), 6.78 (d, J=7.6 Hz, 1H), 5.89 (tt, J=53.1, 2.7 Hz, 1H), 4.88 (t, J=4.0 Hz, 1H), 4.43-4.36 (m, 1H), 4.29 (dd, J=11.0, 3.2 Hz, 1H), 4.18 (dd, J=11.0, 4.9 Hz, 1H), 3.83 (d, J=15.7 Hz, 1H), 3.34 (dd, J=15.7, 9.6 Hz, 1H), 2.46 (brs, 1H); MS (ES) m/z: 652 ($M+H^+$).

Example 79

Cmpd 79

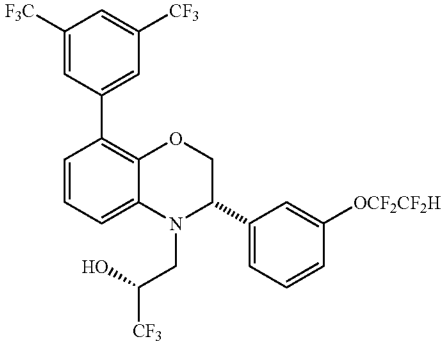

4H-1,4-Benzoxazine-4-ethanol, 2,3-dihydro-3-[3-(1,1,2,2-tetrafluoroethoxy)phenyl]-8-[3,5-bis(trifluoromethyl)phenyl]-α-(trifluoromethyl)-, (3S,αR)—

Spectrums of compound 79 are as following: $^1H$ NMR (400 MHz, $CDCl_3$) δ 7.91 (s, 2H), 7.79 (s, 1H), 7.38 (t, J=7.9 Hz, 1H), 7.19-7.13 (m, 2H), 7.09-7.02 (m, 2H), 6.94 (d, J=8.2 Hz, 1H), 6.78 (d, J=7.6 Hz, 1H), 5.88 (tt, J=53.1, 2.7 Hz, 1H), 4.57 (t, J=3.0 Hz, 1H), 4.34-4.21 (m, 3H), 3.71 (dd, J=15.7, 6.5 Hz, 1H), 3.56 (dd, J=15.8, 5.2 Hz, 1H), 2.27 (brs, 1H); MS (ES) m/z: 652 ($M+H^+$).

Example 80

Cmpd 80

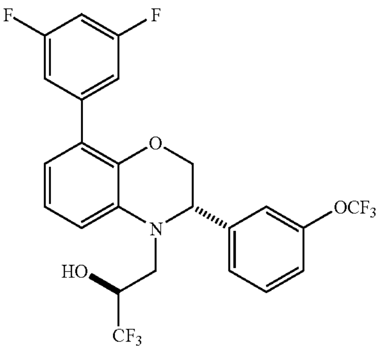

4H-1,4-Benzoxazine-4-ethanol, 2,3-dihydro-3-[3-(trifluoromethoxy)phenyl]-8-[3,5-(difluoro)phenyl]-α-(trifluoromethyl)-, (3S,αS)—

Scheme UU

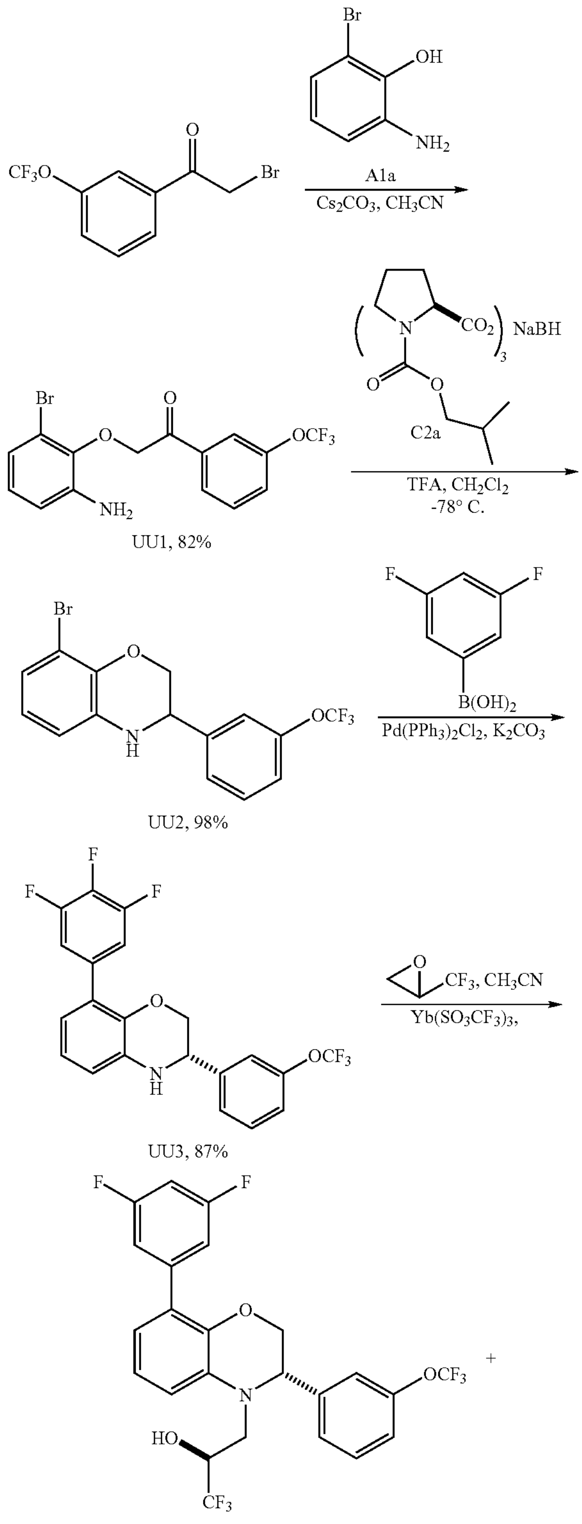

Cmpd 80, 74%

-continued

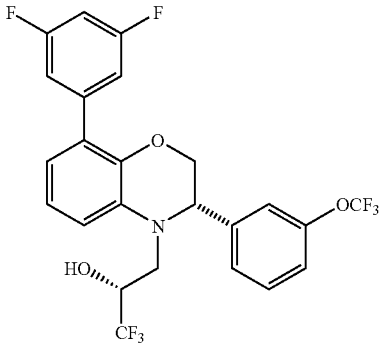

Cmpd 81, 10%

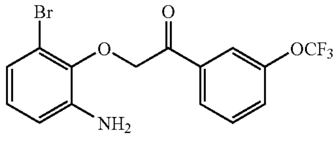

UU1

2-(2-Amino-6-bromo-phenoxy)-1-(3-trifluoromethoxy-phenyl)-ethanone

Replacing A2a with 2-bromo-1-(3-trifluoromethoxy-phenyl)-ethanone and following the same procedure as in the preparation of compound A2b gave compound UU1: $^1H$ NMR (300 MHz, $CDCl_3$) δ 7.86 (s, 1H), 7.77 (d, J=7.9 Hz, 1H), 7.52 (t, J=8.0 Hz, 1H), 7.41-7.35 (m, 3H), 6.93 (t, J=8.0 Hz, 1H), 5.17 (s, 2H).

UU2

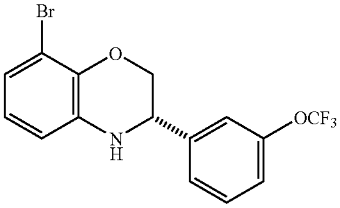

8-Bromo-3-(3-trifluoromethoxy-phenyl)-3,4-dihydro-2H-benzo[1,4]oxazine

Replacing A2b with UU1 and following the same procedure as in the preparation of compound C2b gave compound UU2: $^1H$ NMR (300 MHz, $CDCl_3$) δ 7.42 (t, J=7.7 Hz, 1H), 7.38 (d, J=7.6 Hz, 1H), 7.31-7.25 (m, 2H), 7.03-7.00 (m, 1H), 6.78-6.67 (m, 2H), 4.61 (d, J=8.2 Hz, 1H), 4.50-4.44 (m, 1H), 4.17 (brs, 1H), 4.10 (dd, J=10.7, 8.2 Hz, 1H); MS (ES) m/z: 374 (M).

UU3

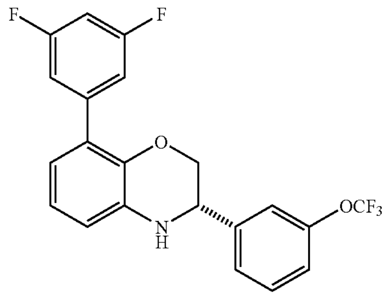

8-(3,5-Difluoro-phenyl)-3-(3-trifluoromethoxy-phenyl)-3,4-dihydro-2H-benzo[1,4]oxazine Replacing C2b with UU2 and following the same procedure as in the preparation of compound C1a gave compound UU3: $^1$H NMR (400 MHz, $CDCl_3$) δ 7.42 (t, J=7.9 Hz, 1H), 7.34 (d, J=7.8 Hz, 1H), 7.28 (s, 1H), 7.20 (d, J=8.0 Hz, 1H), 7.11-7.07 (m, 2H), 6.89 (t, J=7.7 Hz, 1H), 6.78-6.68 (m, 3H), 4.58 (d, J=8.1 Hz, 1H), 4.34-4.30 (m, 1H), 4.15 (brs, 1H), 3.98 (dd, J=10.6, 8.3 Hz, 1H); MS (ES) m/z: 408 (M+H$^+$).

Cmpd 80

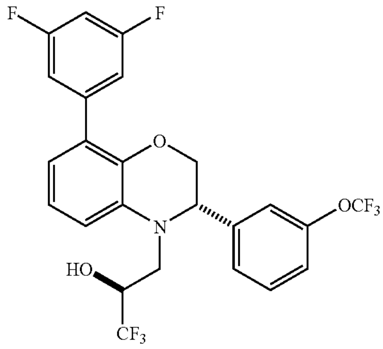

4H-1,4-Benzoxazine-4-ethanol, 2,3-dihydro-3-[3-(trifluoromethoxy)phenyl]-8-[3,5-(difluoro)phenyl]-(1-(trifluoromethyl)-, (3S,αS)—

Replacing A2d with UU3 and following the same procedure as in the preparation of compound 1 and 2 gave compound 80 and 81. Spectrums of compound 80 are as following: $[\alpha]^{20}_D$ −95.40 (c=1, $CHCl_3$); $^1$H NMR (300 MHz, $CDCl_3$) δ 7.39 (t, J=7.9 Hz, 1H), 7.23-7.15 (m, 2H), 7.11 (s, 1H), 7.07-6.98 (m, 3H), 6.82-6.69 (m, 3H), 4.87 (t, J=3.8 Hz, 1H), 4.48-4.32 (m, 1H), 4.27 (dd, J=10.9, 3.2 Hz, 1H), 4.17 (dd, J=10.9, 4.4 Hz, 1H), 3.83 (d, J=15.7 Hz, 1H), 3.31 (dd, J=15.7, 9.6 Hz, 1H), 2.42 (d, J=3.5 Hz, 1H); MS (ES) m/z: 520 (M+H$^+$). Anal. Calcd. For $C_{24}H_{17}F_8NO_3.0.1H_2O$: C, 55.31; H, 3.33; N, 2.69. Found: C, 55.07; H, 3.05; N, 2.60.

Example 81

Cmpd 81

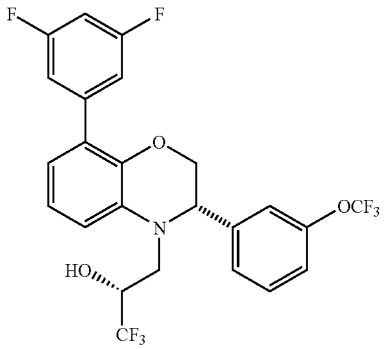

4H-1,4-Benzoxazine-4-ethanol, 2,3-dihydro-3-[3-(trifluoromethoxy)phenyl]-8-[3,5-(difluoro)phenyl]-α-(trifluoromethyl)-, (3S,αR)—

Spectrums of compound 81 are as following: $^1$H NMR (400 MHz, $CDCl_3$) δ 7.38 (t, J=8.0 Hz, 1H), 7.16 (bt, J=6.7 Hz, 2H), 7.07 (s, 1H), 7.03-6.99 (m, 3H), 6.90 (d, J=8.2 Hz, 1H), 6.77-6.70 (m, 2H), 4.56 (s, 1H), 4.37-4.20 (m, 3H), 3.69 (dd, J=15.8, 6.5 Hz, 1H), 3.55 (dd, J=15.7, 5.2 Hz, 1H), 2.36 (brs, 1H); MS (ES) m/z: 520 (M+H$^+$).

Example 82

Cmpd 82

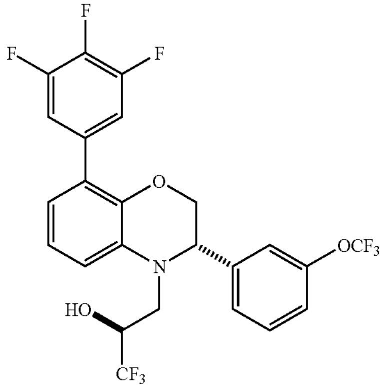

4H-1,4-Benzoxazine-4-ethanol, 2,3-dihydro-3-[3-(trifluoromethoxy)phenyl]-8-[3,4,5-(trifluoro) phenyl]-α-(trifluoromethyl)-, (3S,αS)—

Scheme VV

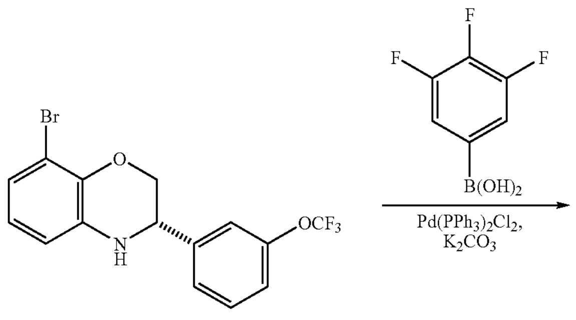

UU2

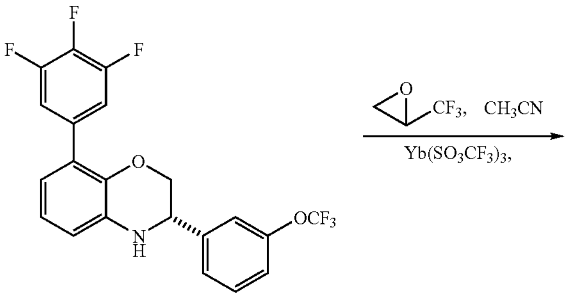

VV1, 60%

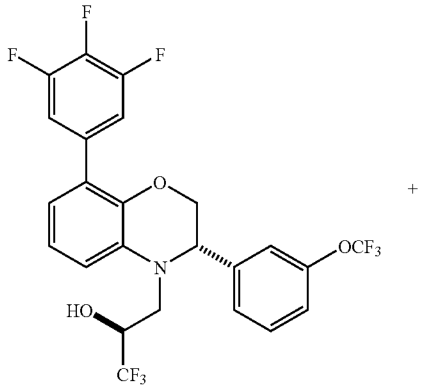

Cmpd 82, 72%

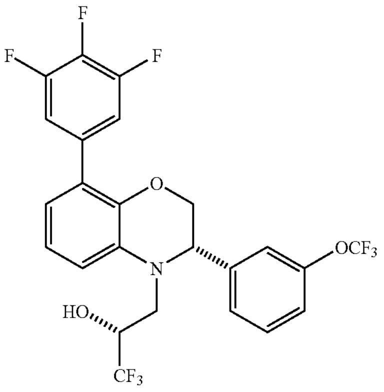

Cmpd 83, 12%

-continued

VV1

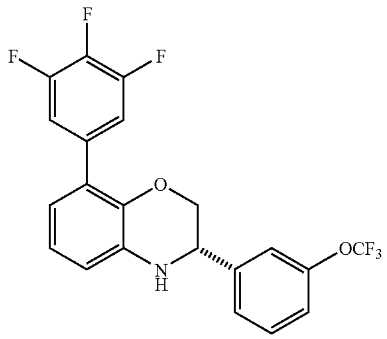

2H-1,4-Benzoxazine, 8-(3,4,5-trifluoro-phenyl)-3,4-dihydro-3-[3-trifluoromethoxy-phenyl]-, (3S)—

Replacing 3,5-difluoro-benzene-boronic acid with 3,4,5-trifluoro-benzene-boronic acid and following the same procedure as in the preparation of compound UU3 gave compound VV1: $^1$H NMR (400 MHz, $CDCl_3$) δ 7.43 (t, J=7.9 Hz, 1H), 7.34 (d, J=7.7 Hz, 1H), 7.26 (d, J=8.4 Hz, 1H), 7.22-7.11 (m, 3H), 6.88 (t, J=7.8 Hz, 1H), 6.74-6.69 (m, 2H), 4.58 (dd, J=8.1, 2.8 Hz, 1H), 4.32 (d, J=10.6 Hz, 1H), 4.16 (s, 1H), 3.98 (dd, J=10.6, 8.2 Hz, 1H); MS (ES) m/z: 426 ($M+H^+$).

Cmpd 82

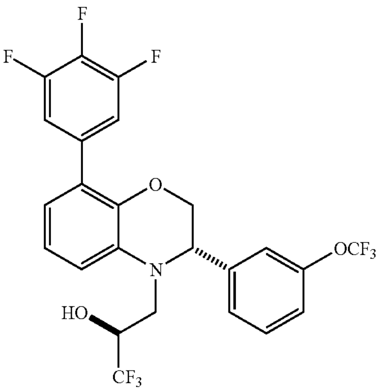

4H-1,4-Benzoxazine-4-ethanol, 2,3-dihydro-3-[3-(trifluoromethoxy)phenyl]-8-[3,4,5-(trifluoro)phenyl]-α-(trifluoromethyl)-, (3S,αS)—

Replacing A2d with VV1 and following the same procedure as in the preparation of compound 1 and 2 gave compound 82 and 83. Spectrums of compound 82 are as following: $[\alpha]^{20}_D$ −87.6° (c=1, $CHCl_3$); $^1$H NMR (400 MHz, $CDCl_3$) δ 7.40 (t, J=7.9 Hz, 1H), 7.19 (d, J=7.7 Hz, 1H), 7.14-7.07 (m, 3H), 7.00 (t, J=7.9 Hz, 1H), 4.87 (t, J=7.9 Hz, 1H), 6.79 (d, J=8.2 Hz, 1H), 6.71 (d, J=7.7 Hz, 1H), 4.87 (t, J=3.7 Hz, 1H), 4.45-4.36 (m, 1H), 4.26 (dd, J=10.9, 3.2 Hz, 1H), 4.17 (dd, J=10.9, 4.4 Hz, 1H), 3.83 (d, J=15.7 Hz, 1H), 3.31 (dd, J=15.7, 9.6 Hz, 1H), 2.37 (d, J=4.6 Hz, 1H); MS (ES) m/z: 538 (M+H$^+$).

Example 83

Cmpd 83

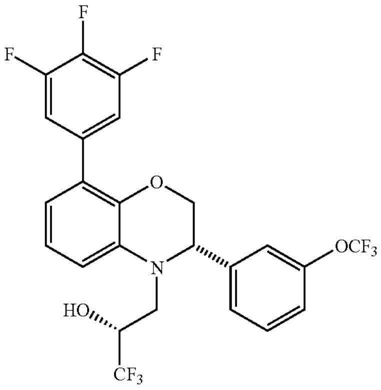

4H-1,4-Benzoxazine-4-ethanol, 2,3-dihydro-3-[3-(trifluoromethoxy)phenyl]-8-[3,4,5-(trifluoro)phenyl]-α-(trifluoromethyl)-, (3S,αR)—

Spectrums of compound 83 are as following: $^1$H NMR (400 MHz, $CDCl_3$) δ 7.38 (t, J=8.0 Hz, 1H), 7.19-6.98 (m, 6H), 6.90 (d, J=8.2 Hz, 1H), 6.73 (d, J=7.7 Hz, 1H), 4.56 (t, J=2.9 Hz, 1H), 4.34-4.26 (m, 1H), 4.24 (d, J=3.0 Hz, 2H), 3.70 (dd, J=15.8, 6.5 Hz, 1H), 3.55 (dd, J=15.8, 5.2 Hz, 1H), 2.22 (d, J=5.7 Hz, 1H); MS (ES) m/z: 538 (M+H$^+$).

Example 84

Cmpd 84

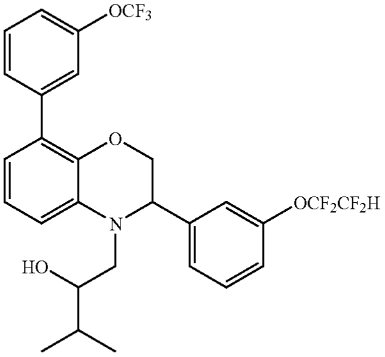

3-Methyl-1-[3-[3-(1,1,2,2-tetrafluoro-ethoxy)-phenyl]-8-(3-trifluoromethoxy-phenyl)-2,3-dihydro-benzo[1,4]oxazin-4-yl]-butan-2-ol Scheme WW

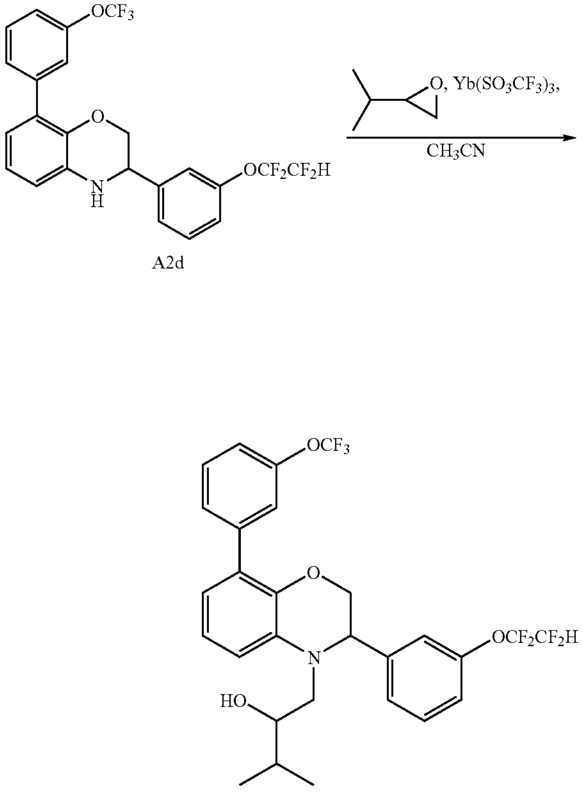

A2d

Cmpd 84, 34%

Replacing 2-trifluoromethyl-oxirane with 2-isopropyl-oxirane and following the same procedure as in the preparation of compound 1 and 2 gave an un-separable mixture compound 84: MS (ES) m/z: 574 (M+H$^+$).

Example 85

Cmpd 85

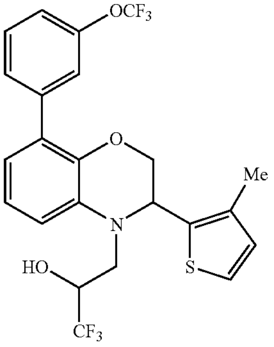

(Higher Rf Cmpd)

1,1,1-Trifluoro-3-[3-(3-methyl-thiophen-2-yl)-8-(3-trifluoromethoxy-phenyl)-2,3-dihydro-benzo[1,4]oxazin-4-yl]-propan-2-ol Scheme XX

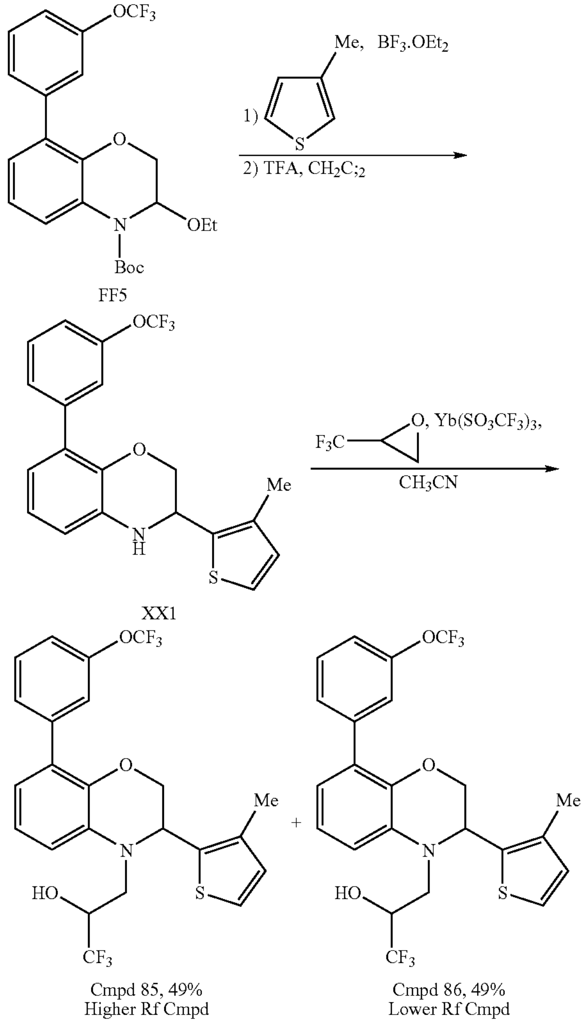

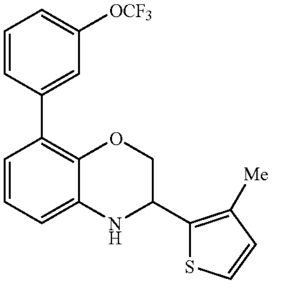

XX1

3-(3-Methyl-thiophen-2-yl)-8-(3-trifluoromethoxy-phenyl)-3,4-dihydro-2H-benzo[1,4]oxazine Replacing 2-methoxy-thiophene with 3-methyl-thiophene and following the same procedure as in the preparation of compound KK1 gave compound XX1: $^1$H NMR (300 MHz, $CDCl_3$) δ 7.52-7.38 (m, 3H), 7.25-7.12 (m, 2H), 6.92-6.82 (m, 2H), 6.76 (d, J=7.6 Hz, 1H), 6.69 (d, J=7.8 Hz, 1H), 4.90 (dd, J=8.6, 3.0 Hz, 1H), 4.31 (dd, J=10.5, 2.9 Hz, 1H), 4.18 (brs, 1H), 4.03 (dd, J=10.6, 8.6 Hz, 1H), 2.27 (s, 3H); MS (ES) m/z: 392 (M+H$^+$).

Cmpd 85

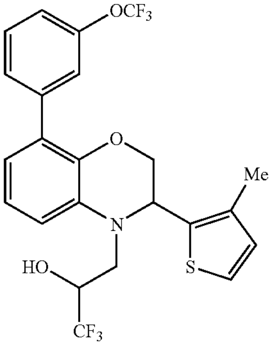

Higher Rf Cmpd 1,1,1-Trifluoro-3-[3-(3-methyl-thiophen-2-yl)-8-(3-trifluoromethoxy-phenyl)-2,3-dihydro-benzo[1,4]oxazin-4-yl]-propan-2-ol Replacing A2d with VV1 and following the same procedure as in the preparation of compound 1 and 2 gave higher Rf compound 85 and lower Rf compound 86 (solvent for PLC: 15% EtOAc in hexane). Spectrums of compound 85 are as following: $^1$H NMR (400 MHz, $CDCl_3$) δ 7.47 (d, J=7.7 Hz, 1H), 7.42-7.38 (m, 2H), 7.21-7.14 (m, 2H), 7.01-6.96 (m, 1H), 6.84 (d, J=5.0 Hz, 1H), 6.78 (d, J=7.9 Hz, 2H), 5.17-5.14 (m, 1H), 4.31-4.22 (m, 2H), 4.18 (dd, J=11.0, 6.1 Hz, 1H), 3.68 (d, J=15.7 Hz, 1H), 3.42 (dd, J=15.7, 9.6 Hz, 1H), 2.41 (d, J=3.8 Hz, 1H), 2.29 (s, 3H); MS (ES) m/z: 504 (M+H$^+$).

Example 86

Cmpd 86

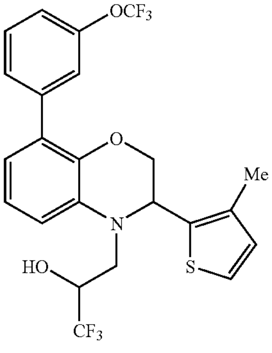

(Lower Rf Cmpd)

1,1,1-Trifluoro-3-[3-(3-methyl-thiophen-2-yl)-8-(3-trifluoromethoxy-phenyl)-2,3-dihydro-benzo[1,4]oxazin-4-yl]-propan-2-ol Spectrums of compound 86 are as following: $^1$H NMR (400 MHz, $CDCl_3$) δ 7.48 (d, J=7.6 Hz, 1H), 7.43-7.37 (m, 2H), 7.19-7.14 (m, 2H), 6.99 (t, J=7.9 Hz, 1H), 6.85-6.78 (m, 3H), 4.85 (t, J=3.4 Hz, 1H), 4.33-4.20 (m, 3H), 3.63 (dd, J=15.7, 4.7 Hz, 1H), 3.54 (dd, J=15.7, 7.1 Hz, 1H), 2.32-2.21 (m, 4H); MS (ES) m/z: 504 (M+H$^+$).

Example 87

Cmpd 87

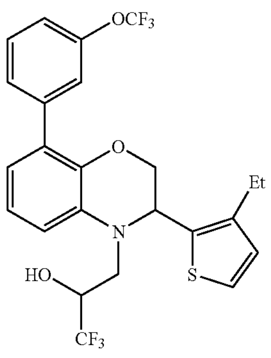

(Higher Rf Cmpd)

3-[3-(3-Ethyl-thiophen-2-yl)-8-(3-trifluoromethoxy-phenyl)-2,3-dihydro-benzo[1,4]oxazin-4-yl]-1,1,1-trifluoro-propan-2-ol Scheme YY

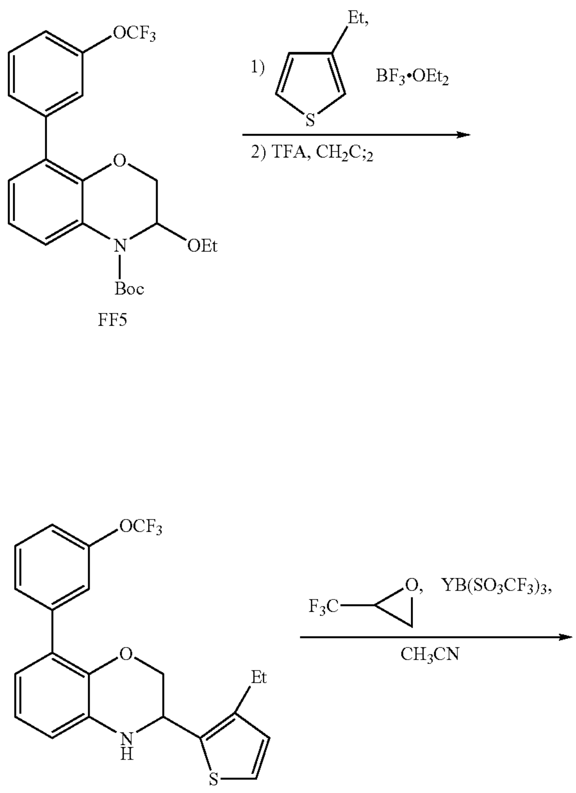

FF5

YY1, 77%

-continued

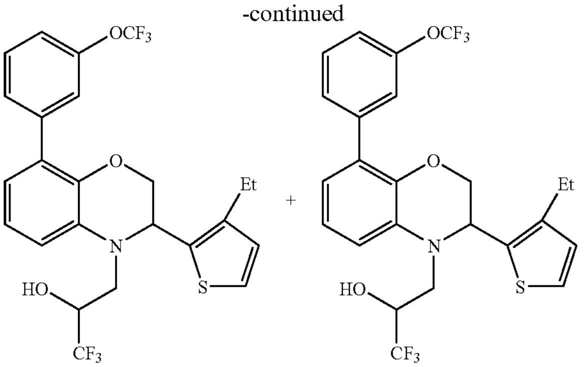

Cmpd 87, 36%
Higher Rf Cmpd

Cmpd 88, 34%
Lower Rf Cmpd

YY1

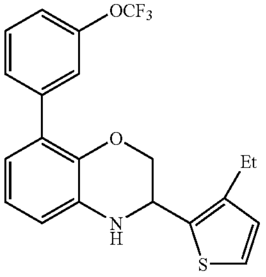

3-(3-Ethyl-thiophen-2-yl)-8-(3-trifluoromethoxy-phenyl)-3,4-dihydro-2H-benzo[1,4]oxazine Replacing 2-methoxy-thiophene with 3-ethyl-thiophene and following the same procedure as in the preparation of compound KK1 gave compound YY1: $^1$H NMR (400 MHz, $CDCl_3$) δ 7.49 (d, J=7.8 Hz, 1H), 7.44-7.39 (m, 2H), 7.24 (d, J=5.1 Hz, 1H), 7.17 (d, J=8.1 Hz, 1H), 6.92 (d, J=5.1 Hz, 1H), 6.88 (t, J=7.7 Hz, 1H), 6.76 (d, J=7.6 Hz, 1H), 6.69 (d, J=7.8 Hz, 1H), 4.93 (dd, J=8.7, 2.7 Hz, 1H), 4.31 (bd, J=10.5 Hz, 1H), 4.18 (brs, 1H), 4.05 (dd, J=10.6, 8.8 Hz, 1H), 2.76-2.59 (m, 2H), 1.23 (t, J=7.6 Hz, 3H); MS (ES) m/z: 406 (M+H$^+$).

Cmpd 87

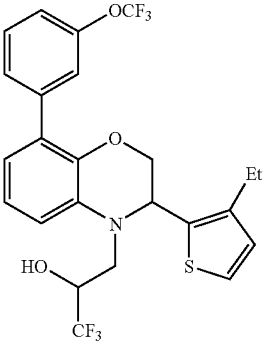

Higher Rf Cmpd

3-[3-(3-Ethyl-thiophen-2-yl)-8-(3-trifluoromethoxy-phenyl)-2,3-dihydro-benzo[1,4]oxazin-4-yl]-1,1,1-trifluoro-propan-2-ol Replacing A2d with YY1 and following the same procedure as in the preparation of compound 1 and 2 gave higher Rf compound 87 and lower Rf compound 88 (solvent for PLC: 15% EtOAc in hexane). Spectrums of compound 87 are as following: $^1$H NMR (400 MHz, $CDCl_3$) δ 7.47 (d, J=7.8 Hz, 1H), 7.43-7.38 (m, 2H), 7.22 (d, J=5.2 Hz, 1H), 7.18-7.15 (m, 1H), 6.98 (t, J=8.1 Hz, 1H), 6.91 (d, J=5.2 Hz, 1H), 6.78 (d, J=7.8 Hz, 2H), 5.18 (dd, J=6.1, 3.4 Hz, 1H), 4.32-4.26 (m, 2H), 4.18 (dd, J=11.0, 6.2 Hz, 1H), 3.67 (d, J=15.7 Hz, 1H), 3.42 (dd, J=15.7, 9.7 Hz, 1H), 2.74-2.62 (m, 2H), 2.43 (d, J=4.0 Hz, 1H), 1.23 (t, J=7.6 Hz, 3H); MS (ES) m/z: 518 (M+H$^+$).

Example 88

Cmpd 88

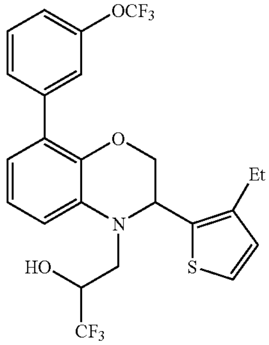

(Lower Rf Cmpd)

3-[3-(3-Ethyl-thiophen-2-yl)-8-(3-trifluoromethoxy-phenyl)-2,3-dihydro-benzo[1,4]oxazin-4-yl]-1,1,1-trifluoro-propan-2-ol Spectrums of compound 88 are as following: $^1$H NMR (400 MHz, $CDCl_3$) δ 7.52-7.38 (m, 3H), 7.21 (d, J=5.2 Hz, 1H), 7.19-7.14 (m, 1H), 7.02-6.92 (m, 1H), 6.91 (d, J=5.2 Hz, 1H), 6.85-6.29 (m, 2H), 4.87 (t, J=3.4 Hz, 1H), 4.35-4.20 (m, 3H), 3.69-3.49 (m, 2H), 2.72-2.58 (m, 2H), 2.27 (d, J=4.6 Hz, 1H), 1.29-1.19 (m, 3H); MS (ES) m/z: 518 (M+H$^+$).

Example 89

Cmpd 89

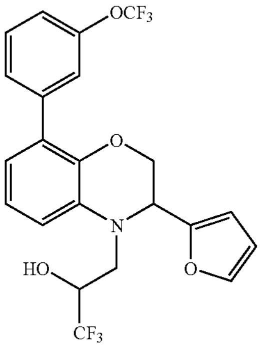

(Higher Rf Cmpd)

1,1,1-Trifluoro-3-[3-furan-2-yl-8-(3-trifluoromethoxy-phenyl)-2,3-dihydro-benzo[1,4]oxazin-4-yl]-propan-2-ol Scheme ZZ

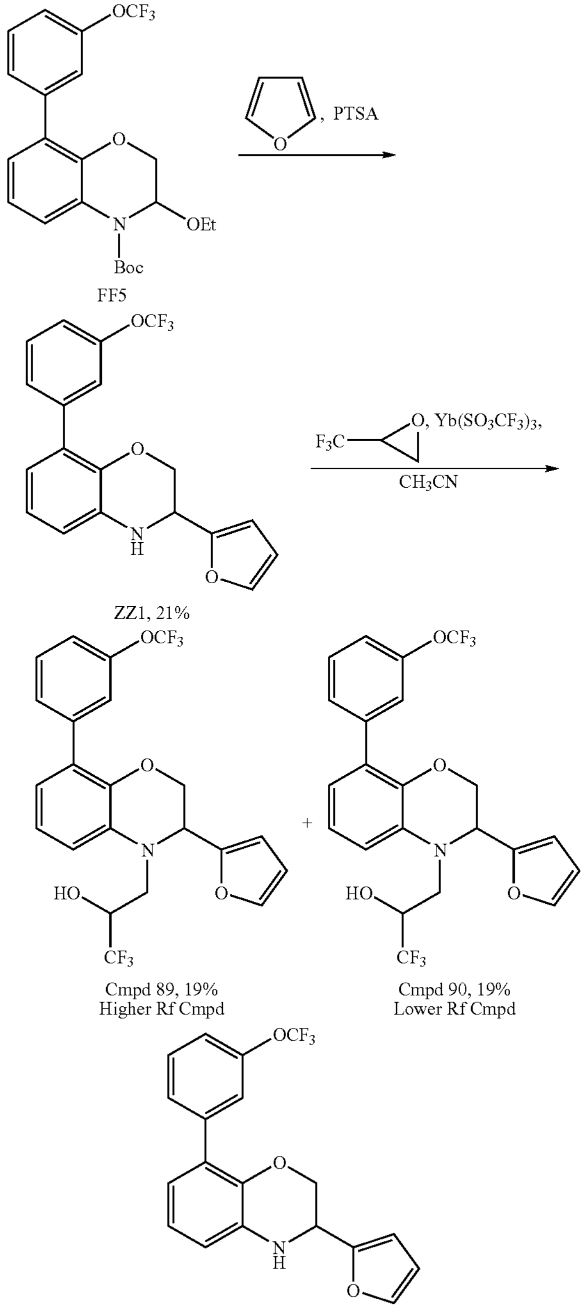

FF5

ZZ1, 21%

Cmpd 89, 19%
Higher Rf Cmpd

Cmpd 90, 19%
Lower Rf Cmpd

ZZ1

3-Furan-2-yl-8-(3-trifluoromethoxy-phenyl)-3,4-dihydro-2H-benzo[1,4]oxazine

A mixture of FF5 (29 mg, 0.066 mmol) and PTSA (25 mg, 0.13 mmol) in furane (1 mL) was stirred at room temperature for 2 d. The mixture was partitioned between $CH_2Cl_2$ and $NaHCO_3$ aqueous solution. The organic layer was dried ($Na_2SO_4$), concentrated and purified by column chromatography to afford 5 mg (21%) of ZZ1 as a yellow oil: $^1$H NMR (400 MHz, $CDCl_3$) δ 7.47 (d, J=7.8 Hz, 1H), 7.43-7.38 (m, 3H), 7.16 (d, J=8.1 Hz, 1H), 6.87 (t, J=7.7 Hz, 1H), 6.74 (d, J=7.6 Hz, 1H), 6.69 (d, J=7.8 Hz, 1H), 6.38-6.29 (m, 2H), 4.68 (dd, J=7.0, 2.9 Hz, 1H), 4.41 (dd, J=10.6, 3.0 Hz, 1H), 4.24-4.15 (m, 2H); MS (ES) m/z: 362 (M+H$^+$).

Cmpd 89

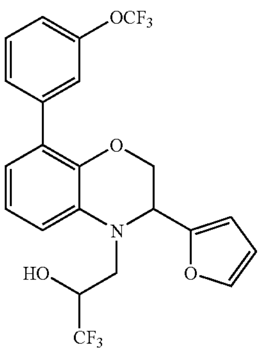

Higher Rf Cmpd 1,1,1-Trifluoro-3-[3-furan-2-yl-8-(3-trifluoromethoxy-phenyl)-2,3-dihydro-benzo[1,4]oxazin-4-yl]-propan-2-ol Replacing A2d with ZZ1 and following the same procedure as in the preparation of compound 1 and 2 gave higher Rf compound 89 and lower Rf compound 90 (solvent for PLC: 15% EtOAc in hexane). Spectrums of compound 89 are as following: $^1$H NMR (400 MHz, $CDCl_3$) δ 7.47-7.36 (m, 4H), 7.16 (d, J=7.5 Hz, 1H), 6.96 (t, J=7.9 Hz, 1H), 6.80-6.74 (m, 2H), 6.35-6.33 (m, 1H), 6.27 (d, J=4.3 Hz, 1H), 4.75 (t, J=3.6 Hz, 1H), 4.46 (dd, J=10.9, 4.2 Hz, 1H), 4.30-4.21 (m, 2H), 3.76 (d, J=15.5 Hz, 1H), 3.52 (dd, J=15.5, 9.7 Hz, 1H), 2.54 (d, J=3.7 Hz, 1H); MS (ES) m/z: 474 (M+H$^+$).

Example 90

Cmpd 90

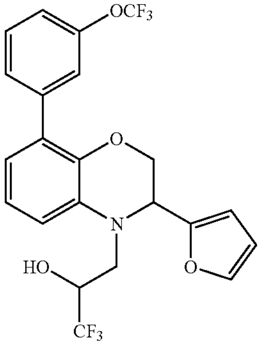

(Lower Rf Cmpd)

1,1,1-Trifluoro-3-[3-furan-2-yl-8-(3-trifluoromethoxy-phenyl)-2,3-dihydro-benzo[1,4]oxazin-4-yl]-propan-2-ol Spectrums of compound 90 are as following: $^1$H NMR (400 MHz, $CDCl_3$) δ 7.47-7.36 (m, 4H), 7.17 (d, J=7.7 Hz, 1H), 6.98 (t, J=7.7 Hz, 1H), 6.82-6.78 (m, 2H), 6.37-6.35 (m, 1H), 6.28 (d, J=3.1 Hz, 1H), 4.58 (t, J=3.2 Hz, 1H), 4.50 (dd, J=11.0, 3.8 Hz, 1H), 4.39-4.30 (m, 1H), 4.26 (dd, J=10.6, 2.8 Hz, 1H), 3.69 (dd, J=15.6, 4.8 Hz, 1H), 3.61 (dd, J=15.3, 7.5 Hz, 1H), 2.60 (d, J=4.9 Hz, 1H); MS (ES) m/z: 474 (M+H$^+$).

Example 91

Cmpd 91

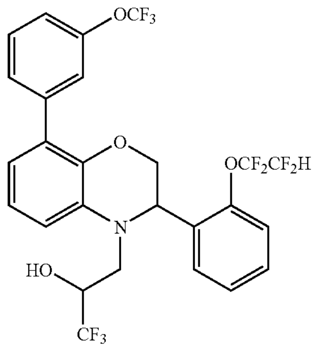

(Higher Rf Cmpd)

1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol Scheme aa

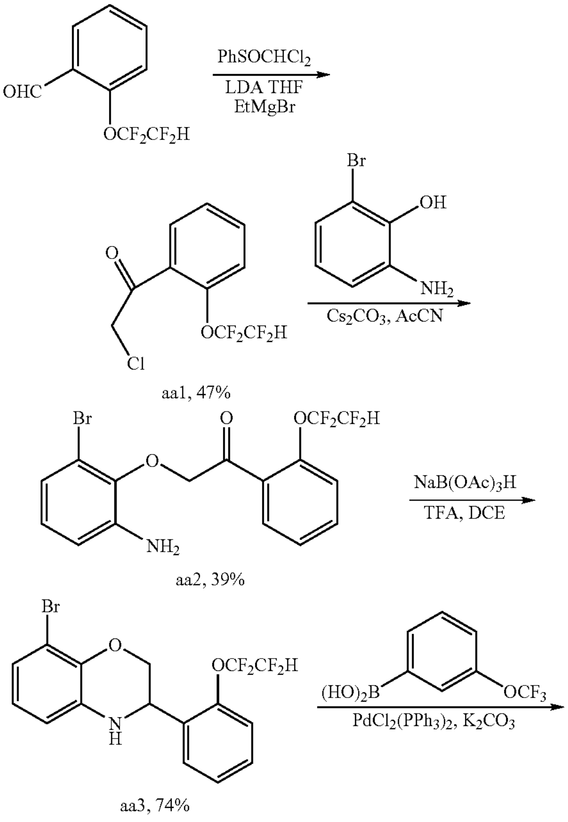

-continued

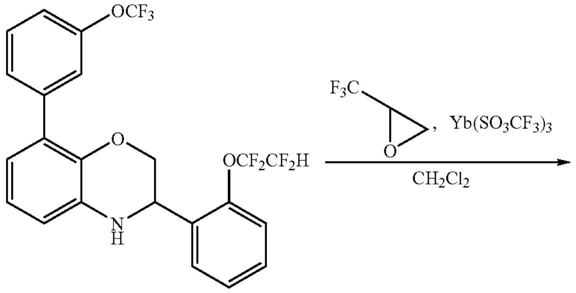

aa4, 59%

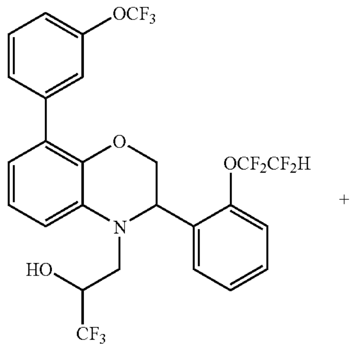

+

Cmpd 91
Higher Rf Cmpd

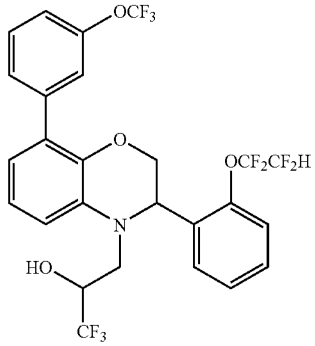

Cmpd 92
Lower Rf Cmpd

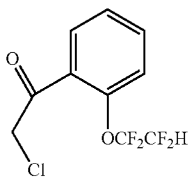

aa1

2-Chloro-1-[2-(1,1,2,2-tetrafluoro-ethoxy)-phenyl] ethanone

Replacing 3-(1,1,2,2-tetrafluoro-ethoxy)-benzaldehyde with 2-(1,1,2,2-tetrafluoro-ethoxy)-benzaldehyde and following the same procedure as in the preparation of compound A2a gave compound aa1 (47%): $^{1}$H NMR (300 MHz, $CDCl_3$) δ 7.78 (d, J=8.0 Hz, 1H), 6.60 (bt, J=7.9 Hz, 1H), 7.43-7.33 (m, 2H), 6.01 (tt, J=52.9, 2.3 Hz, 1H), 4.62 (s, 2H); MS (ES) m/z: 271 ($M+H^+$).

aa2

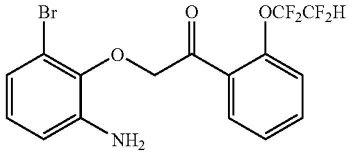

2-(2-Amino-6-bromo-phenoxy)-1-[2-(1,1,2,2-tetrafluoro-ethoxy)-phenyl]-ethanone

Replacing A2a with aa1 and following the same procedure as in the preparation of compound A2b gave compound aa2 (39%): $^{1}$H NMR (300 MHz, $CDCl_3$) δ 7.89 (d, J=7.6 Hz, 1H), 7.52 (bt, J=7.9 Hz, 1H), 7.43-7.34 (m, 4H), 6.94 (d, J=8.0 Hz, 1H), 5.93 (tt, J=52.9, 1.9 Hz, 1H), 4.97 (s, 2H); MS (ES) m/z: 404 ($M-H_2O$).

aa3

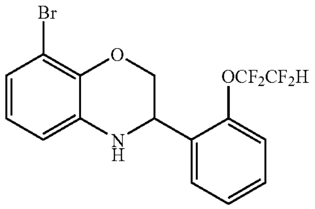

8-Bromo-3-[2-(1,1,2,2-tetrafluoro-ethoxy)-phenyl]-3,4-dihydro-2H-benzo[1,4]oxazine Replacing A2b with aa2 and following the same procedure as in the preparation of compound A2c gave compound aa3 (74%): $^{1}$H NMR (300 MHz, $CDCl_3$) δ 7.90 (d, J=8.1 Hz, 1H), 7.38-7.28 (m, 3H), 6.95 (d, J=7.8 Hz, 1H), 6.72-6.60 (m, 2H), 5.96 (tt, J=53.0, 2.3 Hz, 1H), 4.88 (d, J=7.2 Hz, 1H), 4.44-4.39 (m, 1H), 4.19-4.02 (m, 2H); MS (ES) m/z: 408 (M+2).

aa4

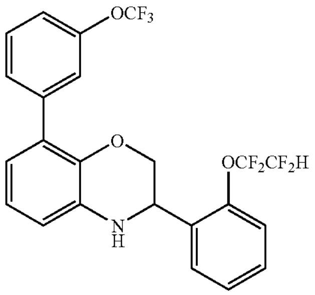

3-[2-(1,1,2,2-Tetrafluoro-ethoxy)-phenyl]-8-(3-trifluoromethoxy-phenyl)-3,4-dihydro-2H-benzo[1,4] oxazine Replacing A2c with aa3 and following the same procedure as in the preparation of compound A2d gave compound aa4 (59%): $^{1}$H NMR (300 MHz, $CDCl_3$) δ 7.57 (dd, J=7.7, 2.2 Hz, 1H), 7.50-7.29 (m, 6H), 7.15 (d, J=8.2 Hz, 1H), 6.89 (t, J=7.7 Hz, 1H), 6.77-6.69 (m, 2H), 5.95 (tt, J=53.0, 2.4 Hz, 1H), 4.93-4.84 (m, 1H), 4.33 (dd, J=10.6, 3.0 Hz, 1H), 4.06-3.99 (m, 2H); MS (ES) m/z: 488 (M+H+).

Cmpd 91

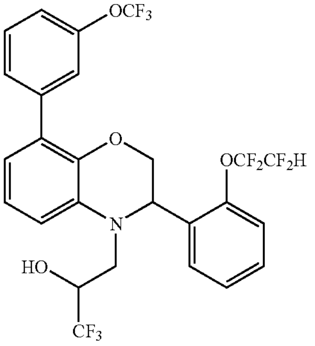

Higher Rf Cmpd 1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol Replacing A2d with aa4 and following the same procedure as in the preparation of compound 1 and 2 gave higher Rf compound 91 and lower Rf compound 92 (solvent for PLC: 15% EtOAc in hexane). Spectrums of compound 91 are as following: $^1$H NMR (300 MHz, $CDCl_3$) δ 7.45-7.20 (m, 7H), 7.14 (d, J=7.7 Hz, 1H), 7.01 (t, J=7.9 Hz, 1H), 6.80-6.75 (m, 2H), 5.95 (tt, J=53.0, 2.2 Hz, 1H), 5.17 (t, J=3.0 Hz, 1H), 4.45-4.20 (m, 3H), 3.81 (dd, J=15.6, 3.2 Hz, 1H), 3.31 (dd, J=15.7, 9.5 Hz, 1H), 2.38 (brs, 1H); MS (ES) m/z: 600 (M+H+).

Example 92

Cmpd 92

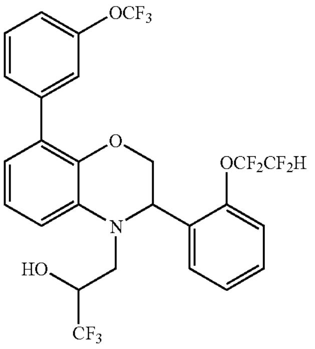

(Lower Rf Cmpd)

1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol Spectrums of compound 92 are as following: $^1$H NMR (300 MHz, $CDCl_3$) δ 7.45-7.30 (m, 5H), 7.25-7.19 (m, 2H), 7.13 (d, J=7.7 Hz, 1H), 7.02 (t, J=7.9 Hz, 1H), 6.90 (d, J=8.2 Hz, 1H), 6.77 (d, J=7.6 Hz, 1H), 5.95 (bt, J=53.0 Hz, 1H), 4.92 (t, J=2.3 Hz, 1H), 4.45-4.20 (m, 3H), 3.69 (dd, J=15.7, 6.7 Hz, 1H), 3.50 (dd, J=15.7, 5.2 Hz, 1H), 2.23 (brs, 1H); MS (ES) m/z: 600 (M+H+).

Example 93

Cmpd 93

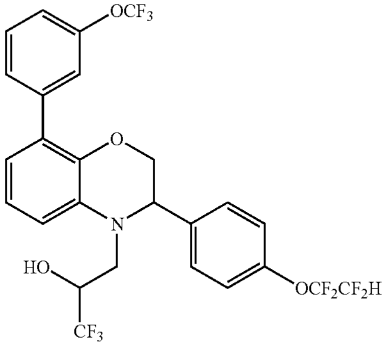

(Higher Rf Cmpd)

1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol Scheme bb

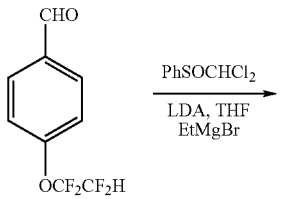

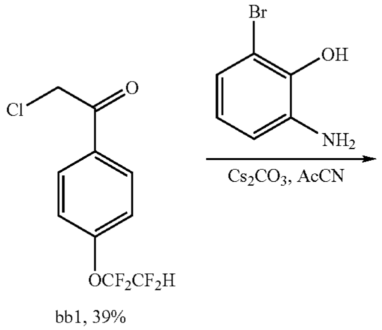

bb1, 39%

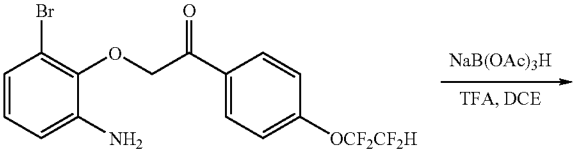

bb2, 48%

-continued

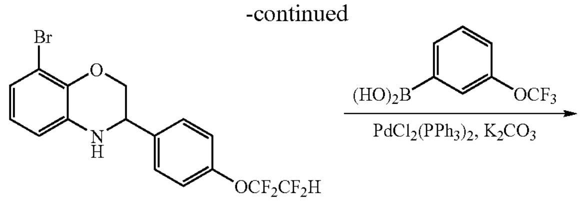

bb3, 50%

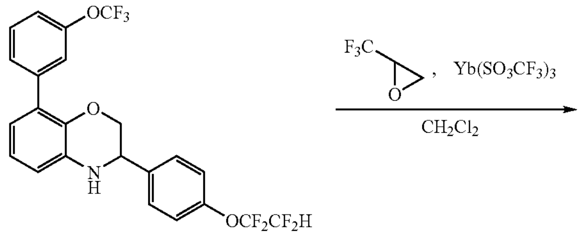

bb4, 52%

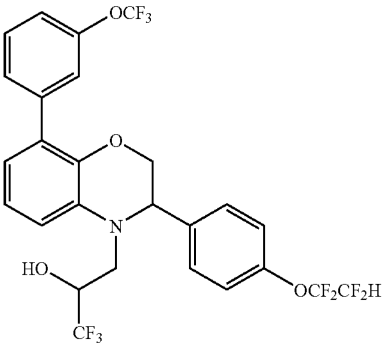

+

Cmpd 93
Higher Rf Cmpd

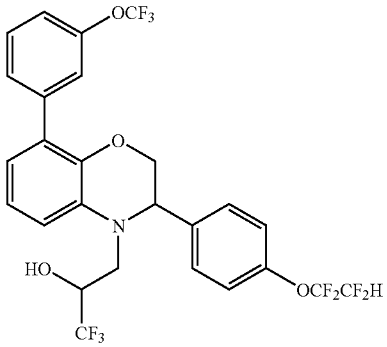

Cmpd 94
Lower Rf Cmpd bb1

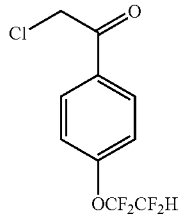

2-Chloro-1-[4-(1,1,2,2-tetrafluoro-ethoxy)phenyl]-ethanone

Replacing 3-(1,1,2,2-tetrafluoro-ethoxy)-benzaldehyde with 4-(1,1,2,2-tetrafluoro-ethoxy)-benzaldehyde and following the same procedure as in the preparation of compound A2a gave compound bbl (39%): $^{1}$H NMR (300 MHz, $CDCl_3$) δ 8.02 (d, J=8.7 Hz, 2H), 7.34 (d, J=8.3 Hz, 2H), 5.94 (tt, J=53.0, 2.7 Hz, 1H), 4.67 (s, 2H).

bb2

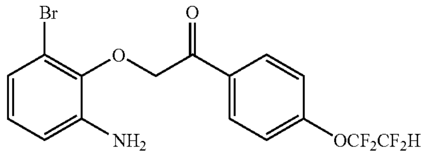

2-(2-Amino-6-bromo-phenoxy)-1-[4-(1,1,2,2-tetrafluoro-ethoxy)-phenyl]-ethanone

Replacing A2a with bb1 and following the same procedure as in the preparation of compound A2b gave compound bb2 (48%): $^{1}$H NMR (300 MHz, $CDCl_3$) δ 7.96 (d, J=8.8 Hz, 2H), 7.45-7.31 (m, 4H), 6.92 (t, J=8.0 Hz, 1H), 5.94 (tt, J=53.0, 2.8 Hz, 1H), 5.17 (s, 2H).

bb3

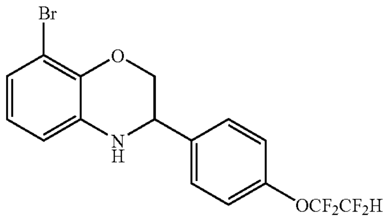

8-Bromo-3-[4-(1,1,2,2-tetrafluoro-ethoxy)-phenyl]-3,4-dihydro-2H-benzo[1,4]oxazine Replacing A2b with bb2 and following the same procedure as in the preparation of compound A2c gave compound bb3 (50%): $^{1}$H NMR (300 MHz, $DCl_3$) δ 7.53-7.39 (m, 3H), 7.28-7.18 (m, 1H), 6.95 (d, J=7.8 Hz, 1H), 6.72-6.60 (m, 2H), 5.92 (tt, J=53.1, 2.8 Hz, 1H), 4.54 (dd, J=8.4, 2.1 Hz, 1H), 4.44-4.38 (m, 1H), 4.22-4.00 (m, 2H); MS (ES) m/z: 408 (M+H$^{+}$).

bb4

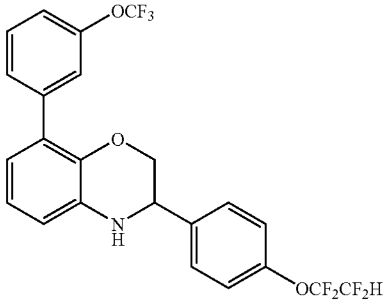

3-[4-(1,1,2,2-Tetrafluoro-ethoxy)-phenyl]-8-(3-trifluoromethoxy-phenyl)-3,4-dihydro-2H-benzo[1,4]oxazine Replacing A2c with bb3 and following the same procedure as in the preparation of compound A2d gave compound bb4

(52%): $^1$H NMR (300 MHz, $CDCl_3$) δ 7.52-7.39 (m, 6H), 7.33-7.11 (m, 2H), 6.89 (t, J=7.7 Hz, 1H), 6.76 (d, J=7.6 Hz, 1H), 6.71 (d, J=7.7 Hz, 1H), 5.91 (bt, J=53.0 Hz, 1H), 4.62-4.54 (m, 1H), 4.36-4.26 (m, 1H), 4.12 (s, 1H), 3.98 (dd, J=10.6, 8.4 Hz, 1H); MS (ES) m/z: 488 (M+H$^+$).

Cmpd 93

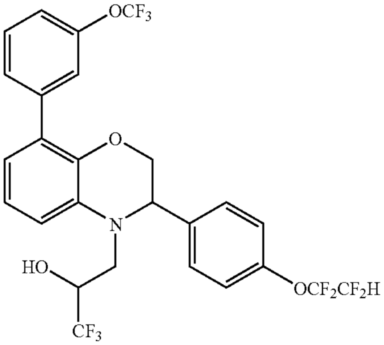

Higher Rf Cmpd 1,1,1-Trifluoro-3-[3-[4-(1,1,2,2-tetrafluoro-ethoxy)-phenyl]-8-(3-trifluoromethoxy-phenyl)-2,3-dihydro-benzo[1,4]oxazin-4-yl]propan-2-ol Replacing A2d with bb4 and following the same procedure as in the preparation of compound 1 and 2 gave higher Rf compound 96 and lower Rf compound 97 (solvent for PLC: 15% EtOAc in hexane). Spectrums of compound 96 are as following: $^1$H NMR (300 MHz, $CDCl_3$) δ 7.50-7.11 (m, 8H), 7.01 (t, J=7.9 Hz, 1H), 6.77 (t, J=7.5 Hz, 2H), 5.90 (tt, J=53.1, 2.8 Hz, 1H), 4.86 (t, J=3.9 Hz, 1H), 4.45-4.33 (m, 1H), 4.27 (dd, J=11.0, 3.2 Hz, 1H), 4.15 (dd, J=10.8, 4.7 Hz, 1H), 3.81 (d, J=15.6 Hz, 1H), 3.31 (dd, J=15.7, 9.6 Hz, 1H), 2.45 (brs, 1H); MS (ES) m/z: 600 (M+H$^+$).

Example 94

Cmpd 94

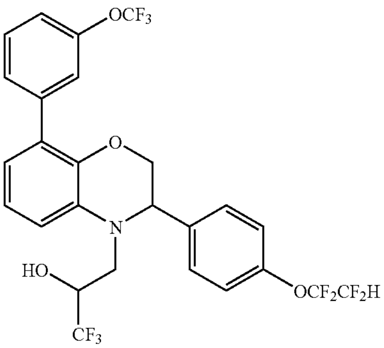

(Lower Rf Cmpd)

1,1,1-Trifluoro-3-[3-[2-(1,1,2,2-tetrafluoro-ethoxy)-phenyl]-8-(3-trifluoromethoxy-phenyl)-2,3-dihydro-benzo[1,4]oxazin-4-yl]-propan-2-ol Spectrums of compound 94 are as following: $^1$H NMR (300 MHz, $CDCl_3$) δ 7.97 (d, J=8.8 Hz, 1H), 7.47-7.11 (m, 7H), 7.02 (t, J=7.7 Hz, 1H), 6.90 (d, J=7.7 Hz, 1H), 6.78 (d, J=7.6 Hz, 1H), 5.90 (tt, J=53.0, 2.7 Hz, 1H), 3.55 (t, J=3.0 Hz, 1H), 4.36-4.19 (m, 3H), 3.70 (dd, J=15.5, 6.7 Hz, 1H), 3.54 (dd, J=15.7, 5.3 Hz, 1H), 2.28 (brs, 1H); MS (ES) m/z: 600 (M+H$^+$).

Example 95

Cmpd 95

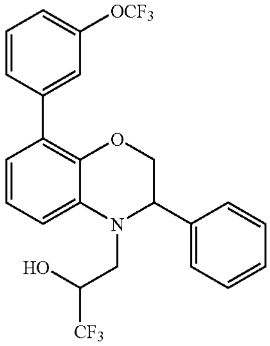

(Higher Rf Cmpd)

1,1,1-Trifluoro-3-[3-phenyl-8-(3-trifluoromethoxy-phenyl)-2,3-dihydro-benzo[1,4]oxazin-4-yl]-propan-2-ol Scheme cc

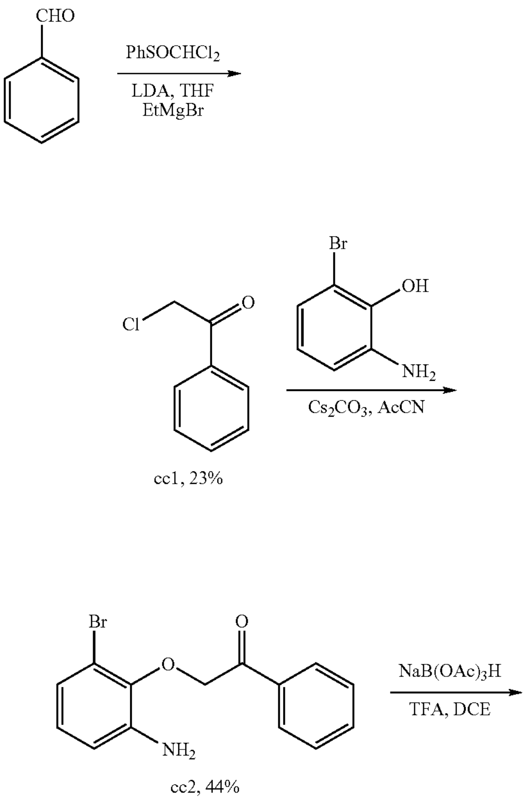

-continued

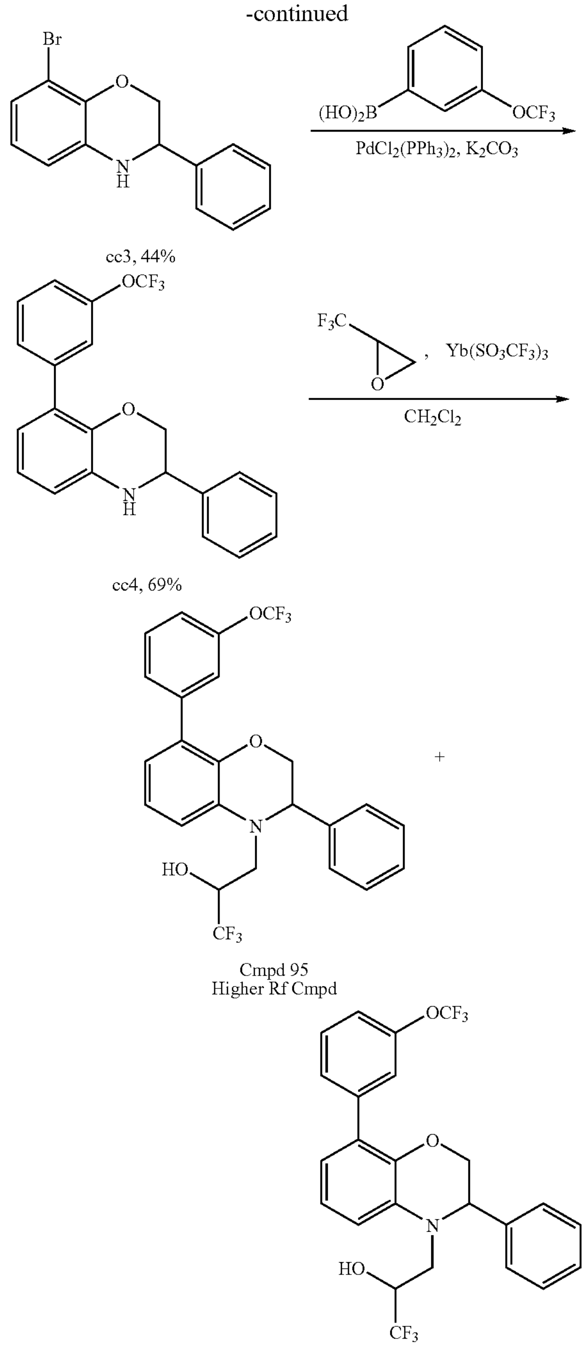

Cmpd 96
Lower Rf Cmpd cc1

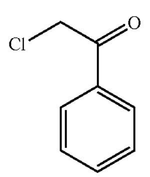

2-Chloro-1-phenyl-ethanone

Replacing 3-(1,1,2,2-tetrafluoro-ethoxy)-benzaldehyde with benzaldehyde and following the same procedure as in the preparation of compound A2a gave compound cc1 (23%): $^{1}$H NMR (300 MHz, $CDCl_3$) δ 7.97 (d, J=7.5 Hz, 2H), 7.65-7.60 (m, 1H), 7.53-7.46 (m, 1H), 7.41-7.37 (m, 1H), 4.72 (s, 2H).

cc2

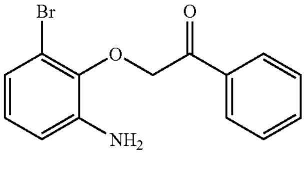

2-(2-Amino-6-bromo-phenoxy)-1-phenyl-ethanone

Replacing A2a with cc1 and following the same procedure as in the preparation of compound A2b gave compound cc2 (44%): $^{1}$H NMR (300 MHz, $CDCl_3$) δ 7.93 (dd, J=7.5, 2.5 Hz, 2H), 7.52-7.45 (m, 3H), 7.40-7.30 (m, 2H), 6.92 (t, J=8.0 Hz, 1H), 5.19 (s, 2H).

cc3

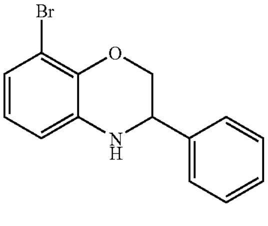

8-Bromo-3-phenyl-3,4-dihydro-2H-benzo[1,4]oxazine

Replacing A2b with cc2 and following the same procedure as in the preparation of compound A2c gave compound cc3 (44%): $^{1}$H NMR (300 MHz, $CDCl_3$) δ 7.47-7.32 (m, 5H), 6.94 (d, J=7.7 Hz, 1H), 6.70-6.59 (m, 2H), 4.52 (d, J=8.5 Hz, 1H), 4.44-4.39 (m, 1H), 4.12-4.00 (m, 2H).

cc4

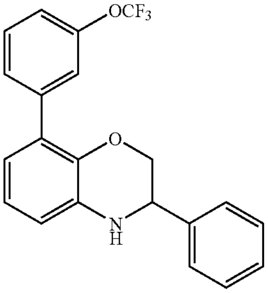

3-Phenyl-8-(3-trifluoromethoxy-phenyl)-3,4-dihydro-2H-benzo[1,4]oxazine

Replacing A2c with cc3 and following the same procedure as in the preparation of compound A2d gave compound cc4 (69%): $^{1}$H NMR (300 MHz, $CDCl_3$) δ 7.51-7.14 (m, 9H), 6.88 (d, J=7.8 Hz, 1H), 6.76-6.69 (m, 2H), 4.55 (dd, J=8.5, 2.9 Hz, 1H), 4.32 (d, J=10.4 Hz, 1H), 4.12 (s, 1H), 4.00 (dd, J=10.5, 8.8 Hz, 1H); MS (ES) m/z: 372 (M+H$^{+}$).

Compound 95

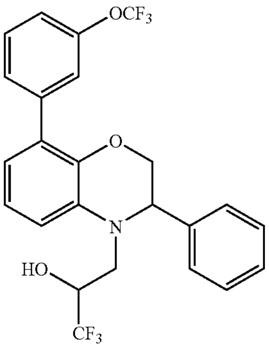

Higher Rf Cmpd 1,1,1-Trifluoro-3-[3-phenyl-8-(3-trifluoromethoxy-phenyl)-2,3-dihydro-benzo[1,4]oxazin-4-yl]-propan-2-ol Replacing A2d with cc4 and following the same procedure as in the preparation of compound 1 and 2 gave higher Rf compound 95 and lower Rf compound 96 (solvent for PLC: 15% EtOAc in hexane). Spectrums of compound 95 are as following: $^1$H NMR (300 MHz, $CDCl_3$) δ 7.50-7.22 (m, 8H), 7.16-7.10 (m, 1H), 7.00 (t, J=7.9 Hz, 1H), 6.82-6.69 (m, 2H), 4.80 (t, J=5.2 Hz, 1H), 4.40-4.23 (m, 2H), 4.17 (dd, J=11.0, 5.3 Hz, 1H), 3.78 (d, J=15.7 Hz, 1H), 3.36 (dd, J=15.7, 9.6 Hz, 1H), 2.40 (d, J=4.4 Hz, 1H); MS (ES) m/z: 484 (M+H$^+$).

Example 96

Cmpd 96

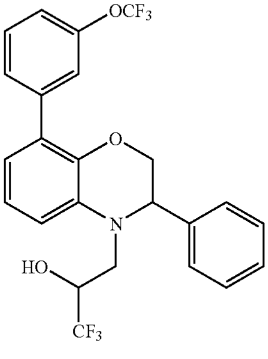

(Lower Rf Cmpd)

1,1,1-Trifluoro-3-[3-phenyl-8-(3-trifluoromethoxy-phenyl)-2,3-dihydro-benzo[1,4]oxazin-4-yl]-propan-2-ol Spectrums of compound 96 are as following: $^1$H NMR (300 MHz, $CDCl_3$) δ 7.48-7.20 (m, 8H), 7.11 (d, J=7.8 Hz, 1H), 7.01 (t, J=7.9 Hz, 1H), 6.88 (d, J=8.2 Hz, 1H), 6.99 (d, J=7.6 Hz, 1H), 4.52 (t, J=3.3 Hz, 1H), 4.33-4.21 (m, 3H), 3.66-3.60 (m, 2H), 2.15 (brs, 1H); MS (ES) m/z: 484 (M+H$^+$).

Example 97

Cmpd 97

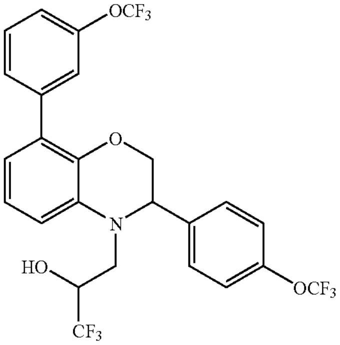

(Higher Rf Cmpd)

1,1,1-Trifluoro-3-[3-(4-trifluoromethoxy-phenyl)-8-(3-trifluoromethoxy-phenyl)-2,3-dihydro-benzo[1,4]oxazin-4-yl]-propan-2-ol Scheme dd

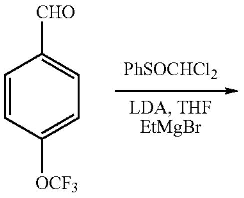

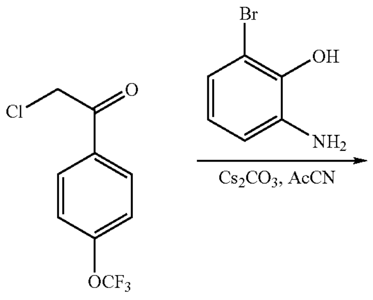

dd1, 23%

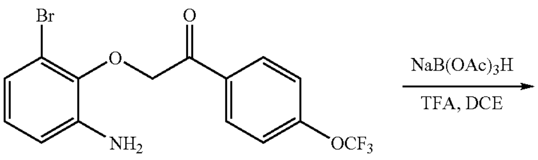

dd2, 44%

-continued

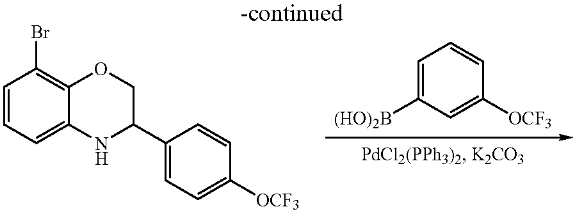

dd3, 44%

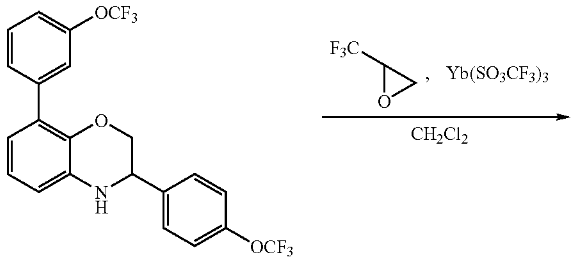

dd4, 69%

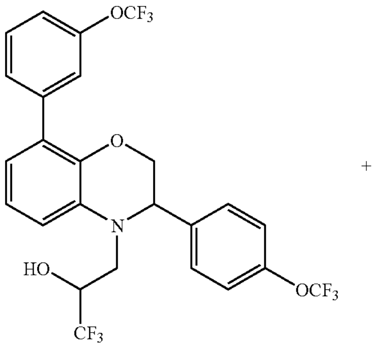

+

Cmpd 97
Higher Rf Cmpd

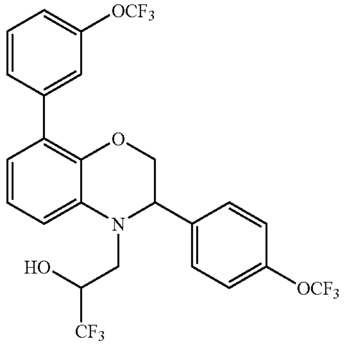

Cmpd 98
Lower Rf Cmpd dd1

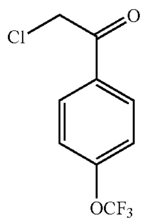

2-Chloro-1-(4-trifluoromethoxy-phenyl)-ethanone

Replacing 3-(1,1,2,2-tetrafluoro-ethoxy)-benzaldehyde with 4-trifluoromethoxy-benzaldehyde and following the same procedure as in the preparation of compound A2a gave compound dd1 (29%): $^1$H NMR (300 MHz, $CDCl_3$) δ 8.03 (d, J=8.8 Hz, 2H), 7.33 (d, J=8.5 Hz, 2H), 4.67 (s, 2H).

dd2

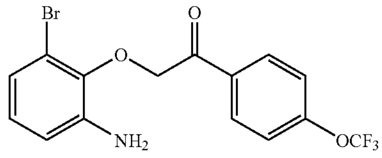

2-(2-Amino-6-bromo-phenoxy)-1-(4-trifluoromethoxy-phenyl)-ethanone

Replacing A2a with dd1 and following the same procedure as in the preparation of compound A2b gave compound dd2 (31%): $^1$H NMR (300 MHz, $CDCl_3$) δ 7.97 (d, J=8.6 Hz, 2H), 7.39-7.31 (m, 4H), 6.93 (t, J=7.9 Hz, 1H), 5.17 (s, 2H); MS (ES) m/z: 372 (M−$H_2O$).

dd3

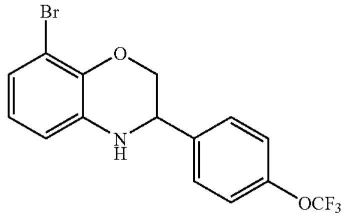

8-Bromo-3-(4-trifluoromethoxy-phenyl)-3,4-dihydro-2H-benzo[1,4]oxazine

Replacing A2b with dd2 and following the same procedure as in the preparation of compound A2c gave compound dd3 (50%): $^1$H NMR (300 MHz, $CDCl_3$) δ 7.42 (d, J=8.7 Hz, 2H), 7.24 (d, J=7.9 Hz, 2H), 6.95 (d, J=7.8 Hz, 1H), 6.72-6.60 (m, 2H), 4.54 (d, J=8.3 Hz, 1H), 4.43-4.37 (m, 1H), 4.14-4.00 (m, 2H).

dd4

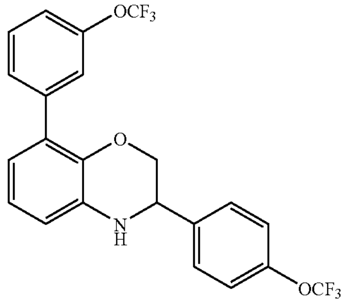

3-(4-Trifluoromethoxy-phenyl)-8-(3-trifluoromethoxy-phenyl)-3,4-dihydro-2H-benzo[1,4]oxazine Replacing A2c with dd3 and following the same procedure as in the preparation of compound A2d gave compound dd4

(74%): $^1$H NMR (300 MHz, $CDCl_3$) δ 7.51-7.38 (m, 5H), 7.29-7.12 (m, 3H), 6.89 (t, J=7.7 Hz, 1H), 6.78-6.69 (m, 2H), 4.58 (d, J=8.1 Hz, 1H), 4.33-4.27 (m, 1H), 4.11 (brs, 1H), 3.98 (dd, J=10.6, 8.4 Hz, 1H); MS (ES) m/z: 456 (M+H$^+$).

Compound 97 Higher Rf Cmpd

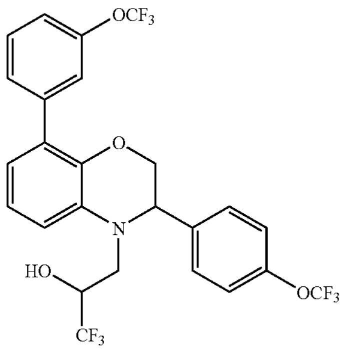

1,1,1-Trifluoro-3-[3-(4-trifluoromethoxy-phenyl)-8-(3-trifluoromethoxy-phenyl)-2,3-dihydro-benzo[1,4]oxazin-4-yl]-propan-2-ol Replacing A2d with dd4 and following the same procedure as in the preparation of compound 1 and 2 gave higher Rf compound 97 and lower Rf compound 98 (solvent for PLC: 15% EtOAc in hexane). Spectrums of compound 97 are as following: $^1$H NMR (300 MHz, $CDCl_3$) δ 7.47-7.11 (m, 8H), 7.01 (t, J=7.9 Hz, 1H), 6.77 (d, J=7.9 Hz, 2H), 4.87 (d, J=3.8 Hz, 1H), 4.45-4.35 (m, 1H), 4.27 (dd, J=10.9, 3.1 Hz, 1H), 4.15 (dd, J=10.7, 4.3 Hz, 1H), 3.82 (d, J=14.5 Hz, 1H), 3.30 (dd, J=15.7, 9.6 Hz, 1H), 2.40 (brs, 1H); MS (ES) m/z: 568 (M+H$^+$).

Example 98

Cmpd 98 (Lower Rf Cmpd)

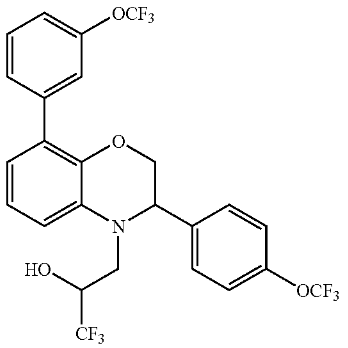

1,1,1-Trifluoro-3-[3-(4-trifluoromethoxy-phenyl)-8-(3-trifluoromethoxy-phenyl)-2,3-dihydro-benzo[1,4]oxazin-4-yl]-propan-2-ol Spectrums of compound 98 are as following: $^1$H NMR (300 MHz, $CDCl_3$) δ 7.45-7.32 (m, 3H), 7.28-7.10 (m, 5H), 7.02 (t, J=7.9 Hz, 1H), 6.89 (d, J=8.1 Hz, 1H), 6.78 (d, J=7.5 Hz, 1H), 4.55 (m, 1H), 4.37-4.18 (m, 3H), 3.70 (dd, J=15.7, 6.5 Hz, 1H), 3.53 (dd, J=15.7, 5.4 Hz, 1H), 2.23 (brs, 1H); MS (ES) m/z: 568 (M+H$^+$).

Example 99

Cmpd 99 (Higher Rf Cmpd)

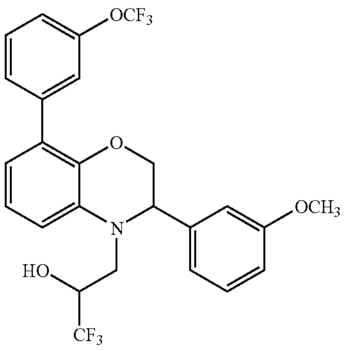

1,1,1-Trifluoro-3-[3-(3-methoxy-phenyl)-8-(3-trifluoromethoxy-phenyl)-2,3-dihydro-benzo[1,4]oxazin-4-yl]-propan-2-ol Scheme ee

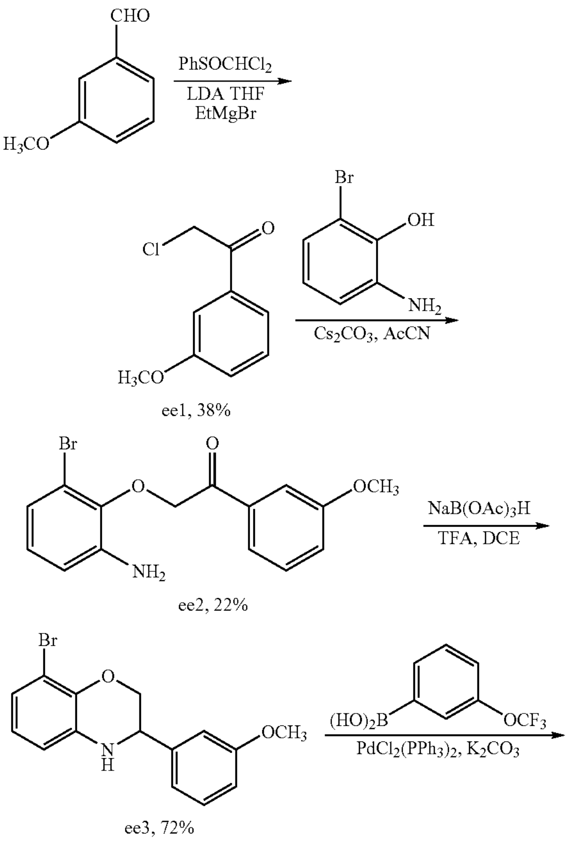

-continued

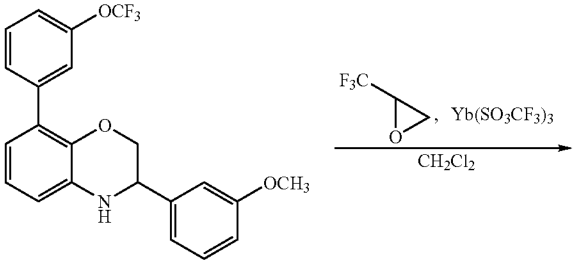

ee4, 57%

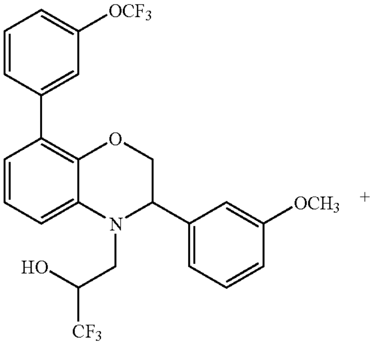

Cmpd 99
Higher Rf Cmpd

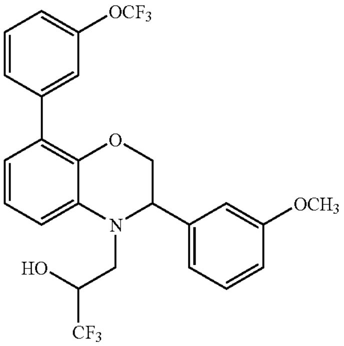

Cmpd 100
Lower Rf Cmpd

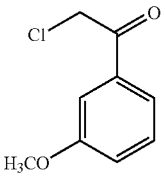

ee1

2-Chloro-1-(3-methoxy-phenyl)-ethanone

Replacing 3-(1,1,2,2-tetrafluoro-ethoxy)-benzaldehyde with 3-methoxy-benzaldehyde and following the same procedure as in the preparation of compound A2a gave compound ee1 (38%): $^1$H NMR (300 MHz, $CDCl_3$) δ 7.55-7.48 (m, 2H), 7.40 (d, J=7.9 Hz, 1H), 7.19-7.14 (m, 1H), 4.70 (s, 2H), 3.87 (s, 3H).

ee2

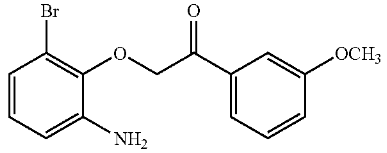

2-(2-Amino-6-bromo-phenoxy)-1-(3-methoxy-phenyl)-ethanone

Replacing A2a with ee1 and following the same procedure as in the preparation of compound A2b gave compound ee2 (22%): $^1$H NMR (300 MHz, $CDCl_3$) δ 7.55 (m, 1H), 7.45-7.32 (m, 4H), 7.10-7.02 (m, 1H), 6.91 (t, J=7.9 Hz, 1H), 5.17 (s, 2H), 3.90 (s, 3H).

ee3

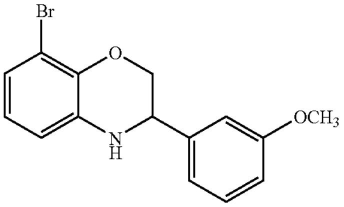

8-Bromo-3-(3-methoxy-phenyl)-3,4-dihydro-2H-benzo[1,4]oxazine

Replacing A2b with ee2 and following the same procedure as in the preparation of compound A2c gave compound ee3 (72%): $^1$H NMR (300 MHz, $CDCl_3$) δ 7.35-7.28 (m, 1H), 7.02-6.91 (m, 4H), 6.71-6.59 (m, 2H), 4.49 (dd, J=8.6, 3.0 Hz, 1H), 4.42 (dd, J=10.6, 3.0 Hz, 1H), 4.12-4.00 (m, 2H), 3.82 (s, 3H); MS (ES) m/z: 320 (M).

ee4

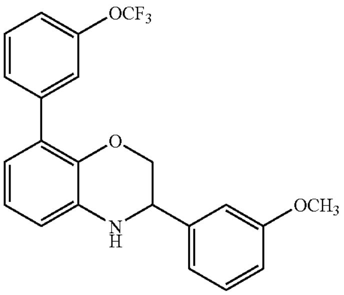

3-(3-Methoxy-phenyl)-8-(3-trifluoromethoxy-phenyl)-3,4-dihydro-2H-benzo[1,4]oxazine Replacing A2c with ee3 and following the same procedure as in the preparation of compound A2d gave compound ee4 (57%): $^1$H NMR (300 MHz, $CDCl_3$) δ 7.52-7.38 (m, 3H), 7.35-7.26 (m, 1H), 7.16 (d, J=7.9 Hz, 1H), 7.02-6.95 (m, 2H), 6.91-6.85 (m, 2H), 6.79-6.68 (m, 2H), 4.53 (dd, J=8.4, 2.7 Hz, 1H), 4.32 (bd, J=10.4 Hz, 1H), 4.11 (brs, 1H), 3.99 (dd, J=10.5, 8.7 Hz, 1H), 3.82 (s, 3H); MS (ES) m/z: 402 ($M+H^+$).

Compound 99 Higher Rf Cmpd

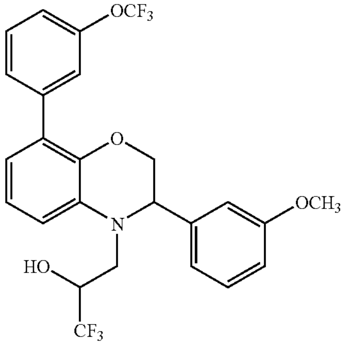

1,1,1-Trifluoro-3-[3-(3-methoxy-phenyl)-8-(3-trifluoromethoxy-phenyl)-2,3-dihydro-benzo[1,4]oxazin-4-yl]-propan-2-ol Replacing A2d with ee4 and following the same procedure as in the preparation of compound 1 and 2 gave higher Rf compound 99 and lower Rf compound 100 (solvent for PLC: 15% EtOAc in hexane). Spectrums of compound 99 are as following: $^1$H NMR (300 MHz, $CDCl_3$) δ 7.49-7.28 (m, 4H), 7.14 (d, J=8.0 Hz, 1H), 6.99 (t, J=7.8 Hz, 1H), 6.90-6.72 (m, 5H), 4.77 (dd, J=5.2, 3.4 Hz, 1H), 4.40-4.21 (m, 2H), 4.16 (dd, J=11.3, 5.6 Hz, 1H), 3.83-3.75 (m, 4H), 3.37 (dd, J=15.6, 9.7 Hz, 1H), 2.37 (brs, 1H); MS (ES) m/z: 514 (M+H$^+$).

Example 100

Cmpd 100 (Lower Rf Cmpd)

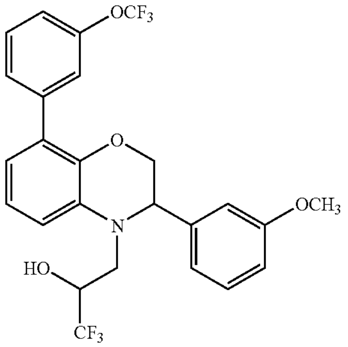

1,1,1-Trifluoro-3-[3-(3-methoxy-phenyl)-8-(3-trifluoromethoxy-phenyl)-2,3-dihydro-benzo[1,4]oxazin-4-yl]-propan-2-ol Spectrums of compound 100 are as following: $^1$H NMR (300 MHz, $CDCl_3$) δ 7.47-7.28 (m, 4H), 7.15 (d, J=7.8 Hz, 1H), 7.00 (t, J=7.9 Hz, 1H), 6.90-6.72 (m, 5H), 4.48 (t, J=3.4

Hz, 1H), 4.35-4.21 (m, 3H), 3.80-3.75 (m, 4H), 3.63 (t, J=5.3 Hz, 1H), 2.17 (brs, 1H); MS (ES) m/z: 514 (M+H$^+$).

Example 101

Cmpd 101 (Higher Rf Cmpd)

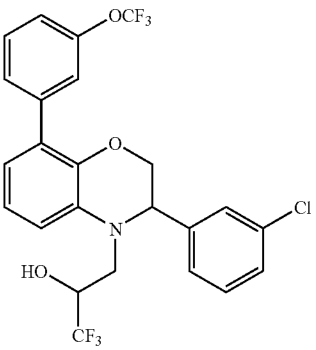

3-[3-(3-Chloro-phenyl)-8-(3-trifluoromethoxy-phenyl)-2,3-dihydro-benzo[1,4]oxazin-4-yl]-1,1,1-trifluoro-propan-2-ol Scheme ff

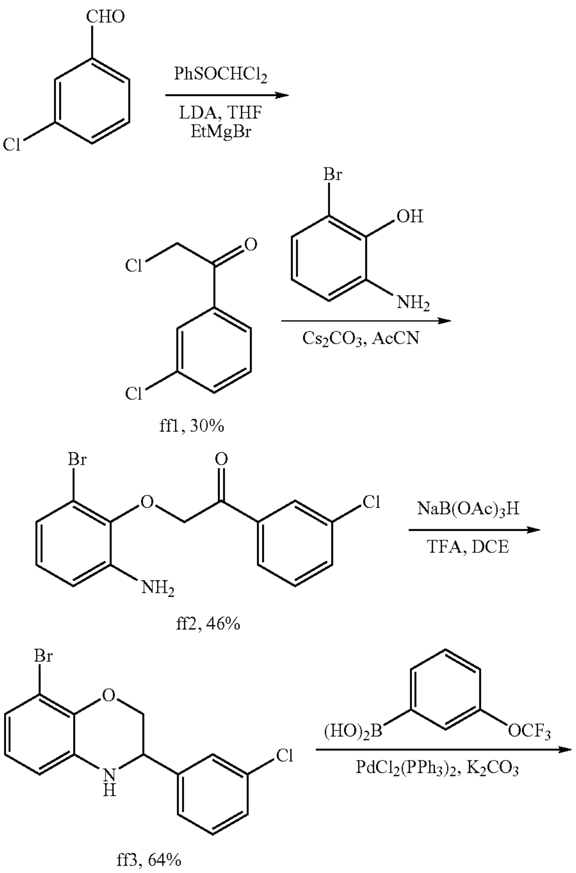

-continued

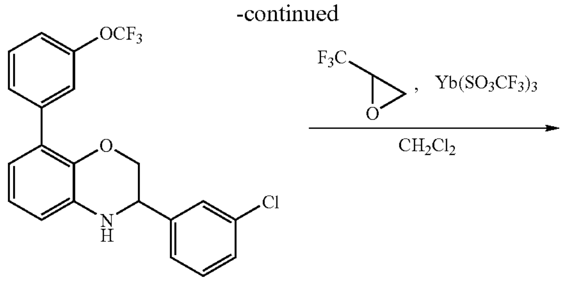

ff4, 63%

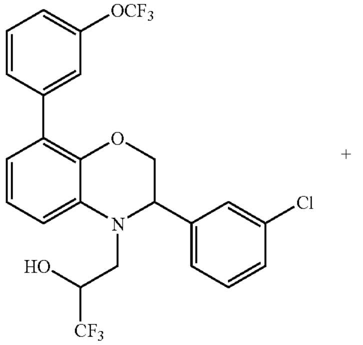

Cmpd 101
Higher Rf Cmpd

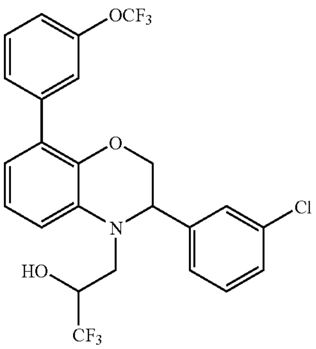

Cmpd 102
Lower Rf Cmpd ff1

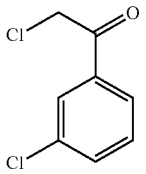

2-Chloro-1-(3-chloro-phenyl)-ethanone

Replacing 3-(1,1,2,2-tetrafluoro-ethoxy)-benzaldehyde with 3-chloro-benzaldehyde and following the same procedure as in the preparation of compound A2a gave compound ff1 (30%): $^1$H NMR (300 MHz, CDCl$_3$) δ 7.94 (s, 1H), 7.84 (d, J=7.8 Hz, 1H), 7.62-7.58 (m, 1H), 7.45 (t, J=7.9 Hz, 1H), 4.67 (s, 2H).

ff2

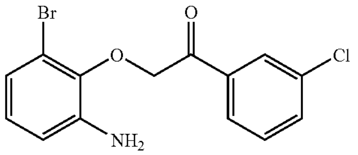

2-(2-Amino-6-bromo-phenoxy)-1-(3-chloro-phenyl)-ethanone

Replacing A2a with ff1 and following the same procedure as in the preparation of compound A2b gave compound ff2 (46%): $^1$H NMR (300 MHz, CDCl$_3$) δ 7.97 (s, 1H), 7.73 (d, J=7.6 Hz, 1H), 7.50-7.35 (m, 4H), 6.93 (t, J=7.9 Hz, 1H), 5.15 (s, 2H); MS (ES) m/z: 362 (M+Na$^+$).

ff3

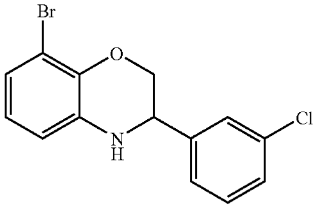

8-Bromo-3-(3-chloro-phenyl)-3,4-dihydro-2H-benzo[1,4]oxazine

Replacing A2b with ff2 and following the same procedure as in the preparation of compound A2c gave compound ff3 (64%): $^1$H NMR (300 MHz, CDCl$_3$) δ 7.45-7.19 (m, 4H), 6.95 (d, J=7.7 Hz, 1H), 6.71-6.60 (m, 2H), 4.50 (d, J=8.3, 2.5 Hz, 1H), 4.42-4.37 (m, 1H), 4.21-3.95 (m, 2H); MS (ES) m/z: 326 (M+H$^+$).

ff4

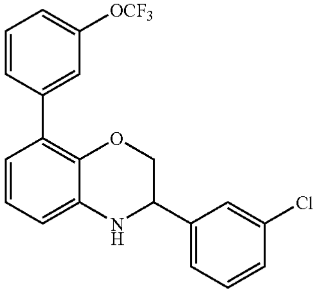

3-(3-Chloro-phenyl)-8-(3-trifluoromethoxy-phenyl)-3,4-dihydro-2H-benzo[1,4]oxazine Replacing A2c with ff3 and following the same procedure as in the preparation of compound A2d gave compound ff4 (63%): $^1$H NMR (300 MHz, CDCl$_3$) δ 7.51-7.22 (s, 7H), 7.16 (d, J=8.0 Hz, 1H), 6.89 (t, J=7.7 Hz, 1H), 6.78-6.69 (m, 2H), 4.54 (d, J=7.3 Hz, 1H), 4.33-4.27 (m, 1H), 4.11 (brs, 1H), 3.97 (d, J=10.6, 8.4 Hz, 1H); MS (ES) m/z: 406 (M+H$^+$).

Compound 101 Higher Rf Cmpd

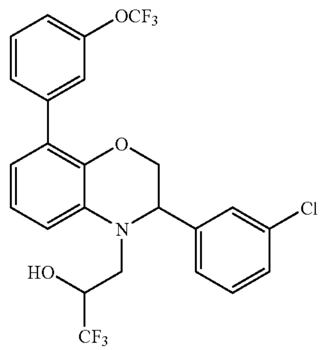

3-[3-(3-Chloro-phenyl)-8-(3-trifluoromethoxy-phenyl)-2,3-dihydro-benzo[1,4]oxazin-4-yl]-1,1,1-trifluoro-propan-2-ol Replacing A2d with ff4 and following the same procedure as in the preparation of compound 1 and 2 gave higher Rf compound 101 and lower Rf compound 102 (solvent for PLC: 15% EtOAc in hexane). Spectrums of compound 101 are as following: $^1$H NMR (300 MHz, $CDCl_3$) δ 7.48-7.33 (m, 4H), 7.32-7.25 (m, 2H), 7.19-7.11 (m, 2H), 7.01 (t, J=7.9 Hz, 1H), 6.77 (t, J=7.9 Hz, 2H), 4.83 (t, J=3.9 Hz, 1H), 4.46-4.35 (m, 1H), 4.25 (dd, J=10.9, 3.2 Hz, 1H), 4.14 (dd, J=10.7, 4.8 Hz, 1H), 3.83 (d, J=15.7 Hz, 1H), 3.31 (dd, J=15.7, 9.6 Hz, 1H), 2.40 (d, J=4.2 Hz, 1H); MS (ES) m/z: 518 (M+H$^+$).

Example 102

Cmpd 102 Lower Rf Cmpd

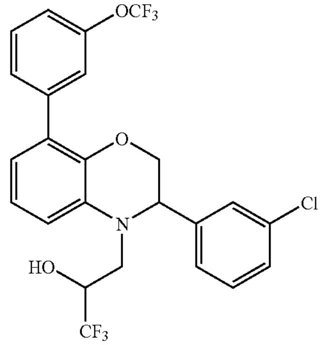

3-[3-(3-Chloro-phenyl)-8-(3-trifluoromethoxy-phenyl)-2,3-dihydro-benzo[1,4]oxazin-4-yl]-1,1,1-trifluoro-propan-2-ol Spectrums of compound 102 are as following: $^1$H NMR (300 MHz, $CDCl_3$) δ 7.45-7.20 (m, 6H), 7.19-7.09 (m, 2H), 7.02 (t, J=7.8 Hz, 1H), 6.89 (d, J=8.0 Hz, 1H), 6.78 (d, J=7.5 Hz, 1H), 4.51 (t, J=2.9 Hz, 1H), 4.36-4.18 (m, 3H), 3.70 (dd, J=15.7, 6.6 Hz, 1H), 3.54 (dd, J=15.7, 5.1 Hz, 1H), 2.23 (d, J=5.1 Hz, 1H); MS (ES) m/z: 518 (M+H$^+$).

Example 103

Cmpd 103 (Higher Rf Cmpd)

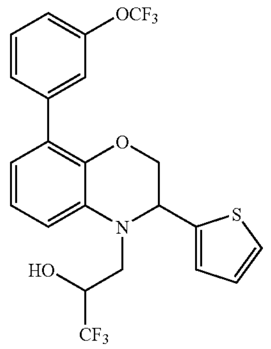

1,1,1-Trifluoro-3-[3-thiophen-2-yl-8-(3-trifluoromethoxy-phenyl)-2,3-dihydro-benzo[1,4]oxazin-4-yl]-propan-2-ol Scheme gg

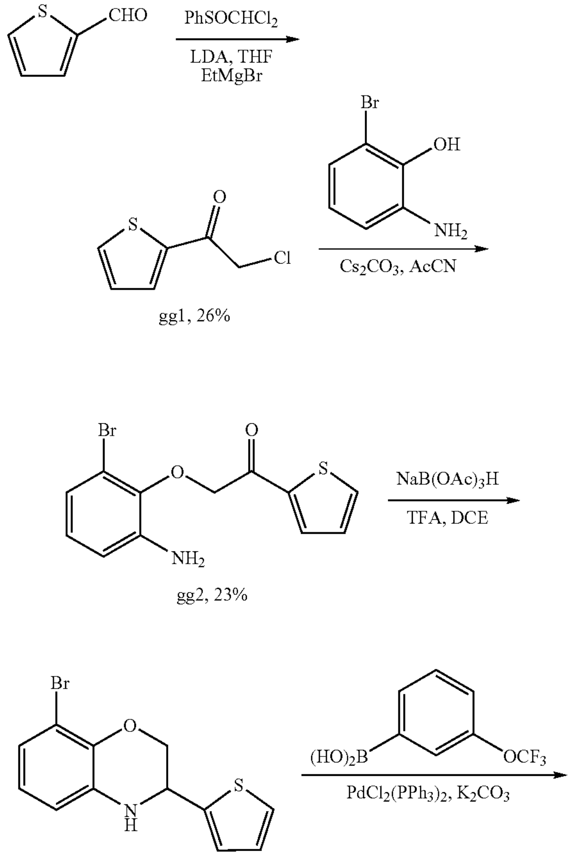

-continued

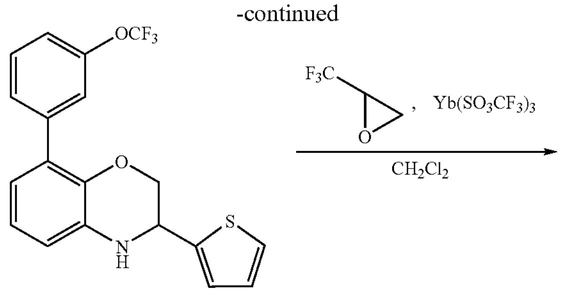

gg4, 89%

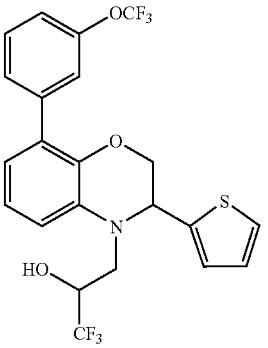

+

Cmpd 103
Higher Rf Cmpd

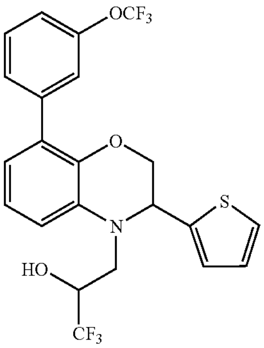

Cmpd 104
Higher Rf Cmpd gg1

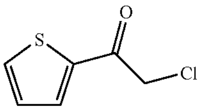

2-Chloro-1-thiophen-2-yl-ethanone

Replacing 3-(1,1,2,2-tetrafluoro-ethoxy)-benzaldehyde with thiophene-2-carbaldehyde and following the same procedure as in the preparation of compound A2a gave compound gg1 (26%): $^1$H NMR (300 MHz, $CDCl_3$) δ 7.79 (d, J=3.7 Hz, 1H), 7.73 (d, J=4.9 Hz, 1H), 7.17 (t, J=4.5 Hz, 1H), 4.59 (s, 2H).

gg2

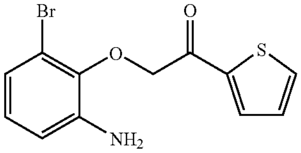

2-(2-Amino-6-bromo-phenoxy)-1-thiophen-2-yl-ethanone

Replacing A2a with gg1 and following the same procedure as in the preparation of compound A2b gave compound gg2 (23%): $^1$H NMR (300 MHz, $CDCl_3$) δ 7.58 (d, J=5.0 Hz, 1H), 7.44 (d, J=3.8 Hz, 1H), 7.34 (d, J=8.0 Hz, 2H), 7.15 (t, J=4.4 Hz, 1H), 6.90 (t, J=7.9 Hz, 1H), 5.11 (s, 2H).

gg3

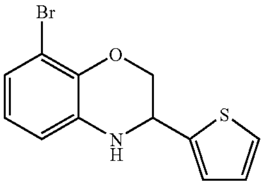

8-Bromo-3-thiophen-2-yl-3,4-dihydro-2H-benzo[1,4]oxazine

Replacing A2b with gg2 and following the same procedure as in the preparation of compound A2c gave compound gg3 (67%): $^1$H NMR (300 MHz, $CDCl_3$) δ 7.31 (d, J=4.9 Hz, 1H), 7.09 (d, J=3.0 Hz, 1H), 7.02 (t, J=4.8 Hz, 1H), 6.95 (d, J=7.9 Hz, 1H), 6.68 (t, J=7.9 Hz, 1H), 6.60 (d, J=7.9 Hz, 1H), 4.86 (d, J=6.5 Hz, 1H), 4.47 (bd, J=10.5 Hz, 1H), 4.21 (brs, 1H), 4.15 (dd, J=10.6, 8.2 Hz, 1H); MS (ES) m/z: 298 (M+2).

gg4

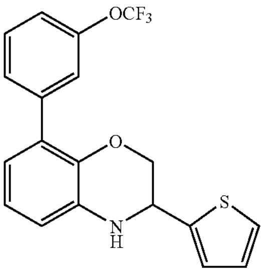

3-Thiophen-2-yl-8-(3-trifluoromethoxy-phenyl)-3,4-dihydro-2H-benzo[1,4]oxazine

Replacing A2c with gg3 and following the same procedure as in the preparation of compound A2d gave compound gg4 (89%): $^1$H NMR (300 MHz, $CDCl_3$) δ 7.51-7.38 (m, 3H), 7.30 (d, J=5.0 Hz, 1H), 7.18-7.14 (m, 1H), 7.09 (d, J=3.4 Hz, 1H), 7.03-6.90 (m, 1H), 6.88 (t, J=7.5 Hz, 1H), 6.76 (d, J=7.6 Hz, 1H), 6.69 (d, J=7.8 Hz, 1H), 4.89 (d, J=6.3 Hz, 1H), 4.36 (bd, J=10.6 Hz, 1H), 4.24 (brs, 1H), 4.10 (dd, J=10.5, 8.1 Hz, 1H); MS (ES) m/z: 378 ($M+H^+$).

Compound 103

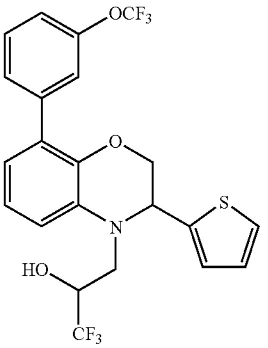

Higher Rf Cmpd 1,1,1-Trifluoro-3-[3-thiophen-2-yl-8-(3-trifluoromethoxy-phenyl)-2,3-dihydro-benzo[1,4]oxazin-4-yl]-propan-2-ol Replacing A2d with gg4 and following the same procedure as in the preparation of compound 1 and 2 gave higher Rf compound 103 and lower Rf compound 104 (solvent for PLC: 15% EtOAc in hexane). Spectrums of compound 103 are as following: $^1$H NMR (300 MHz, $CDCl_3$) δ 7.50-7.36 (m, 3H), 7.31-7.25 (m, 1H), 7.16 (d, J=8.0 Hz, 1H), 7.08-6.93 (m, 3H), 6.77 (t, J=8.1 Hz, 2H), 5.03 (t, J=3.7 Hz, 1H), 4.38-4.25 (m, 3H), 3.72 (d, J=15.7, 2.1 Hz, 1H), 3.48 (dd, J=15.7, 9.5 Hz, 1H), 2.47 (brs, 1H); MS (ES) m/z: 490 (M+H$^+$).

Example 104

Cmpd 104

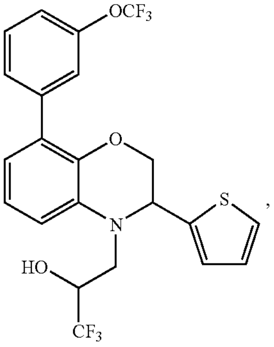

(Lower RF Cmpd)

1,1,1-Trifluoro-3-[3-thiophen-2-yl-8-(3-trifluoromethoxy-phenyl)-2,3-dihydro-benzo[1,4]oxazin-4-yl]-propan-2-ol Spectrums of compound 104 are as following: $^1$H NMR (300 MHz, $CDCl_3$) δ 7.51-7.37 (m, 3H), 7.30-7.23 (m, 1H), 7.16 (d, J=8.1 Hz, 1H), 7.04-6.95 (m, 3H), 6.84-6.78 (m, 2H), 4.77 (t, J=2.7 Hz, 1H), 4.39-4.25 (m, 3H), 3.71-3.52 (m, 2H), 2.31 (brs, 1H); MS (ES) m/z: 490 (M+H$^+$).

Example 105

Cmpd 105

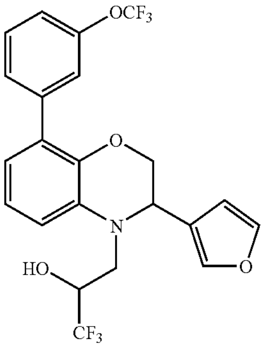

(Higher RF Cmpd)

1,1,1-Trifluoro-3-[3-furan-3-yl-8-(3-trifluoromethoxy-phenyl)-2,3-dihydro-benzo[1,4]oxazin-4-yl]-propan-2-ol Scheme hh

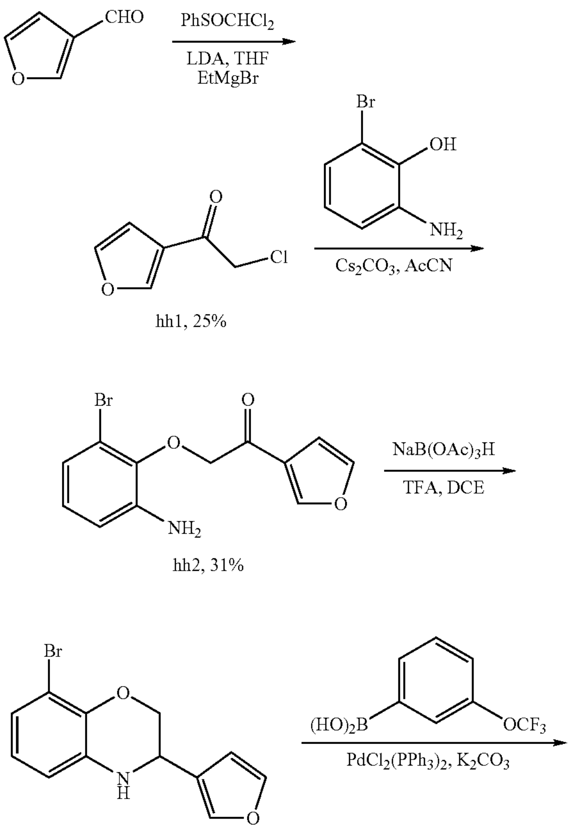

-continued

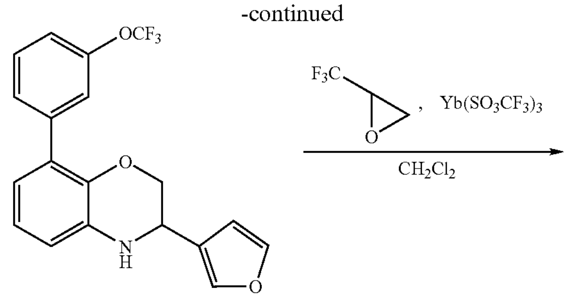

hh4, 63%

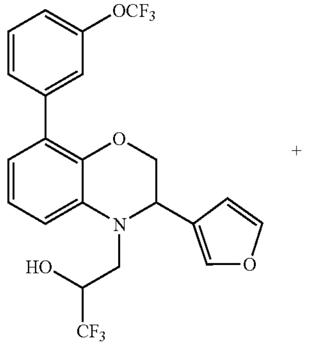

Cmpd 105
Higher Rf Cmpd

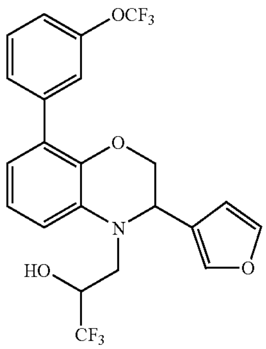

Cmpd 106
Higher Rf Cmpd hh1

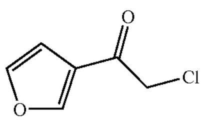

2-Chloro-1-furan-3-yl-ethanone

Replacing 3-(1,1,2,2-tetrafluoro-ethoxy)-benzaldehyde with furan-3-carbaldehyde and following the same procedure as in the preparation of compound A2a gave compound hh1 (25%): $^{1}$H NMR (300 MHz, $CDCl_3$) δ 8.15 (s, 1H), 7.48 (m, 1H), 6.81 (s, 1H), 4.42 (s, 2H).

hh2

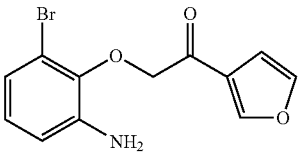

2-(2-Amino-6-bromo-phenoxy)-1-furan-3-yl-ethanone

Replacing A2a with hh1 and following the same procedure as in the preparation of compound A2b gave compound hh2 (31%): $^{1}$H NMR (300 MHz, $CDCl_3$) δ 7.87 (s, 1H), 7.53 (t, J=2.0 Hz, 1H), 7.35-7.31 (m, 2H), 6.97 (s, 1H), 6.90 (t, J=8.0 Hz, 1H), 4.93 (s, 2H).

hh3

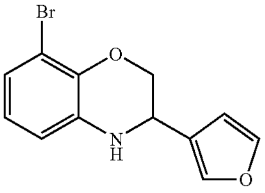

8-Bromo-3-furan-3-yl-3,4-dihydro-2H-benzo[1,4]oxazine

Replacing A2b with hh2 and following the same procedure as in the preparation of compound A2c gave compound hh3 (80%): $^{1}$H NMR (300 MHz, $CDCl_3$) δ 7.48 (s, 1H), 7.43 (s, 1H), 6.93 (d, J=7.8 Hz, 1H), 6.66 (t, J=7.9 Hz, 1H), 6.57 (d, J=7.9 Hz, 1H), 6.40 (s, 1H), 4.52 (d, J=8.1 Hz, 1H), 4.41 (bd, J=10.6 Hz, 1H), 4.09 (dd, J=10.6, 8.2 Hz, 1H), 4.00 (brs, 1H); MS (ES) m/z: 282 (M+2).

hh4

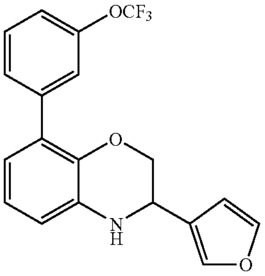

3-Furan-3-yl-8-(3-trifluoromethoxy-phenyl)-3,4-dihydro-2H-benzo[1,4]oxazine

Replacing A2c with hh3 and following the same procedure as in the preparation of compound A2d gave compound hh4 (63%): $^{1}$H NMR (300 MHz, $CDCl_3$) δ 7.50-7.36 (m, 5H), 7.16 (d, J=7.4 Hz, 1H), 6.86 (t, J=7.7 Hz, 1H), 6.74 (d, J=7.7 Hz, 1H), 6.66 (d, J=7.8 Hz, 1H), 6.41 (s, 1H), 4.55 (dd, J=8.2, 2.8 Hz, 1H), 4.31 (dd, J=10.5, 2.9 Hz, 1H), 4.06-3.99 (m, 2H); MS (ES) m/z: 262 ($M+H^+$).

Compound 105

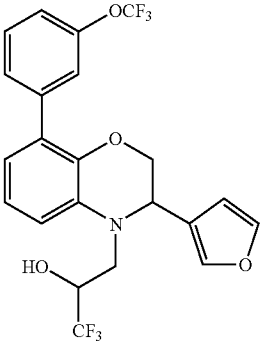

Higher RF Cmpd 1,1,1-Trifluoro-3-[3-furan-3-yl-8-(3-trifluoromethoxy-phenyl)-2,3-dihydro-benzo[1,4]oxazin-4-yl]-propan-2-ol Replacing A2d with hh4 and following the same procedure as in the preparation of compound 1 and 2 gave higher Rf compound 105 and lower Rf compound 106 (solvent for PLC: 15% EtOAc in hexane). Spectrums of compound 105 are as following: $^{1}$H NMR (300 MHz, $CDCl_3$) δ 7.49-7.38 (m, 5H), 7.16 (d, J=7.7 Hz, 1H), 6.96 (t, J=7.9 Hz, 1H), 6.74 (bt, J=7.6 Hz, 2H), 6.34 (s, 1H), 4.68 (t, J=3.9 Hz, 1H), 4.38-4.18 (m, 3H), 3.71 (d, J=15.5 Hz, 1H), 3.46 (dd, J=15.6, 9.4 Hz, 1H), 2.46 (d, J=4.4 Hz, 1H); MS (ES) m/z: 474 ($M+H^+$).

Example 106

Cmpd 106

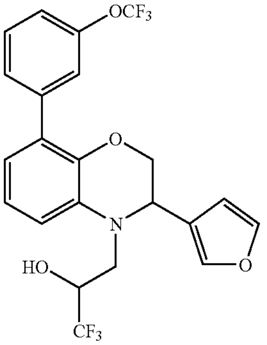

(Lower RF Cmpd)

1,1,1-Trifluoro-3-[3-furan-3-yl-8-(3-trifluoromethoxy-phenyl)-2,3-dihydro-benzo[1,4]oxazin-4-yl]-propan-2-ol Spectrums of compound 106 are as following: $^{1}$H NMR (400 MHz, $CDCl_3$) δ 7.48-7.37 (m, 5H), 7.17-7.14 (m, 1H), 6.96 (t, J=7.9 Hz, 1H), 6.82-6.74 (m, 2H), 6.34 (s, 1H), 4.43 (t, J=3.1 Hz, 1H), 4.32-4.22 (m, 3H), 3.65-3.52 (m, 2H), 2.36 (d, J=4.8 Hz, 1H); MS (ES) m/z: 474 ($M+H^+$).

Compounds 1 through 108 of Formula (I), (Ia), (Ib) or (Ic) in Table 1 were prepared according to the methods described by the Schemes and Examples described herein.

TABLE 1

| Representative Compounds | | |
|---|---|---|
| Cpd No. | Structure | Rf |
| 1 | 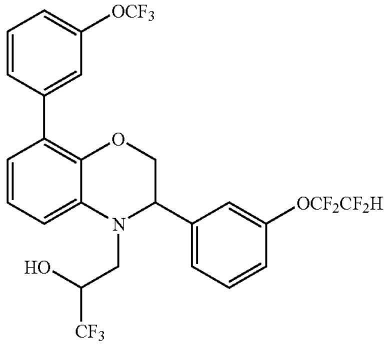 | Higher |
| 2 | 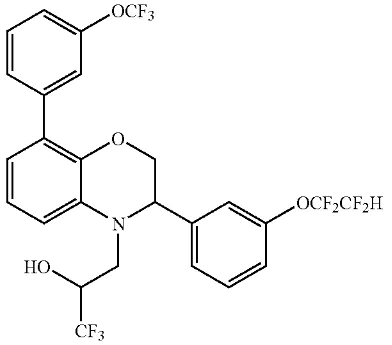 | Lower |
| 3 | 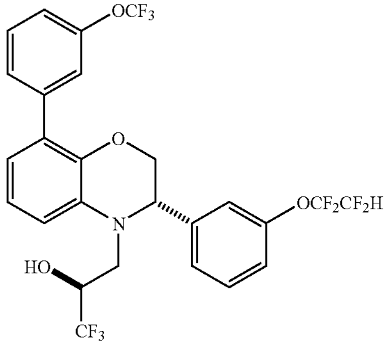 | Not Applicable |
| 4 | 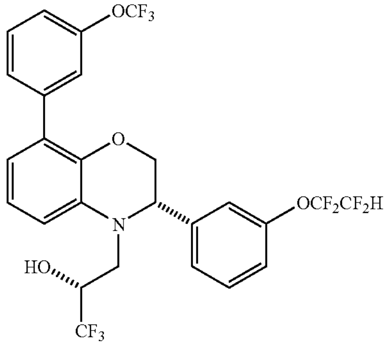 | Not Applicable |

TABLE 1-continued
| Representative Compounds | | |
|---|---|---|
| Cpd No. | Structure | Rf |
| 5 | 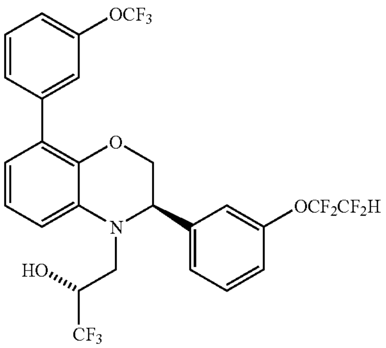 | Not Applicable |
| 6 | 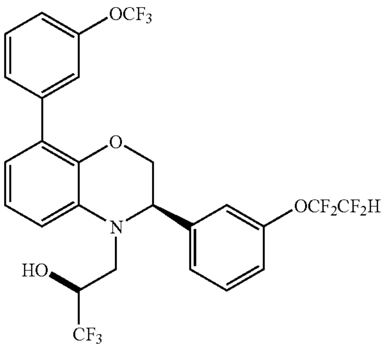 | Not Applicable |
| 7 | 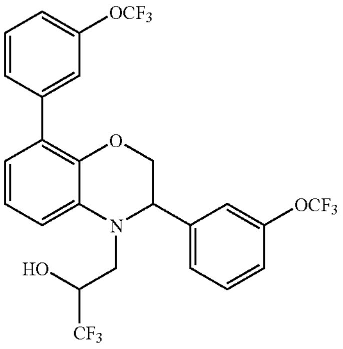 | Higher |
| 8 | 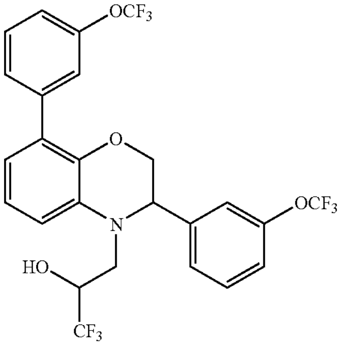 | Lower |
TABLE 1-continued
| Representative Compounds | | |
|---|---|---|
| Cpd No. | Structure | Rf |
| 9 | 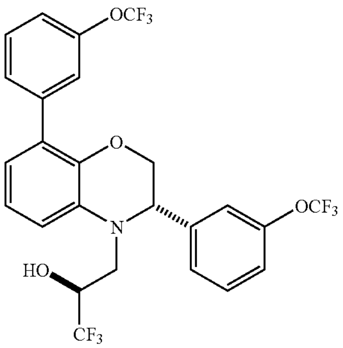 | Not Applicable |
| 10 | 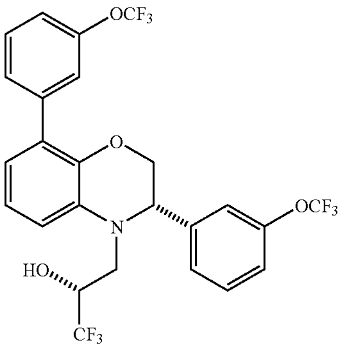 | Not Applicable |
| 11 | 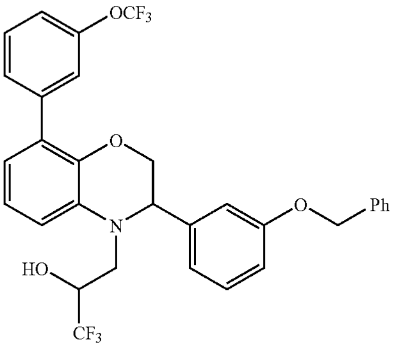 | Higher |
| 12 | 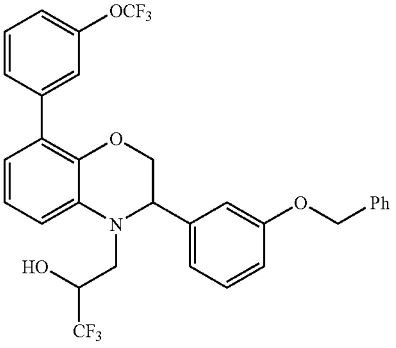 | Lower |

TABLE 1-continued
Representative Compounds
| Cpd No. | Structure | Rf |
|---|---|---|
| 13 | 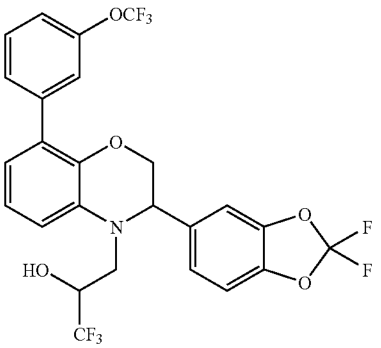 | Higher |
| 14 | 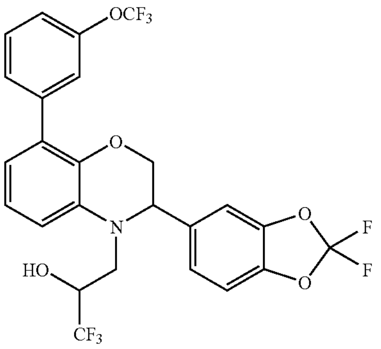 | Lower |
| 15 | 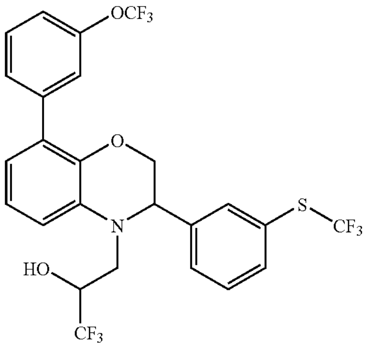 | Higher |
| 16 | 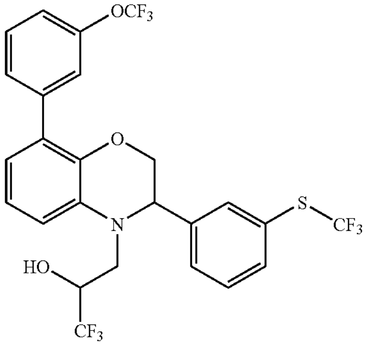 | Lower |
TABLE 1-continued
Representative Compounds
| Cpd No. | Structure | Rf |
|---|---|---|
| 17 | 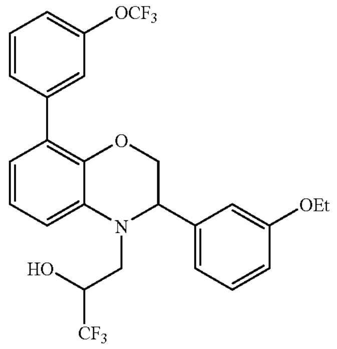 | Higher |
| 18 | 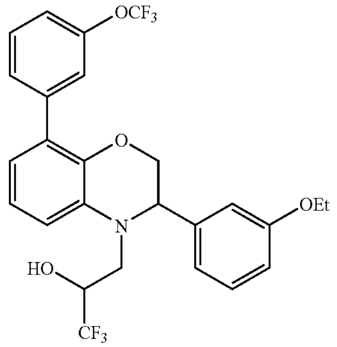 | Lower |
| 19 | 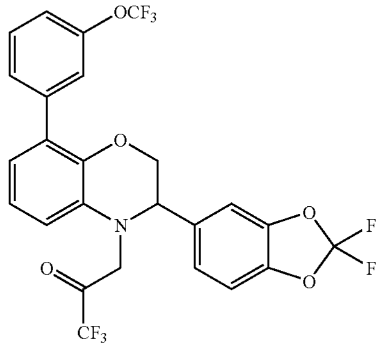 | Not Applicable |
| 20 | 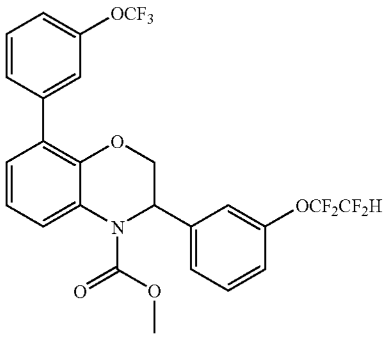 | Not Applicable |

TABLE 1-continued
| Representative Compounds | | |
|---|---|---|
| Cpd No. | Structure | Rf |
| 21 | 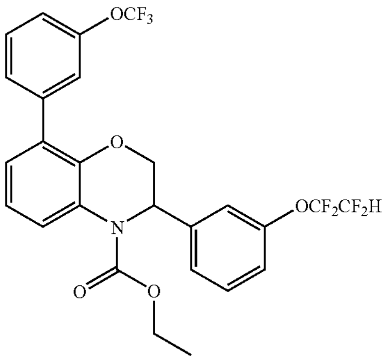 | Not Applicable |
| 22 | 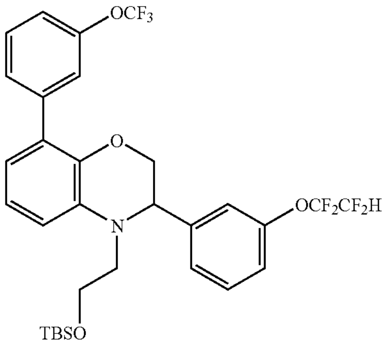 | Not Applicable |
| 23 | 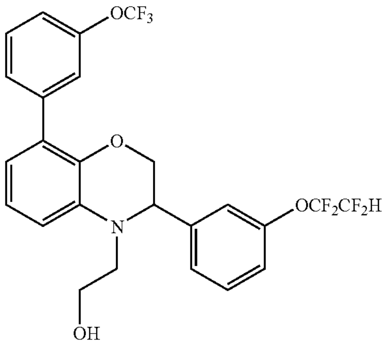 | Not Applicable |
| 24 | 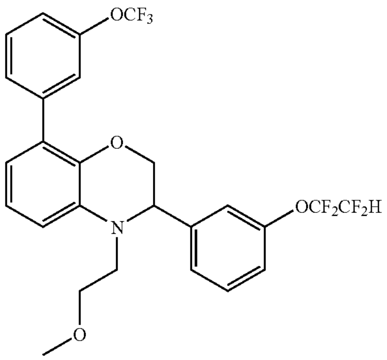 | Not Applicable |
TABLE 1-continued
| Representative Compounds | | |
|---|---|---|
| Cpd No. | Structure | Rf |
| 25 | 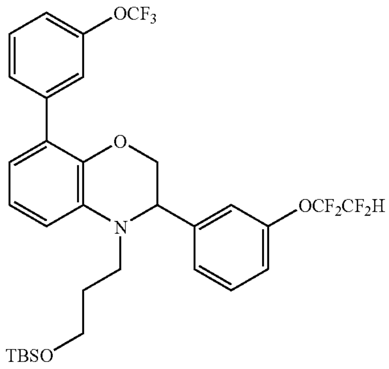 | Not Applicable |
| 26 | 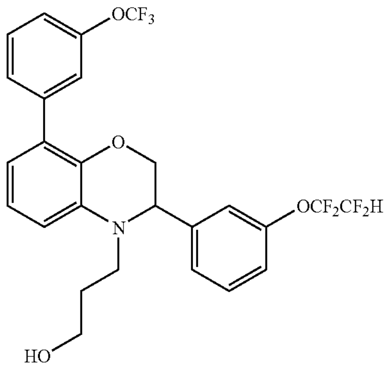 | Not Applicable |
| 27 | 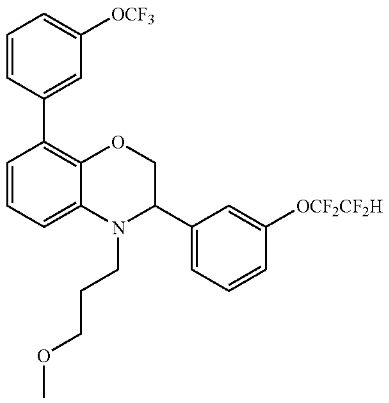 | Not Applicable |
| 28 | 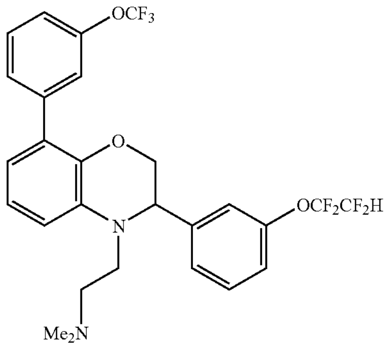 | Not Applicable |

TABLE 1-continued
Representative Compounds
| Cpd No. | Structure | Rf |
|---|---|---|
| 29 | 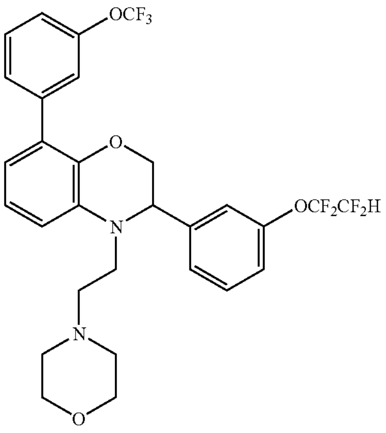 | Not Applicable |
| 30 | 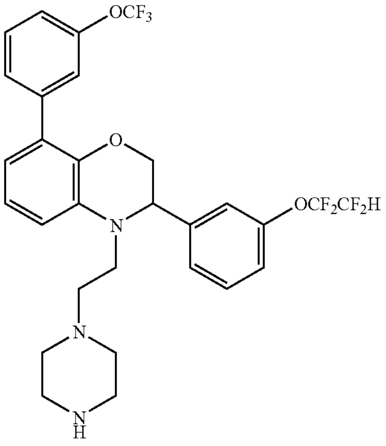 | Not Applicable |
| 31 | 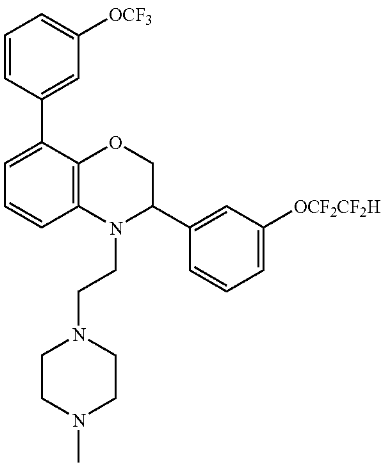 | Not Applicable |
TABLE 1-continued
Representative Compounds
| Cpd No. | Structure | Rf |
|---|---|---|
| 32 | 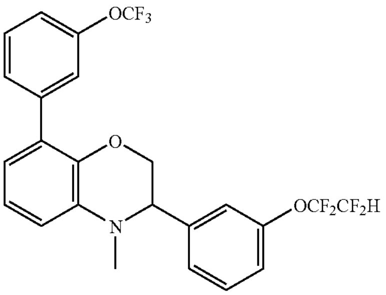 | Not Applicable |
| 33 | 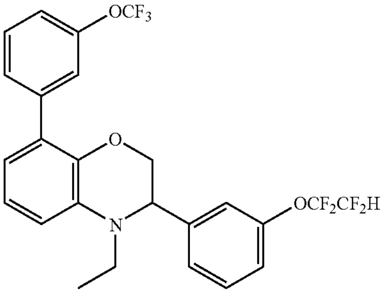 | Not Applicable |
| 34 | 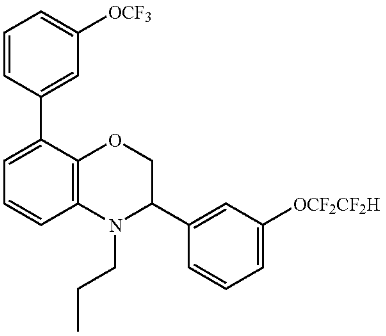 | Not Applicable |
| 35 | 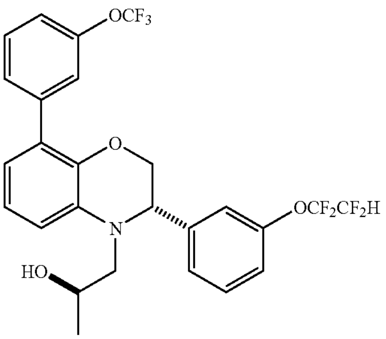 | Not Applicable |

TABLE 1-continued
| Representative Compounds | | |
|---|---|---|
| Cpd No. | Structure | Rf |
| 36 | 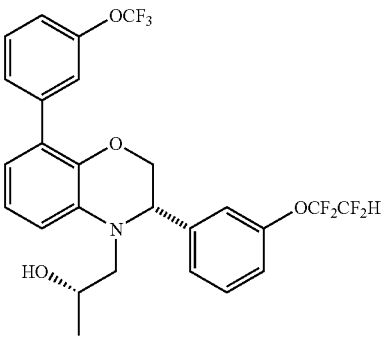 | Not Applicable |
| 37 | 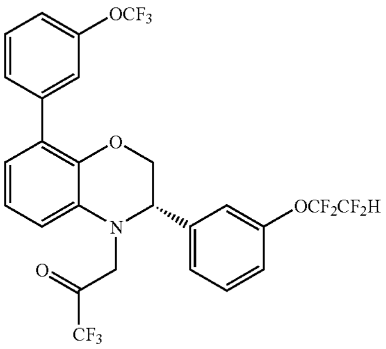 | Not Applicable |
| 38 | 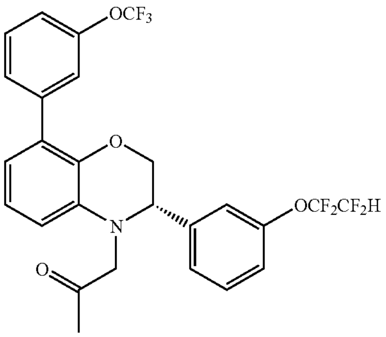 | Not Applicable |
| 39 | 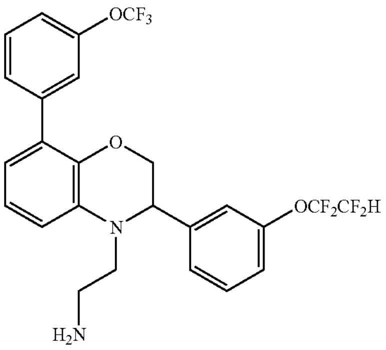 | Not Applicable |
TABLE 1-continued
| Representative Compounds | | |
|---|---|---|
| Cpd No. | Structure | Rf |
| 40 | 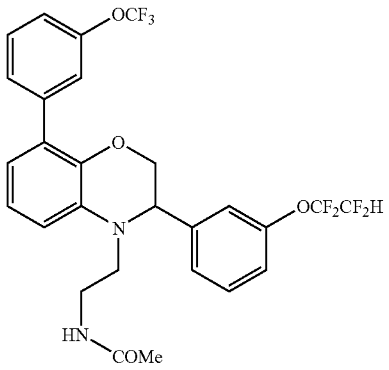 | Not Applicable |
| 41 | 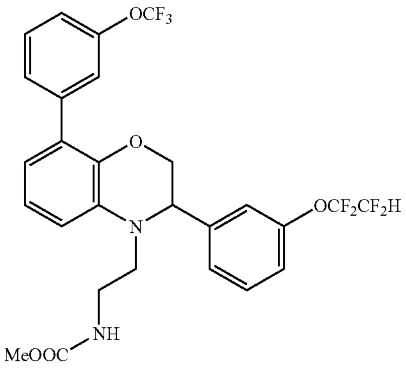 | Not Applicable |
| 42 | 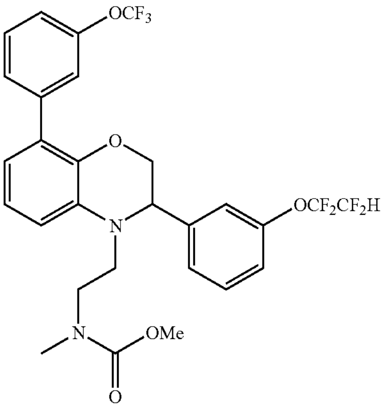 | Not Applicable |
| 43 | 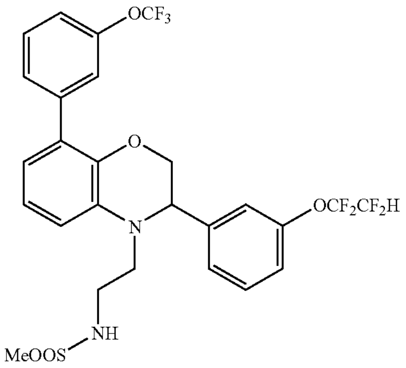 | Not Applicable |

TABLE 1-continued
| Representative Compounds | | |
|---|---|---|
| Cpd No. | Structure | Rf |
| 44 | 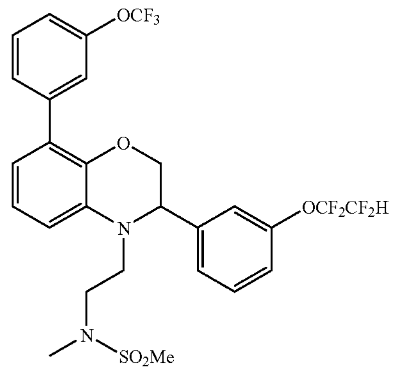 | Not Applicable |
| 45 | 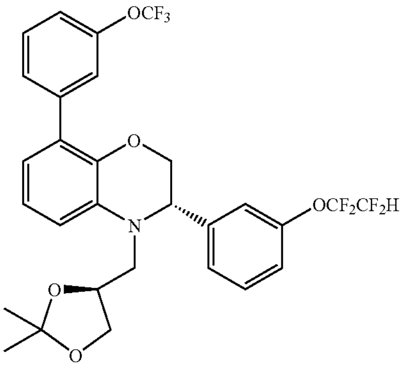 | Not Applicable |
| 46 | 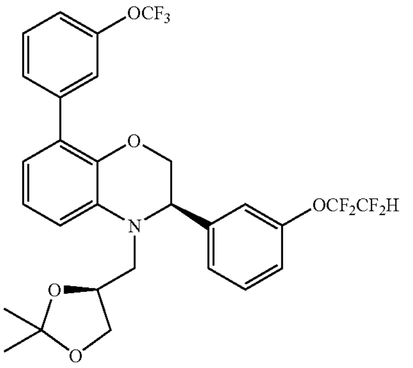 | Not Applicable |
| 47 | 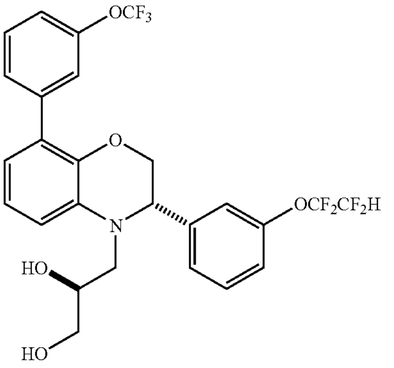 | Not Applicable |
TABLE 1-continued
| Representative Compounds | | |
|---|---|---|
| Cpd No. | Structure | Rf |
| 48 | 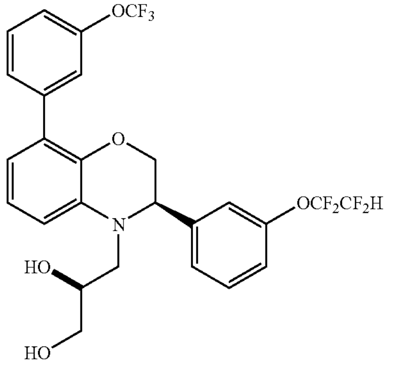 | Not Applicable |
| 49 | 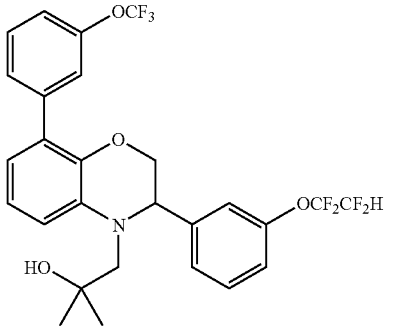 | Not Applicable |
| 50 | 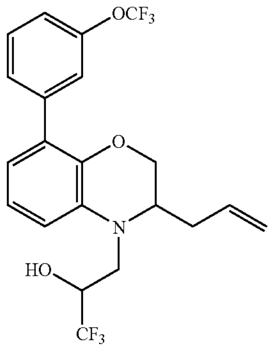 | Higher |
| 51 | 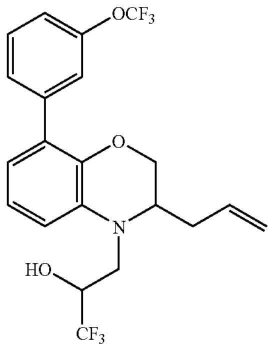 | Lower |

TABLE 1-continued
| Representative Compounds | | |
|---|---|---|
| Cpd No. | Structure | Rf |
| 52 | 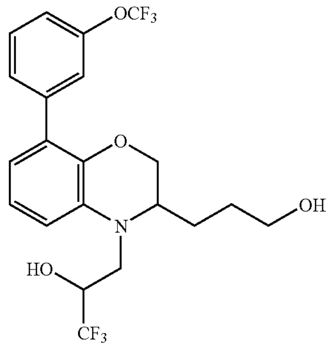 | Not Applicable |
| 53 | 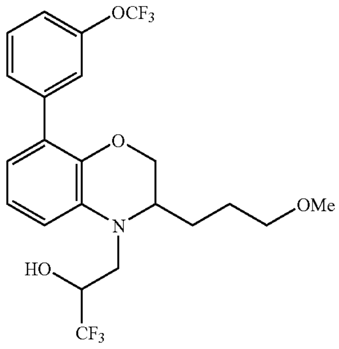 | Not Applicable |
| 54 | 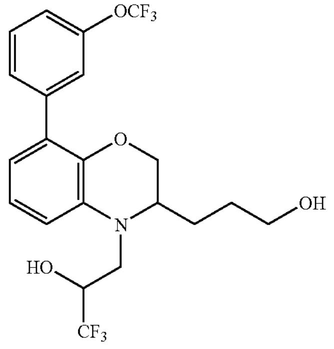 | Not Applicable |
| 55 | 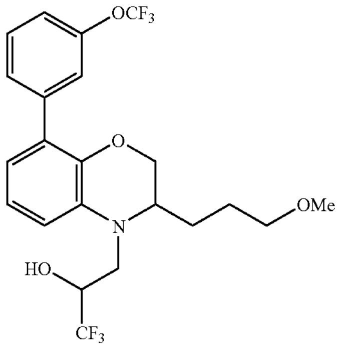 | Not Applicable |
| 56 | 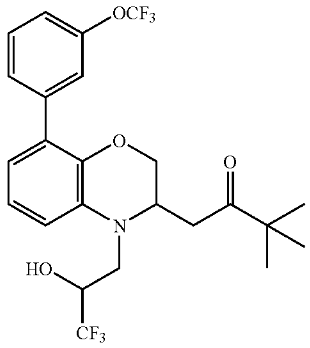 | Higher |
| 57 | 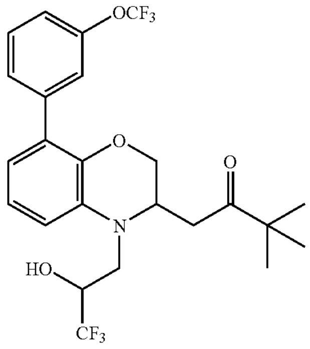 | Lower |
| 58 | 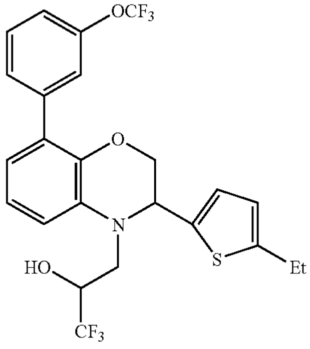 | Higher |
| 59 | 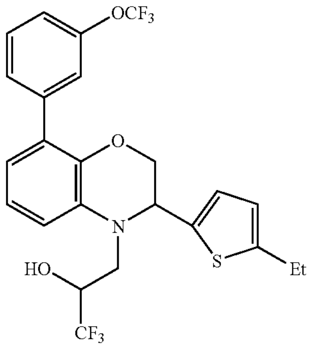 | Lower |

TABLE 1-continued
Representative Compounds
| Cpd No. | Structure | Rf |
|---|---|---|
| 60 | 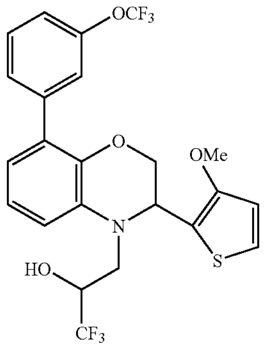 | Higher |
| 61 | 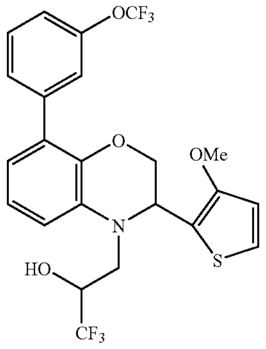 | Lower |
| 62 | 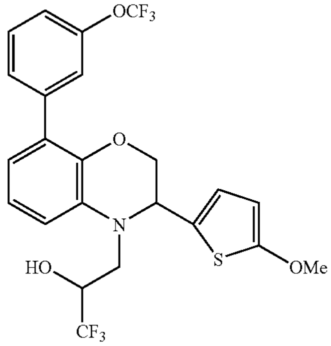 | Higher |
| 63 | 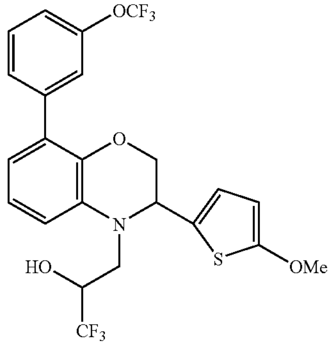 | Lower |
| 64 | 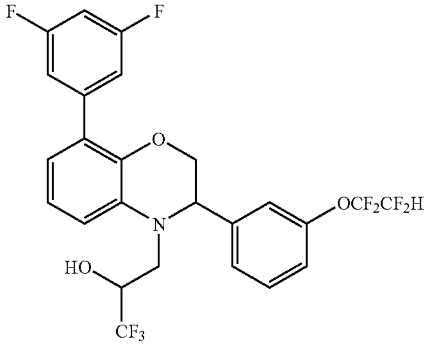 | Higher |
| 65 | 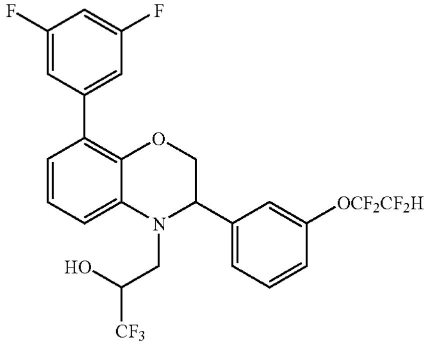 | Lower |
| 66 | 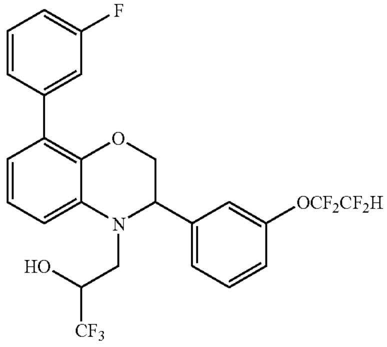 | Higher |
| 67 | 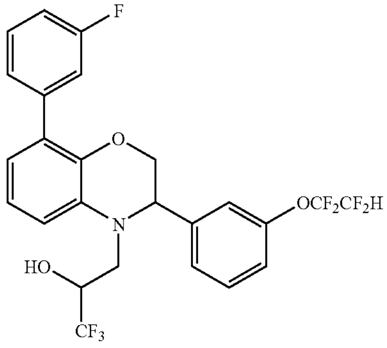 | Lower |

TABLE 1-continued
Representative Compounds
| Cpd No. | Structure | Rf |
|---|---|---|
| 68 | 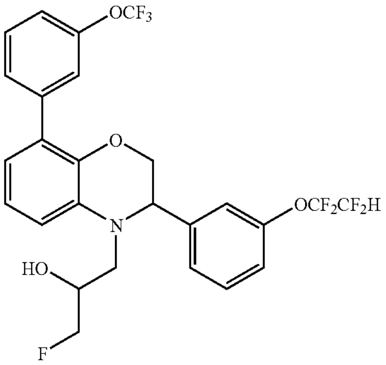 | Higher |
| 69 | 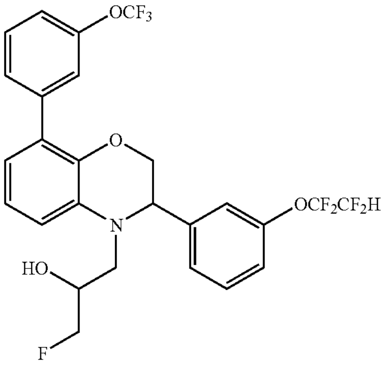 | Lower |
| 70 | 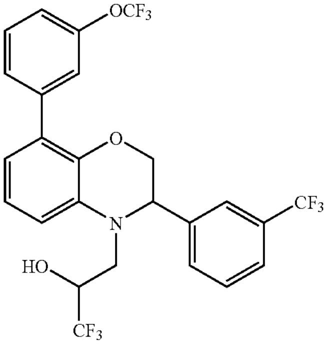 | Higher |
| 71 | 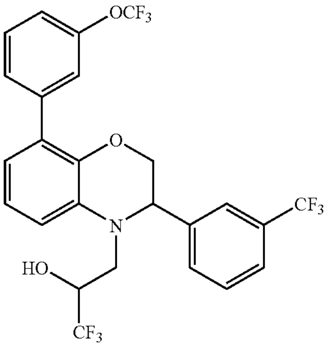 | Lower |
TABLE 1-continued
Representative Compounds
| Cpd No. | Structure | Rf |
|---|---|---|
| 72 | 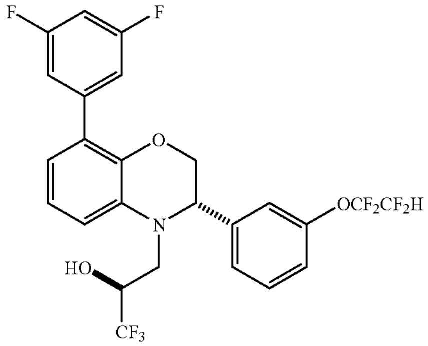 | Not Applicable |
| 73 | 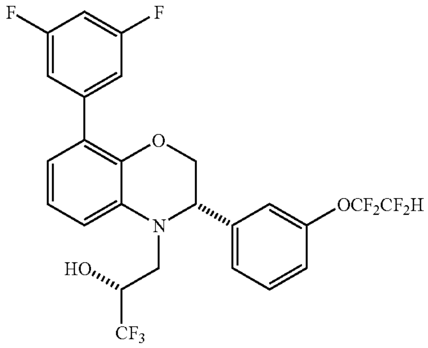 | Not Applicable |
| 74 | 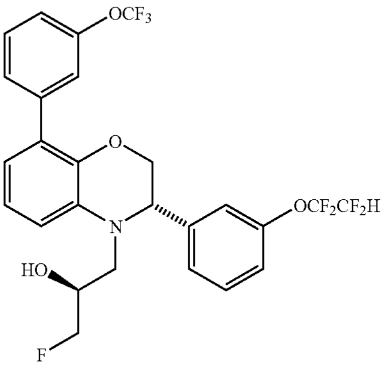 | Not Applicable |
| 75 | 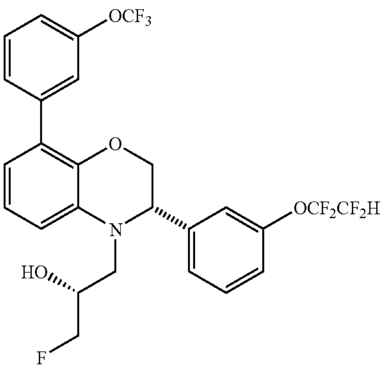 | Not Applicable |

TABLE 1-continued
Representative Compounds
| Cpd No. | Structure | Rf |
|---|---|---|
| 76 | 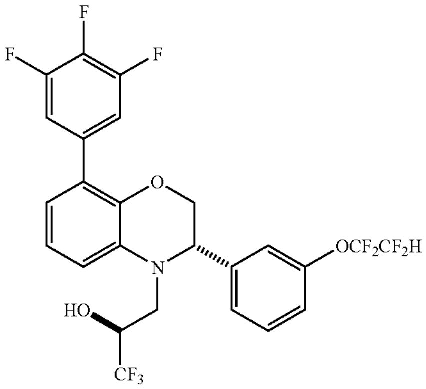 | Not Applicable |
| 77 | 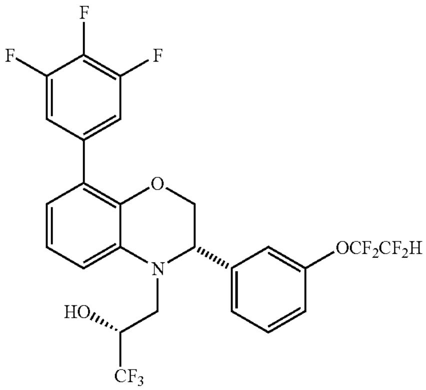 | Not Applicable |
| 78 | 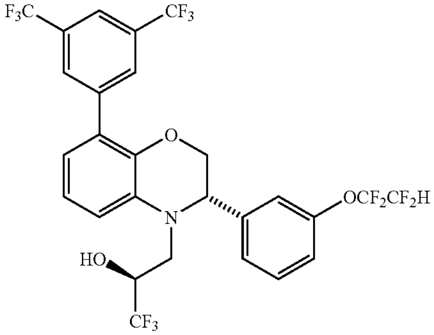 | Not Applicable |
| 79 | 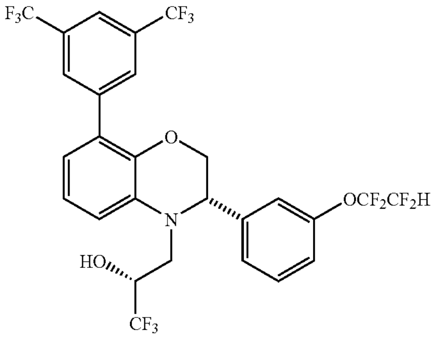 | Not Applicable |
TABLE 1-continued
Representative Compounds
| Cpd No. | Structure | Rf |
|---|---|---|
| 80 | 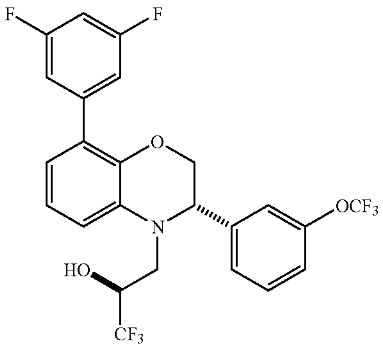 | Not Applicable |
| 81 | 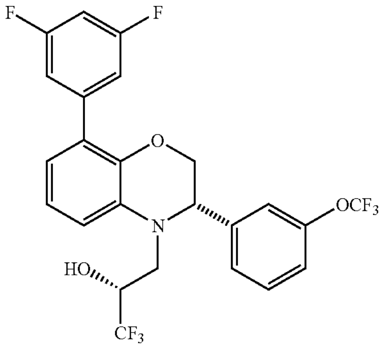 | Not Applicable |
| 82 | 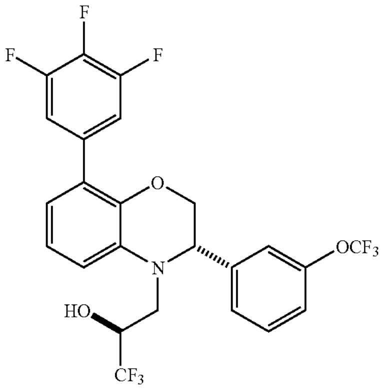 | Not Applicable |
| 83 | 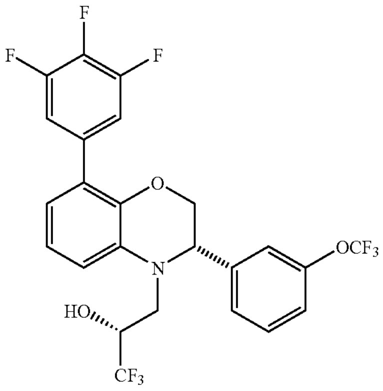 | Not Applicable |

TABLE 1-continued
Representative Compounds
| Cpd No. | Structure | Rf |
|---|---|---|
| 84 | 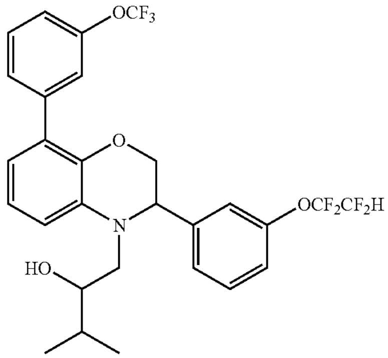 | Not Applicable |
| 85 | 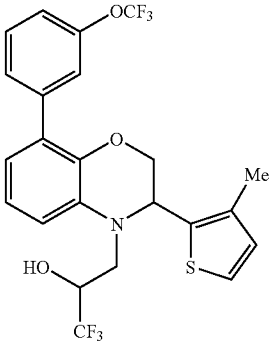 | Higher |
| 86 | 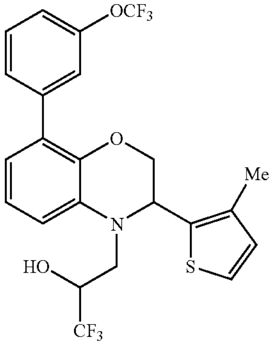 | Lower |
| 87 | 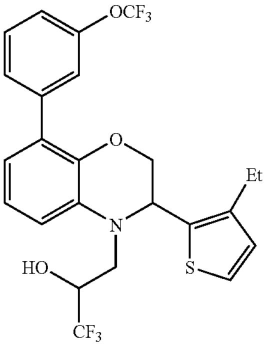 | Higher |
TABLE 1-continued
Representative Compounds
| Cpd No. | Structure | Rf |
|---|---|---|
| 88 | 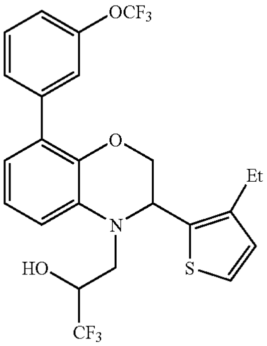 | Lower |
| 89 | 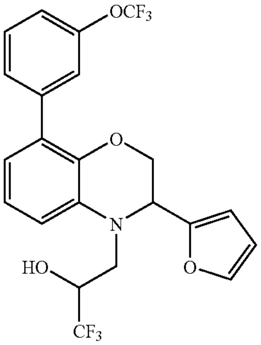 | Higher |
| 90 | 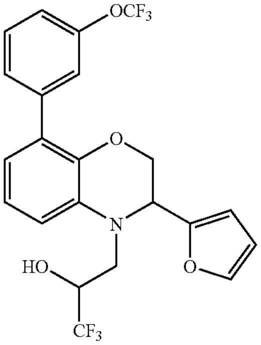 | Lower |
| 91 | 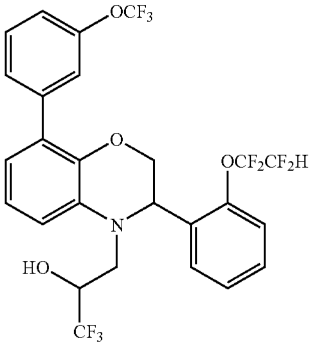 | Higher |

TABLE 1-continued
| Representative Compounds | | |
|---|---|---|
| Cpd No. | Structure | Rf |
| 92 | 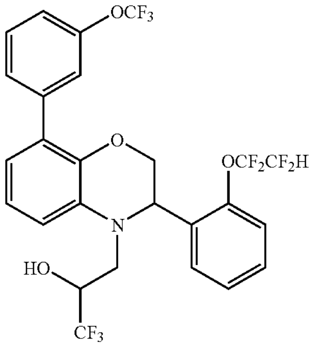 | Lower |
| 93 | 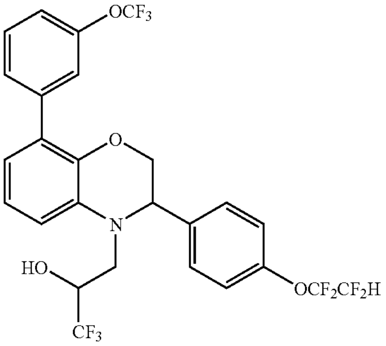 | Higher |
| 94 | 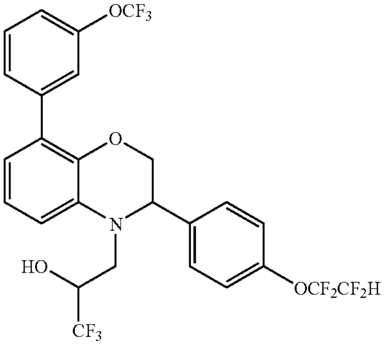 | Lower |
| 95 | 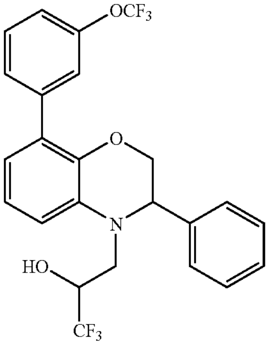 | Higher |
TABLE 1-continued
| Representative Compounds | | |
|---|---|---|
| Cpd No. | Structure | Rf |
| 96 | 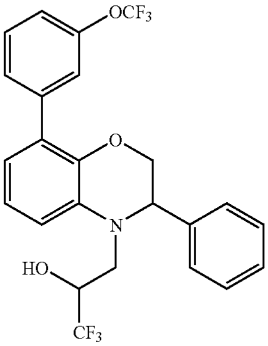 | Lower |
| 97 | 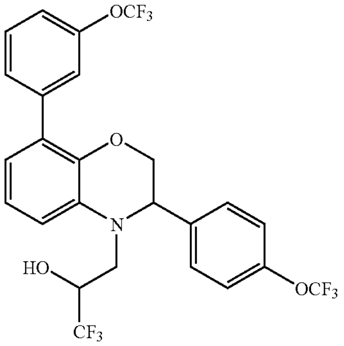 | Higher |
| 98 | 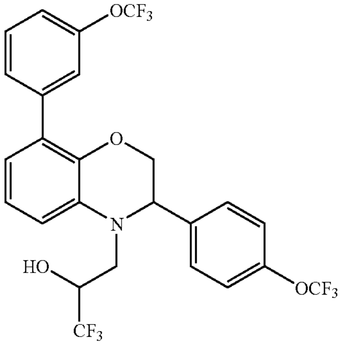 | Lower |
| 99 | 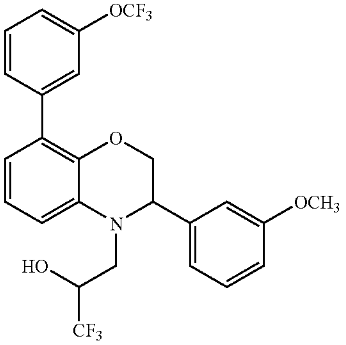 | Higher |

TABLE 1-continued
| Representative Compounds | | |
|---|---|---|
| Cpd No. | Structure | Rf |
| 100 | 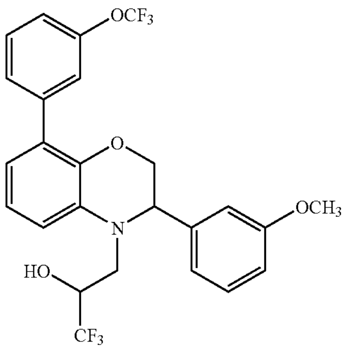 | Lower |
| 101 | 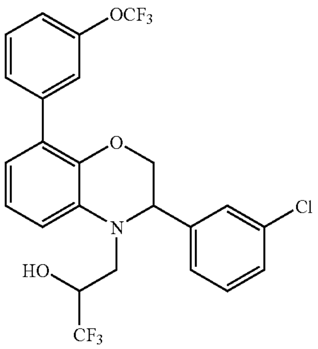 | Higher |
| 102 | 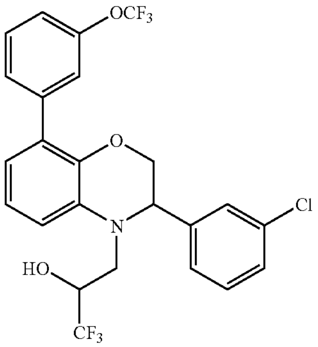 | Lower |
| 103 | 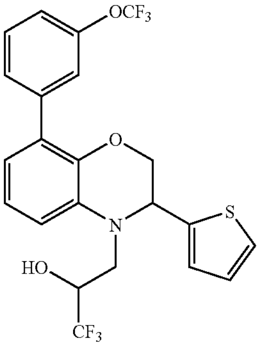 | Higher |
TABLE 1-continued
| Representative Compounds | | |
|---|---|---|
| Cpd No. | Structure | Rf |
| 104 | 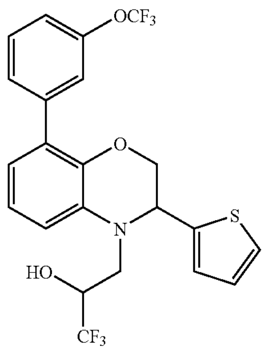 | Lower |
| 105 | 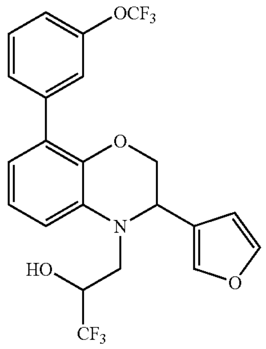 | Higher |
| 106 | 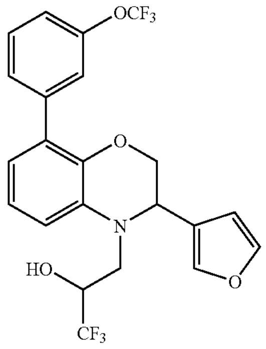 | Lower |
| 107 | 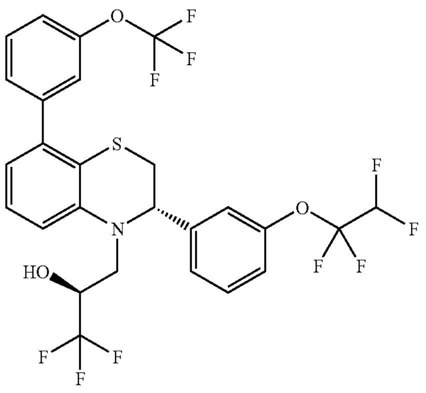 | |

TABLE 1-continued

| Representative Compounds | | |
|---|---|---|
| Cpd No. | Structure | Rf |
| 108 | 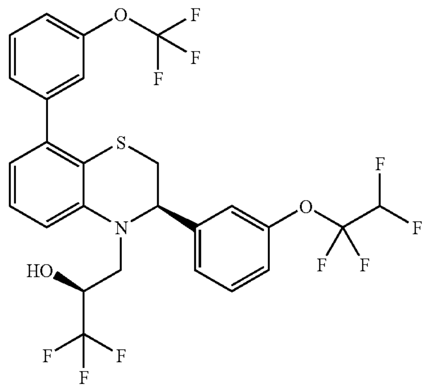 | |

Biological Examples

CETP In Vitro Assay

The CETP inhibitory activity of the compounds was determined using a commercially available kit from Amersham Biosciences (Catalog #TRKQ7005).

For the measurement of inhibitory activity in human plasma, a modified protocol (Connolly, D. T. et al., Biochemistry, 39 13870-13879, 2000) was used. Briefly, 80 μl of human plasma (obtained from normal volunteers), approximately 25 μg/ml (200) of [$^3$H]CE-HDL (Amersham Biosciences from kit TRKQ7005) and 1 μl of compound dissolved in DMSO was incubated for at least 4 hrs at 37° C. and non-specific transfer was determined by incubating a corresponding plate at 4° C. (blank). After the incubation period, 100 of a solution of 1% Dextralip 50/0.5M $MgCl_2$, pH 7.4 was added, vortexed and incubated at room temperature for 10 min. The plate was then centrifuged for 30 min at 10° C. at 3000 rpm in a Sorvall RT6000B centrifuge. Fifty microliters of the supernatant was transferred to a Picoplate (Packard) containing 100 μl of Microscint 40 (Perkin Elmer) and mixed for 30 min using a plate mixer. The radioactivity was counted using a TopCount (Perkin Elmer) and the % control was determined in the samples using the following formula: % transfer relative to vehicle controls (% control)=[cpm blank-cpm test]/cpm blank/cpm control]×100. $IC_{50}$s were calculated from plots of the % control versus compound concentration.

A variety of example compounds have been made and tested, with a range of in vitro results. Below, in Table 2, are representative compounds and the corresponding data; in some cases, where multiple $IC_{50}$'s are shown, multiple measurements were taken. Naturally, different compounds in Formula (I), (Ia), (Ib) and (Ic) may have not activities identical to any one compound below.

TABLE 2

In vitro data of representative compounds of the invention

| Cpd No. | % Inhibition @ 1 μM | $IC_{50}$ (μM) |
|---|---|---|
| 1 | 96 | 0.052, 0.038 |
| 2 | 73 | 0.276, 0.131 |
| 3 | 91 | 0.026 |
| 4 | 26 | Not Determined |
| 5 | 23 | Not Determined |
| 6 | 14 | Not Determined |
| 7 | 64, 66 | 0.104, 0.11 |
| 8 | 21 | Not Determined |
| 9 | 68, 72, 67 | 0.071, 0.195 |
| 10 | 23 | Not Determined |
| 13 | 48 | 0.104, 0.437 |
| 15 | 67, 69 | 0.36 |
| 16 | 20 | Not Determined |
| 17 | 55, 56 | 0.49 |
| 18 | 8 | Not Determined |
| 19 | 0 | Not Determined |
| 20 | 16 | Not Determined |
| 21 | 2 | Not Determined |
| 22 | 13 | Not Determined |
| 23 | 29 | Not Determined |
| 24 | 25 | Not Determined |
| 25 | 13 | Not Determined |
| 26 | 10 | Not Determined |
| 27 | 29 | Not Determined |
| 28 | 9 | Not Determined |
| 29 | 0 | Not Determined |
| 30 | 0 | Not Determined |
| 31 | 17 | Not Determined |
| 32 | 0 | Not Determined |
| 33 | 24 | Not Determined |
| 34 | 38, 39 | 0.190 |
| 35 | 47, 52 | 0.026, 0.117, 0.121 |
| 36 | 28 | Not Determined |
| 37 | 5 | Not Determined |
| 38 | 5 | Not Determined |
| 39 | 2 | Not Determined |
| 40 | 0 | Not Determined |
| 41 | 2 | Not Determined |
| 42 | 8 | Not Determined |
| 43 | 0 | Not Determined |
| 44 | 0 | Not Determined |
| 45 | 25 | Not Determined |
| 46 | 20 | Not Determined |
| 47 | 27 | Not Determined |
| 48 | 13 | Not Determined |
| 49 | 34, 24 | 0.560 |
| 50 | 10 | Not Determined |
| 51 | 0 | Not Determined |
| 52 | 13 | Not Determined |
| 53 | 0 | Not Determined |
| 54 | 1 | Not Determined |
| 55 | 0 | Not Determined |
| 56 | 9 | Not Determined |
| 57 | 0 | Not Determined |
| 58 | 60, 96 | 0.502 |
| 59 | 0 | Not Determined |
| 60 | 0 | Not Determined |
| 61 | 3 | Not Determined |
| 62 | 19 | Not Determined |
| 63 | 17 | Not Determined |
| 64 | 121, 101, 119 | 0.1, 0.117 |
| 65 | 86, 76 | 0.99 |
| 66 | 104, 79, 107 | 0.001, 0.322 |
| 67 | 97, 83 | 0.78 |
| 68 | 79, 91 | 0.127 |
| 69 | 50 | Not Determined |
| 70 | 37 | Not Determined |
| 71 | 2 | Not Determined |
| 72 | 100 | 0.05 |
| 73 | 76 | 0.46 |
| 74 | 77 | 0.014 |
| 75 | 55 | 0.147 |
| 76 | 106, 101 | 0.041 |
| 77 | 80, 82 | 0.22 |
| 78 | 55, 62 | 0.58 |

TABLE 2-continued

| In vitro data of representative compounds of the invention | | |
|---|---|---|
| Cpd No. | % Inhibition @ 1 μM | $IC_{50}$ (μM) |
| 79 | 43, 40 | 5.0 |
| 80 | 100 | 0.193 |
| 82 | 91, 96 | 0.094 |
| 83 | 29 | Not Determined |
| 84 | 84, 87 | 0.1, 0.158 |
| 85 | 20 | Not Determined |
| 86 | 2 | Not Determined |
| 87 | 8 | Not Determined |
| 88 | 12 | Not Determined |
| 89 | 17 | Not Determined |
| 90 | 17 | Not Determined |
| 91 | 6 | Not Determined |
| 92 | 1 | Not Determined |
| 93 | 33 | Not Determined |
| 94 | 11 | Not Determined |
| 95 | 43 | Not Determined |
| 96 | 1 | Not Determined |
| 97 | 38 | Not Determined |
| 98 | 10 | Not Determined |
| 99 | 29 | Not Determined |
| 100 | 6 | Not Determined |
| 101 | 61, 63 | 0.214 |
| 102 | 0 | Not Determined |
| 103 | 20 | Not Determined |
| 104 | 0 | Not Determined |
| 105 | 2 | Not Determined |
| 106 | 0 | Not Determined |
| 107 | 59, 87 | 0.134, 0.198 |
| 108 | 34, 39 | >2.925 |

CETP In Vivo Assay

To determine the in vivo efficacy of a test compound, hamsters are first fed a moderately high cholesterol diet (Research Diets, D5012801) for two weeks before commencing treatment. The animals are orally gavaged with the vehicle (10% solutol, 5% ethanol, 85% D5W) and test compound for 5 days with the last dose being administered 2 hrs before sacrifice. Plasma is obtained and lipid parameters (HDL-C, LDL-C, Total Cholesterol, Triglycerides) are measured.

The results for compound 3 is shown in Table 3.

TABLE 3

| Effect of Compound 3 on lipid parameters in cholesterol-fed hamsters | | | | | |
|---|---|---|---|---|---|
| Dose (mg/kg) | HDL (mg/dL) | LDL (mg/dL) | Total Cholesterol (mg/dL) | Triglycerides (mg/dL) | HDL-C/LDL Ratio |
| Vehicle | 145 ± 7 | 37 ± 2 | 218 ± 11 | 228 ± 20 | 3.9 ± 0.3 |
| 3 mg/kg | 136 ± 6 | 36 ± 3 | 207 ± 7 | 278 ± 21 | 3.7 ± 0.2 |
| 10 mg/kg | 158 ± 10 | 30 ± 2 | 217 ± 12 | 282 ± 16 | 5.2 ± 0.4 |
| 30 mg/kg | 167 ± 5 | 27 ± 2 | 226 ± 5 | 300 ± 36 | 6.2 ± 0.3 |

Data are expressed as the mean ± SEM

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating a disease or condition in a mammal, which disease or condition is affected by the modulation of CETP;

wherein the disease or condition affected by modulation of CETP is selected from the group consisting of atherosclerosis, peripheral vascular disease, dyslipidemia, hyper-LDL-cholesterolemia, hyperbetaliproteinemia, hypoalphalipoproteinemia, familial-hypercholesterolemia, angina, ischemia, cardiac ischemia, myocardial infarction, reperfusion injury, angioplastic restenosis, hypertension, vascular complications of diabetes, obesity and Metabolic Syndrome; and which method comprises administering to a mammal in need of such treatment a therapeutically effective amount of a compound of Formula (I)

Formula (I)

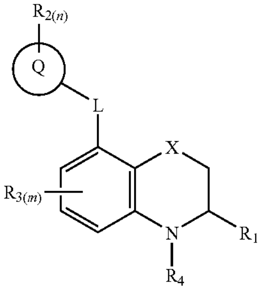

wherein:

L is a covalent bond or O;

X is O;

Q is $C_{6-10}$ aryl or 5- or 6-membered heteroaryl;

n is 0 to 3;

m is 0 to 3;

$R_1$ is $C_{1-10}$ alkyl, $C_{2-10}$ alkenyl, $C_{2-10}$ alkynyl, $C_{3-10}$cycloalkyl, 5- or 6-membered heteroaryl, wherein each of $C_{1-10}$ alkyl, $C_{2-10}$ alkenyl, $C_{2-10}$ alkynyl, $C_{3-10}$cycloalkyl, 5- or 6-membered heteroaryl may be optionally substituted;

or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated$C_{1-4}$alkoxy, optionally substituted $C_{1-4}$ alkylthio, halo, cyano, and hydroxy, or $R_a$ and $R_b$ together with the carbon atoms of the phenyl ring to which they are attached form an optionally substituted 5- or 6-membered heterocyclyl fused to the phenyl ring;

each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;

each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;

$R_4$ is $C_{1-10}$ alkyl optionally substituted with 1-3 members independently selected from halo, oxo, hydroxy, halogenated $C_{1-4}$alkyl, $C_{1-4}$ alkoxy, $C_{3-8}$ cycloalkyl, CN, tert-butyldimethylsilyloxy, optionally substituted heterocyclyl and —$NR_cR_d$, wherein $R_c$ and $R_d$ are independently selected from H, optionally substituted $C_{1-3}$ alkyl, —$C(O)C_{1-3}$alkyl, —C(O)O—$C_{1-3}$ alkyl, and —$SO_2C_{1-3}$ alkyl; or $R_4$ is $C_{1-6}$alkyl substituted with heteroaryl or phenyl substituted with 1 to 3 members independently selected from halo, hydroxy, $C_{1-3}$alkyl, halogenated $C_{1-3}$alkyl, $C_{1-4}$alkoxy, or halogenated $C_{1-4}$alkoxy;

or an enantiomer, diastereomer, tautomer, or pharmaceutically acceptable salt thereof.

2. The method of claim 1, which comprises increasing HDL-C in said mammal.

3. The method of claim 1, which comprises increasing the ratio of HDL-C/total cholesterol in said mammal.

4. The method of claim 1, which comprises increasing the ratio of HDL-C/LDL-C in said mammal.

5. The method of claim 1, which comprises lowering either or both of LDL-C and non-HDL-C cholesterol in said mammal.

6. The method of claim 1, wherein said therapeutically effective amount comprises a dose range of from about 0.01 mg to about 1,000 mg.

7. The method of claim 1 wherein said therapeutically effective amount comprises a dose range of from about 10 mg to about 800 mg.

8. The method of claim 1 wherein said therapeutically effective amount comprises a dose range of from about 50 mg to about 400 mg.

9. The method of claim 1, wherein the disease or condition affected by modulation of CETP is selected from the group consisting of atherosclerosis, hypertriglyceridemia, hypercholesterolemia, mixed hyperlipidemia, and hypo-HDL-cholesterolemia.

10. The method of claim 1, wherein m is 0.

11. The method of claim 1, wherein n is 1 or 2.

12. The method of claim 1, wherein L is a covalent bond.

13. The method of claim 1, wherein Q is phenyl.

14. The method of claim 1, wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, hydroxy, halogenated $C_{1-4}$alkylthio, or an optionally substituted five membered heterocyclyl ring fused to the phenyl ring forming a bicyclic ring system.

15. The method of claim 1, wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

16. The method of claim 1, wherein $R_1$ is phenyl substituted with halogenated $C_{1-4}$alkyl or halogenated $C_{1-4}$alkoxy.

17. The method of claim 1, wherein $R_1$ is phenyl substituted with $-OCF_2CF_2H$, $-CF_3$, or $-OCF_3$.

18. The method of claim 1, wherein $R_1$ is $C_{1-6}$ alkyl substituted with hydroxy, $C_{1-4}$alkoxy, oxo, halo, or cyano.

19. The method of claim 1, wherein $R_1$ is furanyl or thienyl optionally substituted with $C_{1-3}$alkyl, $C_{1-3}$alkoxy, hydroxy, or cyano.

20. The method of claim 1, wherein n is 1, 2, or 3 and each $R_2$ is independently selected from halo, halogenated $C_{1-4}$alkyl, and halogenated $C_{1-4}$alkoxy.

21. The method of claim 1, wherein each $R_2$ is independently selected from $-OCF_2CF_2H$, $-OCF_3$ or F.

22. The method of claim 1, wherein n is 1 and $R_2$ is halogenated $C_{1-4}$alkoxy.

23. The method of claim 1, wherein $R_2$ is $-OCF_2CF_2H$.

24. The method of claim 1, wherein $R_4$ is $C_{1-5}$ alkyl optionally substituted with 1 or 2 members each independently selected from halo, oxo, hydroxy, halogenated$C_{1-4}$alkyl, and optionally substituted heterocyclyl.

25. The method of claim 1, wherein $R_4$ is $C_{1-3}$ alkyl substituted with 2 members each independently selected from halo, hydroxy, and halogenated$C_{1-3}$alkyl.

* * * * *